(12) United States Patent
Cho et al.

(10) Patent No.: US 10,844,062 B2
(45) Date of Patent: Nov. 24, 2020

(54) PYRIDINE DERIVATIVE INHIBITING RAF KINASE AND VASCULAR ENDOTHELIAL GROWTH FACTOR RECEPTOR, METHOD FOR PREPARING SAME, PHARMACEUTICAL COMPOSITION CONTAINING SAME, AND USE THEREOF

(71) Applicants: SAMJIN PHARMACEUTICAL CO., LTD., Seoul (KR); INCHEON UNIVERISTY INDUSTRY ACADEMIC COOPERATION FOUNDATION, Incheon (KR); BAMICHEM CO., LTD., Incheon (KR)

(72) Inventors: Eui Hwan Cho, Seoul (KR); Hee Jong Shin, Gyeonggi-do (KR); Min Hyo Ki, Gyeonggi-do (KR); Ho Seok Kwon, Gyeonggi-do (KR); Jae Woong Lee, Gyeonggi-do (KR); Jeong Ho Joo, Gyeonggi-do (KR); Keun Kuk Lee, Gyeonggi-do (KR); Jong Min Kim, Seoul (KR); Yong Bin Park, Gyeonggi-do (KR); Sung Hyun Kang, Seoul (KR); Hyoung Min Cho, Gyeonggi-do (KR); Hyun Tae Kim, Gyeonggi-do (KR); Soon Kil Ahn, Seoul (KR); Sung Pyo Hong, Gyeonggi-do (KR); Sung Hye Kim, Gyeonggi-do (KR)

(73) Assignees: Incheon University Industry Academic Cooperation Foundation, Incheon (KR); Samjin Pharmaceutical Co., Ltd., Seoul (KR); Bamichem Co., Ltd., Incheon (KR)

( * ) Notice: Subject to any disclaimer, the term of this patent is extended or adjusted under 35 U.S.C. 154(b) by 0 days.

(21) Appl. No.: 16/074,950

(22) PCT Filed: Jan. 11, 2017

(86) PCT No.: PCT/KR2017/000387
§ 371 (c)(1),
(2) Date: Aug. 2, 2018

(87) PCT Pub. No.: WO2017/135589
PCT Pub. Date: Aug. 10, 2017

(65) Prior Publication Data
US 2019/0300531 A1 Oct. 3, 2019

(30) Foreign Application Priority Data
Feb. 3, 2016 (KR) ........................ 10-2016-0013643

(51) Int. Cl.
C07D 473/00 (2006.01)
A61P 35/00 (2006.01)
C07D 487/04 (2006.01)
C07D 401/04 (2006.01)
C07D 401/14 (2006.01)
A61K 31/52 (2006.01)
A61K 31/519 (2006.01)

(52) U.S. Cl.
CPC .......... *C07D 473/00* (2013.01); *A61K 31/519* (2013.01); *A61K 31/52* (2013.01); *A61P 35/00* (2018.01); *C07D 401/04* (2013.01); *C07D 401/14* (2013.01); *C07D 487/04* (2013.01)

(58) Field of Classification Search
CPC ... C07D 473/00; C07D 401/04; C07D 401/14
See application file for complete search history.

(56) References Cited

U.S. PATENT DOCUMENTS

| | | | |
|---|---|---|---|
| 2010/0273764 | A1 | 10/2010 | Andrews et al. |
| 2014/0296261 | A1* | 10/2014 | Xiao .................... C07D 473/00 514/263.22 |

FOREIGN PATENT DOCUMENTS

| | | |
|---|---|---|
| CA | 2820550 | 5/2013 |
| CN | 103102349 | 5/2013 |
| CN | 103387576 | 11/2013 |
| KR | 1020120007540 | 1/2012 |
| KR | 1020120060744 | 6/2012 |
| WO | WO 2008/153947 | 12/2008 |
| WO | 2013/071865 A1 | 5/2013 |

OTHER PUBLICATIONS

Schubbert. Nature Reviews: Cancer, 2007, 7, 295-308 (Year: 2007).*
"Treatment of obesity", http://www.guideline.gov/summary/summary.aspx?doc_id=9854&nbr=5278&ss=6&xl=999, accessed Oct. 16, 2008, primary reference 2006 (Year: 2006).*
"Can childhood leukemia be prevented?", https://www.cancer.org/cancer/leukemia-in-children/causes-risks-prevention/prevention.html, accessed Oct. 25, 2018, last revised Feb. 3, 2016 (Year: 2016).*
Silverman. The Organic Chemistry of Drug Design and Drug Action, 2004, 25-34 (Year: 2004).*
Longbin L. et al., "Purinylpyridinylamino-based DFG-in/aC-helix-out B-Raf inhibitors: Applying mutant versus wild-type B-Raf selectivity indices for compound profiling", Bioorganic & Medicinal Chemistry, (2016) pp. 2215-2234, vol. 24, No. 10.

(Continued)

*Primary Examiner* — Noble E Jarrell
(74) *Attorney, Agent, or Firm* — Brinks Gilson & Lione

(57) ABSTRACT

The present invention provides a novel pyridine derivative, a pharmaceutically acceptable salt thereof, a method for preparing the same, and a pharmaceutical composition containing the same as an active ingredient. The pyridine derivative according to the present invention inhibits Raf kinase (B-Raf, Raf-1, or B-RafV600E) and a vascular endothelial growth factor receptor (VEGFR2) involved in angiogenesis, and thus, can be favorably used for the prevention or treatment of melanoma, colorectal cancer, prostate cancer, thyroid cancer, lung cancer, pancreatic cancer, ovarian cancer, or the like, which is induced by RAS mutation.

7 Claims, 3 Drawing Sheets

(56) References Cited

OTHER PUBLICATIONS

Ahn, J-H et al., "Oncogenic BRAF inhibitor UAI-201 induces cell cycle arrest and autophagy in BRAF mutant glioma cells" Life Sciences, 2014, p. 38-46, vol. 104.
New Zealand Office Action for NZ745003, dated Nov. 15, 2018.
Korean Office Action for KR20170004155, dated Jan. 2, 2019.
Yang, Weimin et al. "Design, synthesis and biological evaluation of bisarylureas and amides based on 2-amino-3-purinylpyridine scaffold as DFG-out B-Raf kinase inhibitors", European Journal of Medicinal Chemistry, 2015, pp. 581-591, vol. 89, and Supplementary data, pp. SI-S5.
Chapman, Paul B. et al. "Improved Survival with Vemurafenib in Melanoma with BRAF V600E Mutation", The New England Journal of Medicine, 2011, p. 2507-2516, vol. 364.
Connolly, Daniel, et al. "Human Vascular Permeability Factor", The Journal of Biological Chemistry, Nov. 25, 1989, p. 20017-20024, vol. 264, No. 33.
Davies, Helen et al. "Mutations of the BRAF gene in human cancer", Nature, Jun. 27, 2002, p. 949-954, vol. 417.
English translation of the International Search Report dated Apr. 20, 2017, prepared in International Application No. PCT/KR2017/000387.
English translation of the Written Opinion dated Apr. 20, 2017, prepared in International Application No. PCT/KR2017/000387.
Fan, Tai-Pinf D., et al. "Controlling the vasculature: angiogenesis, anti-angiogenesis and vascular targeting of gene therapy", Trends Pharmacol. Sci., 1995, pp. 57-66, vol. 16.
Folkman, Judah, "Angiogenesis in cancer, vascular, rheumatoid and other disease", Nature Medicine, Nov. 1, 1995, pp. 27-31, vol. 1.
Hagemann, Carsten et al. "Isotype-Specific Functions of Raf Kinases", Experimental Cell Research, 1999, pp. 34-46 vol. 253.
Hatzivassiliou, Georgia, et al. "RAF inhibitors prime wild-type RAF to activate the MARK pathway and enhance growth" Nature, Mar. 18, 2010, pp. 431-435, vol. 464.
Heidorn, Sonja J. et al. "Kinase-Dead BRAF and Oncogenic RAS Cooperate to Drive Tumor Progression through CRAF", Cell, 2010, pp. 209-221, vol. 140.
Jakeman, Lyn B., et al. "Developmental Expression of Binding Sites and Messenger Ribonucleic Acid for Vascular Endothelial Growth Factor Suggests a Role for This Protein in Vasculogenesis and Angiogenesis", Endocrinology, 1993, pp. 848-859, vol. 133.
Karreth, Floriain A., "C-Raf is Required for the Initiation of Lung Cancer by K-Ras G12D", Cancer Discovery, 2011, pp. 128-136, vol. 1.
Kim, K. Jin et al. "Inhibition of vascular endothelial growth factor-induced angiogenesis suppresses tumour growth in vivo", Nature, Apr. 29, 1993, pp. 841-844, vol. 362.
Kolch, Walter, et al. "Regulation of the expression of the VEGF/VPS and its receptors: role in tumor angiogenesis", Breast cancer Research and Treatment, 1995, pp. 139-155, vol. 36.
Mercer, Kathryn E., et al. "Raf proteins and cancer: B-Raf is identified as a mutational target", Biochimica et Biophysica Acta, 2003, pp. 25-40, vol. 1653.
Sanchez-Laorden, Berta et al. "BRAF Inhibitors Induce Metastasis in RAS Mutant or Inhibitor-Resistant Melanoma Cells by Reactivating MEK and ERK Signaling" Science Signaling, Mar. 25, 2014, pp. 1-12, vol. 7, issue 318 ra30.
Yang, Weimin et al. "Design, synthesis and biological evaluation of bis-aryl ureas and amides based on 2-amino-3-purinylpyridine scaffold as DFG-out B-Raf kinase inhibitors", European Journal of Medicinal Chemistry, 2015, pp. 581-591, vol. 89.

\* cited by examiner

【Figure 1】
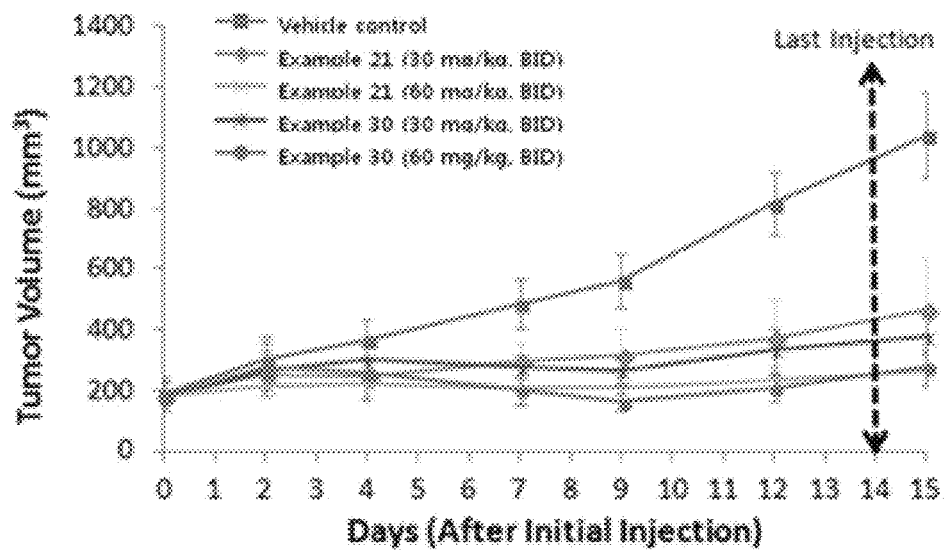
【Figure 2】
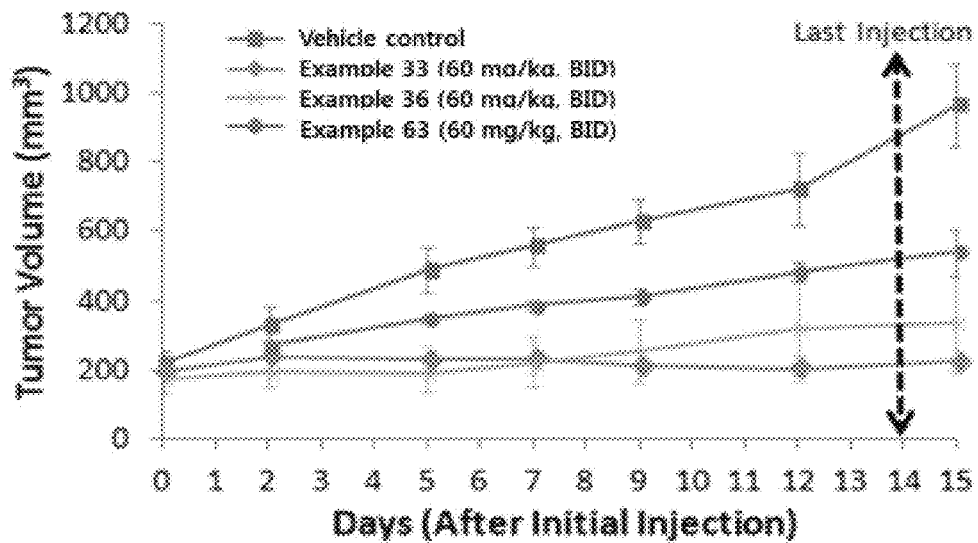

【Figure 3】
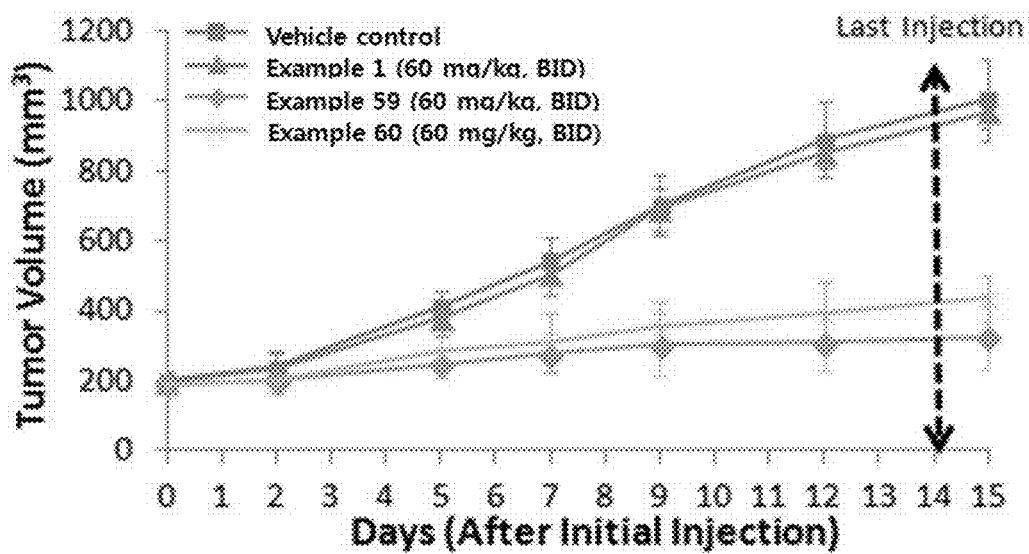
【Figure 4】
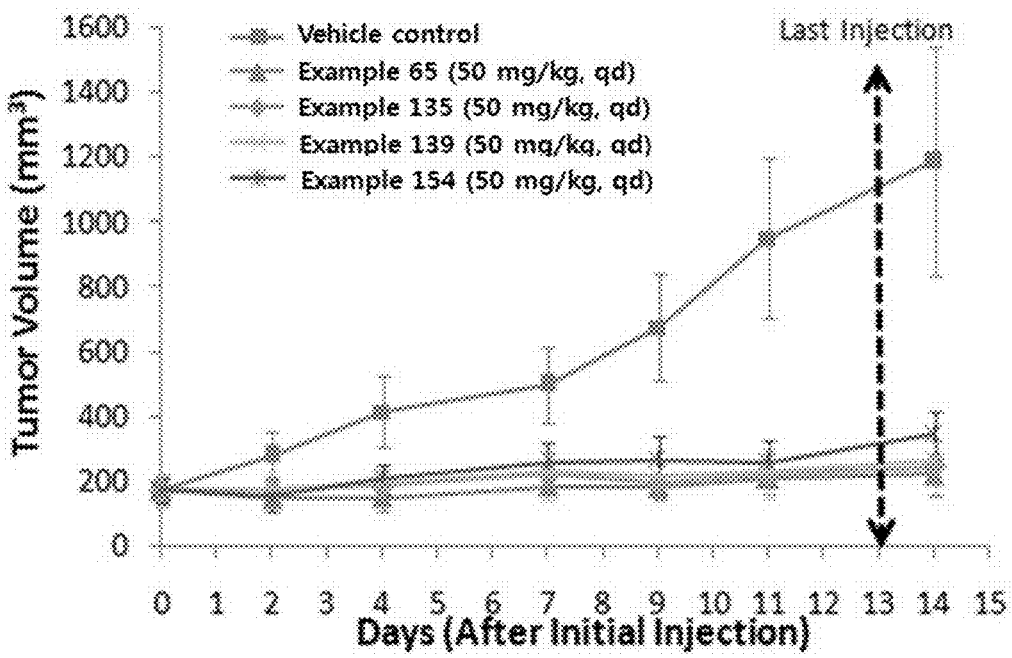

[Figure 5]
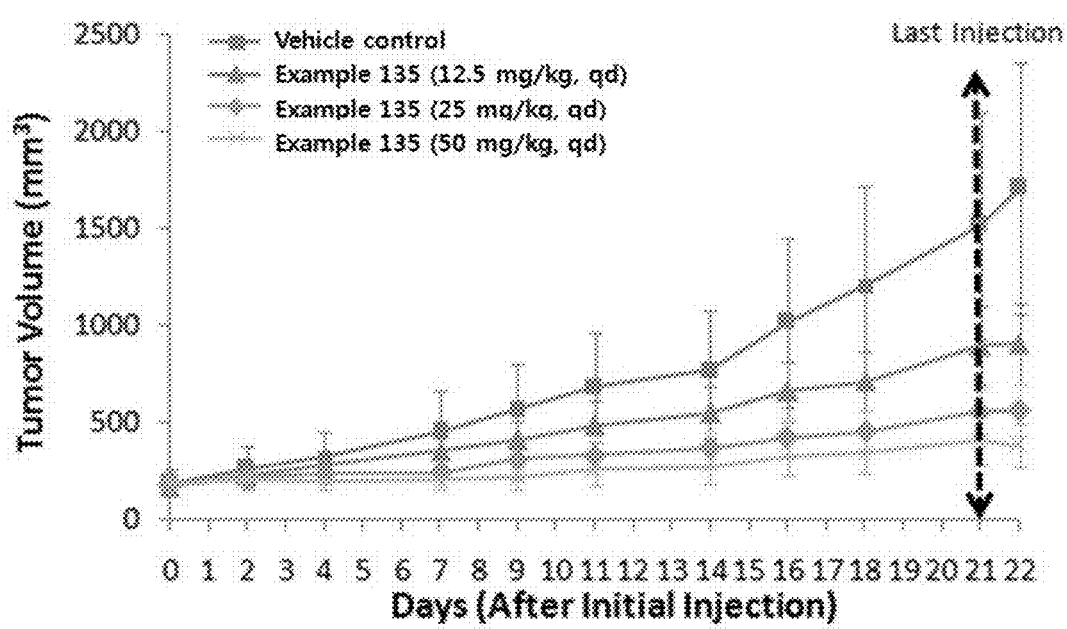

PYRIDINE DERIVATIVE INHIBITING RAF KINASE AND VASCULAR ENDOTHELIAL GROWTH FACTOR RECEPTOR, METHOD FOR PREPARING SAME, PHARMACEUTICAL COMPOSITION CONTAINING SAME, AND USE THEREOF

This application is a National Stage application of International Application No. PCT/KR2017/000387, filed Jan. 11, 2017. This application also claims priority under 35 U.S.C. § 119 to Korean Patent Application No. 10-2016-0013643, filed Feb. 3, 2016.

TECHNICAL FIELD

The present invention relates to a pyridine derivative that inhibits tyrosine kinases, particularly all Raf kinases and vascular endothelial growth factor 2 (VEGFR2), a method for preparing the same, a pharmaceutical composition containing the same, and the use thereof.

BACKGROUND ART

Cancer is a fatal disease that is one of the leading causes of adult deaths worldwide, and the incidence thereof is increasing. Currently, various drugs are used for the purpose of treating cancer. Most of the drugs treat cancer through their cytotoxicity, but show side effects, including cytotoxicity even against normal cells due to their low selectivity for cancer cells. Furthermore, resistance to anticancer drugs makes it more difficult to treat cancer. In an effort to overcome these problems, many new molecular-level targets have recently been identified through human genome sequencing and have become available for therapeutic use. Thus, studies have been actively conducted to maximize therapeutic effects while minimizing adverse effects by developing anticancer agents that selectively act on targets in cells, rather than using previous mechanisms of action that attack cells themselves.

Intracellular signaling pathways are functionally connected to each other and thereby form complex mechanisms that regulate cell proliferation, growth, metastasis, death and the like. Protein tyrosine kinases in signaling pathways play an important role in regulating intracellular functions, and abnormal expression and mutation thereof are commonly observed in cancer cells. Protein tyrosine kinases are enzyme which catalyzes the transfer of phosphate groups from ATP to tyrosines located on protein substrates. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, normal signaling by these receptors can become impossible, leading to various diseases. In addition, protein tyrosine kinase receptors play an important role in biochemical signaling cascades through the cellular plasma membrane. These transmembrane molecules typically contain an intracellular tyrosine kinase domain and an extracellular ligand-binding domain, which are linked to each other in the plasma membrane. Receptor-ligand binding simulates phosphorylation of tyrosine kinase residues between the receptor and another intracellular molecule, and changes caused by tyrosine phosphorylation elicit signaling through various cellular responses. Protein tyrosine kinases are classified into several families in association with growth factors. In particular, studies on vascular endothelial growth factor receptor (VEGFR) tyrosine kinases associated with VEGF have been actively conducted.

VEGFR tyrosine kinases consist of a receptor portion and a tyrosine kinase portion and are transmembrane proteins that transduce extracellular signals into cells. VEGFR tyrosine kinases are divided into VEGFR1, VEGFR2 and VEGFR3, and the major VEGFR involved in angiogenesis is known as VEGFR2 (KDR). Undesirable pathological angiogenesis is related to diseases such as retinopathy in diabetic patients, psoriasis, cancer, rheumatoid arthritis, atheroma, Kaposi's sarcoma, angioma and the like [Trends Pharmacol. Sci, 1995, 16, 57-66 and Nature Medicine, 1995, 1, 27-31]. In contrast to FGFs, VEGF growth factors are relatively active only in certain endothelial cells due to limited expression of their receptors. It was recently reported that VEGFs act as an important stimulator of normal and pathological angiogenesis [Jakeman et al., Endocrimology 133: 848-859, 1993; and Kolch et al., Breast Cancer Research and Treatment 36: 139-155, 1995] and vascular permeability [Connolly et al., J. Biol. Chem. 264: 20017-20024, 1989], and that antagonism of VEGF action by sequestration of VEGF with antibody can result in inhibition of tumor growth [Nature, 1993, 362, 841-844].

The processes involved in tumor growth, progression and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and RAF, and RAF plays an important role in MEK signaling in the Ras-Raf-MEK-ERK signaling pathway and plays a major role in tumor formation [Nature 2002, 417, 949-954]. Raf proteins include three isoforms (A-raf, B-raf, and C-raf) [Biochim. Biophys. Acta., 2003, 1653, 25-40], and among them, B-raf and C-raf play an important role in transducing signals from Ras to MEK. These Raf isoforms have very similar amino acid sequences, but have different biochemical activities and biological functions [Exp. Cell. Res. 1999, 253, 34-46]. Until now, the most frequent mutation of B-raf is a mutation of valine 600 to glutamic acid (V600E), which has been observed in more than 90% of human cancers. Therefore, anticancer agents that selectively target B-raf have been approved by the FDA and used as therapeutic agents against malignant skin melanoma. However, it is known that these therapeutic agents stimulate the binding of B-raf to C-raf by paradoxical activation in RAS-mutated cells and activate the RAF dimer, thus stimulating cell proliferation [Nature 2010, 464, 431-435 and Cell, 2010, 140, 209-221]. This is because not only B-raf but also C-raf plays an important role in the growth of cancer cells with RAS mutations, and thus the inhibition of only B-raf cannot inhibit downstream signals [Cancer Discov, 2011, 1, 128-136]. In addition, clinical tests indicated that selective B-raf inhibitors caused adverse effects such as cutaneous squamous cell carcinoma associated with RAS mutation [N. Engl. J. Med., 2011, 364, 2507-2516], and preclinical animal tests also indicated that selective B-raf inhibitors rather stimulated the growth and metastasis of cancer cells with RAS mutations [Nature, 2010, 464, 431-435 and Sci. Signal, 2014, 7, ra30].

Thus, in order to inhibit the growth and proliferation of cancer cells with RAS mutations, all Raf kinases (B-raf, raf-1, and B-raf V600E) should be inhibited, and in order to exhibit greater effects in vivo, vascular endothelial growth factor receptor 2 (VEGFR2) should also be inhibited.

International Patent Publication No. WO 2008/153947 and Korean Patent Publication No. 2012-0060744 disclose 3-(9H-purin-6-yl)-pyridin-2-ylamino-based derivative compounds which inhibit only B-raf among tyrosine kinase receptors.

PRIOR ART DOCUMENTS

Patent Documents

International Patent Publication No. WO 2008/153947;
Korean Patent Publication No. 2012-0060744.

DISCLOSURE

Technical Problem

It is an object of the present invention to provide a pyridine derivative, a method for preparing the same, a pharmaceutical composition comprising the same, and the use thereof.

Another object of the present invention is to provide a pharmaceutical composition comprising the pyridine derivative or a pharmaceutically acceptable salt thereof as an active ingredient, which is used to prevent or treat an abnormal cell growth disease caused by RAS mutation, by inhibiting all Raf kinases (B-Raf, Raf-1, and B-Raf V600E) and vascular endothelial growth factor receptor 2 (VEGFR2) which is involved in angiogenesis.

Technical Solution

The present inventors have found that a pyridine derivative according to the present invention inhibits all Raf kinases (B-Raf, Raf-1, and B-Raf V600E) and vascular endothelial growth factor receptor 2 (VEGFR2) which is involved in angiogenesis, thereby completing the present invention.

Advantageous Effects

A pyridine derivative and pharmaceutically acceptable salt thereof according to the present invention may be used to prevent or treat an abnormal cell growth disease caused by RAS mutation, by inhibiting all Raf kinases (B-Raf, Raf-1, and B-Raf V600E) and vascular endothelial growth factor receptor 2 (VEGFR2) which is involved in angiogenesis.

DESCRIPTION OF DRAWINGS

FIG. 1 shows the results of observing the in vivo antitumor effects of Examples 21 and 30.

FIG. 2 shows the results of observing the in vivo antitumor effects of Examples 33, 36 and 63.

FIG. 3 shows the results of observing the in vivo antitumor effects of Examples 59 and 60 and Comparative Example 1.

FIG. 4 shows the results of observing the in vivo antitumor effects of Examples 65, 135, 139 and 154.

FIG. 5 shows the results of observing the in vivo antitumor effects depending on concentration of Example 135.

BEST MODE FOR INVENTION

To achieve the above objects, the present invention provides a pyridine derivative, a method for preparing the same, a pharmaceutical composition containing the same, and the use thereof.

Hereinafter, the present invention will be described in further detail.

Pyridine Derivative Compound

The present invention provides a pyridine derivative represented by the following formula 1 and a pharmaceutically acceptable salt thereof:

[Formula 1]

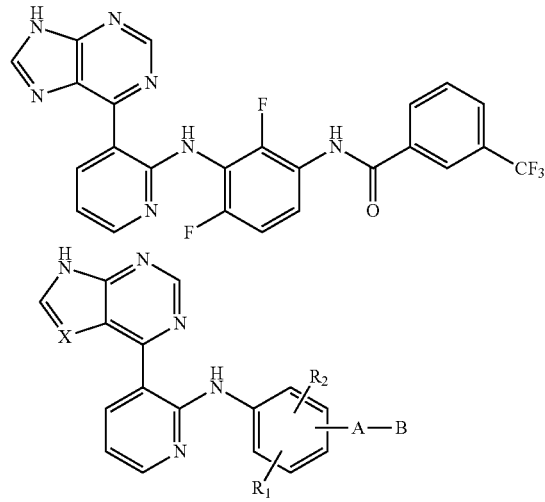

wherein
X is CH or N;
$R_1$ and $R_2$ are each independently hydrogen, halogen, cyano, $C_{1-6}$ alkyl, or $C_{1-6}$ alkoxy, wherein one or more hydrogen atoms in the $C_{1-6}$ alkyl may be substituted with halogen;

A is 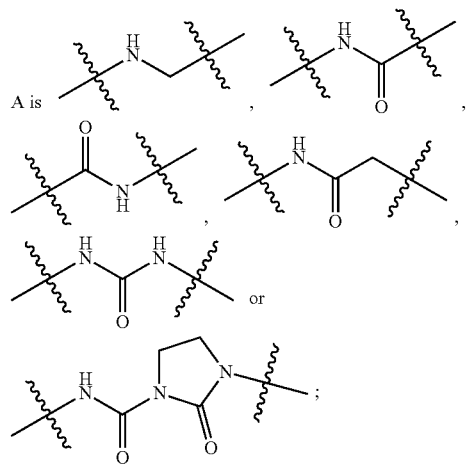

and

B is C$_{1-8}$ alkyl, aryl, or heteroaryl,
wherein one or more hydrogen atoms in the aryl or heteroaryl may be each independently substituted with a substituent selected from the group consisting of halogen, —CF$_3$, —NO$_2$, —OH, —SH, —CN, —NR$_3$R$_4$, —NHC(O)OR$_5$, —SO$_2$R$_6$, C$_{1-8}$ alkoxy, C$_{1-8}$ thioalkoxy, C$_{1-8}$ alkyl, C$_{3-6}$ cycloalkyl, 3- to 6-membered heterocycloalkyl, C$_{5-8}$ aryl, and 5- to 8-membered heteroaryl,
wherein one or more hydrogen atoms in the C$_{1-8}$ alkoxy among the substituents may be each independently substituted with halogen,
one or more hydrogen atoms in the C$_{1-8}$ alkyl or C$_{3-6}$ cycloalkyl among the substituents may be each independently substituted with 3- to 6-membered heterocycloalkyl which is unsubstituted or substituted with C$_{1-8}$ alkyl, —CN or —C(O)NH$_2$,
one or more hydrogen atoms in the 3 to 6-membered heterocycloalkyl among the substituents may be each independently substituted with C$_{1-8}$ alkyl or OH;
one or more hydrogen atoms in the C$_{5-8}$ aryl or 5- to 8-membered heteroaryl among the substituents may be each independently substituted with halogen, —CF$_3$, —NO$_2$, —OH, —SH, —CN, —NR$_3$R$_4$, —NHC(O)OR$_5$, —C(O)NR$_3$R$_4$, C$_{1-8}$ alkoxy, C$_{1-8}$ thioalkoxy, or C$_{1-8}$ alkyl,
wherein R$_3$, R$_4$, R$_5$ and R$_6$ are each independently hydrogen or C$_{1-6}$ alkyl, wherein one or more atoms in the C$_{1-6}$ alkyl may be substituted with halogen.

According to one embodiment of the present invention, the compound represented by formula 1 may be a pyridine derivative represented by the following formula 4:

[Formula 4]

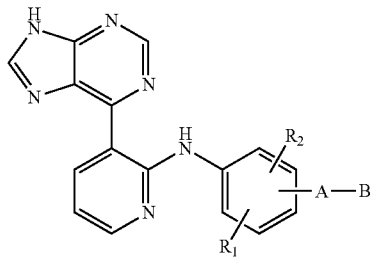

wherein
X is CH or N;
R$_1$ and R$_2$ are each independently hydrogen, halogen, C$_{1-6}$ alkyl, or C$_{1-6}$ alkoxy, wherein one or more hydrogen atoms in the C$_{1-6}$ alkyl may be substituted with halogen;
A is

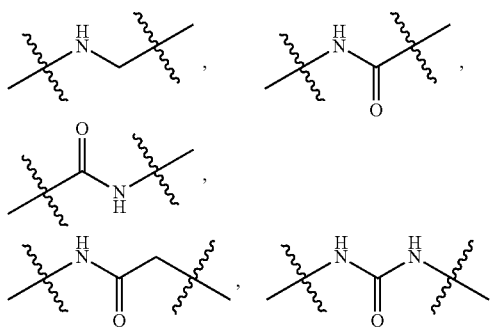

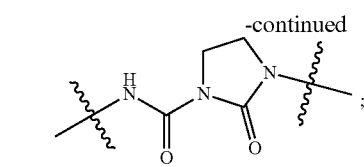

and
B is C$_{1-8}$ alkyl, aryl or heteroaryl,
wherein one or more hydrogen atoms in the aryl or heteroaryl may be each independently substituted with a substituent selected from the group consisting of halogen, —CF$_3$, —NO$_2$, —CN, —NR$_3$R$_4$, —NHC(O)OR$_5$, —SO$_2$R$_6$, C$_{1-8}$ alkoxy, C$_{1-8}$ alkyl, C$_{3-6}$ cycloalkyl, 3 to 6-membered heterocycloalkyl, C$_{5-8}$ aryl, and 5- to 8-membered heteroaryl,
wherein one or more hydrogen atoms in the C$_{1-8}$ alkoxy among the substituents may be each independently substituted with halogen,
one or more hydrogen atoms in the C$_{1-8}$ alkyl or C$_{3-6}$ cycloalkyl among the substituents may be each independently substituted with 3- to 6-membered heterocycloalkyl which is unsubstituted or substituted with C$_{1-8}$ alkyl, —CN or —C(O)NH$_2$,
one or more hydrogen atoms in the 3- to 6-membered heterocycloalkyl among the substituents may be each independently substituted with C$_{1-8}$ alkyl or OH;
one or more hydrogen atoms in the C$_{5-8}$ aryl or 5- to 8-membered heteroaryl among the substituents may be each independently substituted with halogen, —CF$_3$, —NO$_2$, —CN, —NR$_3$R$_4$, —NHC(O)OR$_5$, —C(O)NR$_3$R$_4$, C$_{1-8}$ alkoxy, or C$_{1-8}$ alkyl,
wherein R$_3$, R$_4$, R$_5$ and R$_6$ are each independently hydrogen or C$_{1-6}$ alkyl, wherein one or more atoms in the C$_{1-6}$ alkyl may be substituted with halogen.

According to another embodiment of the present invention, the compound represented by formula 1 may be a pyridine derivative represented by the following formula 5:

[Formula 5]

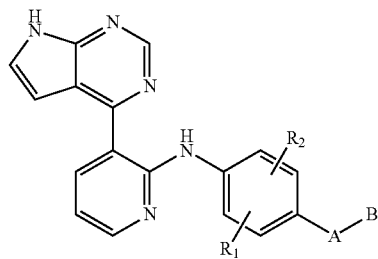

Wherein
X is a nitrogen atom;
R$_1$ and R$_2$ are each independently hydrogen or halogen;
A is

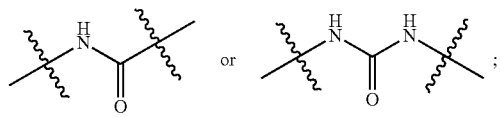 [SMILES: *NC(*)=O ; *NC(=O)N*]

and
B is aryl or heteroaryl,
wherein one or more hydrogen atoms in the aryl or heteroaryl may be each independently substituted with a substituent selected from the group consisting of halogen, —CF$_3$, and C$_{1-8}$ alkyl,
wherein one or more hydrogen atoms in the C$_{1-8}$ alkyl among the substituents may be each independently substituted with —CN.

According to still another embodiment of the present invention, in the formula 1 above, X is a nitrogen atom;

R$_1$ and R$_2$ are each independently hydrogen, halogen, C$_{1-4}$ alkyl, or C$_{1-4}$ alkoxy, wherein one or more hydrogen atoms in the C$_{1-4}$ alkyl may be substituted with halogen;

A is

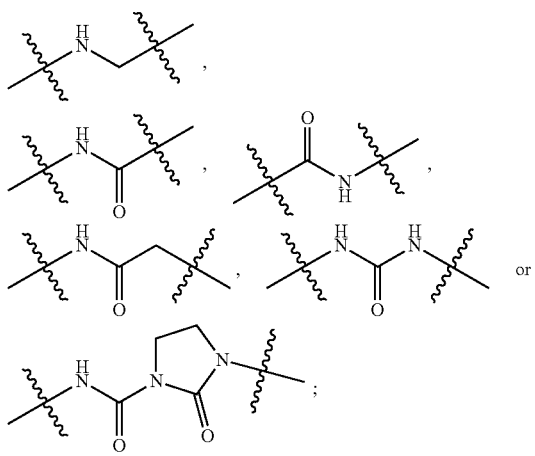

and

B is C$_{1-8}$ alkyl, aryl or heteroaryl, wherein one or more hydrogen atoms in the aryl or heteroaryl may be each independently substituted with a substituent selected from the group consisting of halogen, —CF$_3$, —NO$_2$, —CN, —NR$_3$R$_4$, —NHC(O)OR$_5$, —SO$_2$R$_6$, C$_{1-4}$ alkoxy, C$_{1-4}$ alkyl, C$_{3-6}$ cycloalkyl, 3- to 6-membered heterocycloalkyl, C$_{5-8}$ aryl, and 5- to 8-membered heteroaryl, one or more hydrogen atoms in the C$_{1-8}$ alkoxy among the substituents may be each independently substituted with halogen;

one or more hydrogen atoms in the C$_{1-4}$ alkyl or C$_{3-6}$ cycloalkyl among the substituents may be each independently substituted with 3- to 6-membered heterocycloalkyl which is unsubstituted or substituted with C$_{1-4}$ alkyl, —CN or —C(O)NH$_2$, one or more hydrogen atoms in the 3- to 6-membered heterocycloalkyl among the substituents may each independently substituted with C$_{1-8}$ alkyl or —OH, one or more hydrogen atoms in the C$_{5-8}$ aryl or 5- to 8-membered heteroaryl among the substituents may be each independently substituted with halogen or C$_{1-4}$ alkyl.

According to still another embodiment of the present invention, in the formula 1 above, X is CH;

R$_1$ and R$_2$ are each independently hydrogen, halogen, C$_{1-4}$ alkyl, or C$_{1-4}$ alkoxy, wherein one or more hydrogen atoms in the C$_{1-4}$ alkyl may be substituted with halogen;

A is

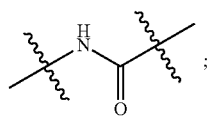

and

B is aryl, wherein one or more hydrogen atoms in the aryl may be each independently substituted with a substituent selected from the group consisting of halogen, —CF$_3$, C$_{1-4}$ alkoxy or C$_{1-4}$ alkyl, wherein one or more hydrogen atoms in the C$_{1-4}$ alkyl among the substituents may be each independently substituted with —CN or —C(O)NH$_2$.

The term 'halogen' as used herein refers to fluorine, chlorine, bromine or iodine, unless otherwise indicated.

The term 'alkyl' as used herein refers to a straight, cyclic or branched hydrocarbon residue, unless otherwise indicated.

The term 'cycloalkyl' as used herein refers to a cyclic alkyl including cyclopropyl, etc., unless otherwise indicated.

The term 'aryl' as used herein refers to an aromatic group including phenyl, naphthyl, etc., unless otherwise indicated.

The term 'heterocycloalkyl' as used herein refers to a cyclic alkyl, e.g., mono-, bi- or polycyclic alkyl, which contains at least one, preferably one to four heteroatoms, selected from O, N and S, unless otherwise indicated. Examples of monoheterocycloalkyl include, but are not limited to, piperidinyl, morpholinyl, thiamorpholinyl, pyrrolidinyl, imidazolidinyl, tetrahydrofuranyl, piperazinyl, and groups similar thereto.

The term 'heteroaryl' as used herein refers to a mono-, bi- or polycyclic aromatic group, which contains at least one heteroatom, preferably one to four heteroatoms, selected from O, N and S, and in which one or more carbon atoms of the ring is substituted with C═O, unless otherwise indicated. Examples of monocyclic heteroaryl include, but are not limited to, thiazolyl, oxazolyl, thiophenyl, furanyl, pyrrolyl, imidazolyl, isooxazolyl, pyrazolyl, triazolyl, thiadiazolyl, tetrazolyl, oxadiazolyl, pyridinyl, pyridazinyl, pyrimidinyl, pyrazinyl and groups similar thereto. Examples of bicyclic heteroaryl include, but are not limited to, indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, furinyl, furopyridinyl, oxochromene, dioxoisoindoline and groups similar thereto.

According to a preferred embodiment of the present invention, the pyridine derivative represented by formula 1 may be selected from the group consisting of the following compounds:

1) N-(3-(3-(9H-purin-6-yl)pyridin-2-ylamino)-2,4-difluorophenyl)-3-(trifluoromethyl)benzamide;
2) N-(3-(3-(9H-purin-6-yl)pyridin-2-ylamino)-2,4-difluorophenyl)-3-(4-methyl-1H-imidazol-1-yl)-5-(trifluoromethyl)benzamide;
3) N-(3-(3-(9H-purin-6-yl)pyridin-2-ylamino)-2,4-difluorophenyl)-4-((4-ethylpiperazin-1-yl)methyl)-3-(trifluoromethyl)benzamide;
4) N-(3-(3-(9H-purin-6-yl)pyridin-2-ylamino)-2,4-difluorophenyl)isobutylamide;
5) N-(3-(3-(9H-purin-6-yl)pyridin-2-ylamino)-2,4-difluorophenyl)thiophene-2-carboxamide;
6) N-(3-(3-(9H-purin-6-yl)pyridine-2-ylamino)-2,4-difluorophenyl)furan-2-carboxamide;

7) N-(3-(3-(9H-purin-6-yl)pyridin-2-ylamino)-2,4-difluorophenyl)isoxazole-5-carboxamide;
8) N-(3-(3-(9H-purin-6-yl)pyridin-2-ylamino)-2,4-difluorophenyl)thiazole-5-carboxamide;
9) N-(3-(3-(9H-purin-6-yl)pyridin-2-ylamino)-2,4-difluorophenyl)-3-(2-cyanopropan-2-yl)benzamide;
10) N-(3-(3-(9H-purin-6-yl)pyridin-2-ylamino)-2,4-difluorophenyl)-3-(4-methylpiperazin-1-yl)-5-(trifluoromethyl)benzamide;
11) N-(3-(3-(9H-purin-6-yl)pyridin-2-ylamino)-2,4-difluorophenyl)-3-thiomorpholino-5-(trifluoromethyl)benzamide;
12) N-(3-(3-(9H-purin-6-yl)pyridin-2-ylamino)-2,4-difluorophenyl)-3-(4-hydroxypiperidin-1-yl)-5-(trifluoromethyl)benzamide;
13) N-(3-(3-(9H-purin-6-yl)pyridin-2-ylamino)-2,4-difluorophenyl)-3-(4-methylpiperidin-1-yl)-5-(trifluoromethyl)benzamide;
14) N-(3-(3-(9H-purin-6-yl)pyridin-2-ylamino)-2,4-difluorophenyl)-4-thiomorpholino-3-(trifluoromethyl)benzamide;
15) N-(3-(3-(9H-purin-6-yl)pyridin-2-ylamino)-2,4-difluorophenyl)-4-(4-methylpeperidin-1-yl)-3-(trifluoromethyl)benzamide;
16) N-(3-(3-(9H-purin-6-yl)pyridin-2-ylamino)-2,4-difluorophenyl)-4-chloro-3-(trifluoromethyl)benzamide;
17) N-(3-(3-(9H-purin-6-yl)pyridin-2-ylamino)-2,4-difluorophenyl)-2,3-dihydrobenzo[b][1,4]dioxine-6-carboxamide;
18) N-(3-(3-(9H-purin-6-yl)pyridin-2-ylamino)-2,4-difluorophenyl)-3-morpholino-5-(trifluoromethyl)benzamide;
19) N-(3-(3-(9H-purin-6-yl)pyridin-2-ylamino)-2,4-difluorophenyl)-4-(pyrrolidin-1-yl)-3-(trifluoromethyl)benzamide;
20) N-(3-(3-(9H-purin-6-yl)pyridin-2-ylamino)-2,4-difluorophenyl)-3-(1-cyanocyclopropyl)benzamide;
21) N-(5-(3-(9H-purin-6-yl)pyridin-2-ylamino)-2-fluorophenyl)-3-(2-cyanopropan-2-yl)benzamide;
22) N-(3-(3-(9H-purin-6-yl)pyridin-2-ylamino)-2,4-difluorophenyl)-3-(1-amino-2-methyl-1-oxopropan-2-yl)benzamide;
23) N-(3-(3-(9H-purin-6-yl)pyridin-2-ylamino)phenyl)-3-(2-cyanopropan-2-yl)benzamide;
24) N-(5-(3-(9H-purin-6-yl)pyridin-2-ylamino)-2-chlorophenyl)-3-(2-cyanopropan-2-yl)benzamide;
25) N-(3-(3-(9H-purin-6-yl)pyridin-2-ylamino)-2,6-difluorophenyl)-3-(2-cyanopropan-2-yl)benzamide;
26) N-(3-(3-(9H-purin-6-yl)pyridin-2-ylamino)-2,4-difluorophenyl)-2-(trifluoromethyl)benzamide;
27) N-(3-(3-(9H-purin-6-yl)pyridin-2-ylamino)-2,4-difluorophenyl)-4-(trifluoromethyl)benzamide;
28) N-(3-(3-(9H-purin-6-yl)pyridin-2-ylamino)-2,4-difluorophenyl)-3-fluoro-5-(trifluoromethyl)benzamide;
29) N-(3-(3-(9H-purin-6-yl)pyridin-2-ylamino)-2-fluorophenyl)-3-(2-cyanopropan-2-yl)benzamide;
30) N-(5-(3-(9H-purin-6-yl)pyridin-2-ylamino)-2-fluorophenyl)-3-(trifluoromethyl)benzamide;
31) N-(5-(3-(9H-purin-6-yl)pyridin-2-ylamino)-2,4-difluorophenyl)-3-(trifluoromethyl)benzamide;
32) N-(5-(3-(9H-purin-6-yl)pyridin-2-ylamino)-2,4-difluorophenyl)-3-(2-cyanopropan-2-yl)benzamide;
33) N-(5-(3-(9H-purin-6-yl)pyridin-2-ylamino)-2-fluorophenyl)-3-(2-cyanopropan-2-yl)-5-fluorobenzamide;
34) N-(3-(3-(9H-purin-6-yl)pyridin-2-ylamino)-2,4-difluorophenyl)-3-nitrobenzamide;
35) N-(3-(3-(9H-purin-6-yl)pyridin-2-ylamino)-2,4-difluorophenyl)-3-methoxybenzamide;
36) N-(5-(3-(9H-purin-6-yl)pyridin-2-ylamino)-2-fluorophenyl)-3-fluoro-5-(trifluoromethyl)benzamide;
37) N-(3-(3-(9H-purin-6-yl)pyridin-2-ylamino)-2,4-difluorophenyl)-3-cyanobenzamide;
38) N-(3-(3-(9H-purin-6-yl)pyridin-2-ylamino)-2,4-difluorophenyl)-4-methoxy-3-(trifluoromethyl)benzamide;
39) N-(4-(3-(9H-purin-6-yl)pyridin-2-ylamino)-3-fluorophenyl)-3-(2-cyanopropan-2-yl)benzamide;
40) N-(3-(3-(9H-purin-6-yl)pyridin-2-ylamino)-2,4-difluorophenyl)-3-nitro-5-(trifluoromethyl)benzamide;
41) N-(3-(3-(9H-purin-6-yl)pyridin-2-ylamino)-2,4-difluorophenyl)-4-chloro-3-(2-cyanopropan-2-yl)benzamide;
42) N-(3-(3-(9H-purin-6-yl)pyridin-2-ylamino)-2,4-difluorophenyl)-2-chloro-3-(2-cyanopropan-2-yl)benzamide;
43) N-(3-(3-(9H-purin-6-yl)pyridin-2-ylamino)-2,4-difluorophenyl)-3-(2-cyanopropan-2-yl)-5-fluorobenzamide;
44) N-(3-(3-(9H-purin-6-yl)pyridin-2-ylamino)-2,4-difluorophenyl)-3-(2-cyanopropan-2-yl)-4,5-difluorobenzamide;
45) N-(3-(3-(9H-purin-6-yl)pyridin-2-ylamino)-2,4-difluorophenyl)-3-chlorobenzamide;
46) N-(3-(3-(9H-purin-6-yl)pyridin-2-ylamino)-2,4-difluorophenyl)-3-(dimethylamino)benzamide;
47) N-(3-(3-(9H-purin-6-yl)pyridin-2-ylamino)-2,4-difluorophenyl)-3-methylbenzamide;
48) N-(3-(3-(9H-purin-6-yl)pyridin-2-ylamino)phenyl)-3-chlorobenzamide;
49) N-(3-(3-(9H-purin-6-yl)pyridin-2-ylamino)-4-fluorophenyl)-3-(2-cyanopropan-2-yl)benzamide;
50) N-(3-(3-(9H-purin-6-yl)pyridin-2-ylamino)-4-fluorophenyl)-3-(trifluoromethyl)benzamide;
51) N-(3-(3-(9H-purin-6-yl)pyridin-2-ylamino)phenyl)-3-(trifluoromethyl)benzamide;
52) N-(3-(3-(9H-purin-6-yl)pyridin-2-ylamino)-2,4-difluorophenyl)-4-nitrobenzamide;
53) N-(3-(3-(9H-purin-6-yl)pyridin-2-ylamino)-2,4-difluorophenyl)-4-methoxybenzamide;
54) N-(3-(3-(9H-purin-6-yl)pyridin-2-ylamino)-2,4-difluorophenyl)-3-aminobenzamide;
55) methyl 3-(3-(3-(9H-purin-6-yl)pyridin-2-ylamino)-2,4-difluorophenylcarbamoyl)phenylcarbamate;
56) N-(3-(3-(9H-purin-6-yl)pyridin-2-ylamino)-2,4-difluorophenyl)pyrazine-2-carboxamide;
57) N-(3-(3-(9H-purin-6-yl)pyridin-2-ylamino)-2,4-difluorophenyl)benzamide;
58) N-{2,4-difluoro-3-[3-(9H-purin-6-yl)pyridin-2-ylamino)-phenyl}-3,5-bistrifluoromethylbenzamide;
59) 1-(3-(3-(9H-purin-6-yl)pyridin-2-ylamino)-2,4-difluorophenyl)-3-(3-(4-methyl-1H-imidazol-1-yl)-5-(trifluoromethyl)phenyl)urea;
60) 1-(3-(3-(9H-purin-6-yl)pyridin-2-ylamino)-2,4-difluorophenyl)-3-(4-((4-ethylpiperazin-1-yl)methyl)-3-(trifluoromethyl)phenyl)urea;
61) 4-chloro-N-{2-fluoro-5-[3-(9H-purin-6-yl)pyridin-2-ylamino)phenyl}-3-(trifluoromethyl)benzamide;
62) N-{2-fluoro-5-[3-(9H-purin-6-yl)pyridin-2-ylamino)phenyl}-3-nitro-5-(trifluoromethyl)benzamide;
63) N-{2-fluoro-5-[3-(9H-purin-6-yl)pyridin-2-ylamino)phenyl}-3-methoxy-5-(trifluoromethyl)benzamide;
64) N-{2-fluoro-5-[3-(9H-purin-6-yl)pyridin-2-ylamino)phenyl}-(6-methylpyridin-2-yl)benzamide;
65) N-{2-fluoro-5-[3-(9H-purin-6-yl)pyridin-2-ylamino)phenyl}-3,5-bis(trifluoromethyl)benzamide;
66) N-{2-chloro-5-[3-(9H-purin-6-yl)pyridin-2-ylamino)phenyl}-3-trifluoromethylbenzamide;
67) N-{2-chloro-5-[3-(9H-purin-6-yl)pyridin-2-ylamino)phenyl}-3-fluoro-5-trifluoromethylbenzamide;

68) N-{2-methyl-5-[3-(9H-purin-6-yl)pyridin-2-ylamino)phenyl}-3-trifluoromethylbenzamide;
69) N-{2-methoxy-5-[3-(9H-purin-6-yl)pyridin-2-ylamino)phenyl}-3-trifluoromethylbenzamide;
70) N-{4-methoxy-5-[3-(9H-purin-6-yl)pyridin-2-ylamino)phenyl}-3-trifluoromethylbenzamide;
71) N-{4-methyl-5-[3-(9H-purin-6-yl)pyridin-2-ylamino)phenyl}-3-trifluoromethylbenzamide;
72) N-{2,6-difluoro-3-[3-(9H-purin-6-yl)pyridin-2-ylamino)phenyl}-3-trifluoromethylbenzamide;
73) 2-fluoro-5-[3-(9H-purin-6-yl)pyridin-2-ylamino]-N-(3-trifluoromethylphenyl)benzamide;
74) 1-(4-chloro-3-trifluoromethylphenyl)-3-{2-fluoro-5-[3-(9H-purin-6-yl)pyridin-2-ylamino]phenyl}urea;
75) 1-{3-fluoro-4-[3-(9H-purin-6-yl)pyridin-2-ylamino]phenyl}-3-(3-trifluoromethylphenyl)urea;
76) N-{2-fluoro-5-[3-(9H-purin-6-yl)pyridin-2-ylamino]phenyl}-2-(3-trifluoromethylphenyl)acetamide;
77) N-(3-cyanomethylphenyl)-4-fluoro-3-[3-(9H-purin-6-yl)pyridin-2-ylamino]benzamide;
78) N-4-[(3-(9H-purin-6-yl)pyridin-2-yl)amino]-3-fluoro-phenyl-4-(cyanomethyl)benzamide;
79) N-4-[3-(9H-purin-6-yl)pyridin-2-ylamino]phenyl-3-trifluoromethylbenzamide;
80) N-2-methoxy-4-[3-(9H-purin-6-yl)pyridin-2-ylamino]phenyl-3-trifluoromethylbenzamide;
81) N-(3-(3-(9H-purin-6-yl)pyridin-2-ylamino)-2,4-difluorophenyl)-3-(4-fluorophenyl)-2-oxoimidazolidine-1-carboxamide;
82) N-(4-(3-(9H-purin-6-yl)pyridin-2-ylamino)-3-fluorophenyl)-3-(2-cyanopropan-2-yl)benzamide;
83) N-(3-(3-(7H-pyrrolo[2,3-d]pyrimidin-4-yl)pyridin-2-ylamino)-2,4-difluorophenyl)-3-(1-amino-2-methyl-1-oxopropan-2-yl)benzamide;
84) N-(5-(3-(7H-pyrrolo[2,3-d]pyrimidin-4-yl)pyridin-2-ylamino)-2,4-diflurophenyl)-3-(2-cyanopropan-2-yl)benzamide;
85) N-(3-(3-(7H-pyrrolo[2,3-d]pyrimidin-4-yl)pyridin-2-ylamino)-2,4-difluorophenyl)-3-(2-cyanopropan-2-yl)benzamide;
86) N-(3-(3-(7H-pyrrolo[2,3-d]pyrimidin-4-yl)pyridin-2-ylamino)-2-fluorophenyl)-3-(2-cyanopopan-2-yl)benzamide;
87) N-2-fluoro-5-[3-(7H-pyrrolo[2,3-d]pyrimidin-4-yl)pyridin-2-ylamino]phenyl-3-trifluoromethyl benzamide;
88) 3-fluoro-N-2-fluoro-5-[3-(7H-pyrrolo[2,3-d]pyrimidin-4-yl)pyridin-2-ylamino]phenyl-5-trifluoromethyl benzamide;
89) 4-chloro-N-2-fluoro-5-[3-(7H-pyrrolo[2,3-d]pyrimidin-4-yl)pyridin-2-ylamino]phenyl-5-trifluoromethyl benzamide;
90) N-2-fluoro-5-[3-(7H-pyrrolo[2,3-d]pyrimidin-4-yl)pyridin-2-ylamino]phenyl-3,5-bistrifluoromethyl benzamide;
91) 3-(2-cyanopropan-2-yl)-N-2-fluoro-5-[3-(7H-pyrrolo[2,3-d]pyrimidin-4-yl)pyridin-2-ylamino]phenyl benzamide;
92) 3-(2-cyanopropan-2-yl)-5-fluoro-N-2-fluoro-5-[3-(7H-pyrrolo[2,3-d]pyrimidin-4-yl)pyridin-2-ylamino]phenyl benzamide;
93) 4-chloro-3-(2-cyanopropan-2-yl)-N-2-fluoro-5-[3-(7H-pyrrolo[2,3-d]pyrimidin-4-yl)pyridin-2-ylamino]phenyl benzamide;
94) 3-(2-cyanopropan-2-yl)-N-3-[3-(7H-pyrrolo[2,3-d]pyrimidin-4-yl)pyridin-2-ylamino]phenyl benzamide;
95) 3-(2-cyanopropan-2-yl)-N-4-fluoro-3-[3-(7H-pyrrolo[2,3-d]pyrimidin-4-yl)pyridin-2-ylamino]phenyl benzamide;
96) 3-(2-cyanopropan-2-yl)-N-2,6-difluoro-3-[3-(7H-pyrrolo[2,3-d]pyrimidin-4-yl)pyridin-2-ylamino]phenyl benzamide;
97) N-{2-chloro-5-[3-(7H-pyrrolo[2,3-d]pyrimidin-4-yl)pyridin-2-ylamino]phenyl}-3-(2-cyanopropan-2-yl)benzamide;
98) 3-(2-cyanopropan-2-yl)-N-3-fluoro-5-[3-(7H-pyrrolo[2,3-d]pyrimidin-4-yl)pyridin-2-ylamino]phenyl benzamide;
99) 3-(2-cyanopropan-2-yl)-N-4-methyl-3-[3-(7H-pyrrolo[2,3-d]pyrimidin-4-yl)pyridin-2-ylamino]phenylbenzamide;
100) 3-(2-cyanopropan-2-yl)-N-{4-methoxy-3-[3-(7H-pyrrolo[2,3-d]pyrimidin-4-yl)pyridin-2-ylamino]phenyl}benzamide;
101) N-{3-[3-(7H-pyrrolo[2,3-d]pyrimidin-4-yl)pyridin-2-ylamino]phenyl}-3-trifluoromethylbenzamide;
102) N-2-fluoro-3-[3-(7H-pyrrolo[2,3-d]pyrimidin-4-yl)pyridin-2-ylamino]phenyl-3-trifluoromethylbenzamide;
103) N-4-fluoro-3-[3-(7H-pyrrolo[2,3-d]pyrimidin-4-yl)pyridin-2-ylamino]phenyl-3-trifluoromethylbenzamide;
104) N-2,4-difluoro-3-[3-(7H-pyrrolo[2,3-d]pyrimidin-4-yl)pyridin-2-ylamino]phenyl-3-trifluoromethylbenzamide;
105) N-2,6-difluoro-3-[3-(7H-pyrrolo[2,3-d]pyrimidin-4-yl)pyridin-2-ylamino]phenyl-3-trifluoromethylbenzamide;
106) N-2,4-difluoro-5-[3-(7H-pyrrolo[2,3-d]pyrimidin-2-yl)pyridin-2-ylamino]phenyl-3-trifluoromethylbenzamide;
107) N-2-chloro-5-[3-(7H-pyrrolo[2,3-d]pyrimidin-4-yl)pyridin-2-ylamino]phenyl-3-trifluoromethylbenzamide;
108) N-4-methyl-3-[3-(7H-pyrrolo[2,3-d]pyrimidin-4-yl)pyridin-2-ylamino]phenyl-3-trifluoromethylbenzamide;
109) N-4-methoxy-3-[3-(7H-pyrrolo[2,3-d]pyrimidin-4-yl)pyridin-2-ylamino]phenyl-3-trifluoromethylbenzamide;
110) N-3-fluoro-5-[3-(7H-pyrrolo[2,3-d]pyrimidin-4-yl)pyridin-2-ylamino]phenyl-3-trifluoromethylbenzamide;
111) N-5-[(3-(9H-purin-6-yl)pyridin-2-yl)amino]-2-fluorophenyl-4-fluoro-3-(trifluoromethyl)benzamide;
112) 5-[3-(9H-purin-6-yl)amino]-N-[3-(2-cyanopropan-2-yl)phenyl]-2-fluorobenzamide;
113) N-5-[(3-(9H-purin-6-yl)pyridin-2-yl)amino]-2-fluorophenyl-3-fluorobenzamide;
114) 5-[3-(9H-purin-6-yl)pyridin-2-yl]amino-N-(3,4-difluorophenyl)-2-fluorobenzamide;
115) 5-[3-(9H-purin-6-yl)pyridin-2-yl]amino-N-(3,5-difluorophenyl)-2-fluorobenzamide;
116) N-5-[(3-(9H-purin-6-yl)pyridin-2-yl)amino]-2-fluoropheny-3-(2-cyanopropan-2-yl)-4-fluorobenzamide;
117) N-5-[(3-(9H-purin-6-yl)pyridin-2-yl)amino]-2-fluorophenyl-4-chloro-3-(2-cyanopropan-2-yl)benzamide;
118) 1-5-[(3-(9H-purin-6-yl)pyridin-2-yl)amino]-2-fluorophenyl-3-[3-(trifluoromethyl)phenyl]urea;
119) N-5-[(3-(9H-purin-6-yl)pyridin-2-yl)amino]-2-fluorophenyl-6-(2-cyanopropan-2-yl)picolinamide;
120) N-5-[(3-(9H-purin-6-yl)pyridin-2-yl)amino]-2-fluorophenyl-2-fluoro-5-(trifluoromethyl)benzamide;
121) N-5-[(3-(9H-purin-6-yl)pyridin-2-yl)amino]-2-fluorophenyl-2-fluoro-3-(trifluoromethyl)benzamide;
122) N-3-[(3-(9H-purin-6-yl)pyridin-2-yl)amino]-2-fluorophenyl-3-(trifluoromethyl)benzamide;
123) 1-5-[(3-(9H-purin-6-yl)pyridin-2-yl)amino]-2-fluorophenyl-3-[4-(trifluoromethyl)phenyl]urea;
124) N-5-[(3-(9H-purin-6-yl)pyridin-2-yl)amino]-2-chlorophenyl-3,5-bis(trifluoromethyl)benzamide;

125) N-5-[(3-(9H-purin-6-yl)pyridin-2-yl)amino]-2-fluorophenyl-3-(methylthio)benzamide;
126) N-5-[(3-(9H-purin-6-yl)pyridin-2-yl)amino]-2-fluorophenyl-3-(methylsulfonyl)benzamide;
127) N-5-[(3-(9H-purin-6-yl)pyridin-2-yl)amino]-2-chlorophenyl-3-(2-cyanopropan-2-yl)-5-fluorobenzamide;
128) N-5-[(3-(9H-purin-6-yl)pyridin-2-yl)amino]-2-fluorophenyl-2,4-bis(trifluoromethyl)benzamide;
129) N-5-[(3-(9H-purin-6-yl)pyridin-2-yl)amino]-2-fluorophenyl-3,4-bis(trifluoromethyl)benzamide;
130) N-5-[(3-(9H-purin-6-yl)pyridin-2-yl)amino]-2-fluorophenyl-2,5-bis(trifluoromethyl)benzamide;
131) N-5-[(3-(9H-purin-6-yl)pyridin-2-yl)amino]-2-fluorophenyl-3-(trifluoromethoxy)benzamide;
132) N-5-[(3-(9H-purin-6-yl)pyridin-2-yl)amino]-2-fluorophenyl-3,5-dimethoxybenzamide;
133) N-5-[(3-(9H-purin-6-yl)pyridin-2-yl)amino]-2-fluorophenyl-3-fluoro-4-(trifluoromethyl)benzamide;
134) N-5-[(3-(9H-purin-6-yl)pyridin-2-yl)amino]-2-fluorophenyl-4-methoxy-3-(trifluoromethyl)benzamide;
135) N-5-[(3-(9H-purin-6-yl)pyridin-2-yl)amino]-2-fluorophenyl-3-chloro-5-(trifluoromethyl)benzamide;
136) N-5-[(3-(9H-purin-6-yl)pyridin-2-yl)amino]-2-fluorophenyl-6-(trifluoromethyl)picolinamide;
137) N-5-[(3-(9H-purin-6-yl)pyridin-2-yl)amino]-2-fluorophenyl-4-fluoro-3-methylbenzamide;
138) N-5-[(3-(9H-purin-6-yl)pyridin-2-yl)amino]-2-fluorophenyl-4-methyl-3-(trifluoromethyl)benzamide;
139) N-5-[(3-(9H-purin-6-yl)pyridin-2-yl)amino]-2-fluorophenyl-3-methyl-5-(trifluoromethyl)benzamide;
140) N-5-[(3-(9H-purin-6-yl)pyridin-2-yl)amino]-2-fluorophenyl-3-methoxy-5-(trifluoromethoxy)benzamide;
141) N-5-[(3-(9H-purin-6-yl)pyridin-2-yl)amino]-2-fluorophenyl-3-cyclopropylbenzamide;
142) N-5-[(3-(9H-purin-6-yl)pyridin-2-yl)amino]-2-fluorophenyl-3-chloro-5-(trifluoromethoxy)benzamide;
143) N-5-[(3-(9H-purin-6-yl)pyridin-2-yl)amino]-2-fluorophenyl-4-fluoro-3-(trifluoromethoxy)benzamide;
144) N-5-[(3-(9H-purin-6-yl)pyridin-2-yl)amino]-2-fluorophenyl-4-(trifluoromethyl)picolinamide;
145) N-5-[(3-(9H-purin-6-yl)pyridin-2-yl)amino]-2-fluorophenyl-3-methylbenzamide;
146) N-5-[(3-(9H-purin-6-yl)pyridin-2-yl)amino]-2-fluorophenyl-3-chlorobenzamide;
147) N-5-[(3-(9H-purin-6-yl)pyridin-2-yl)amino]-2-fluorophenyl-4-chloro-3-(trifluoromethoxy)benzamide;
148) N-5-[(3-(9H-purin-6-yl)pyridin-2-yl)amino]-2-fluorophenyl-3-fluoro-2-(trifluoromethyl)isonicotinamide;
149) N-5-[(3-(9H-purin-6-yl)pyridin-2-yl)amino]-2-fluorophenyl-5-(trifluoromethyl)nicotinamide;
150) N-5-[(3-(9H-purin-6-yl)pyridin-2-yl)amino]-2-fluorophenyl-4-methoxy-3-(trifluoromethoxy)benzamide;
151) N-5-[(3-(9H-purin-6-yl)pyridin-2-yl)amino]-2-fluorophenyl-2-(trifluoromethyl)isonicotinamide;
152) N-3-[(3-(9H-purin-6-yl)pyridin-2-yl)amino]-4-methoxyphenyl-3-(2-cyanopropan-2-yl)benzamide;
153) N-3-[(3-(9H-purin-6-yl)pyridin-2-yl)amino]-4-methylphenyl-3-(2-cyanopropan-2-yl)benzamide;
154) N-5-[(3-(9H-purin-6-yl)pyridin-2-yl)amino]-2-fluorophenyl-3-(2-cyanopropan-2-yl)-5-(trifluoromethyl)benzamide;
155) N-5-[(3-(9H-purin-6-yl)pyridin-2-yl)amino]-2-fluorophenyl-3-(2-cyanopropan-2-yl)-5-methylbenzamide;
156) N-5-[(3-(9H-purin-6-yl)pyridin-2-yl)amino]-2-fluorophenyl-2-bromo-3-(2-cyanopropan-2-yl)-5-methoxybenzamide;
157) N-5-[(3-(9H-purin-6-yl)pyridin-2-yl)amino]-2-fluorophenyl-3-cyano-5-(trifluoromethyl)benzamide; and
158) N-5-[(3-(9H-purin-6-yl)pyridin-2-yl)amino]-2-fluorophenyl-3-bromo-5-(trifluoromethyl)benzamide.

The compounds according to the present invention may form pharmaceutically acceptable salts. These pharmaceutically acceptable salts may be those formed from acids that form nontoxic acid addition salts containing pharmaceutically acceptable anions, but the scope of the present invention is not limited thereto. Examples of such salts include acid addition salts formed with inorganic acids such as hydrochloric acid, sulfuric acid, nitric acid, phosphoric acid, hydrobromic acid, hydriodic acid, and like; organic carbonic acids such as tartaric acid, formic acid, citric acid, acetic acid, trichloroacetic acid, trifluoroacetic acid, gluconic acid, benzoic acid, lactic acid, fumaric acid, maleic acid, and the like; and sulfonic acids such as methanesulfonic acid, benzenesulfonic acid, p-toluenesulfonic acid, naphthalensulfonic acid, and the like.

In addition, the compounds of formula 1 or pharmaceutically acceptable salts thereof according to the present invention may also exist as solvates or hydrates.

In addition, the compounds represented by formula 1 according to the present invention may contain one or more asymmetric carbon atoms, and thus occur as racemates, racemic mixtures, single enantiomers, diastereomeric mixtures and individual diastereomers. These isomers may be resolved using conventional methods. For example, isomers of the compounds represented by formula 1 may be resolved by column chromatography or HPLC. Alternatively, enantiomers and other compounds with chiral centers may be synthesized by stereospecific synthesis using optically pure starting materials and/or reagents of known configuration.

Method for Preparation of Pyridine Derivative

The present invention provides a method for preparing the pyridine derivative of the present invention, the method comprising a step of reacting a compound of formula 2 with a compound of formula 3 according to the following reaction scheme 1, thereby obtaining a compound of formula 1:

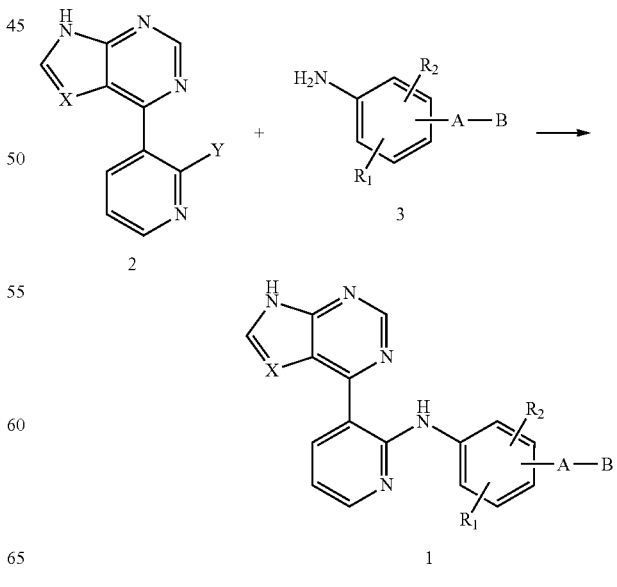

wherein X, A, B, R$_1$ and R$_2$ are as defined in formula 1 above, and Y is halogen.

In the preparation method according to the present invention, lithium(bistrimethylsilyl)amide may be used as a base, and tetrahydrofuran may be used as a solvent. Specifically, the pyridine derivative of formula 1 may be prepared by dissolving the compound of formula 2 and the compound of formula 3 in tetrahydrofuran as the solvent, and then adding lithium(bistrimethylsilyl)amide as the base, slowly thereto at 0° C., followed by stirring at room temperature for 1 hour.

Pharmaceutical Composition Comprising Pyridine Derivative as Active Ingredient, Use Thereof, and Treatment Method Using the Same The present invention provides a pharmaceutical composition for prevention or treatment of an abnormal cell growth disease caused by RAS mutation, the composition containing, as an active ingredient, the pyridine derivative represented by the following formula 1 or a pharmaceutically acceptable salt thereof:

[Formula 1]

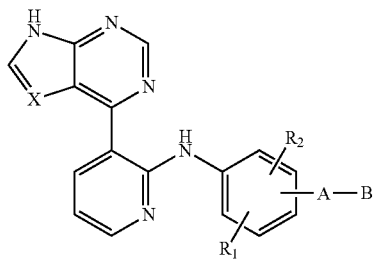

wherein X, A, B, R$_1$ and R$_2$ are as defined above.

The pyridine derivative or pharmaceutically acceptable salt thereof according to the present invention exhibits the effect of inhibiting all Raf kinases (B-Raf, Raf-1, and B-RafV600E) and vascular endothelial growth factor receptor (VEGFR2) which is involved in angiogenesis. Thus, a pharmaceutical composition containing, as an active ingredient, the pyridine derivative or pharmaceutically acceptable salt thereof according to the present invention, may be effectively used for the prevention or treatment of an abnormal cell growth disease (a disease caused by abnormal activation) caused by excessive activity of Raf kinases and vascular endothelial growth factor receptor which is involved in angiogenesis. Namely, the pharmaceutical composition may be effectively used for the prevention or treatment of an abnormal cell growth disease caused by RAS mutation.

In the present invention, the abnormal cell growth disease caused by RAS mutation may be any one selected from the group consisting of gastric cancer, lung cancer, liver cancer, colorectal cancer, small bowel cancer, pancreatic cancer, brain cancer, bone cancer, melanoma, breast cancer, sclerosing adenosis, uterine cancer, cervical cancer, ovarian cancer, head and neck cancer, esophageal cancer, thyroid cancer, parathyroid cancer, renal cancer, sarcoma, prostate cancer, urethral cancer, bladder cancer, leukemia, multiple myeloma, blood cancer, lymphoma, fibroadenoma, inflammation, diabetes, obesity, psoriasis, rheumatoid arthritis, hemangioma, acute or chronic renal disease, coronary artery restenosis, autoimmune diseases, asthma, neurodegenerative diseases, acute infection, and ocular diseases caused by vascular disorders. More preferably, the abnormal cell growth disease caused by RAS mutation may be any one selected from the group consisting of melanoma, colorectal cancer, prostate cancer, thyroid cancer, and ovarian cancer.

The pharmaceutical composition according to the present invention may further contain an agent selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, apoptosis inhibitors, inflammation inhibitors, and P-glycoprotein inhibitors. The pharmaceutical composition according to the present invention may be administered or formulated in combination with the additional agent.

The pharmaceutical composition according to the present invention may be administered orally or parenterally (e.g., intravenously, subcutaneously, intraperitoneally or topically) according to the intended use. The dose of the pharmaceutical composition varies depending on the patient's weight, age, sex, health condition and diet, the time of administration, the mode of administration, excretion rate, the severity of the disease, and the like. The compound represented by formula 1 according to the present invention may be administered once or several times at a daily dose of about 1 to 1000 mg/kg, preferably 5 to 100 mg/kg.

The pharmaceutical composition according to the present invention may contain a conventional pharmaceutically acceptable carrier, excipient or additive. The pharmaceutical composition according to the present invention may be formulated according to a conventional method, and may be provided as various oral dosage forms such as tablets, pills, powders, capsules, syrups, emulsions, microemulsions and the like, or dosage forms for parenteral administration such as intramuscular, intravenous or subcutaneous administration.

When the pharmaceutical composition of the present invention is prepared as an oral formulation, examples of additives or carriers that may be used include cellulose, calcium silicate, corn starch, lactose, sucrose, dextrose, calcium phosphate, stearic acid, magnesium stearate, calcium stearate, gelatin, talc, surfactants, suspending agents, emulsifiers, diluents and the like. When the pharmaceutical composition of the present invention is prepared as an injectable formulation, examples of additives or carriers that may be used include water, saline, aqueous glucose solution, sugar-like solution, alcohol, glycol, ether (e.g., polyethyleneglycol 400), oil, fatty acid, fatty acid ester, glyceride, surfactants, suspending agents, emulsifiers and the like. In addition, the pharmaceutical composition according to the present invention may further contain a pharmaceutically acceptable additive. The phrase "pharmaceutically acceptable" refers to additives or compositions that are physiologically tolerable and do not typically produce an allergic or similar untoward reaction, such as gastric upset, dizziness and the like, when administered to humans. Examples of the additives include carriers, excipients, diluents and the like. Examples of the additives include carriers, excipients and diluents include lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, and mineral oil. In addition, the composition may further contain a filler, an anticoagulant, a lubricant, a wetting agent, fragrance, an emulsifier, a preservative and the like.

The present invention also provides the use of the pyridine derivative of formula 1 or a pharmaceutically acceptable salt thereof in the prevention or treatment of an abnormal cell growth disease caused by RAS mutation.

The present invention also provide the use of the pyridine derivative of formula 1 or a pharmaceutically acceptable salt thereof in preparation of a medicament for preventing or treating an abnormal cell growth disease caused by RAS mutation.

The present invention also provide a preventing or treating an abnormal cell growth disease caused by RAS mutation, the method comprising administering a therapeutically effective amount of the pyridine derivative represented by formula 1 or a pharmaceutically acceptable salt thereto to a subject in need of prevention or treatment of the abnormal cell growth disease caused by RAS mutation. In the present invention, the "subject" includes mammals, particularly humans.

As used herein, the term "therapeutically effective amount" refers to an amount of the pyridine derivative represented by formula 1, which is effective for prevention or treatment of the abnormal cell growth disease caused by RAS mutation.

MODE FOR INVENTION

Hereinafter, the present invention will be described in detail with reference to examples and experimental examples. It is to understood, however, that these examples are only for better understanding of the present invention and are not intended to limit the scope of the present invention.

Example 1. Preparation of N-(3-(3-(9H-Purin-6-Yl) Pyridin-2-Ylamino)-2,4-Difluorophenyl)-3-(Trifluoromethyl)Benzamide

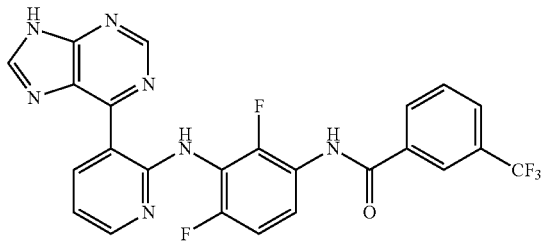 [SMILES: O=C(Nc1ccc(F)c(Nc2ncccc2-c2ncnc3[nH]cnc23)c1F)c1cccc(C(F)(F)F)c1]

Step 1: Preparation of 2,6-Difluoro-3-Nitrobenzoic Acid

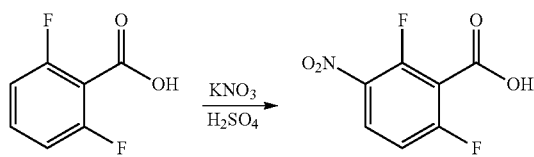

To 2,6-difluorobenzoic acid (1.4 g, 9 mmol), concentrated sulfuric acid (5 mL) was added, and potassium nitrate (1 g, 9.9 mmol) was added in small portions at 0° C. The reaction mixture was warmed to room temperature and stirred for 24 hours. Next, ice water was poured into the reaction solution, extracted with ethyl acetate, dried with anhydrous magnesium sulfate, and then concentrated under reduced pressure. The residue was filtered under reduced pressure, and the obtained solid was washed with diethyl ether and dried to afford the title compound.

$^1$H NMR (400 MHz, DMSO-d$_6$): δ 8.37 (td, J=9.2, 5.6 Hz, 1H), 7.46 (t, J=9.2 Hz, 1H)

Step 2: Preparation of t-Butyl 2,6-Difluoro-3-Nitrophenyl Carbamate

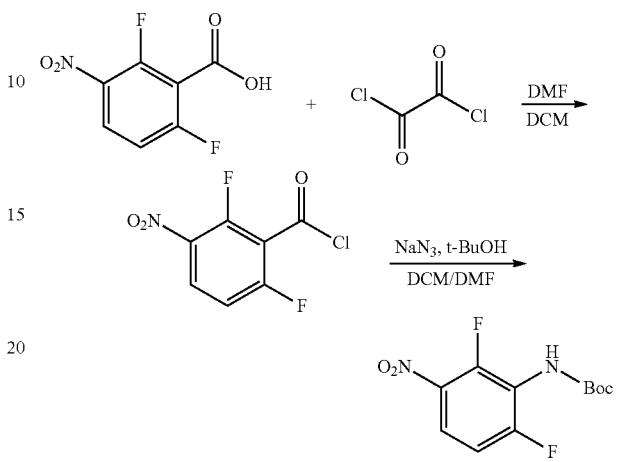

To a mixed solvent of dichloromethane and N,N-dimethylformamide, 2,6-difluoro-3-nutrobenzoic acid (16 g, 79 mmol) prepared in step 1 was added and oxalyl chloride (14 mL, 158 mmol) was added slowly. The reaction mixture was stirred at room temperature for 18 hours and concentrated the solvent, and the residue was diluted with dichloromethane and N,N-dimethylformamide and cooled to 0° C. Sodium azide (5.6 g, 87 mmol) was added thereto in small portions. After the solution was stirred at room temperature for 30 minutes, t-butanol (40 mL) was added thereto. The reaction solution was stirred under reflux for 3 hours. After completion of the reaction, the reaction solution was concentrated under reduced pressure. After concentration, the residue was washed with aqueous sodium hydrogen carbonate solution and brine and extracted with ethyl acetate. The organic layer was concentrated, dried with anhydrous magnesium sulfate, and then purified by column chromatography to afford the title compound.

$^1$H NMR (400 MHz, CDCl$_3$): δ 8.00 (m, 1H), 7.08 (m, 1H), 6.46 (bs, 1H), 1.51 (s, 9H)

Step 3: Preparation of t-Butyl 3-Amino-2,6-Difluorophenyl Carbamate

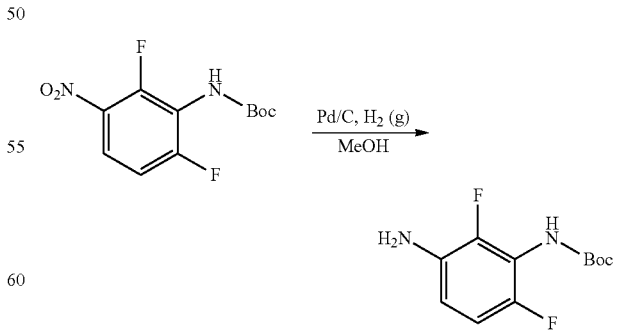

t-butyl 2,6-difluoro-3-nitrophenyl carbamate (1 g, 3.6 mmol) prepared in step 2 was dissolved in a methanol solvent, and palladium carbon (100 mg) was added thereto, followed by stirring for 15 hours under a hydrogen pressure.

After completion of the reaction, the reaction solution was filtered through celite, concentrated under reduced pressure, and purified by column chromatography to afford the title compound.

$^1$H NMR (400 MHz, CDCl$_3$): δ 6.74 (m, 1H), 6.59 (m, 1H), 5.95 (bs, 1H), 3.62 (bs, 2H), 1.51 (s, 9H)

Step 4: Preparation of t-Butyl 2,6-Difluoro-3-(3-(Trifluoromethyl)Benzamido)Phenyl Carbamate

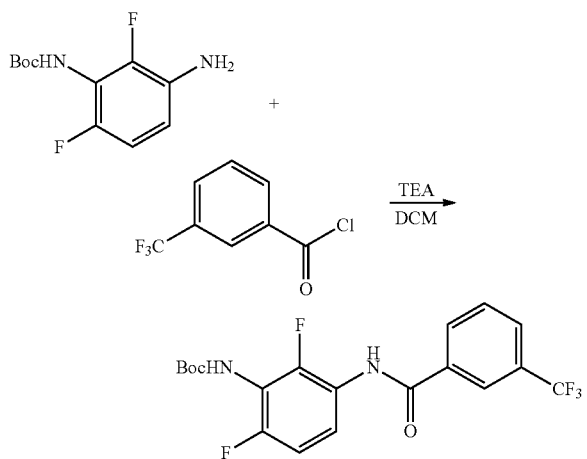

t-butyl (3-amino-2,6-difluorophenyl)carbamate (30 mg, 0.12 mmol) prepared in step 3 was added to and dissolved in a dichloromethane solvent. To the reaction solution, 3-(trifluoromethyl)benzoyl chloride (19 μL, 0.13 mmol) and triethylamine (25 μL, 0.18 mmol) were added, followed by stirring at room temperature for 1 hour. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

$^1$H NMR (400 MHz, CDCl$_3$): δ 8.25 (m, 1H), 8.16 (s, 1H), 8.07 (d, J=7.6 Hz, 1H), 7.99 (s, 1H), 7.86 (d, J=7.6 Hz, 1H), 7.68 (d, J=8.0 Hz, 1H), 7.02 (td, J=9.2, 1.6 Hz, 1H) 6.06 (s, 1H), 1.54 (s, 9H)

Step 5: Preparation of 6-Chloro-9-(Tetrahydro-2H-Pyran-2-Yl)-9H-Purine

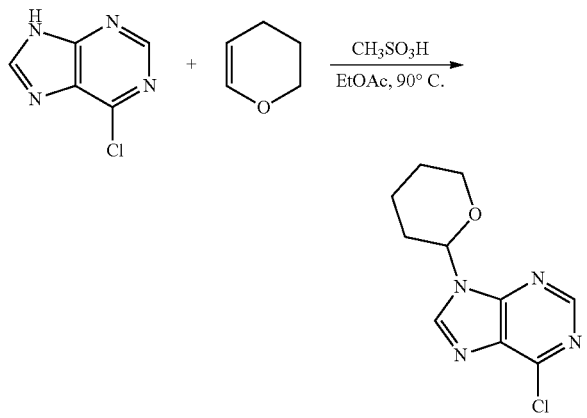

6-chloro-9H-purine (500 mg, 3.2 mmol), 4-methanesulfonic acid (12 mg, 0.07 mmol) and 3,4-dihydro-2H-pyran (0.9 mL, 9.7 mmol) were added to an ethyl acetate solvent, followed by stirring. The reaction mixture was stirred at 90° C. for about 1 hour until the solid was completely dissolved. After the solvent was removed by concentration, the residue was purified by column chromatography to afford the title compound.

$^1$H NMR (400 MHz, CDCl$_3$): δ 8.77 (s, 1H), 8.36 (s, 1H), 5.80 (dd, J=10.4, 2.8 Hz, 1H), 4.21 (m, 1H), 3.80 (m, 1H), 2.21-1.67 (m, 6H)

Step 6: Preparation of 6-(2-Fluoropyridin-3-Yl)-9-(Tetrahydro-2H-Pyran-2-Yl)-9H-Purine

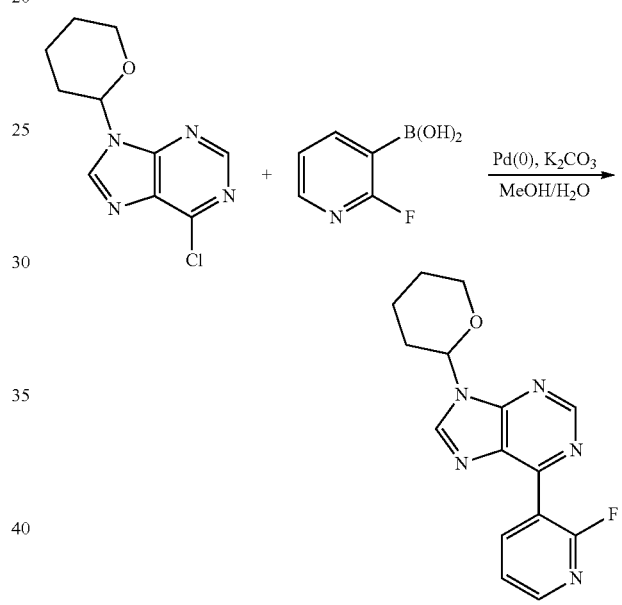

To a mixed solvent of ethanol and water (5/1 v/v), 6-chloro-9-(tetrahydro-2H-pyran-2-yl)-9H-purine (239 mg, 1 mmol) prepared in step 5, 2-fluoropyridin-3-yl boronic acid (189 mg, 1.3 mmol), potassium acetate (216 mg, 2.2 mmol) and bis(di-t-butyl-(4-dimethylaminophenyl)phosphine)dichloropalladium (14 mg, 0.02 mmol) were added. The reaction mixture was stirred under reflux under a nitrogen atmosphere at 80° C. for 2 hours. After completion of the reaction, the solution was concentrated, washed with water and brine, and extracted with ethyl acetate. The organic layer was dried with anhydrous magnesium sulfate and concentrated under reduced pressure, and the residue was purified by column chromatography to afford the title compound.

$^1$H NMR (400 MHz, CDCl$_3$): δ 9.09 (s, 1H), 8.91 (s, 1H), 8.56 (m, 1H), 8.47 (m, 1H), 7.62 (m, 1H), 5.84 (dd, J=10.8, 2.0 Hz, 1H), 4.04 (m, 1H), 3.76 (m, 1H), 2.38 (m, 1H), 2.03 (dd, J=12.8, 2.6 Hz, 2H), 1.79-1.60 (m, 3H)

Step 7: Preparation of N-(2,4-Difluoro-3-(3-(9-(Tetrahydro-2H-Pyran-2-Yl)-9H-Purin-6-Yl)Pyridin-2-Ylamino)Phenyl)-3-(Trifluoromethyl)Benzamide

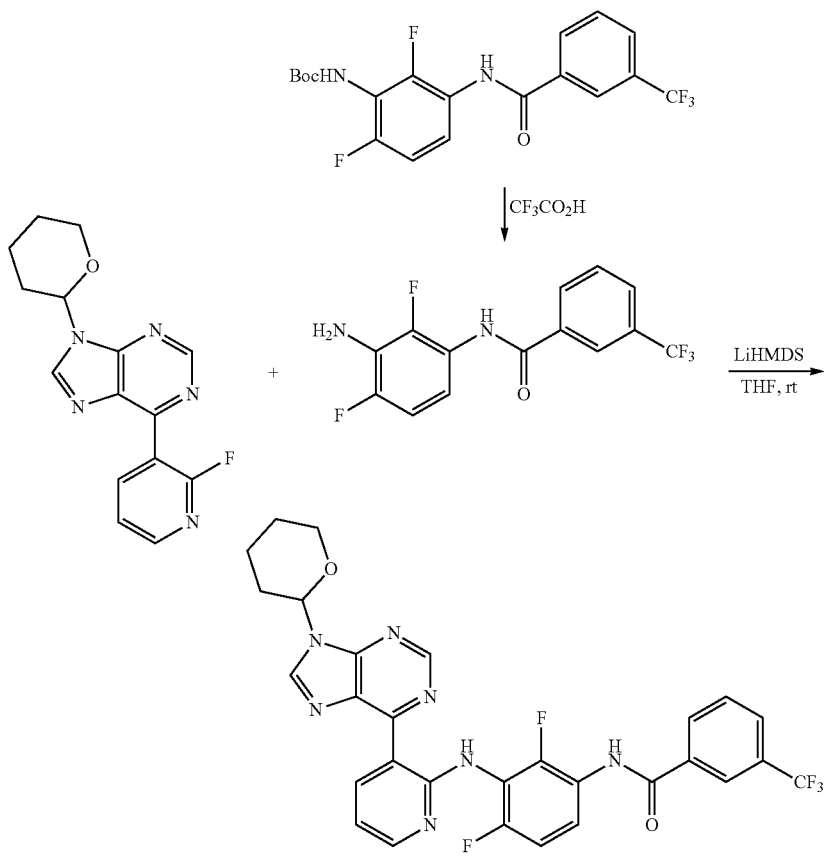

t-butyl-2,6-difluoro-3-(3-(trifluoromethyl)benzamido)phenyl carbamate (30 mg, 0.09 mmol) prepared in step 4 was dissolved in an ethyl acetate solvent, and 4 M hydrogen chloride solution (4 M solution in 1,4-dioxane) was added thereto, followed by stirring at room temperature for 2 hours. After completion of the reaction, the solvent was concentrated, and the filtration under reduced pressure was performed to afford N-(3-amino-2,4-difluorophenyl)-3-(trifluoromethyl)benzamide.

N-(3-amino-2,4-difluorophenyl)-3-(trifluoromethyl)benzamide (19 mg, 0.06 mmol) obtained by the above and 6-(2-fluoropyridin-3-yl)-9-(tetrahydro-2H-pyran-2-yl)-9H-purine (16 mg, 0.054 mmol) prepared in step 6 were added to and dissolved in a tetrahydrofuran solvent, and then lithium(bistrimethylsilyl)amide (270 μL, 1.0 M solution in THF) was added slowly thereto at 0° C. The reaction solution was stirred at room temperature for 1 hour. After completion of the reaction, water was added to the reaction solution, followed by extraction with ethyl acetate. The organic layer was dried with anhydrous magnesium sulfate, concentrated under reduced pressure, and then purified by column chromatography to afford the title compound.

$^1$H NMR (400 MHz, CDCl$_3$): δ 11.66 (s, 1H), 9.68 (dd, J=8.0, 2.0 Hz, 1H), 9.05 (s, 1H), 8.40 (s, 1H), 8.30 (dd, J=4.8, 1.6 Hz, 1H), 8.23 (m, 1H), 8.19 (s, 1H), 8.07 (m, 2H), 7.84 (d, J=7.6 Hz, 1H), 7.66 (t, J=7.6 Hz, 1H), 7.09 (td, J=9.2, 2.0 Hz, 1H), 6.98 (dd, J=8.0, 4.8 Hz, 1H), 5.91 (dd, J=10.8, 2.4 Hz, 1H), 4.25 (m, 1H), 3.86 (m, 1H), 2.24-1.61 (m, 6H)

Step 8: Preparation of N-(3-(3-(9H-Purin-6-Yl)Pyridin-2-Ylamino)-2,4-Difluorophenyl)-3-(Trifluorometrhyl)Benzamide

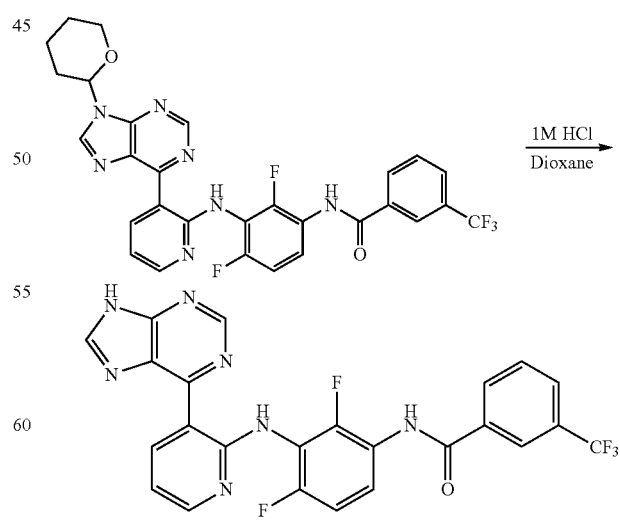

N-(2,4-difluoro-3-(3-(9-(tetrahydro-2H-pyran-2-yl)-9H-purin-6-yl)pyridin-2-ylamino)phenyl)-3-(trifluoromethyl)

benzamide (20 mg, 0.034 mmol) prepared in step 7 was added to 1M hydrochloric acid aqueous solution and stirred under reflux for 2 hours. After completion of the reaction, the reaction solution was washed with aqueous sodium hydrogen carbonate solution and brine and extracted with ethyl acetate. The organic layer was dried with anhydrous magnesium sulfate, concentrated under reduced pressure, and then purified by column chromatography to afford the title compound.

$^1$H NMR (400 MHz, DMSO-d$_6$): δ 9.72 (bs, 1H), 9.04 (s, 1H), 8.55 (s, 1H), 8.31 (s, 1H), 8.26 (d, J=7.2 Hz, 1H), 8.19 (dd, J=4.0, 1.6 Hz, 1H), 7.93 (d, J=7.6 Hz, 1H), 7.77 (t, J=8.0 Hz, 1H), 7.63 (m, 1H), 7.15 (t, J=9.6 Hz, 1H), 7.03 (dd, J=8.0, 4.8 Hz, 1H)

Example 2. Preparation of N-(3-(3-(9H-purin-6-yl)pyridin-2-ylamino)-2,4-difluorophenyl)-3-(4-methyl-1H-imidazol-1-yl)-5-(trifluoromethyl)benzamide

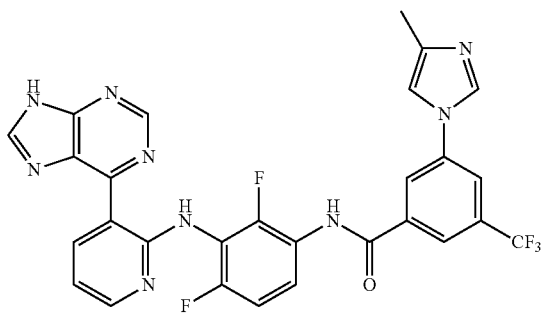 [SMILES: Cc1cn(-c2cc(C(=O)Nc3ccc(F)c(Nc4ncccc4-c4ncnc5[nH]cnc45)c3F)cc(C(F)(F)F)c2)cn1]

Step 1: Preparation of t-Butyl 2,6-Difluoro-3-(3-(4-Methyl-1H-Imidazol-1-Yl)-5-(Trifluoromethyl)Benzamido)Phenyl Carbamate

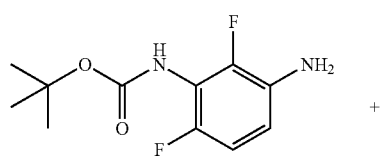

+

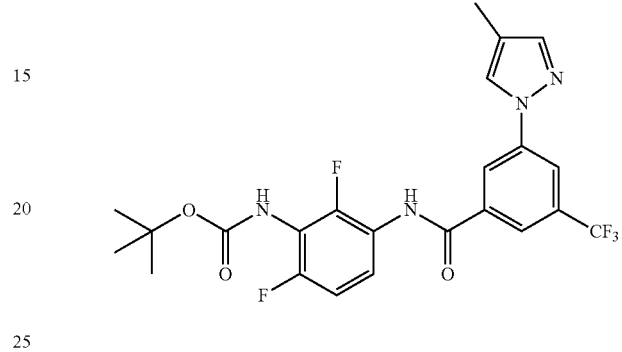

To a dichloromethane solvent, t-butyl-3-amino-2,6-difluorophenyl carbamate (30 mg, 0.12 mmol) prepared in step 3 of Example 1, 3-(4-methyl-1H-imidazol-1-yl)-5-(trifluoromethyl)benzoic acid (48 mg, 0.18 mmol), 1-ethyl-3-(3-dimethylaminopropyl)carbodiimide (35 mg, 0.18 mmol) and N,N-dimethylaminopyridine (15 mg, 0.12 mmol) were added, and the mixture was stirred at room temperature for 2 hours. After completion of the reaction, the reaction solution was washed with water and brine and extracted with dichloromethane. The organic layer was dried with anhydrous magnesium sulfate, concentrated under reduced pressure and then purified by column chromatography to afford the title compound.

$^1$H NMR (400 MHz, MeOD): δ 8.42 (s, 1H), 8.28 (d, J=1.6 Hz, 1H), 8.26 (s, 1H), 8.16 (s, 1H), 7.64 (d, J=Hz, 1H), 7.52 (s, 1H), 7.09 (td, J=Hz, 1H), 2.30 (s, 3H), 1.52 (s, 9H)

Step 2: Preparation of N-(2,4-difluoro-3-(3-(9-(tetrahydro-2H-pyran-2-yl)-9H-purin-6-yl)pyridin-2-ylamino)phenyl)-3-(4-methyl-1H-imidazol-1-yl)-5-(trifluoromethyl)benzamide

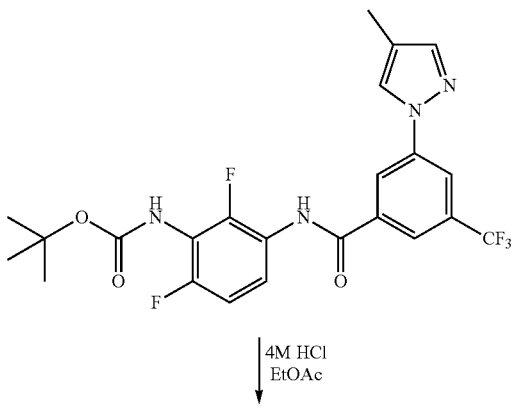

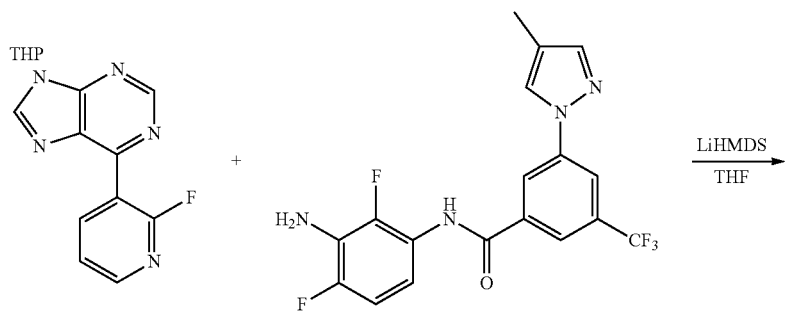

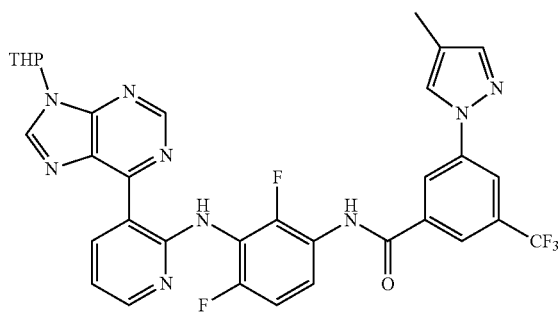

t-butyl 2,6-difluoro-3-(3-(4-methyl-1H-imidazol-1-yl)-5-(trifluoromethyl)benzamido)phenyl carbamate (30 mg, 0.06 mmol) prepared in step 1 was added to an ethyl acetate solvent, and hydrogen chloride solution (4 M solution in 1,4-dioxane) was added thereto, followed by stirring at room temperature for 2 hours. After completion of the reaction, the solvent was concentrated, and the filtration under reduced pressure was performed to afford N-(3-amino-2,4-difluorophenyl)-3-(4-methyl-1H-pyrazol-1-yl)-5-(trifluoromethyl)benzamide.

N-(3-amino-2,4-difluorophenyl)-3-(4-methyl-1H-pyrazol-1-yl)-5-(trifluoromethyl)benzamide (26 mg, 0.07 mmol) obtained by the above processes and 6-(2-fluoropyridin-3-yl)-9-(tetrahydro-2H-pyran-2-yl)-9H-purine (18 mg, 0.059 mmol) prepared in step 6 of Example 1 were added to and dissolved in a tetrahydrofuran solvent, and then lithium (bistrimethylsilyl)amide (295 μL, 1.0 M solution in THF) was added slowly thereto at 0° C. The reaction solution was stirred at room temperature for 1 hour. After completion of the reaction, water was added to the reaction solution, followed by extraction with ethyl acetate. The organic layer was dried with anhydrous magnesium sulfate, concentrated under reduced pressure, and then purified by column chromatography to afford the title compound.

$^1$H NMR (400 MHz, CDCl$_3$): δ 11.69 (s, 1H), 9.67 (dd, J=8.0, 2.0 Hz, 1H), 9.04 (s, 1H), 8.45 (s, 1H), 8.42 (s, 2H), 8.24 (dd, J=4.8, 1.6 Hz, 1H), 8.10 (s, 1H), 8.02 (s, 1H), 7.87 (s, 1H), 7.76 (s, 1H), 7.10 (m, 2H), 6.95 (dd, J=8.0, 4.8 Hz, 1H), 5.90 (m, 1H), 4.23 (m, 1H), 3.85 (m, 1H), 2.29 (s, 3H), 2.24-1.73 (m, 6H)

Step 3: Preparation of N-(3-(3-(9H-Purin-6-Yl)Pyridin-2-Ylamino)-2,4-Difluorophenyl)-3-(4-Methyl-1H-Imidazol-1-Yl)-5-(Trifluoromethyl)Benzamide

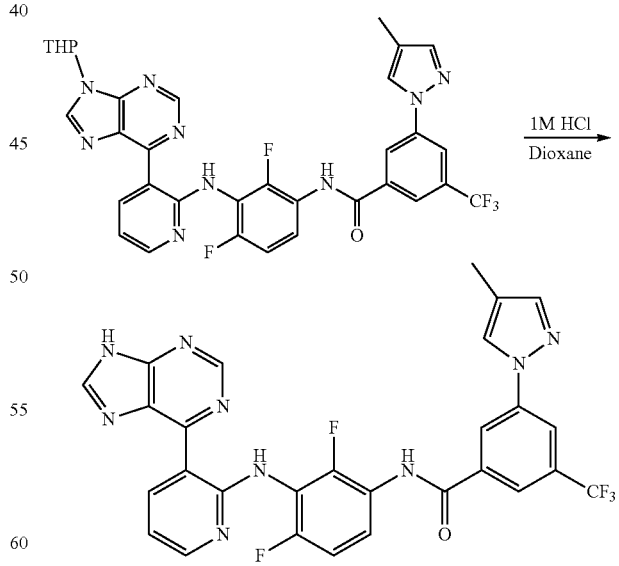

N-(2,4-difluoro-3-(3-(9-(tetrahydro-2H-pyran-2-yl)-9H-purin-6-yl)pyridin-2-ylamino)phenyl)-3-(4-methyl-1H-imidazol-1-yl)-5-(trifluoromethyl)benzamide (20 mg, 0.030 mmol) prepared in step 2 was added to 1M hydrochloric acid aqueous solution and stirred under reflux for 2 hours. After completion of the reaction, the reaction solution was washed with aqueous sodium hydrogen carbonate solution and brine and extracted with ethyl acetate. The organic layer was dried with anhydrous magnesium sulfate, concentrated under reduced pressure, and then purified by column chromatography to afford the title compound.

$^1$H NMR (400 MHz, DMSO-$d_6$): δ 9.65 (bs, 1H), 9.04 (s, 1H), 8.55 (s, 1H), 8.45 (s, 1H), 8.29 (s, 2H), 8.19 (d, J=4.8 Hz, 1H), 8.17 (s, 1H), 7.67 (m, 1H), 7.53 (s, 1H), 7.16 (t, J=9.2 Hz, 1H), 7.04 (dd, J=7.6, 4.8 Hz, 1H), 2.30 (s, 3H)

Example 3. Preparation of N-(3-(3-(9H-Purin-6-Yl)Pyridin-2-Ylamino)-2,4-Difluorophenyl)-4-((4-Ethylpiperazin-1-Yl)Methyl)-3-(Trifluoromethyl)Benzamide

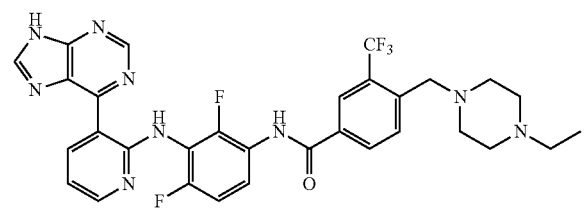 [SMILES: CCN1CCN(Cc2ccc(C(=O)Nc3ccc(F)c(Nc4ncccc4-c4ncnc5[nH]cnc45)c3F)cc2C(F)(F)F)CC1]

Step 1: Preparation of t-Butyl-3-(4-((4-Ethylpiperazin-1-Yl)Methyl)-3-(Trifluoromethy)Benzamido)-2,6-Difluorophenyl Carbamate

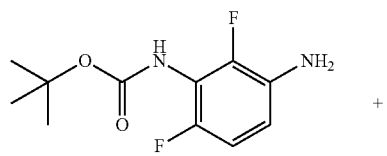 +

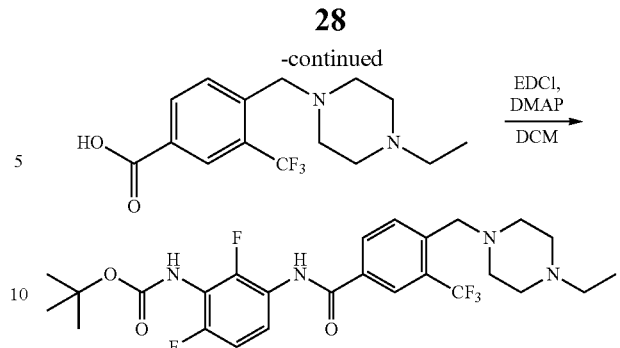

To a dichloromethane solvent, t-butyl-3-amino-2,6-difluorophenylcarbamate (30 mg, 0.12 mmol) prepared in step 3 of Example 1, 4-((4-ethylpiperazin-1-yl)methyl)-3-(trifluoromethyl)benzoic acid (50 mg, 0.18 mmol), 1-ethyl-3-(3-dimethylaminopropyl)carbodiimide (35 mg, 0.18 mmol) and N,N-dimethylaminopyridine (15 mg, 0.12 mmol) were added. The mixture was stirred at room temperature for 2 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

$^1$H NMR (400 MHz, CDCl$_3$): δ 8.16-7.98 (s, 5H), 6.98 (t, J=9.2 Hz, 1H), 6.33 (s, 1H), 3.74 (s, 2H), 2.57 (bs, 8H), 2.47 (q, J=7.2 Hz, 2H), 1.52 (s, 9H), 1.12 (t, J=7.2 Hz, 3H)

Step 2: Preparation of N-(2,4-Difluoro-3-(3-(9-(Tetrahydro-2H-Pyran-2-Yl)-9H-Purin-6-Yl)Pyridin-2-Ylamino)Phenyl)-4-((4-Ethylpiperazin-1-Yl)Methyl)-3-(Trifluoromethyl)Benzamide

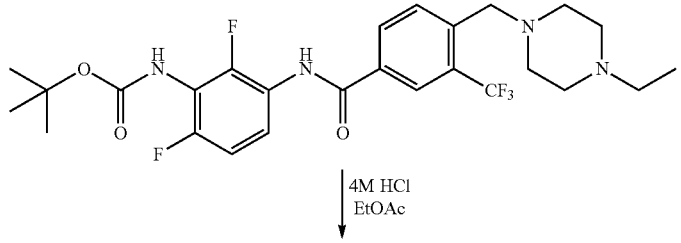

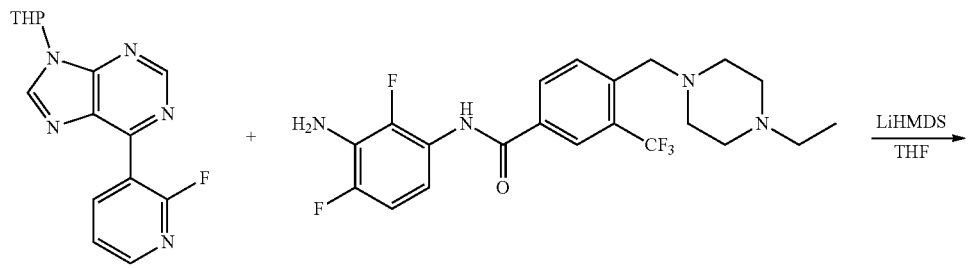

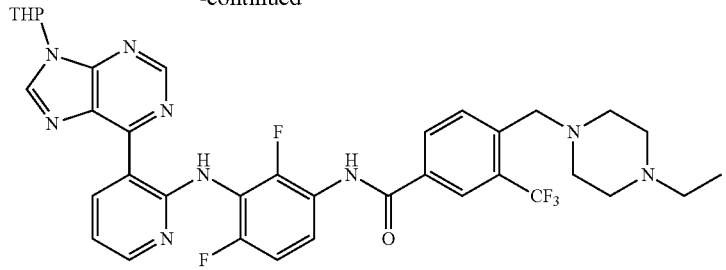

t-butyl-3-(4-((4-ethylpiperazin-1-yl)methyl)-3-(trifluoromethyl)benzamido)-2,6-difluorophenyl carbamate (30 mg, 0.06 mmol) prepared in step 1 was added to an ethyl acetate solvent, and hydrogen chloride solution (4 M solution in 1,4-dioxane) was added thereto, followed by stirring at room temperature for 2 hours. After completion of the reaction, the solvent was removed by concentration, and the residue was filtered under reduced pressure to afford N-(3-amino-2,4-difluorophenyl)-4-((4-ethylpiperazin-1-yl)methyl)-3-(trifluoromethyl)benzamide.

N-(3-amino-2,4-difluorophenyl)-4-((4-ethylpiperazin-1-yl)methyl)-3-(trifluoromethyl)benzamide (22 mg, 0.05 mmol) obtained by the above processes and 6-(2-fluoropyridin-3-yl)-9-(tetrahydro-2H-pyran-2-yl)-9H-purine (14 mg, 0.05 mmol) prepared in step 6 of Example 1 were added to and dissolved in a tetrahydrofuran solvent, and lithium (bistrimethylsilyl)amide (225 μL, 1.0 M solution in THF) was added slowly thereto at 0° C. The solution was stirred at room temperature for 1 hour. After completion of the reaction, water was added to the reaction solution and an extraction with ethyl acetate was performed. The organic layer was dried with anhydrous magnesium sulfate, concentrated under reduced pressure, and then purified by column chromatography to afford the title compound.

¹H NMR (400 MHz, CDCl₃): δ 11.65 (s, 1H), 9.68 (dd, J=8.0, 2.0 Hz, 1H) 9.05 (s, 1H), 8.41 (s, 1H), 8.31 (dd, J=4.8, 1.6 Hz, 1H), 8.18 (s, 1H), 8.02 (m, 3H), 7.07 (td, J=9.2, 1.6 Hz, 1H), 6.99 (dd, J=8.0, 4.8 Hz, 1H), 5.91 (dd, J=10.4, 2.4 Hz, 1H), 4.23 (m, 1H), 3.86 (m, 1H), 2.47 (m, 10H), 2.25-1.71 (m, 6H), 1.10 (t, J=7.6 Hz, 3H)

Step 3: Preparation of N-(3-(3-(9H-Purin-6-Yl)Pyridin-2-Ylamino)-2,4-Difluorophenyl)-4-((4-Ethylpiperazin-1-Yl)Methyl)-3-(Trifluoromethyl)Benzamide

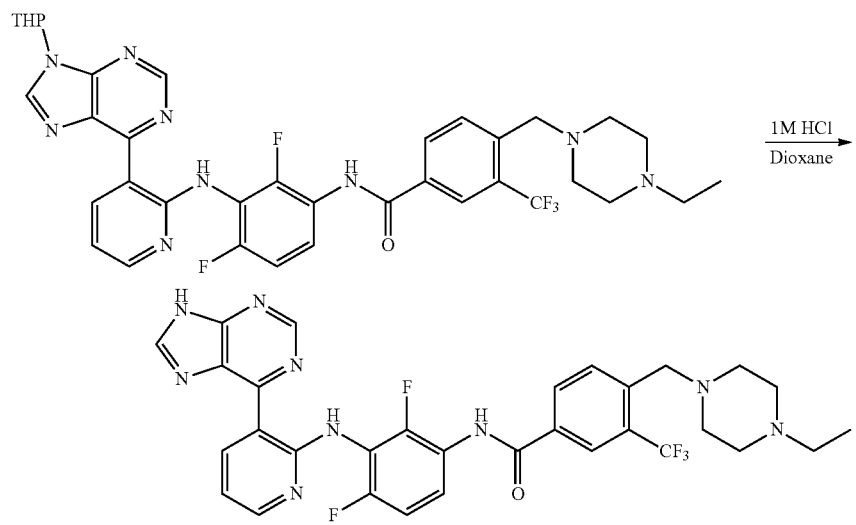

To N-(2,4-difluoro-3-(3-(9-(tetrahydro-2H-pyran-2-yl)-9H-purin-6-yl)pyridin-2-ylamino)phenyl)-4-((4-ethylpiperazin-1-yl)methyl)-3-(trifluoromethyl)benzamide (20 mg, 0.03 mmol) prepared in step 2, 1M hydrochloric acid aqueous solution was added, and the mixture was stirred under reflux for 2 hours. After completion of the reaction, the reaction solution was cooled to room temperature, and the produced solid was filtered under reduced pressure, washed with water and dichloromethane, and dried at room temperature to afford the title compound.

¹H NMR (400 MHz, DMSO-d₆): δ 10.50 (dd, J=8.0, 1.6 Hz, 1H), 9.13 (bs, 1H), 8.71 (s, 1H), 8.39 (s, 1H), 8.31 (d, J=8.4 Hz, 1H), 8.19 (dd, J=8.0, 1.6 Hz, 1H), 7.87 (m, 1H), 7.49 (dd, J=7.6, 6.4 Hz, 1H), 7.43 (t, J=9.2 Hz, 1H), 4.15 (s, 2H), 3.54 (m, 2H), 3.26 (m, 6H), 2.80 (m, 2H), 1.39 (t, J=7.6 Hz, 3H)

Example 4. Preparation of N-(3-(3-(9H-Purin-6-Yl)Pyridin-2-Ylamino)-2,4-Difluorophenyl)Isobutylamide

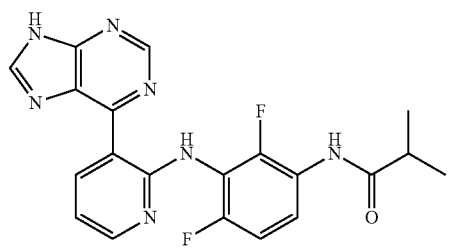 [SMILES: CC(C)C(=O)Nc1ccc(F)c(Nc2ncccc2-c2ncnc3[nH]cnc23)c1F]

Step 1: Preparation of Benzyl t-Butyl(2,4-Difluoro-1,3-Phenylene)Dicarbamate

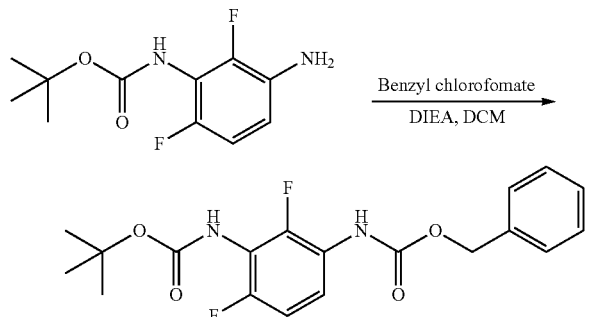

To a dichloromethane solvent, t-butyl 2,6-difluoro-3-aminophenylcarbamate (305 mg, 1.25 mmol) prepared in step 3 of Example 1, diisopropylethylamine (371 μL, 2.13 mmol) and benzyl chloride (194 μL, 1.38 mmol) were added. The mixture was stirred at room temperature for 5 hours. After completion of the reaction, the reaction solution was washed with water and brine and extracted with ethyl acetate. The organic layer was dried with anhydrous magnesium sulfate, filtered under reduced pressure, and then concentrated. The residue was purified by column chromatography to afford the title compound.

$^1$H NMR (400 MHz, CDCl$_3$): δ 7.94 (bs, 1H), 7.39 (m, 5H), 6.93 (td, J=9.2, 1.6 Hz, 1H), 6.82 (bs, 1H), 5.98 (bs, 1H), 5.23 (s, 2H), 1.52 (s, 9H).

Step 2: Preparation of Benzyl 3-Amino-2,4-Difluorophenylcarbamate

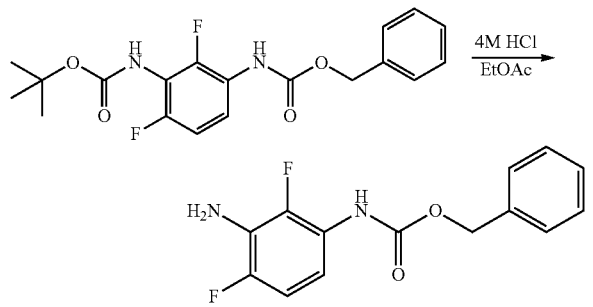

t-butyl(2,4-difluoro-1,3-phenylene)dicarbamate (400 mg, 1.06 mmol) prepared in step 1 was added to an ethyl acetate solvent, and 4 M hydrogen chloride solution (4 M solution in 1,4-dioxane) was added thereto, followed by stirring at room temperature for 5 hours. After completion of the reaction, the solid obtained by concentrating the solvent and being filtered under reduced pressure was washed with diethyl ether, thereby obtaining the title compound.

$^1$H NMR (400 MHz, CDCl$_3$): δ 7.40 (m, 6H), 6.80 (dd, J=9.6, 2.0 Hz, 1H), 6.74 (bs, 1H), 5.23 (s, 2H), 3.76 (bs, 2H)

Step 3: Preparation of Benzyl-2,4-Difluoro-3-(3-(9-(Tetrahydro-2H-Pyran-2-Yl)-9H-Purin-6-Yl)Pyridin-2-Ylamino)Phenyl Carbamate

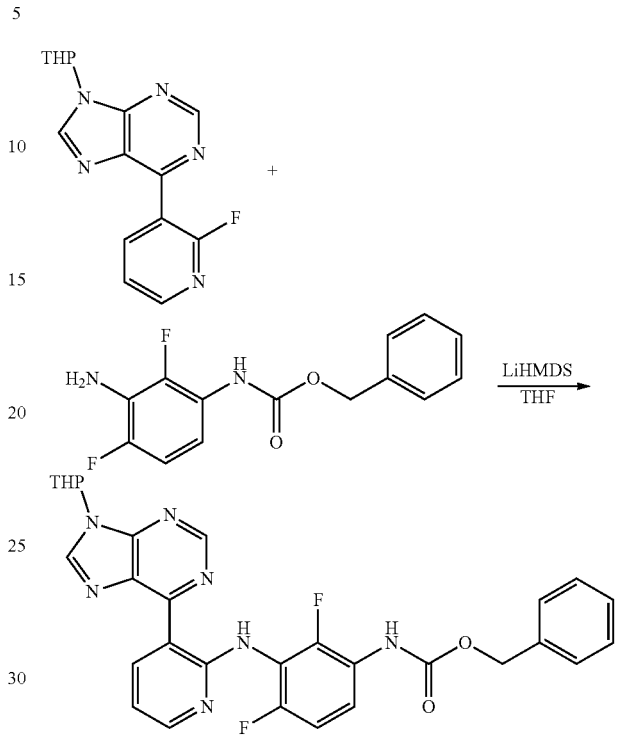

3-amino-2,4-difluorophenylcarbamate (100 mg, 0.32 mmol) prepared in step 2 and 6-(2-fluoropyridin-3-yl)-9-(tetrahydro-2H-pyran-2-yl)-9H-purine (86 mg, 0.29 mmol) prepared in step 6 of Example were added to and dissolved in anhydrous tetrahydrofuran, and then lithium(bistrimethylsilyl)amide (1.0 M solution in THF, 1.45 mL) was added slowly thereto at 0° C. The reaction mixture was stirred for 1 hour. After completion of the reaction, water was added to the reaction solution, followed by extraction with ethyl acetate. The organic layer was dried with anhydrous magnesium sulfate, concentrated under reduced pressure, and then purified by column chromatography to afford the title compound.

$^1$H NMR (400 MHz, CDCl$_3$): δ 11.57 (s, 1H), 9.66 (dd, J=8.0, 2.0 Hz, 1H), 9.02 (s, 1H), 8.39 (s, 1H), 8.28 (dd, J=4.4, 1.6 Hz, 1H), 7.92 (bs, 1H), 7.40 (m, 5H), 6.98 (m, 3H), 5.89 (dd, J=10.4, 2.4 Hz, 1H), 5.24 (s, 2H), 4.22 (m, 1H), 3.84 (m, 1H), 2.23-1.68 (m, 6H)

Step 4: Preparation of 2,6-Difluoro-N-(3-(9-(Tetrahydro-2H-Pyran-2-Yl)-9H-Purin-6-Yl)Pyridin-2-Yl)Benzene-1,3-Diamine

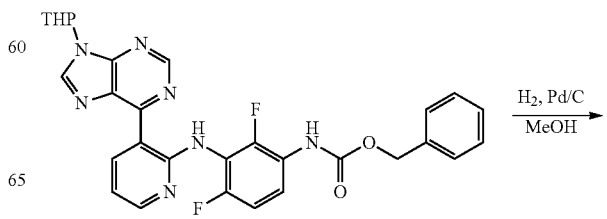

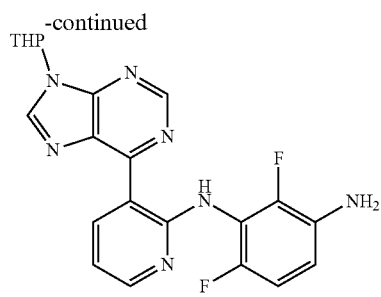

Benzyl-2,4-difluoro-3-(3-(9-(tetrahydro-2H-pyran-2-yl)-9H-purin-6-yl)pyridin-2-ylamino)phenyl carbamate (100 mg, 0.18 mmol) prepared in step 3 was dissolved in a methanol solvent, and palladium carbon (50 mg) was added thereto, followed by stirring under a hydrogen pressure for 1 hour. After completion of the reaction, the reaction solution was filtered through celite, concentrated under reduced pressure, and then purified by column chromatography to afford the title compound.

$^1$H NMR (400 MHz, CDCl$_3$): δ 11.49 (s, 1H), 9.63 (dd, J=7.6, 1.6 Hz, 1H), 9.01 (s, 1H), 8.37 (s, 1H), 8.30 (dd, J=4.8, 1.6 Hz, 1H), 6.92 (m, 1H), 6.82 (td, J=9.2, 2.0 Hz, 1H), 6.60 (td, J=9.2, 5.2 Hz, 1H), 5.88 (dd, J=10.4, 2.4 Hz, 1H), 4.23 (m, 1H), 3.83 (m, 1H), 3.49 (bs, 2H), 2.22-1.69 (m, 6H)

Step 5: Preparation of N-(2,4-Difluoro-3-(3-(9-(Tetrahydro-2H-Pyran-2-Yl)-9H-Purin-6-Yl)Pyridin-2-Ylamino)Phenyl)Isobutylamide

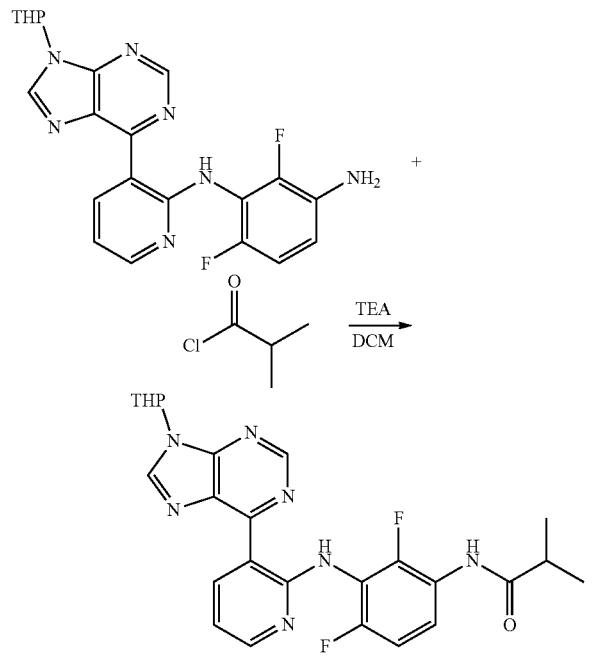

2,6-difluoro-N-(3-(9-(tetrahydro-2H-pyran-2-yl)-9H-purin-6-yl)pyridin-2-yl)benzene-1,3-diamine (30 mg, 0.07 mmol) prepared in step 4, isobutyryl chloride (8 μL, 0.078 mmol) and triethylamine (20 μL, 0.14 mmol) were added to a dichloromethane solvent, followed by stirring at room temperature for 2 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

$^1$H NMR (400 MHz, CDCl$_3$): δ 11.57 (s, 1H), 9.67 (dd, J=8.0, 2.0 Hz, 1H), 9.03 (s, 1H), 8.40 (s, 1H), 8.28 (m, 1H), 7.42 (s, 1H), 6.99 (m, 2H), 5.90 (dd, J=10.8, 2.4 Hz, 1H), 4.23 (m, 1H), 3.85 (m, 1H), 2.58 (m, 1H), 2.23-1.68 (m, 6H), 1.29 (d, J=6.8 Hz, 6H)

Step 6: Preparation of N-(3-(3-(9H-Purin-6-Yl)Pyridin-2-Ylamino)-2,4-Difluorophenyl)Isobutylamide

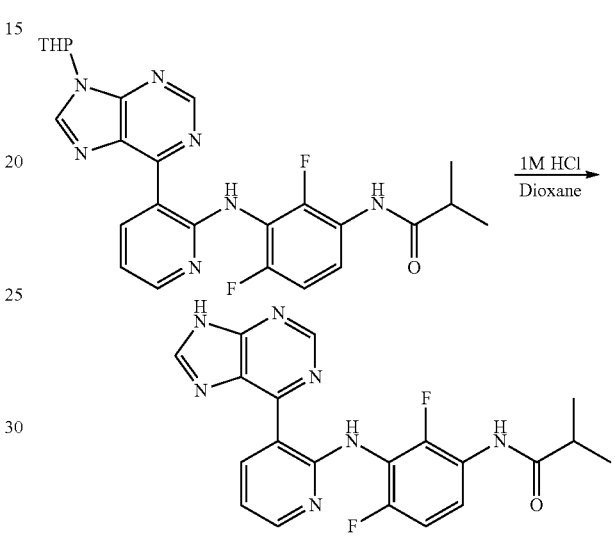

To N-(2,4-difluoro-3-(3-(9-(tetrahydro-2H-pyran-2-yl)-9H-purin-6-yl)pyridin-2-ylamino)phenyl)isobutylamide (20 mg, 0.040 mmol) prepared in step 5, 1M hydrochloric acid aqueous solution was added, followed by stirring under reflux for 2 hours. After completion of the reaction, the reaction solution was washed with aqueous sodium hydrogen carbonate solution and brine and extracted with ethyl acetate. The organic layer was dried with anhydrous magnesium sulfate, concentrated under reduced pressure, and then purified by column chromatography to afford the title compound.

$^1$H NMR (400 MHz, DMSO-d$_6$): δ 11.69 (s, 1H), 9.67 (m, 2H), 8.98 (s, 1H), 8.64 (s, 1H), 8.19 (dd, J=4.8, 1.6 Hz, 1H), 7.63 (m, 1H), 7.14 (t, J=9.2 Hz, 1H), 7.02 (dd, J=7.6, 4.8 Hz, 1H), 2.71 (m, 1H), 1.10 (d, J=6.8 Hz, 6H).

Example 5. Preparation of N-(3-(3-(9H-Purin-6-Yl)Pyridin-2-Ylamino)-2,4-Difluorophenyl)Thiophene-2-Carboxamide

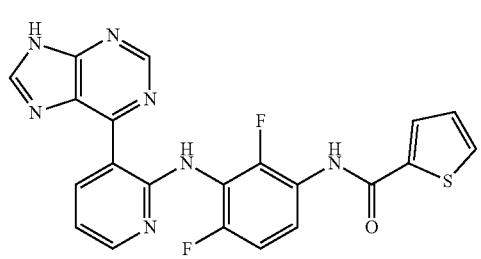

Step 1: Preparation of N-(2,4-Difluoro-3-(3-(9-(Tetrahydro-2H-Pyran-2-Yl)-9H-Purin-6-Yl)Pyridin-2-Ylamino)Phenyl)Thiophene-2-Carboxamide

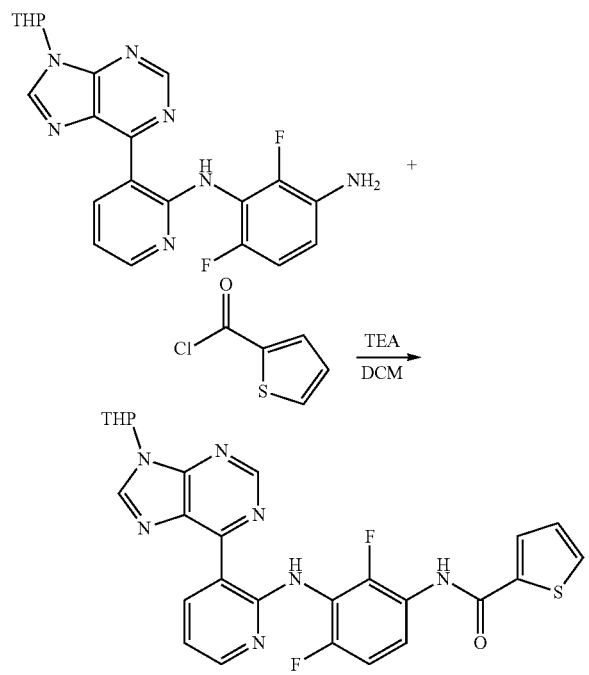

2,6-difluoro-N-(3-(9-(tetrahydro-2H-pyran-2-yl)-9H-purin-6-yl)pyridin-2-yl)benzene-1,3-diamine (30 mg, 0.07 mmol) prepared in step 4 of Example 4, thiophene-2-carbonyl chloride (8.3 μL, 0.078 mmol) and triethylamine (20 μL, 0.14 mmol) were added to a dichloromethane solvent. The mixture was stirred at room temperature for 2 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

$^1$H NMR (400 MHz, CDCl$_3$): δ 11.61 (s, 1H), 9.65 (m, 1H), 9.02 (d, J=5.2 Hz, 1H), 8.37 (d, J=6.8 Hz, 1H), 8.22 (m, 1H), 7.60 (m, 3H), 7.14 (m, 1H), 7.03 (m, 2H), 6.94 (m, 1H), 5.88 (m, 1H), 4.22 (m, 1H), 3.83 (m, 1H), 2.22-1.61 (m, 6H)

Step 2: Preparation of N-(3-(3-(9H-Purin-6-Yl)Pyridin-2-Ylamino)-2,4-Difluorophenyl)Thiophene-2-Carboxamide

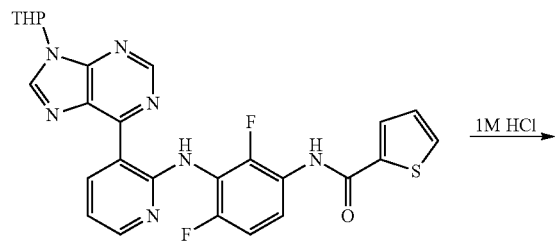

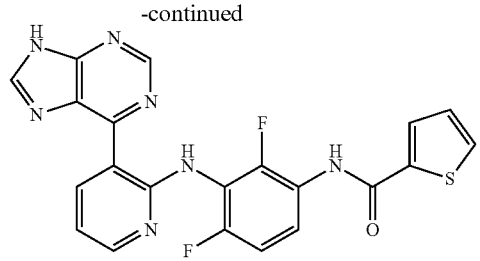

To N-(2,4-difluoro-3-(3-(9-(tetrahydro-2H-pyran-2-yl)-9H-purin-6-yl)pyridin-2-ylamino)phenyl)thiophene-2-carboxamide (20 mg, 0.037 mmol), prepared in step 1, 1M hydrochloric acid aqueous solution was added, followed by stirring under reflux for 2 hours. After completion of the reaction, the reaction solution was washed with aqueous sodium hydrogen carbonate solution and brine and extracted with ethyl acetate. The organic layer was dried with anhydrous magnesium sulfate, concentrated under reduced pressure, and then purified by column chromatography to afford the title compound.

$^1$H NMR (400 MHz, DMSO-d$_6$): δ 11.65 (s, 1H), 10.26 (s, 1H), 9.68 (dd, J=7.6, 1.6 Hz, 1H), 9.05 (s, 1H), 8.75 (s, 1H), 8.23 (dd, J=4.8, 1.6 Hz, 1H), 8.03 (m, 1H), 7.88 (dd, J=5.2, 1.2 Hz, 1H), 7.46 (m, 1H), 7.21 (m, 2H), 7.05 (m, 1H).

Example 6. Preparation of N-(3-(3-(9H-Purin-6-Yl)Pyridine-2-Ylamino)-2,4-Difluorophenyl)Furan-2-Carboxamide

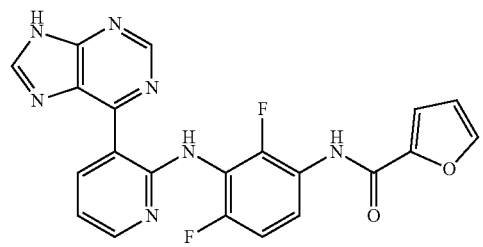 [SMILES: O=C(Nc1ccc(F)c(Nc2ncccc2-c2ncnc3[nH]cnc23)c1F)c1ccco1]

Step 1: Preparation of N-(2,4-Difluoro-3-(3-(9-(Tetrahydro-2H-Pyran-2-Yl)-9H-Purin-6-Yl)Pyridin-2-Ylamino)Phenyl)Furan-2-Carboxamide

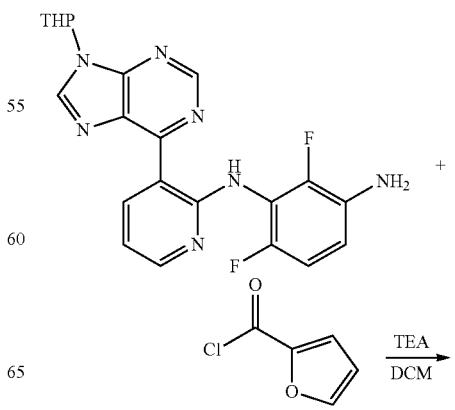

-continued

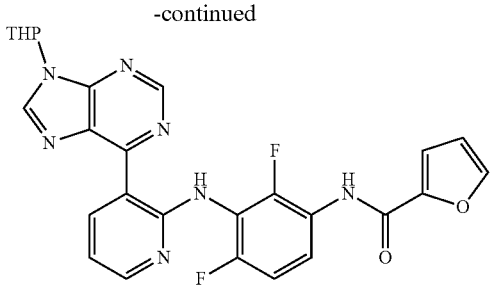

2,6-difluoro-N-(3-(9-(tetrahydro-2H-pyran-2-yl)-9H-purin-6-yl)pyridin-2-yl)benzene-1,3-diamine (30 mg, 0.07 mmol) prepared in step 4 of Example 4, furan-2-carbonyl chloride (8 μL, 0.078 mmol) and triethylamine (20 μL, 0.14 mmol) were added to a dichloromethane solvent. The mixture was stirred at room temperature for 2 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

$^1$H NMR (400 MHz, CDCl$_3$): δ 11.62 (s, 1H), 9.65 (m, 1H), 9.02 (s, 1H), 8.37 (s, 1H), 8.25 (m, 1H), 7.51 (s, 1H), 7.17 (d, J=3.6 Hz, 1H), 6.94 (m, 2H), 6.48 (dd, J=3.6, 1.6 Hz, 1H), 5.88 (m, 1H), 4.24 (m, 1H), 3.83 (m, 1H), 2.22-1.69 (m, 6H)

Step 2: Preparation of N-(3-(3-(9H-Purin-6-Yl)Pyridin-2-Ylamino)-2,4-Difluorophenyl)Furan-2-Carboxamide

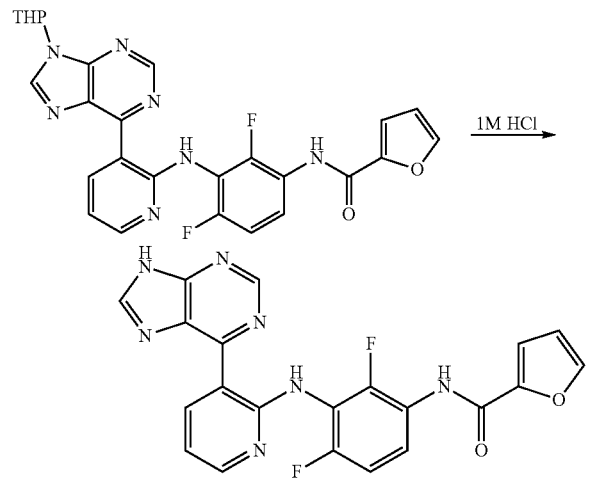

To N-(2,4-difluoro-3-(3-(9-(tetrahydro-2H-pyran-2-yl)-9H-purin-6-yl)pyridin-2-ylamino)phenyl)furan-2-carboxamide (20 mg, 0.038 mmol) prepared in step 1, 1M hydrochloric acid aqueous solution was added, followed by stirring under reflux for 2 hours. After completion of the reaction, the reaction solution was cooled to room temperature, and the produced solid was filtered under reduced pressure, washed with water and dichloromethane, and dried to afford the title compound.

$^1$H NMR (400 MHz, DMSO-d$_6$): δ 13.86 (s, 1H), 11.61 (s, 1H), 10.10 (s, 1H), 9.69 (s, 1H), 9.05 (s, 1H), 8.74 (s, 1H), 8.22 (m, 1H), 7.95 (m, 1H), 7.35 (m, 4H), 7.05 (m, 1H), 6.70 (m, 1H)

Example 7. Preparation of N-(3-(3-(9H-Purin-6-Yl)Pyridin-2-Ylamino)-2,4-Difluorophenyl)Isoxazole-5-Carboxamide

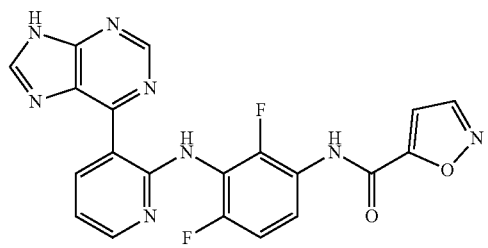 [SMILES: O=C(Nc1ccc(F)c(Nc2ncccc2-c2ncnc3[nH]cnc23)c1F)c1ccno1]

Step 1: Preparation of N-(2,4-Difluoro-3-(3-(9-(Tetrahydro-2H-Pyran-2-Yl)-9H-Purin-6-Yl)Pyridin-2-Ylamino)Phenyl)Isoxazole-5-Carboxamide

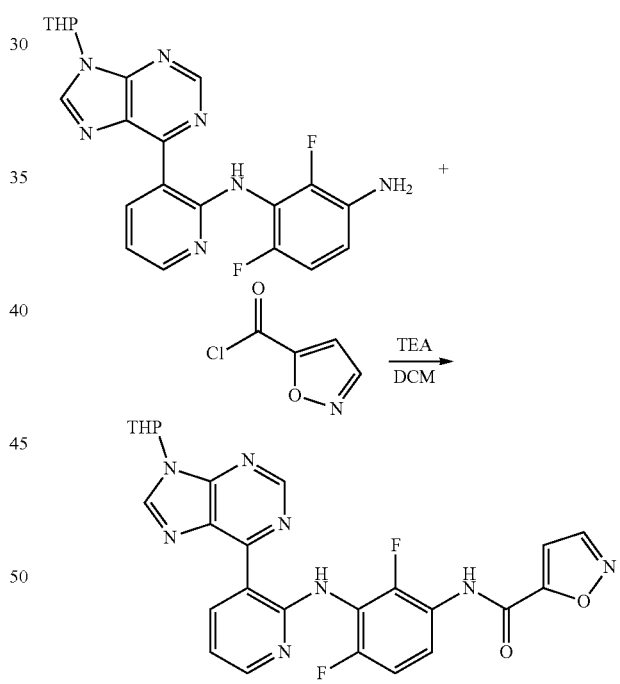

2,6-difluoro-N-(3-(9-(tetrahydro-2H-pyran-2-yl)-9H-purin-6-yl)pyridin-2-yl)benzene-1,3-diamine (20 mg, 0.047 mmol) prepared in step 4 of Example 4, idoxazole-5-carbonyl chloride (5.0 μL, 0.052 mmol) and triethylamine (7.9 μL, 0.056 mmol) were added to a dichloromethane solvent. The mixture was stirred at room temperature for 2 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

¹H NMR (400 MHz, CDCl₃): δ 11.67 (s, 1H), 9.69 (dd, J=7.6, 1.6 Hz, 1H), 9.05 (s, 1H), 8.46 (s, 1H), 8.42 (d, J=1.6 Hz, 1H), 8.39 (s, 1H), 8.31 (dd, J=4.8, 1.6 Hz, 1H), 8.22 (m, 1H), 7.08 (s, 2H), 7.00 (dd, J=8.0, 4.8 Hz, 1H), 5.91 (dd, J=10.8, 2.4 Hz, 1H), 4.25 (m, 1H), 3.86 (m, 1H), 2.25-1.74 (m, 6H).

Step 2: Preparation of N-(3-(3-(9H-Purin-6-Yl)Pyridin-2-Ylamino)-2,4-Difluorophenyl)Isoxazole-5-Carboxamide

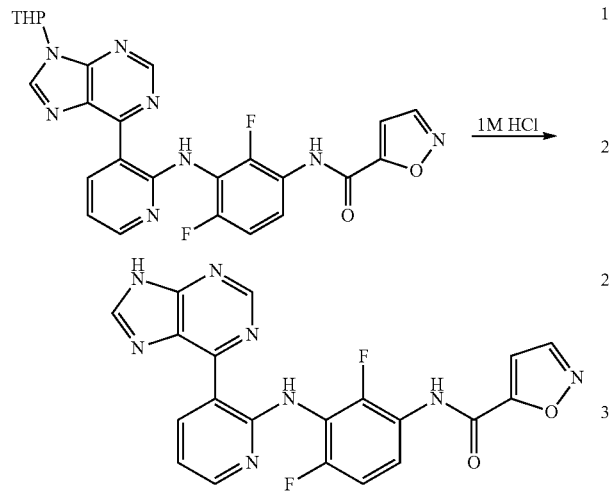

To N-(2,4-difluoro-3-(3-(9-(tetrahydro-2H-pyran-2-yl)-9H-purin-6-yl)pyridin-2-ylamino)phenyl)isoxazole-5-carboxamide (20 mg, 0.039 mmol) prepared in step 1, 1M hydrochloric acid aqueous solution was added, followed by stirring under reflux for 2 hours. After completion of the reaction, the reaction solution was cooled to room temperature, and the produced solid was filtered under reduced pressure, washed with water and dichloromethane, and dried to afford the title compound.

¹H NMR (400 MHz, DMSO-d₆): δ 11.64 (s, 1H), 10.76 (s, 1H), 9.67 (s, 1H), 9.03 (s, 1H), 8.84 (d, J=1.6 Hz, 1H), 8.72 (s, 1H), 8.22 (dd, J=4.8, 2.0 Hz, 1H), 7.46 (m, 1H), 7.27 (m, 2H), 7.05 (dd, J=8.0, 4.8 Hz, 1H)

Example 8. Preparation of N-(3-(3-(9H-Purin-6-Yl)Pyridin-2-Ylamino)-2,4-Difluorophenyl)Thiazole-5-Carboxamide Step 1: Preparation of N-(2,4-Difluoro-3-(3-(9-(Tetrahydro-2H-Pyran-2-Yl)-9H-Purin-6-Yl)Pyridin-2-Ylamino)Phenyl)Thiazole-5-Carboxyamide

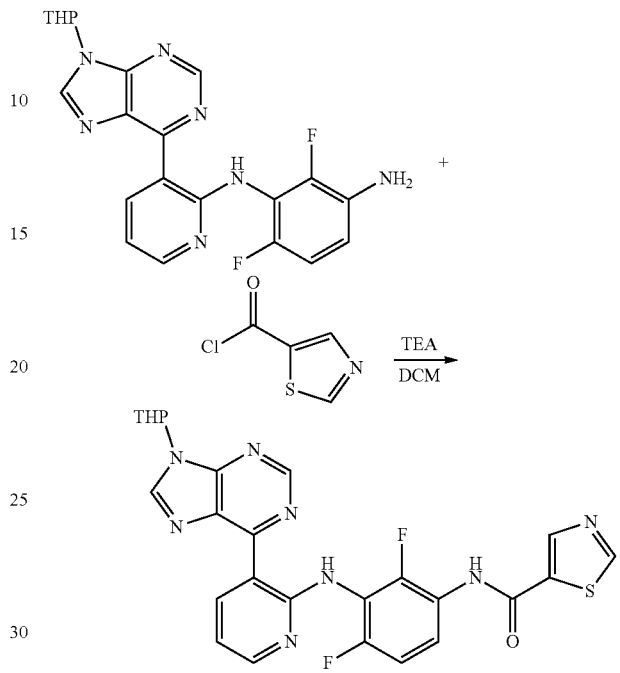

2,6-dlfluoro-N-(3-(9-(tetrahydro-2H-pyran-2-yl)-9H-purin-6-yl)pyridin-2-yl)benzene-1,3-diamine (30 mg, 0.07 mmol) prepared in step 4 of Example 4, thiazole-5-carbonyl chloride (11 mg, 0.078 mmol) and triethylamine (11.8 μL, 0.084 mmol) were added to a dichloromethane solvent. Next, the reaction was stirred at room temperature for 3 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

¹H NMR (400 MHz, CDCl₃): δ 11.64 (s, 1H), 9.67 (dd, J=8.0, 1.6 Hz, 1H), 9.52 (s, 1H), 9.04 (s, 1H), 8.83 (d, J=2.0 Hz, 1H), 8.34 (m, 4H), 7.08 (td, J=6.0, 2.0 Hz, 1H), 6.97 (dd, J=8.0, 4.8 Hz, 1H), 5.90 (dd, J=10.4, 2.4 Hz, 1H), 4.24 (m, 1H), 3.85 (m, 1H), 2.24-1.73 (m, 6H).

Step 2: Preparation of N-(3-(3-(9H-Purin-6-Yl)Pyridin-2-Ylamino)-2,4-Difluorophenyl)Thiazole-5-Carboxamide

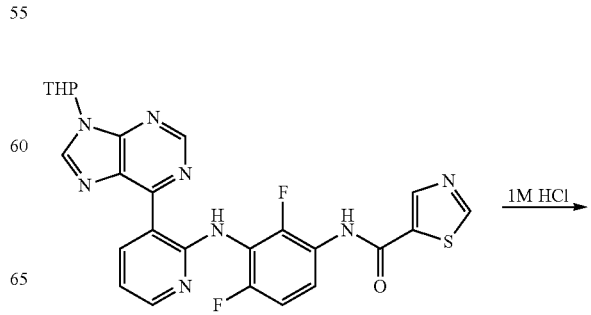

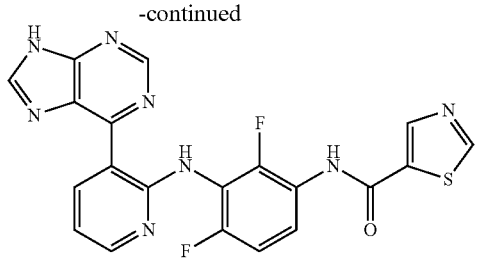

To N-(2,4-difluoro-3-(3-(9-(tetrahydro-2H-pyran-2-yl)-9H-purin-6-yl)pyridin-2-ylamino)phenyl)thiazole-5-carboxyamide (20 mg, 0.037 mmol) prepared in step 1, 1M hydrochloric acid aqueous solution was added, followed by stirring under reflux for 2 hours. After completion of the reaction, the reaction solution was cooled to room temperature, and the produced solid was filtered under reduced pressure, washed with water and dichloromethane, and dried to afford the title compound.

¹H NMR (400 MHz, DMSO-d₆): δ 11.69 (s, 1H), 10.10 (s, 1H), 9.68 (dd, J=8.0, 2.0 Hz, 1H), 9.29 (s, 1H), 9.06 (s, 1H), 8.76 (s, 1H), 8.55 (d, J=2.0 Hz, 1H), 8.23 (dd, J=4.8, 2.0 Hz, 1H), 7.76 (m, 1H), 7.24 (td, J=9.2, 1.6 Hz, 1H), 7.07 (dd, J=8.0, 4.8 Hz, 1H)

Example 9. Preparation of N-(3-(3-(9H-Purin-6-Yl)Pyridin-2-Ylamino)-2,4-Difluorophenyl)-3-(2-Cyanopropan-2-Yl)Benzamide

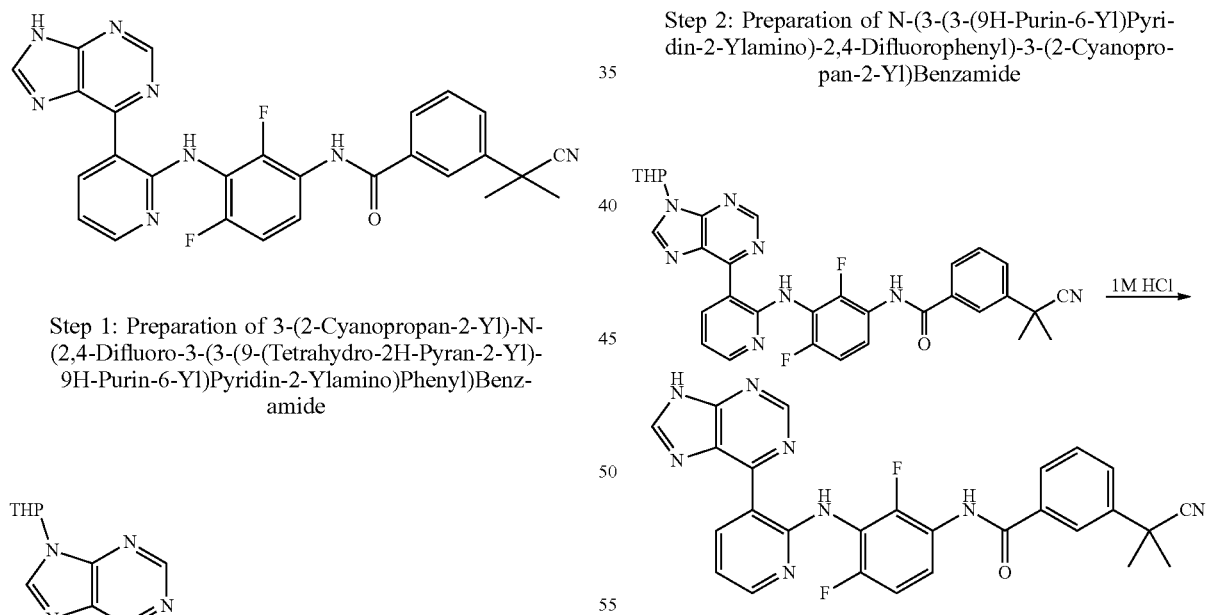

Step 1: Preparation of 3-(2-Cyanopropan-2-Yl)-N-(2,4-Difluoro-3-(3-(9-(Tetrahydro-2H-Pyran-2-Yl)-9H-Purin-6-Yl)Pyridin-2-Ylamino)Phenyl)Benzamide

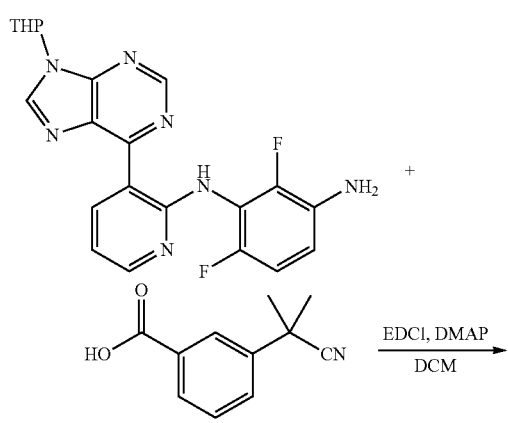

2,6-difluoro-N-(3-(9-(tetrahydro-2H-pyran-2-yl)-9H-purin-6-yl)pyridin-2-yl)benzene-1,3-diamine (40 mg, 0.095 mmol) prepared in step 4 of Example 4, 3-(2-cyanopropan-2-yl)benzoic acid (20 mg, 0.11 mmol), 1-ethyl-3-(3-dimethylaminopropyl)carbodiimide (27 mg, 0.14 mmol) and N,N-dimethylaminopyridine (17 mg, 0.14 mmol) were added to a dichloromethane solvent, followed by stirring at room temperature for 18 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

¹H NMR (400 MHz, CDCl₃): δ 11.64 (s, 1H), 9.68 (dd, J=8.0, 2.0 Hz, 1H), 9.05 (s, 1H), 8.40 (s, 1H), 8.30 (dd, J=4.8, 1.6 Hz, 1H), 8.22 (m, 2H), 7.77 (m, 2H), 7.55 (t, J=7.8 Hz, 1H), 7.08 (td, J=9.2, 1.6 Hz, 1H), 6.98 (dd, J=8.0, 4.8 Hz, 1H), 5.91 (dd, J=10.4, 2.4 Hz, 1H), 4.24 (m, 1H), 3.85 (m, 1H), 2.24-1.70 (m, 12H)

Step 2: Preparation of N-(3-(3-(9H-Purin-6-Yl)Pyridin-2-Ylamino)-2,4-Difluorophenyl)-3-(2-Cyanopropan-2-Yl)Benzamide

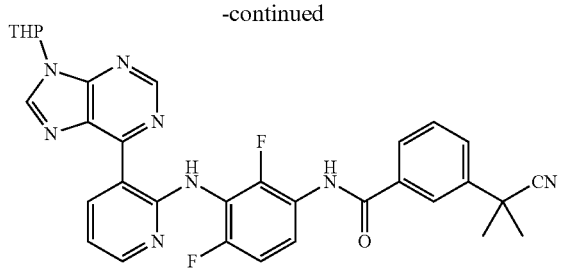

To 3-(2-cyanopropan-2-yl)-N-(2,4-difluoro-3-(3-(9-(tetrahydro-2H-pyran-2-yl)-9H-purin-6-yl)pyridin-2-ylamino)phenyl)benzamide (20 mg, 0.034 mmol) prepared in step 1, 1M hydrochloric acid aqueous solution was added, followed by stirring under reflux for 2 hours. After completion of the reaction, the reaction solution was washed with saturated aqueous sodium hydrogen carbonate solution and brine and extracted with ethyl acetate. The organic layer was dried with anhydrous magnesium sulfate, concentrated under reduced pressure, and then purified by column chromatography to afford the title compound.

¹H NMR (400 MHz, DMSO-d₆): δ 11.62 (s, 1H), 10.32 (s, 1H), 9.67 (dd, J=7.6, 1.6 Hz, 1H), 9.05 (s, 1H), 8.74 (s, 1H), 8.23 (dd, J=4.8, 1.6 Hz, 1H), 8.11 (m, 1H), 7.97 (d, J=7.6 Hz, 1H), 7.77 (m, 1H), 7.61 (t, J=8.0 Hz, 1H), 7.49 (td, J=8.4, 5.6 Hz, 1H), 7.24 (td, J=10.4, 1.2 Hz, 1H), 7.06 (dd, J=8.0, 4.8 Hz, 1H), 1.75 (s, 6H).

Example 10. Preparation of N-(3-(3-(9H-Purin-6-Yl)Pyridin-2-Ylamino)-2,4-d Fluorophenyl)-3-(4-Methylpiperazin-1-Yl)-5-(Trifluoromethyl)Benzamide

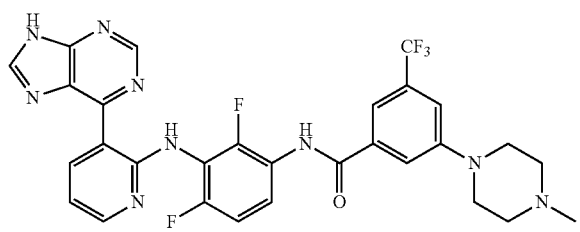 [SMILES: CN1CCN(c2cc(C(=O)Nc3ccc(F)c(Nc4ncccc4-c4ncnc5[nH]cnc45)c3F)cc(C(F)(F)F)c2)CC1]

The title compound was synthesized in the same manner as described in Example 2, except that 3-(4-methylpiperazin-1-yl)-5-(trifluoromethyl)benzoic acid was used instead of 3-(4-methyl-1H-imidazol-1-yl)-5-(trifluoromethyl)benzoic acid in step 1 of Example 2.

¹H NMR (400 MHz, CDCl₃): δ 11.67 (s, 1H), 9.74 (d, J=6.8 Hz, 1H), 9.06 (s, 1H), 8.33 (m, 2H), 8.20 (m, 1H), 8.03 (d, J=2.4 Hz, 1H), 7.61 (s, 1H), 7.46 (s, 1H), 7.08 (td, J=7.6, 1.2 Hz, 1H), 7.00 (m, 1H), 3.38 (t, J=4.8 Hz, 4H), 2.66 (s, 4H), 2.42 (s, 3H).

Example 11. Preparation of N-(3-(3-(9H-Purin-6-Yl)Pyridin-2-Ylamino)-2,4-Difluorophenyl)-3-Thiomorpholino-5-(Trifluoromethyl)Benzamide

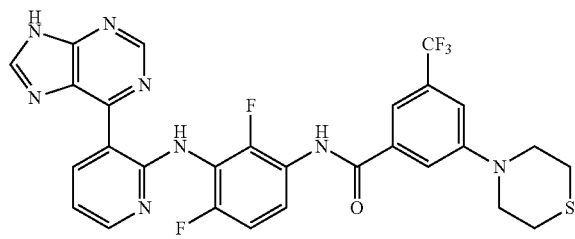 [SMILES: O=C(Nc1ccc(F)c(Nc2ncccc2-c2ncnc3[nH]cnc23)c1F)c1cc(N2CCSCC2)cc(C(F)(F)F)c1]

The title compound was synthesized in the same manner as described in Example 2, except that 3-thiomorpholino-5-(trifluoromethyl)benzoic acid was used instead of 3-(4-methyl-1H-imidazol-1-yl)-5-(trifluoromethyl)benzoic acid in step 1 of Example 2.

¹H NMR (400 MHz, DMSO-d₆): δ 11.62 (s, 1H), 10.36 (s, 1H), 9.67 (d, J=6.4 Hz, 1H), 9.04 (s, 1H), 8.73 (s, 1H), 8.22 (dd, J=2.8, 1.6 Hz, 1H), 7.72 (s, 1H), 7.61 (s, 1H), 7.48 (m, 1H), 7.39 (s, 1H), 7.24 (t, J=9.2 Hz, 1H), 7.04 (dd, J=4.8, 2.8 Hz, 1H), 3.72 (m, 4H), 2.70 (s, 4H).

Example 12. Preparation of N-(3-(3-(9H-purin-6-yl)pyridin-2-ylamino)-2,4-difluorophenyl)-3-(4-hydroxypiperidin-1-yl)-5-(trifluoromethyl)benzamide

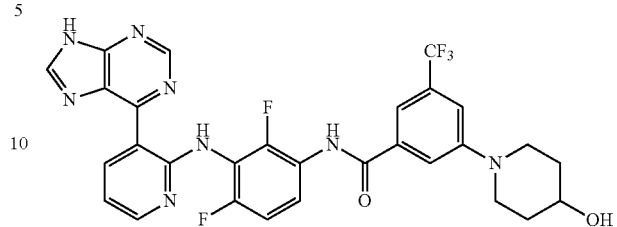

The title compound was synthesized in the same manner as described in Example 2, except that 3-(4-hydroxypiperidin-1-yl)-5-(trifluoromethyl)benzoic acid was used instead of 3-(4-methyl-1H-imidazol-1-yl)-5-(trifluoromethyl)benzoic acid in step 1 of Example 2.

¹H NMR (400 MHz, MeOD): δ 9.53 (d, J=7.2 Hz, 1H), 9.00 (s, 1H), 8.52 (s, 1H), 8.52 (dd, J=3.2, 1.6 Hz, 1H), 7.75 (s, 1H), 7.62 (s, 1H), 7.58 (m, 1H), 7.36 (s, 1H), 7.10 (t, J=9.2 Hz, 1H), 7.00 (dd, J=4.8, 3.2 Hz, 1H), 3.74 (m, 3H), 3.07 (m, 2H), 2.00 (m, 2H), 1.65 (s, 2H).

Example 13. Preparation of N-(3-(3-(9H-Purin-6-Yl)Pyridin-2-Ylamino)-2,4-Difluorophenyl)-3-(4-Methylpiperidin-1-Yl)-5-(Trifluoromethyl)Benzamide

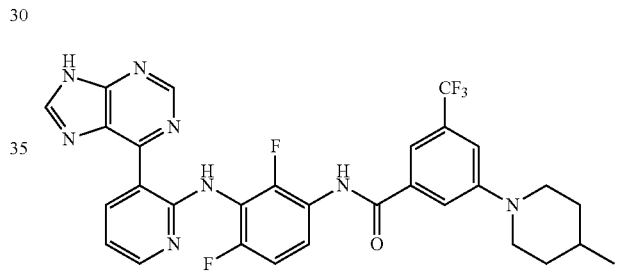

The title compound was synthesized in the same manner as described in Example 2, except that 3-(4-methylpiperidin-1-yl)-5-(trifluoromethyl)benzoic acid was used instead of 3-(4-methyl-1H-imidazol-1-yl)-5-(trifluoromethyl)benzoic acid in step 1 of Example 2.

¹H NMR (400 MHz, CDCl₃): δ 11.67 (s, 1H), 9.74 (s, 1H), 9.06 (d, J=6.8 Hz, 1H), 8.32 (m, 2H), 8.14 (m, 2H), 7.59 (s, 1H), 7.30 (m, 2H), 7.00 (m, 2H), 3.79 (d, J=9.2 Hz, 2H), 2.84 (m, 2H), 1.77 (m, 2H), 1.68 (m, 1H), 1.32 (m, 2H), 1.00 (s, 3H)

Example 14. Preparation of N-(3-(3-(9H-Purin-6-Yl)Pyridin-2-Ylamino)-2,4-Difluorophenyl)-4-Thiomorpholino-3-(Trifluoromethyl)Benzamide

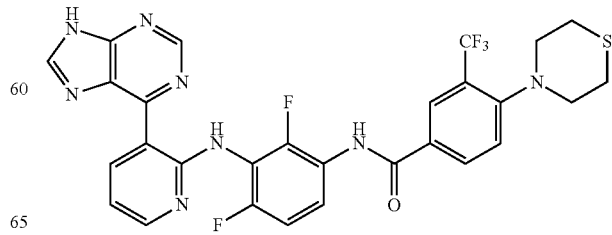

The title compound was synthesized in the same manner as described in Example 2, except that 4-thiomorpholino-3-(trifluoromethyl)benzoic acid was used instead of 3-(4-methyl-1H-imidazol-1-yl)-5-(trifluoromethyl)benzoic acid in step 1 of Example 2.

$^1$H NMR (400 MHz, CDCl$_3$): δ 11.67 (s, 1H), 9.74 (d, J=6.8 Hz, 1H), 9.07 (s, 1H), 8.34 (s, 1H), 8.32 (dd, J=3.2, 1.6 Hz, 1H), 8.17 (m, 2H), 8.04 (m, 2H), 7.40 (d, J=8.4 Hz, 1H), 7.07 (m, 1H), 7.00 (m, 1H), 3.23 (t, J=4.8 Hz, 4H), 2.82 (t, J=4.8 Hz, 4H).

Example 15. Preparation of N-(3-(3-(9H-Purin-6-Yl)Pyridin-2-Ylamino)-2,4-Difluorophenyl)-4-(4-Methylpeperidin-1-Yl)-3-(Trifluoromethyl)Benzamide

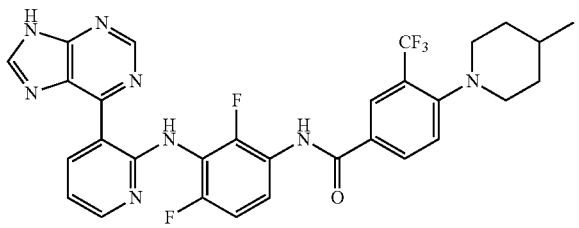 [SMILES: CC1CCN(c2ccc(C(=O)Nc3ccc(F)c(Nc4ncccc4-c4ncnc5[nH]cnc45)c3F)cc2C(F)(F)F)CC1]

The title compound was synthesized in the same manner as described in Example 2, except that 4-(4-methylpiperidin-1-yl)-3-(trifluoromethyl)benzoic acid was used instead of 3-(4-methyl-1H-imidazol-1-yl)-5-(trifluoromethyl)benzoic acid in step 1 of Example 2.

$^1$H NMR (400 MHz, CDCl$_3$): δ 11.66 (s, 1H), 9.72 (d, J=7.2 Hz, 1H), 9.06 (s, 1H), 8.32 (m, 2H), 8.17 (m, 2H), 7.97 (m, 2H), 7.32 (d, J=8.8 Hz, 1H), 7.05 (m, 1H), 6.99 (m, 1H), 3.22 (d, J=11.6 Hz, 2H), 2.77 (t, J=11.2 Hz, 2H), 1.71 (d, J=12.8 Hz, 2H), 1.53 (m, 1H), 1.47 (m, 2H), 1.01 (d, J=6.0 Hz, 3H)

Example 16. Preparation of N-(3-(3-(9H-Purin-6-Yl)Pyridin-2-Ylamino)-2,4-Difluorophenyl)-4-Chloro-3-(Trifluoromethyl)Benzamide

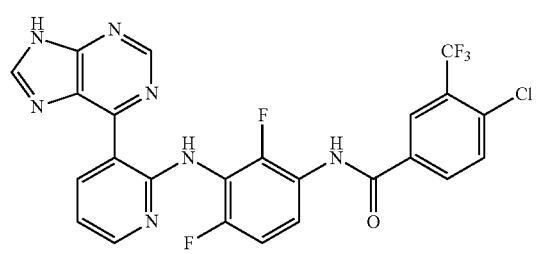 [SMILES: O=C(Nc1ccc(F)c(Nc2ncccc2-c2ncnc3[nH]cnc23)c1F)c1ccc(Cl)c(C(F)(F)F)c1]

The title compound was synthesized in the same manner as described in Example 2, except that 4-chloro-3-(trifluoromethyl)benzoic acid was used instead of 3-(4-methyl-1H-imidazol-1-yl)-5-(trifluoromethyl)benzoic acid in step 1 of Example 2.

$^1$H NMR (400 MHz, CDCl$_3$): δ 9.63 (d, J=7.2 Hz, 1H), 9.00 (s, 1H), 8.33 (d, J=12.8 Hz, 2H), 8.20 (d, J=3.2 Hz, 1H), 8.11 (d, J=8.0 Hz, 1H), 7.77 (m, 1H), 7.65 (d, J=8.4 Hz, 1H), 7.06 (t, J=9.2 Hz, 1H), 7.00 (m, 1H)

Example 17. Preparation of N-(3-(3-(9H-Purin-6-Yl)Pyridin-2-Ylamino)-2,4-Difluorophenyl)-2,3-Dihydrobenzo[b][1,4]Dioxine-6-Carboxamide

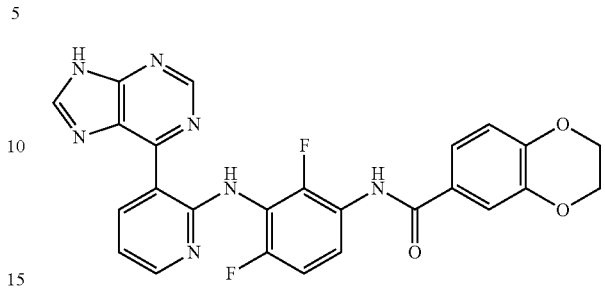

The title compound was synthesized in the same manner as described in Example 2, except that 2,3-dihydrobenzo[b][1,4]dioxine-6-carboxylic acid was used instead of 3-(4-methyl-1H-imidazol-1-yl)-5-(trifluoromethyl)benzoic acid in step 1 of Example 2.

$^1$H NMR (400 MHz, CDCl$_3$): δ 11.64 (s, 1H), 9.74 (d, J=7.2 Hz, 1H), 9.05 (s, 1H), 8.33 (s, 2H), 8.25 (d, J=5.2 Hz, 1H), 7.92 (s, 1H), 7.46 (s, 1H), 7.40 (d, J=10 Hz, 1H), 7.05 (m, 1H), 6.96 (m, 2H), 4.33 (m, 4H)

Example 18. Preparation of N-(3-(3-(9H-Purin-6-Yl)Pyridin-2-Ylamino)-2,4-Difluorophenyl)-3-Morpholino-5-(Trifluoromethyl)Benzamide

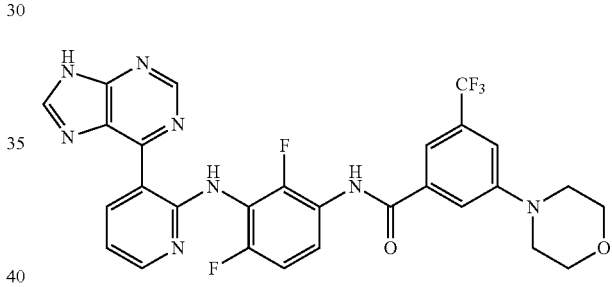

The title compound was synthesized in the same manner as described in Example 2, except that 3-morpholino-5-(trifluoromethyl)benzoic acid was used instead of 3-(4-methyl-1H-imidazol-1-yl)-5-(trifluoromethyl)benzoic acid in step 1 of Example 2.

$^1$H NMR (400 MHz, CDCl$_3$): δ 11.68 (s, 1H), 11.55 (brs, 1H), 9.75 (d, J=6.8 Hz, 1H), 9.06 (s, 1H), 8.32 (m, 2H), 8.19 (m, 1H), 8.05 (s, 1H), 7.62 (s, 1H), 7.50 (s, 1H), 7.27 (s, 1H), 7.08 (m, 1H), 7.00 (m, 1H), 3.90 (m, 4H), 3.29 (m, 2H)

Example 19. Preparation of N-(3-(3-(9H-Purin-6-Yl)Pyridin-2-Ylamino)-2,4-Difluorophenyl)-4-(Pyrrolidin-1-Yl)-3-(Trifluoromethyl)Benzamide

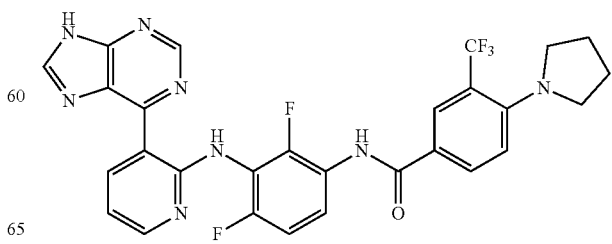

The title compound was synthesized in the same manner as described in Example 2, except that 4-(pyrrolidin-1-yl)-3-(trifluoromethyl)benzoic acid was used instead of 3-(4-methyl-1H-imidazol-1-yl)-5-(trifluoromethyl)benzoic acid in step 1 of Example 2.

$^1$H NMR (400 MHz, CDCl$_3$): δ 11.64 (s, 1H), 9.73 (d, J=6.4 Hz, 1H), 9.06 (s, 1H), 8.32 (m, 2H), 8.24 (m, 2H), 8.17 (d, J=2.4 Hz, 1H), 7.85 (m, 2H), 7.06 (d, J=7.2, 5.0 Hz, 1H), 7.00 (m, 1H), 6.90 (d, J=8.8 Hz, 1H), 3.50 (m, 2H), 2.02 (m, 2H)

Example 20. Preparation of N-(3-(3-(9H-Purin-6-Yl)Pyridin-2-Ylamino)-2,4-Difluorophenyl)-3-(1-Cyanocyclopropyl)Benzamide

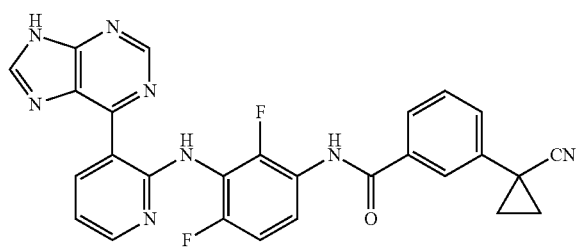 [SMILES: N#CC1(c2cccc(C(=O)Nc3ccc(F)c(Nc4ncccc4-c4ncnc5[nH]cnc45)c3F)c2)CC1]

The title compound was synthesized in the same manner as described in Example 2, except that 3-(1-cyanocyclopropyl)benzoic acid was used instead of 3-(4-methyl-1H-imidazol-1-yl)-5-(trifluoromethyl)benzoic acid in step 1 of Example 2.

$^1$H NMR (400 MHz, DMSO-d$_6$): δ 11.69 (brs, 1H), 10.29 (s, 1H), 9.67 (d, J=7.2 Hz, 1H), 9.01 (s, 1H), 8.67 (s, 1H), 8.21 (dd, J=2.0, 2.8 Hz, 1H), 7.91 (m, 2H), 7.58 (m, 2H), 7.47 (m, 1H), 7.23 (t, J=8.0 Hz, 1H), 7.03 (m, 1H), 1.82 (m, 2H), 1.62 (m, 2H)

Example 21. Preparation of N-(5-(3-(9H-Purin-6-Yl)Pyridin-2-Ylamino)-2-Fluorophenyl)-3-(2-Cyanopropan-2-Yl)Benzamide

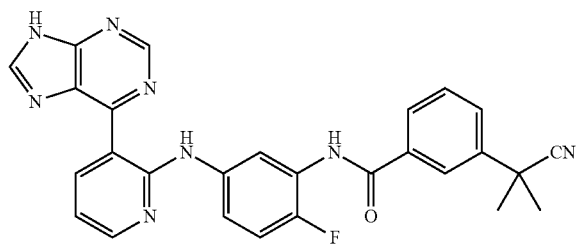 [SMILES: CC(C)(C#N)c1cccc(C(=O)Nc2cc(Nc3ncccc3-c3ncnc4[nH]cnc34)ccc2F)c1]

The title compound was synthesized in the same manner as described in Example 2, except that, in step 1 of Example 2, t-butyl(3-amino-4-fluorophenyl)carbamate was used instead of t-butyl(3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 12.68 (brs, 1H), 10.30 (s, 1H), 9.77 (brs, 1H), 9.11 (s, 1H), 8.69 (s, 1H), 8.36 (dd, J=1.6, 2.8 Hz, 1H), 8.10 (m, 2H), 7.99 (d, J=8.0 Hz, 1H), 7.78 (d, J=8.0 Hz, 1H), 7.71 (m, 1H), 7.63 (t, J=8.0 Hz, 1H), 7.29 (t, J=9.6 Hz, 1H), 7.04 (m, 1H), 1.77 (s, 6H)

Example 22: Preparation of N-(3-(3-(9H-Purin-6-Yl)Pyridin-2-Ylamino)-2,4-Difluorophenyl)-3-(1-Amino-2-Methyl-1-Oxopropan-2-Yl)Benzamide

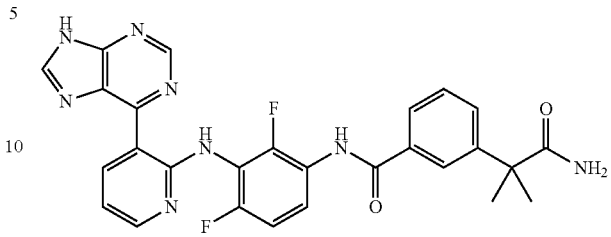

The title compound was synthesized in the same manner as described in Example 2, except that 3-(1-amino-2-methyl-1-oxopropan-2-yl)benzoic acid was used instead of 3-(4-methyl-1H-imidazol-1-yl)-5-(trifluoromethyl)benzoic acid in step 1 of Example 2.

$^1$H NMR (400 MHz, CDCl$_3$): δ 12.40 (brs, 1H), 11.67 (s, 1H), 9.71 (d, J=7.2 Hz, 1H), 8.98 (s, 1H), 8.31 (s, 1H), 8.27 (dd, J=1.6, 2.8 Hz, 1H), 8.24 (s, 1H), 8.14 (brs, 1H), 7.99 (s, 1H), 7.77 (d, J=7.6 Hz, 1H), 7.61 (d, J=8.4 Hz, 1H), 7.48 (t, J=7.6 Hz, 1H), 7.04 (t, J=9.2 Hz, 1H), 6.96 (m, 1H), 6.11 (brs, 1H), 5.53 (brs, 1H), 1.64 (s, 6H)

Example 23. Preparation of N-(3-(3-(9H-Purin-6-Yl)Pyridin-2-Ylamino)Phenyl)-3-(2-Cyanopropan-2-Yl)Benzamide

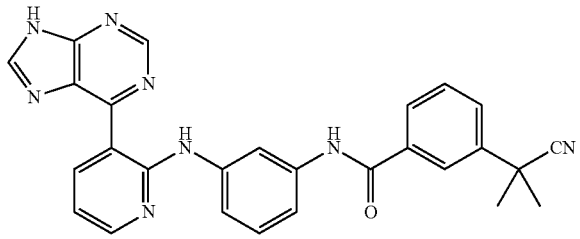 [SMILES: CC(C)(C#N)c1cccc(C(=O)Nc2cccc(Nc3ncccc3-c3ncnc4[nH]cnc34)c2)c1]

The title compound was synthesized in the same manner as described in Example 2, except that, in step 1 of Example 2, t-butyl (3-aminophenyl)carbamate was used instead of t-butyl (3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 12.29 (brs, 1H), 9.65 (brs, 1H), 8.85 (s, 1H), 8.33 (d, J=2.8 Hz, 1H), 8.24 (s, 1H), 8.16 (s, 1H), 8.17 (s, 1H), 8.04 (s, 1H), 7.81 (d, J=7.6 Hz, 1H), 7.70 (d, J=7.6 Hz, 1H), 7.51 (t, J=7.6 Hz, 1H), 7.40 (m, 1H), 7.30 (m, 2H), 6.90 (m, 1H), 1.78 (s, 6H)

Example 24. Preparation of N-(5-(3-(9H-Purin-6-Yl)Pyridin-2-Ylamino)-2-Chlorophenyl)-3-(2-Cyanopropan-2-Yl)Benzamide

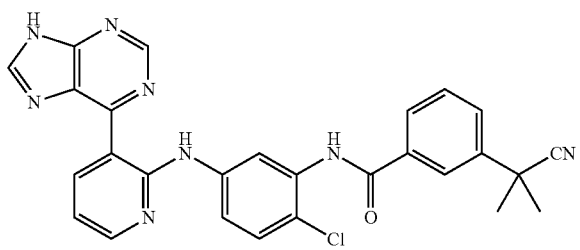 [SMILES: CC(C)(C#N)c1cccc(C(=O)Nc2cc(Nc3ncccc3-c3ncnc4[nH]cnc34)ccc2Cl)c1]

The title compound was synthesized in the same manner as described in Example 2, except that, in step 1 of Example 2, t-butyl (3-amino-4-chlorophenyl)carbamate was used instead of t-butyl (3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 13.86 (brs, 1H), 12.75 (brs, 1H), 10.26 (s, 1H), 9.75 (brs, 1H), 9.14 (s, 1H), 8.71 (s, 1H), 8.39 (dd, J=2.0, 2.8 Hz, 1H), 8.15 (m, 2H), 8.01 (d, J=7.6 Hz, 1H), 7.84 (dd, J=2.8, 6.0 Hz, 1H), 7.80 (m, 1H), 7.63 (t, J=8.0 Hz, 1H), 7.51 (d, J=8.8 Hz, 1H), 7.08 (m, 1H), 1.77 (s, 6H)

Example 25. Reparation of N-(3-(3-(9H-Purin-6-Yl)Pyridin-2-Ylamino)-2,6-Difluorophenyl)-3-(2-Cyanopropan-2-Yl)Benzamide

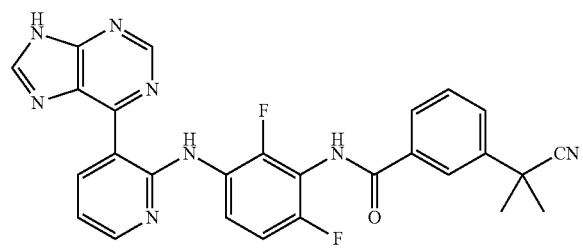 [SMILES: CC(C)(C#N)c1cccc(C(=O)Nc2c(F)ccc(Nc3ncccc3-c3ncnc4[nH]cnc34)c2F)c1]

The title compound was synthesized in the same manner as described in Example 2, except that, in step 1 of Example 2, t-butyl (3-amino-2,4-difluorophenyl)carbamate was used instead of t-butyl (3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 13.02 (brs, 1H), 10.36 (s, 1H), 9.92 (brs, 1H), 8.92 (s, 1H), 8.59 (m, 2H), 8.37 (d, J=2.8 Hz, 1H), 8.17 (s, 1H), 8.03 (d, J=8.0 Hz, 1H), 7.82 (d, J=8.4 Hz, 1H), 7.65 (t, J=7.6 Hz, 1H), 7.23 (m, 1H), 7.09 (m, 1H), 1.78 (s, 6H)

Example 26. Preparation of N-(3-(3-(9H-Purin-6-Yl)Pyridin-2-Ylamino)-2,4-Difluorophenyl)-2-(Trifluoromethyl)Benzamide

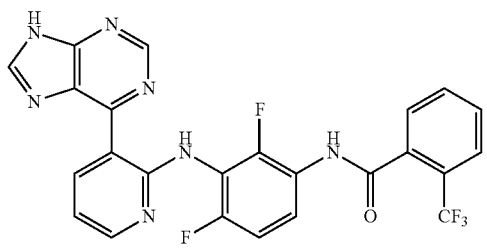 [SMILES: O=C(Nc1ccc(F)c(Nc2ncccc2-c2ncnc3[nH]cnc23)c1F)c1ccccc1C(F)(F)F]

The title compound was synthesized in the same manner as described in Example 1, except that 2-(trifluoromethyl)benzoyl chloride was used instead of 3-(trifluoromethyl)benzoyl chloride in step 4 of Example 1.

$^1$H NMR (400 MHz, DMSO-d$_6$): δ 11.63 (s, 1H), 10.45 (s, 1H), 9.67 (d, J=7.6 Hz, 1H), 9.02 (s, 1H), 8.68 (s, 1H), 8.21 (dd, J=2.0, 2.8 Hz, 1H), 7.80 (m, 4H), 7.61 (m, 1H), 7.22 (m, 1H), 7.03 (m, 1H)

Example 27. Preparation of N-(3-(3-(9H-Purin-6-Yl)Pyridin-2-Ylamino)-2,4-Difluorophenyl)-4-(Trifluoromethyl)Benzamide

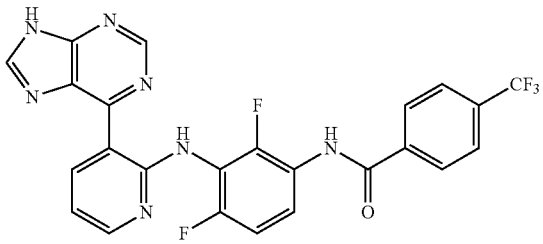 [SMILES: O=C(Nc1ccc(F)c(Nc2ncccc2-c2ncnc3[nH]cnc23)c1F)c1ccc(C(F)(F)F)cc1]

The title compound was synthesized in the same manner as described in Example 1, except that 4-(trifluoromethyl)benzoyl chloride was used instead of 3-(trifluoromethyl)benzoyl chloride in step 4 of Example 1.

$^1$H NMR (400 MHz, DMSO-d$_6$): δ 13.85 (brs, 1H), 11.60 (s, 1H), 10.44 (s, 1H), 9.68 (brs, 1H), 9.05 (s, 1H), 8.73 (s, 1H), 8.23 (dd, J=1.6, 2.8 Hz, 1H), 8.18 (d, J=8.0 Hz, 2H), 7.93 (d, J=8.4 Hz, 2H), 7.50 (m, 1H), 7.24 (m, 1H), 7.04 (m, 1H)

Example 28. Preparation of N-(3-(3-(9H-Purin-6-Yl)Pyridin-2-Ylamino)-2,4-Difluorophenyl)-3-Fluoro-5-(Trifluoromethyl)Benzamide

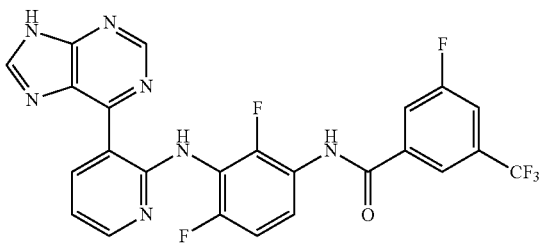 [SMILES: O=C(Nc1ccc(F)c(Nc2ncccc2-c2ncnc3[nH]cnc23)c1F)c1cc(F)cc(C(F)(F)F)c1]

The title compound was synthesized in the same manner as described in Example 2, except that 3-fluoro-5-(trifluoromethyl)benzoic acid was used instead of 3-(4-methyl-1H-imidazol-1-yl)-5-(trifluoromethyl)benzoic acid in step 1 of Example 2.

$^1$H NMR (400 MHz, DMSO-d$_6$): δ 11.63 (brs, 1H), 10.54 (brs, 1H), 9.66 (d, J=7.6 Hz, 1H), 9.03 (s, 1H), 8.71 (s, 1H), 8.22 (m, 2H), 8.12 (d, J=9.2 Hz, 2H), 8.00 (d, J=8.4 Hz, 1H), 7.51 (m, 1H), 7.25 (m, 1H), 7.03 (m, 1H)

Example 29. Preparation of N-(3-(3-(9H-Purin-6-Yl)Pyridin-2-Ylamino)-2-Fluorophenyl)-3-(2-Cyanopropan-2-Yl)Benzamide

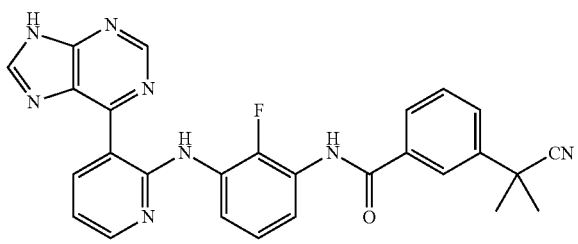 [SMILES: CC(C)(C#N)c1cccc(C(=O)Nc2cccc(Nc3ncccc3-c3ncnc4[nH]cnc34)c2F)c1]

The title compound was synthesized in the same manner as described in Example 2, except that, in step 1 of Example 2, t-butyl (3-amino-2-fluorophenyl)carbamate was used instead of t-butyl (3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 11.61 (brs, 1H), 10.29 (s, 1H), 9.66 (d, J=6.0 Hz, 1H), 9.04 (s, 1H), 8.72 (s, 1H), 8.23 (dd, J=2.0, 2.8 Hz, 1H), 8.11 (t, J=1.6 Hz, 1H), 7.97 (m, 1H), 7.77 (m, 1H), 7.61 (t, J=8.0 Hz, 1H), 7.49 (m, 1H), 7.23 (m, 1H), 7.03 (m, 1H), 1.76 (s, 6H)

Example 30. Preparation of N-(5-(3-(9H-Purin-6-Yl)Pyridin-2-Ylamino)-2-Fluorophenyl)-3-(Trifluoromethyl)Benzamide

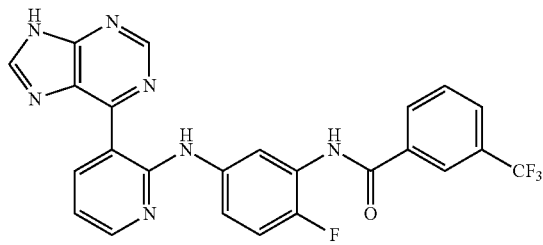 [SMILES: O=C(Nc1cc(Nc2ncccc2-c2ncnc3[nH]cnc23)ccc1F)c1cccc(C(F)(F)F)c1]

The title compound was synthesized in the same manner as described in Example 1, except that t-butyl (3-amino-4-fluorophenyl)carbamate was used instead of t-butyl (3-amino-2,6-difluorophenyl)carbamate in step 4 of Example 1.

$^1$H NMR (400 MHz, DMSO-d$_6$): δ 12.76 (brs, 1H), 10.46 (s, 1H), 9.78 (d, J=7.2 Hz, 1H), 9.04 (s, 1H), 8.59 (s, 1H), 8.33 (m, 3H), 8.12 (m, 1H), 8.01 (d, J=7.6 Hz, 1H), 7.81 (t, J=7.6 Hz, 1H), 7.72 (m, 1H), 7.29 (t, J=9.6 Hz, 1H), 7.03 (m, 1H)

Example 31. Preparation of N-(5-(3-(9H-Purin-6-Yl)Pyridin-2-Ylamino)-2,4-Difluorophenyl)-3-(Trifluoromethyl)Benzamide

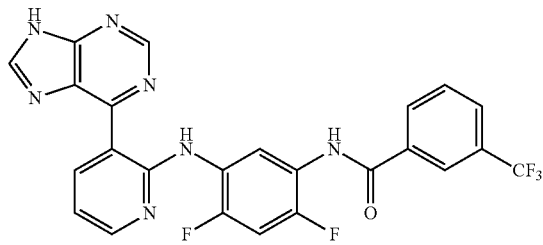 [SMILES: O=C(Nc1cc(Nc2ncccc2-c2ncnc3[nH]cnc23)c(F)cc1F)c1cccc(C(F)(F)F)c1]

The title compound was synthesized in the same manner as described in Example 1, except that t-butyl (5-amino-2,4-difluorophenyl)carbamate was used instead of t-butyl (3-amino-2,6-difluorophenyl)carbamate in step 4 of Example 1.

$^1$H NMR (400 MHz, DMSO-d$_6$): δ 13.90 (brs, 1H), 12.88 (brs, 1H), 10.50 (s, 1H), 9.86 (brs, 1H), 9.07 (s, 1H), 8.80 (t, J=8.4 Hz, 1H), 8.74 (s, 1H), 8.39 (dd, J=2.0, 2.8 Hz, 1H), 8.36 (s, 1H), 8.31 (d, J=7.6 Hz, 1H), 8.01 (d, J=7.2 Hz, 1H), 7.82 (t, J=7.6 Hz, 1H), 7.53 (t, J=10.4 Hz, 1H), 7.11 (m, 1H)

Example 32. Preparation of N-(5-(3-(9H-Purin-6-Yl)Pyridin-2-Ylamino)-2,4-Difluorophenyl)-3-(2-Cyanopropan-2-Yl)Benzamide

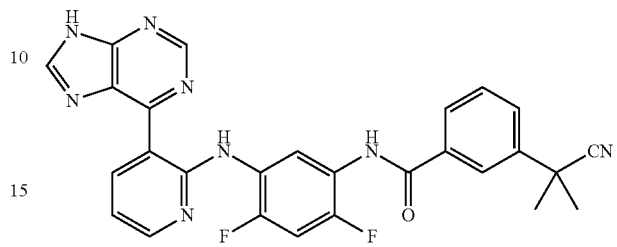

The title compound was synthesized in the same manner as described in Example 2, except that, in step 1 of Example 2, t-butyl (5-amino-2,4-difluorophenyl)carbamate was used instead of t-butyl (3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 13.89 (brs, 1H), 12.87 (s, 1H), 10.32 (s, 1H), 9.85 (brs, 1H), 9.05 (s, 1H), 8.78 (t, J=8.4 Hz, 1H), 8.72 (s, 1H), 8.38 (dd, J=2.0, 2.8 Hz, 1H), 8.13 (s, 1H), 7.99 (d, J=7.6 Hz, 1H), 7.78 (m, 1H), 7.62 (t, J=8.0 Hz, 1H), 7.52 (t, J=10.0 Hz, 1H), 7.11 (m, 1H), 1.77 (s, 6H)

Example 33. Preparation of N-(5-(3-(9H-Purin-6-Yl)Pyridin-2-Ylamino)-2-Fluorophenyl)-3-(2-Cyanopropan-2-Yl)-5-Fluorobenzamide

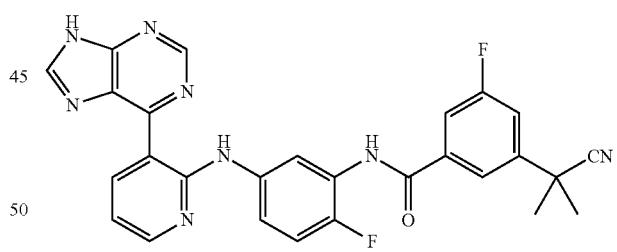

The title compound was synthesized in the same manner as described in Example 2, except that, in step 1 of Example 2, t-butyl (5-amino-4-fluorophenyl)carbamate was used instead of t-butyl (3-amino-2,6-difluorophenyl)carbamate, and 3-(2-cyanopropan-2-yl)-5-fluoro-benzoic acid was used instead of 3-(4-methyl-1H-imidazol-1-yl)-5-(trifluoromethyl)benzoic acid.

$^1$H NMR (400 MHz, DMSO-d$_6$): δ 13.85 (s, 1H), 12.64 (brs, 1H), 10.38 (s, 1H), 9.78 (brs, 1H), 9.13 (s, 1H), 8.72 (s, 1H), 8.36 (dd, J=1.6, 2.8 Hz, 1H), 8.12 (m, 1H), 8.02 (s, 1H), 7.81 (d, J=8.4 Hz, 1H), 7.72 (m, 2H), 7.30 (t, J=9.2 Hz, 1H), 7.06 (m, 1H), 1.78 (s, 6H)

Example 34. Preparation of N-(3-(3-(9H-Purin-6-Yl)Pyridin-2-Ylamino)-2,4-Difluorophenyl)-3-Nitrobenzamide

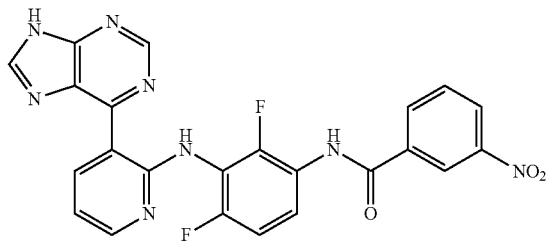

The title compound was synthesized in the same manner as described in Example 2, except that 3-nitrobenzoyl chloride was used instead of 3-(trifluoromethyl)benzoyl chloride in step 4 of Example 1.

$^1$H NMR (400 MHz, DMSO-$d_6$): δ 11.67 (brs, 1H), 10.62 (s, 1H), 9.67 (brs, 1H), 9.03 (s, 1H), 8.23 (s, 1H), 8.70 (s, 1H), 8.50 (m, 3H), 8.22 (dd, J=1.6, 3.2 Hz, 1H), 7.87 (m, 1H), 7.51 (m, 1H), 7.25 (t, J=8.4 Hz, 1H), 7.04 (m, 1H)

Example 35. Preparation of N-(3-(3-(9H-Purin-6-Yl)Pyridin-2-Ylamino)-2,4-Difluorophenyl)-3-Methoxybenzamide

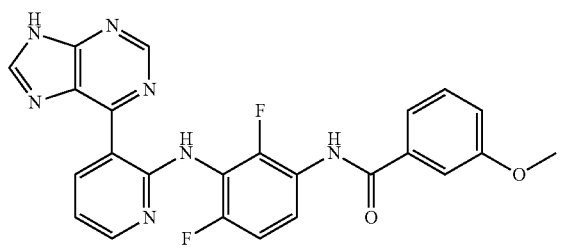 [SMILES: COc1cccc(C(=O)Nc2ccc(F)c(Nc3ncccc3-c3ncnc4[nH]cnc34)c2F)c1]

The title compound was synthesized in the same manner as described in Example 1, except that 3-methoxybenzoyl chloride was used instead of 3-(trifluoromethyl)benzoyl chloride in step 4 of Example 1.

$^1$H NMR (400 MHz, DMSO-$d_6$): δ 13.92 (brs, 1H), 11.65 (brs, 1H), 10.16 (s, 1H), 9.72 (brs, 1H), 9.05 (s, 1H), 8.73 (s, 1H), 8.23 (dd, J=3.2, 1.6 Hz, 1H), 7.52 (m, 4H), 7.21 (m, 2H), 7.04 (m, 1H), 3.84 (s, 3H)

Example 36. Preparation of N-(5-(3-(9H-Purin-6-Yl)Pyridin-2-Ylamino)-2-Fluorophenyl)-3-Fluoro-5-(Trifluoromethyl)Benzamide

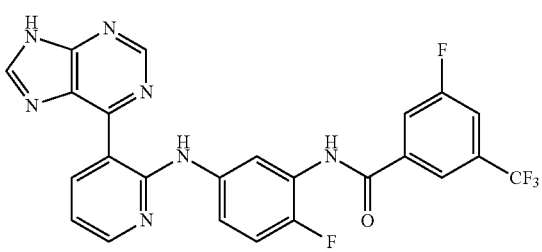

The title compound was synthesized in the same manner as described in Example 2, except that, in step 1 of Example 2, t-butyl (3-amino-4-fluorophenyl)carbamate was used instead of t-butyl (3-amino-2,6-difluorophenyl)carbamate, and 3-fluoro-5-(trifluoromethyl)benzoic acid was used instead of 3-(4-methyl-1H-imidazol-1-yl)-5-(trifluoromethyl)benzoic acid.

$^1$H NMR (400 MHz, DMSO-$d_6$): δ 13.87 (brs, 1H), 12.65 (brs, 1H), 10.55 (s, 1H), 9.79 (brs, 1H), 9.13 (s, 1H), 8.73 (s, 1H), 8.36 (dd, J=2.8, 1.6 Hz, 1H), 8.24 (s, 1H), 8.15 (d, J=9.2 Hz, 1H), 7.72 (m, 1H), 7.31 (t, J=9.6 Hz, 1H), 7.05 (m, 1H)

Example 37. Preparation of N-(3-(3-(9H-Purin-6-Yl)Pyridin-2-Ylamino)-2,4-Difluorophenyl)-3-Cyanobenzamide

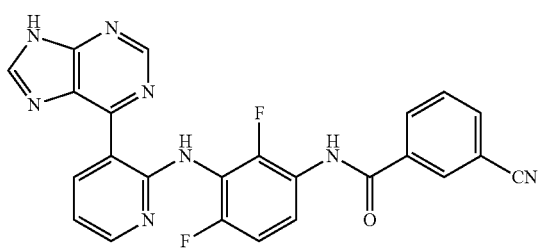 [SMILES: N#Cc1cccc(C(=O)Nc2ccc(F)c(Nc3ncccc3-c3ncnc4[nH]cnc34)c2F)c1]

The title compound was synthesized in the same manner as described in Example 2, except that, in step 1 of Example 2, 3-cyanobenzoic acid was used instead of 3-(4-methyl-1H-imidazol-1-yl)-5-(trifluoromethyl)benzoic acid.

$^1$H NMR (400 MHz, DMSO-$d_6$): δ 13.88 (brs, 1H), 11.64 (s, 1H), 10.43 (s, 1H), 9.71 (d, J=6.8 Hz, 1H), 9.05 (s, 1H), 8.74 (s, 1H), 8.42 (s, 1H), 8.28 (d, J=7.6 Hz, 1H), 8.23 (dd, J=1.6, 2.8 Hz, 1H), 8.09 (d, J=7.6 Hz, 1H), 7.77 (t, J=8.0 Hz, 1H), 7.50 (m, 1H), 7.23 (m, 1H), 7.04 (m, 1H)

Example 38. Preparation of N-(3-(3-(9H-Purin-6-Yl)Pyridin-2-Ylamino)-2,4-Difluorophenyl)-4-Methoxy-3-(Trifluoromethyl)Benzamide

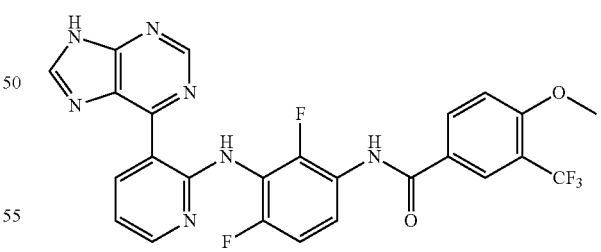

The title compound was synthesized in the same manner as described in Example 2, except that, in step 1 of Example 2, 4-methoxy-3-(trifluoromethyl)benzoic acid was used instead of 3-(4-methyl-1H-imidazol-1-yl)-5-(trifluoromethyl)benzoic acid.

$^1$H NMR (400 MHz, DMSO-$d_6$): δ 13.87 (brs, 1H), 11.63 (brs, 1H), 10.31 (s, 1H), 9.72 (brs, 1H), 9.05 (s, 1H), 8.74 (s, 1H), 8.29 (m, 2H), 8.23 (dd, J=3.2, 1.6 Hz, 1H), 7.46 (m, 2H), 7.23 (t, J=8.8 Hz, 1H), 7.04 (m, 1H), 3.99 (s, 3H)

Example 39: Preparation of N-(4-(3-(9H-Purin-6-Yl)Pyridin-2-Ylamino)-3-Fluorophenyl)-3-(2-Cyanopropan-2-Yl)Benzamide

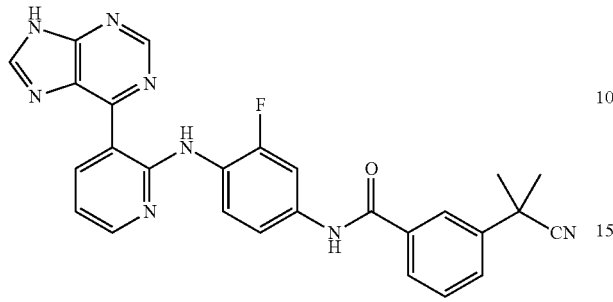

The title compound was synthesized in the same manner as described in Example 2, except that, in step 1 of Example 2, t-butyl (4-amino-2-fluorophenyl)carbamate was used instead of t-butyl (3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 13.88 (brs, 1H), 12.88 (s, 1H), 10.45 (s, 1H), 9.85 (d, J=7.6 Hz, 1H), 9.02 (s, 1H), 8.67 (s, 1H), 8.62 (t, J=9.2 Hz, 1H), 8.39 (dd, J=2.8, 2.0 Hz, 1H), 8.07 (s, 1H), 7.96 (d, J=7.6 Hz, 1H), 7.88 (dd, J=11.6, 2.0 Hz, 1H), 7.77 (d, J=7.6 Hz, 1H), 7.62 (t, J=8.0 Hz, 1H), 7.52 (d, J=8.8 Hz, 1H), 7.08 (m, 1H), 1.77 (s, 6H)

Example 40. Preparation of N-(3-(3-(9H-Purin-6-Yl)Pyridin-2-Ylamino)-2,4-Difluorophenyl)-3-Nitro-5-(Trifluoromethyl)Benzamide

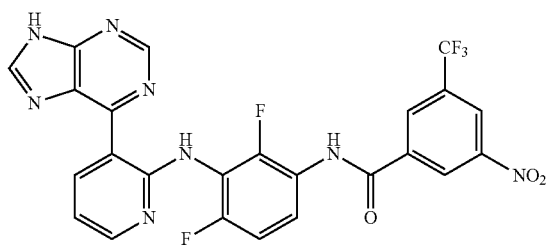

The title compound was synthesized in the same manner as described in Example 2, except that, in step 1 of Example 2, 3-nitro-5-(trifluoromethyl)benzoic acid was used instead of 3-(4-methyl-1H-imidazol-1-yl)-5-(trifluoromethyl)benzoic acid.

$^1$H NMR (400 MHz, DMSO-d$_6$): δ 13.87 (brs, 1H), 11.71 (brs, 1H), 10.83 (s, 1H), 9.74 (brs, 1H), 9.05 (m, 2H), 8.75 (m, 2H), 8.23 (dd, J=1.6, 2.8 Hz, 1H), 7.55 (m, 1H), 7.27 (t, J=9.2 Hz, 1H), 7.04 (m, 1H)

Example 41. Preparation of N-(3-(3-(9H-Purin-6-Yl)Pyridin-2-Ylamino)-2,4-Difluorophenyl)-4-Chloro-3-(2-Cyanopropan-2-Yl)Benzamide

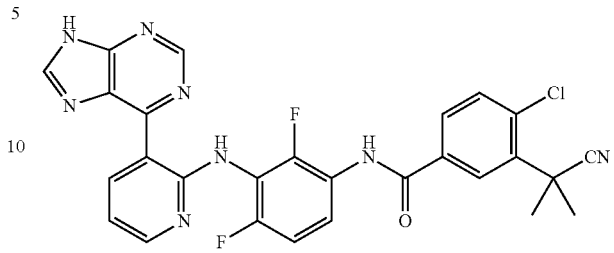

The title compound was synthesized in the same manner as described in Example 2, except that, in step 1 of Example 2, 4-chloro-3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 11.69 (s, 1H), 10.38 (s, 1H), 9.66 (d, J=8 Hz, 1H), 8.99 (s, 1H), 8.64 (S, 1H), 8.2 (m, 1H), 8.07 (s, 1H), 7.99 (d, J=6.8 Hz, 1H), 7.74 (d, J=8.4 Hz, 1H), 7.47 (m, 1H), 7.03 (dd, J=7.8 Hz, 4.4 Hz, 1H), 1.87 (S, 6H)

Example 42: Preparation of N-(3-(3-(9H-Purin-6-Yl)Pyridin-2-Ylamino)-2,4-Difluorophenyl)-2-Chloro-3-(2-Cyanopropan-2-Yl)Benzamide

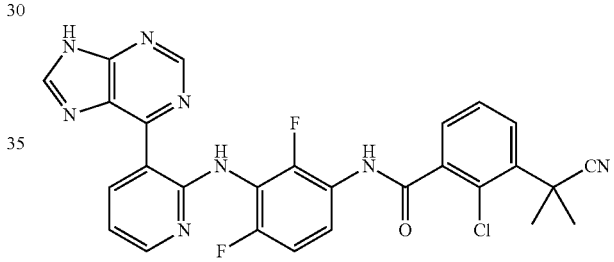

The title compound was synthesized in the same manner as described in Example 2, except that, in step 1 of Example 2, 2-chloro-3-(2-cyanopropan-2-yl)benzoic acid was used instead of 3-(4-methyl-1H-imidazol-1-yl)-5-(trifluoromethyl)benzoic acid.

$^1$H NMR (400 MHz, DMSO-d$_6$): δ 11.66 (s, 1H), 10.50 (s, 1H), 9.66 (d, J=6.4 Hz, 1H), 9.00 (s, 1H), 8.66 (s, 1H) 8.21 (dd, J=4.8 Hz, 1.6 Hz, 1H), 7.67 (m, 2H), 7.59 (m, 1H), 7.53 (m, 1H), 7.23 (m, 1H), 7.03 (dd, J=7.6 Hz, 4.8 Hz, 1H), 1.84 (s, 6H)

Example 43. Preparation of N-(3-(3-(9H-Purin-6-Yl)Pyridin-2-Ylamino)-2,4-Difluorophenyl)-3-(2-Cyanopropan-2-Yl)-5-Fluorobenzamide

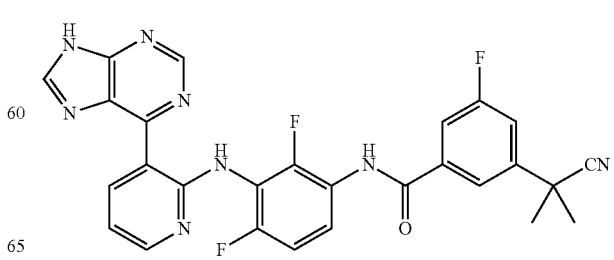

The title compound was synthesized in the same manner as described in Example 2, except that, in step 1 of Example 2, 3-(2-cyanopropan-2-yl)-5-fluorobenzoic acid was used instead of 3-(4-methyl-1H-imidazol-1-yl)-5-(trifluoromethyl)benzoic acid.

¹H NMR (400 MHz, DMSO-d₆): δ 11.64 (brs, 1H), 10.40 (s, 1H), 9.67 (brs, 1H), 9.03 (s, 1H), 8.71 (s, 1H), 8.22 (dd, J=4.8 Hz, 1.6 Hz, 1H), 7.99 (s, 1H), 7.79 (d, J=8.8 Hz, 1H), 7.66 (m, 1H), 7.48 (m, 1H), 7.25 (t, J=8.4 Hz, 1H), 7.04 (dd, J=8 Hz, 4.8 Hz, 1H), 1.76 (s, 6H)

Example 44. Preparation of N-(3-(3-(9H-Purin-6-Yl)Pyridin-2-Ylamino)-2,4-Difluorophenyl)-3-(2-Cyanopropan-2-Yl)-4,5-Difluorobenzamide

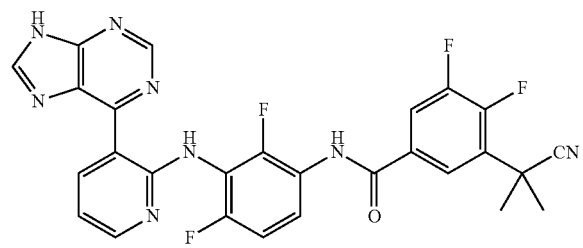 [SMILES: CC(C)(C#N)c1cc(C(=O)Nc2ccc(F)c(Nc3ncccc3-c3ncnc4[nH]cnc34)c2F)cc(F)c1F]

The title compound was synthesized in the same manner as described in Example 2, except that, in step 1 of Example 2, 3-(2-cyanopropan-2-yl)-4,5-difluorobenzoic acid was used instead of 3-(4-methyl-1H-imidazol-1-yl)-5-(trifluoromethyl)benzoic acid.

¹H NMR (400 MHz, DMSO-d₆): δ 11.68 (brs, 1H), 10.41 (s, 1H), 9.67 (brs, 1H), 9.01 (s, 1H), 8.68 (s, 1H), 8.21 (dd, J=4.8 Hz, 1.6 Hz, 1H), 8.09 (m, 1H), 7.91 (d, J=5.6 Hz, 1H), 7.46 (m, 1H), 7.24 (m, 1H), 7.03 (dd, J=8 Hz, 4.8 Hz, 1H), 1.82 (s, 1H)

Example 45. Preparation of N-(3-(3-(9H-Purin-6-Yl)Pyridin-2-Ylamino)-2,4-Difluorophenyl)-3-Chlorobenzamide

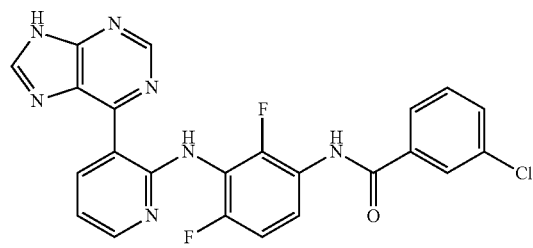 [SMILES: O=C(Nc1ccc(F)c(Nc2ncccc2-c2ncnc3[nH]cnc23)c1F)c1cccc(Cl)c1]

The title compound was synthesized in the same manner as described in Example 2, except that, in step 1 of Example 2, 3-chlorobenzoic acid was used instead of 3-(4-methyl-1H-imidazol-1-yl)-5-(trifluoromethyl)benzoic acid.

¹H NMR (400 MHz, DMSO-d₆): δ 13.88 (brs, 1H), 11.61 (brs, 1H), 10.34 (s, 1H), 9.71 (brs, 1H), 9.05 (s, 1H), 8.74 (s, 1H), 8.23 (dd, J=4.8 Hz, 2 Hz, 1H), 8.03 (m, 1H), 7.95 (d, J=7.6 Hz, 1H), 7.69 (m, 1H), 7.58 (t, J=7.6 Hz, 1H), 7.47 (m, 1H), 7.23 (m, 1H), 7.04 (dd, J=4.8 Hz, 2 Hz, 1H)

Example 46. Preparation of N-(3-(3-(9H-Purin-6-Yl)Pyridin-2-Ylamino)-2,4-Difluorophenyl)-3-(Dimethylamino)Benzamide

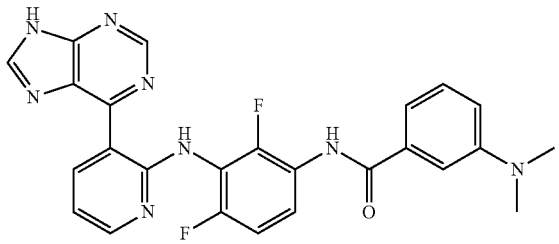 [SMILES: CN(C)c1cccc(C(=O)Nc2ccc(F)c(Nc3ncccc3-c3ncnc4[nH]cnc34)c2F)c1]

The title compound was synthesized in the same manner as described in Example 2, except that, in step 1 of Example 2, 3-(dimethylamino)benzoic acid was used instead of 3-(4-methyl-1H-imidazol-1-yl)-5-(trifluoromethyl)benzoic acid.

¹H NMR (400 MHz, DMSO-d₆): δ 11.64 (brs, 1H), 10.05 (s, 1H), 9.68 (brs, 1H), 9.02 (s, 1H), 8.69 (s, 1H), 8.22 (dd, J=4.6 Hz, 2 Hz, 1H), 7.45 (m, 1H), 7.28 (m, 5H), 7.03 (dd, J=7.6 Hz, 4.2 Hz, 1H), 6.94 (m, 1H), 2.96 (s, 6H)

Example 47. Preparation of N-(3-(3-(9H-Purin-6-Yl)Pyridin-2-Ylamino)-2,4-Difluorophenyl)-3-Methylbenzamide

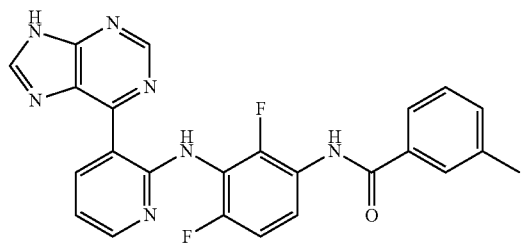 [SMILES: Cc1cccc(C(=O)Nc2ccc(F)c(Nc3ncccc3-c3ncnc4[nH]cnc34)c2F)c1]

The title compound was synthesized in the same manner as described in Example 2, except that, in step 1 of Example 2, 3-methylbenzoic acid was used instead of 3-(4-methyl-1H-imidazol-1-yl)-5-(trifluoromethyl)benzoic acid.

¹H NMR (400 MHz, DMSO-d₆): δ 13.87 (brs, 1H), 11.59 (brs, 1H), 10.13 (s, 1H), 9.67 (brs, 1H), 9.04 (s, 1H), 8.72 (s, 1H), 8.22 (dd, J=4.6 Hz, 2 Hz, 1H), 7.81 (s, 1H), 7.78 (m, 1H), 7.45 (m, 3H), 7.21 (m, 1H), 7.04 (dd, J=7.6 Hz, 4.8 Hz, 1H), 2.40 (s, 3H)

Example 48. Preparation of N-(3-(3-(9H-Purin-6-Yl)Pyridin-2-Ylamino)Phenyl)-3-Chlorobenzamide

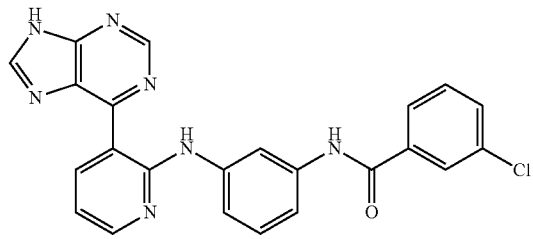 [SMILES: O=C(Nc1cccc(Nc2ncccc2-c2ncnc3[nH]cnc23)c1)c1cccc(Cl)c1]

The title compound was synthesized in the same manner as described in Example 2, except that, in step 1 of Example 2, t-butyl (3-aminophenyl)carbamate was used instead of t-butyl (3-amino-2,6-difluorophenyl)carbamate, and 3-chlorobenzoic acid was used instead of 3-(4-methyl-1H-imidazol-1-yl)-5-(trifluoromethyl)benzoic acid.

¹H NMR (400 MHz, DMSO-d₆): δ 12.67 (brs, 1H), 10.35 (s, 1H), 9.77 (brs, 1H), 9.04 (s, 1H), 8.61 (s, 1H), 8.36 (m, 1H), 8.22 (s, 1H), 8.05 (s, 1H), 7.95 (m, 1H), 7.68 (m, 1H), 7.60 (m, 2H), 7.48 (m, 1H), 7.31 (t, J=7.6 Hz, 1H), 7.04 (m, 1H)

Example 49. Preparation of N-(3-(3-(9H-Purin-6-Yl)Pyridin-2-Ylamino)-4-Fluorophenyl)-3-(2-Cyanopropan-2-Yl)Benzamide

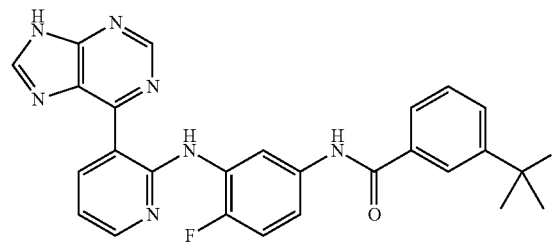

The title compound was synthesized in the same manner as described in Example 2, except that, in step 1 of Example 2, t-butyl (5-amino-2-fluorophenyl)carbamate was used instead of t-butyl (3-amino-2,6-difluorophenyl)carbamate, and 3-(2-cyanopropan-2-yl)benzoic acid was used instead of 3-(4-methyl-1H-imidazol-1-yl)-5-(trifluoromethyl)benzoic acid.

¹H NMR (400 MHz, DMSO-d₆): δ 12.85 (brs, 1H), 10.39 (s, 1H), 9.84 (brs, 1H), 9.04 (s, 1H), 8.96 (m, 1H), 8.41 (m, 1H), 8.06 (m, 1H), 7.97 (d, J=7.6 Hz, 1H), 7.76 (m, 1H), 7.61 (t, J=7.6 Hz, 1H), 7.47 (m, 1H), 7.30 (dd, J=8.8 Hz, 2.4 Hz, 1H), 7.11 (dd, J=4.8 Hz, 2.8 Hz, 1H), 1.76 (s, 6H)

Example 50. Preparation of N-(3-(3-(9H-Purin-6-Yl)Pyridin-2-Ylamino)-4-Fluorophenyl)-3-(Trifluoromethyl)Benzamide

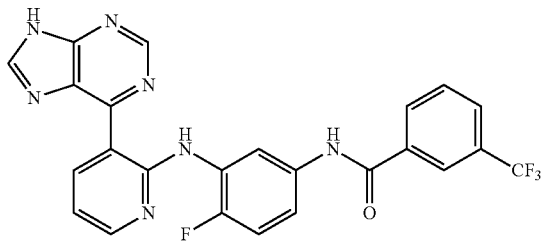

The title compound was synthesized in the same manner as described in Example 2, except that, in step 1 of Example 2, t-butyl (5-amino-2-fluorophenyl)carbamate was used instead of t-butyl (3-amino-2,6-difluorophenyl)carbamate, and 3-(trifluoromethyl)benzoic acid was used instead of 3-(4-methyl-1H-imidazol-1-yl)-5-(trifluoromethyl)benzoic acid.

¹H NMR (400 MHz, DMSO-d₆): δ 12.91 (brs, 1H), 10.55 (s, 1H), 9.84 (d, J=8 Hz, 1H), 9.02 (s, 1H), 8.99 (dd, J=7.6 Hz, 2.4 Hz, 1H), 8.68 (s, 1H), 8.42 (dd, J=4.6 Hz, 1.6 Hz, 1H), 8.30 (m, 2H), 7.98 (d, J=7.2 Hz, 1H), 7.80 (t, J=8 Hz, 1H), 7.50 (m, 1H), 7.31 (m, 1H), 7.12 (dd, J=8 Hz, 4.8 Hz, 1H)

Example 51. Preparation of N-(3-(3-(9H-Purin-6-Yl)Pyridin-2-Ylamino)Phenyl)-3-(Trifluoromethyl)Benzamide

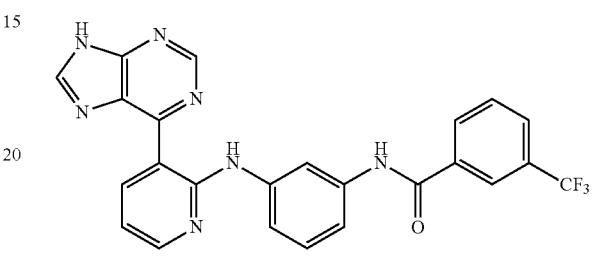

The title compound was synthesized in the same manner as described in Example 2, except that, in step 1 of Example 2, t-butyl (3-aminophenyl)carbamate was used instead of t-butyl (3-amino-2,6-difluorophenyl)carbamate, and 3-(trifluoromethyl)benzoic acid was used instead of 3-(4-methyl-1H-imidazol-1-yl)-5-(trifluoromethyl)benzoic acid.

¹H NMR (400 MHz, DMSO-d₆): δ 12.61 (brs, 1H), 10.50 (s, 1H), 9.71 (brs, 1H), 9.10 (s, 1H), 8.72 (s, 1H), 8.39 (dd, J=4.4 Hz, 2 Hz, 1H), 8.31 (m, 3H), 7.98 (d, J=8 Hz, 1H), 7.80 (t, J=7.6 Hz, 1H), 7.58 (m, 1H), 7.49 (m, 1H), 7.34 (m, 1H), 7.34 (t, J=8 Hz, 1H), 7.06 (dd, J=8 Hz, 4.8 Hz, 1H)

Example 52. Preparation of N-(3-(3-(9H-Purin-6-Yl)Pyridin-2-Ylamino)-2,4-Difluorophenyl)-4-Nitrobenzamide

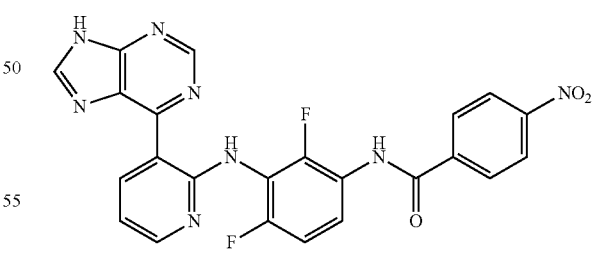

The title compound was synthesized in the same manner as described in Example 2, except that, in step 1 of Example 2, 4-nitrobenzoic acid was used instead of 3-(4-methyl-1H-imidazol-1-yl)-5-(trifluoromethyl)benzoic acid.

¹H NMR (400 MHz, DMSO-d₆): δ 11.60 (brs, 1H), 10.54 (s, 1H), 9.66 (brs, 1H), 9.03 (s, 1H), 8.71 (s, 1H), 8.38 (d, J=8.8 Hz, 2H), 8.22 (m, 3H), 7.51 (m, 1H), 7.24 (t, J=8.8 Hz, 1H), 7.04 (dd, J=8 Hz, 4.4 Hz, 1H)

Example 53. Preparation of N-(3-(3-(9H-Purin-6-Yl)Pyridin-2-Ylamino)-2,4-Difluorophenyl)-4-Methoxybenzamide

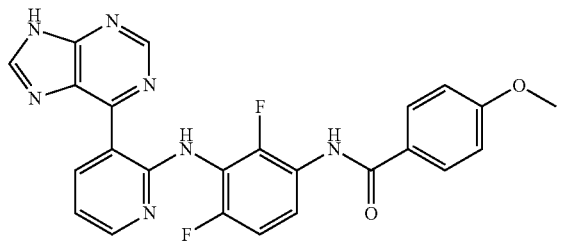 [SMILES: COc1ccc(C(=O)Nc2ccc(F)c(Nc3ncccc3-c3ncnc4[nH]cnc34)c2F)cc1]

The title compound was synthesized in the same manner as described in Example 2, except that, in step 1 of Example 2, 4-methoxybenzoic acid was used instead of 3-(4-methyl-1H-imidazol-1-yl)-5-(trifluoromethyl)benzoic acid.

$^1$H NMR (400 MHz, DMSO-d$_6$): δ 11.61 (brs, 1H), 10.00 (s, 1H), 9.66 (brs, 1H), 9.03 (m, 1H), 8.70 (m, 1H), 8.21 (m, 1H), 7.97 (d, J=9.2 Hz, 2H), 7.46 (m, 1H), 7.19 (t, J=9.2 Hz, 1H), 7.04 (m, 3H), 3.84 (s, 3H)

Example 54. Preparation of N-(3-(3-(9H-Purin-6-Yl)Pyridin-2-Ylamino)-2,4-Difluorophenyl)-3-Aminobenzamide

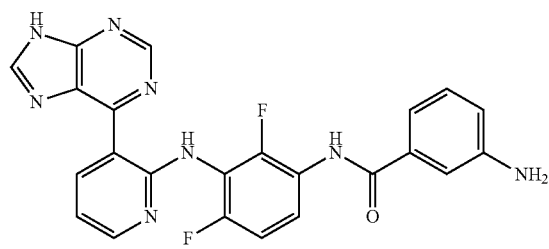

The title compound was synthesized in the same manner as described in Example 2, except that, in step 1 of Example 2, 3-aminobenzoic acid was used instead of 3-(4-methyl-1H-imidazol-1-yl)-5-(trifluoromethyl)benzoic acid.

$^1$H NMR (400 MHz, DMSO-d$_6$): δ 11.60 (s, 1H), 9.95 (s, 1H), 9.66 (d, J=6.8 Hz, 1H), 9.03 (s, 1H), 8.70 (s, 1H), 8.22 (dd, J=4.8 Hz, 2 Hz, 1H), 7.43 (m, 1H), 7.15 (m, 4H), 7.03 (dd, J=7.6 Hz, 3.2 Hz, 1H), 6.75 (d, J=7.6 Hz, 1H), 5.32 (s, 2H)

Example 55. Preparation of Methyl 3-(3-(3-(9H-Purin-6-Yl)Pyridin-2-Ylamino)-2,4-Difluorophenylcarbamoyl)Phenylcarbamate

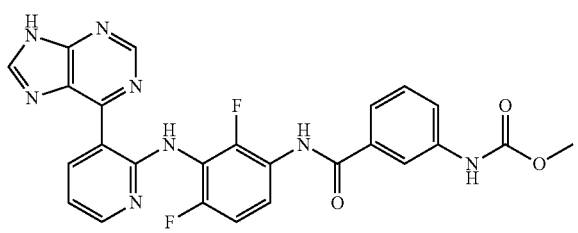 [SMILES: COC(=O)Nc1cccc(C(=O)Nc2ccc(F)c(Nc3ncccc3-c3ncnc4[nH]cnc34)c2F)c1]

The title compound was synthesized in the same manner as described in Example 2, except that, in step 1 of Example 2, 3-methoxycarbonylaminobenzoic acid was used instead of 3-(4-methyl-1H-imidazol-1-yl)-5-(trifluoromethyl)benzoic acid.

$^1$H NMR (400 MHz, DMSO-d$_6$): δ 11.62 (s, 1H), 10.19 (s, 1H), 9.87 (s, 1H), 9.67 (brs, 1H), 9.03 (s, 1H), 8.71 (s, 1H), 8.22 (dd, J=4.8 Hz, 1.6 Hz, 1H), 8.03 (s, 1H), 7.68 (d, J=7.6 Hz, 1H), 7.61 (d, J=8 Hz, 1H), 7.45 (m, 2H), 7.21 (t, J=9.2 Hz, 1H), 7.03 (dd, J=7.6 Hz, 4.8 Hz, 1H), 3.68 (s, 3H)

Example 56. Preparation of N-(3-(3-(9H-Purin-6-Yl)Pyridin-2-Ylamino)-2,4-Difluorophenyl)Pyrazine-2-Carboxamide

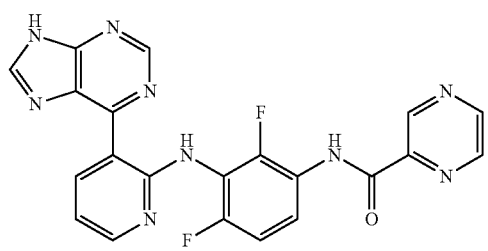 [SMILES: O=C(Nc1ccc(F)c(Nc2ncccc2-c2ncnc3[nH]cnc23)c1F)c1cnccn1]

The title compound was synthesized in the same manner as described in Example 2, except that, in step 1 of Example 2, pyrazine-2-carboxylic acid was used instead of 3-(4-methyl-1H-imidazol-1-yl)-5-(trifluoromethyl)benzoic acid.

$^1$H NMR (400 MHz, DMSO-d$_6$): δ 13.85 (s, 1H), 11.63 (s, 1H), 10.51 (s, 1H), 9.68 (s, 1H), 9.31 (s, 1H), 9.05 (t, 1H), 8.97 (d, J=2.4 Hz 1H), 8.84 (t, 1H), 8.73 (s, 1H), 8.24-8.23 (m, 1H), 7.75-7.70 (m, 1H), 7.26 (t, 1H), 7.06-7.03 (m, 1H)

Example 57. Preparation of N-(3-(3-(9H-Purin-6-Yl)Pyridin-2-Ylamino)-2,4-Difluorophenyl)Benzamide

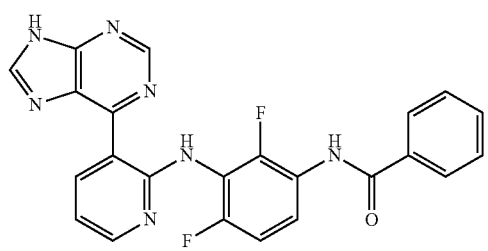 [SMILES: O=C(Nc1ccc(F)c(Nc2ncccc2-c2ncnc3[nH]cnc23)c1F)c1ccccc1]

The title compound was synthesized in the same manner as described in Example 2, except that, in step 1 of Example 2, benzoic acid was used instead of 3-(4-methyl-1H-imidazol-1-yl)-5-(trifluoromethyl)benzoic acid.

$^1$H NMR (400 MHz, DMSO-d$_6$): δ 13.85 (s, 1H), 11.60 (s, 1H), 10.18 (s, 1H), 9.69 (s, 1H), 9.05 (d, J=7.2 Hz, 1H), 8.73 (s, 1H), 8.24-8.22 (m, 1H), 8.00 (d, J=7.2 Hz, 2H), 7.63-7.60 (m, 1H), 7.56-7.45 (m, 3H), 7.22 (t, 1H), 7.06-7.03 (m, 1H)

Example 58. Preparation of N-2,4-Difluoro-3-[3-(9H-Purin-6-Yl)Pyridin-2-Ylamino)-Phenyl-3,5-Bistrifluoromethylbenzamide

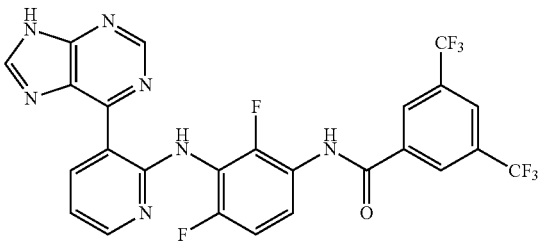 [SMILES: O=C(Nc1ccc(F)c(Nc2ncccc2-c2ncnc3[nH]cnc23)c1F)c1cc(C(F)(F)F)cc(C(F)(F)F)c1]

The title compound was synthesized in the same manner as described in Example 2, except that, in step 1 of Example 2, 3,5-bistrifluoromethylbenzoic acid was used instead of 3-(4-methyl-1H-imidazol-1-yl)-5-(trifluoromethyl)benzoic acid.
$^1$H NMR (400 MHz, DMSO-$d_6$): δ 13.85 (s, 1H), 11.59 (s, 1H), 10.71 (s, 1H), 9.65 (s, 1H), 9.62 (d, 1H), 9.02 (s, 1H), 8.62 (s, 1H), 8.41 (s, 1H), 8.21 (q, 1H), 7.54-7.50 (m, 1H), 7.24 (t, 1H), 7.05-7.02 (m, 1H)

Example 59. Preparation of 1-(3-(3-(9H-Purin-6-Yl)Pyridin-2-Ylamino)-2,4-Difluorophenyl)-3-(3-(4-Methyl-1H-Imidazol-1-Yl)-5-(Trifluoromethyl)Phenyl)Urea

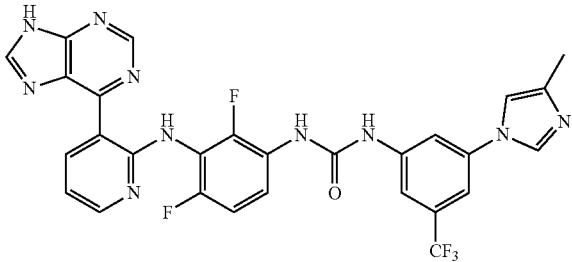 [SMILES: Cc1cn(-c2cc(NC(=O)Nc3ccc(F)c(Nc4ncccc4-c4ncnc5[nH]cnc45)c3F)cc(C(F)(F)F)c2)cn1]

The title compound was synthesized in the same manner as described in Example 2, except that, in step 2 of Example 2, t-butyl 2,6-difluoro-[3-(3-(4-methyl-1H-imidazol-1-yl)-5-(trifluoromethyl)phenylureido]phenylcarbamate was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-$d_6$): δ 11.66 (bs, 1H), 9.64 (d, J=6.8 Hz, 1H), 9.53 (bs, 1H), 8.99 (s, 1H), 8.83 (s, 1H), 8.65 (s, 1H), 8.21 (s, 2H), 7.85 (m, 3H), 7.59 (s, 1H), 7.50 (s, 1H), 7.16 (t, J=9.6 Hz, 1H), 7.03 (m, 1H), 2.17 (s, 3H)

Example 60. Preparation of 1-(3-(3-(9H-Purin-6-Yl)Pyridin-2-Ylamino)-2,4-Difluorophenyl)-3-(4-((4-Ethylpiperazin-1-Yl)Methyl)-3-(Trifluoromethyl)Phenyl)Urea

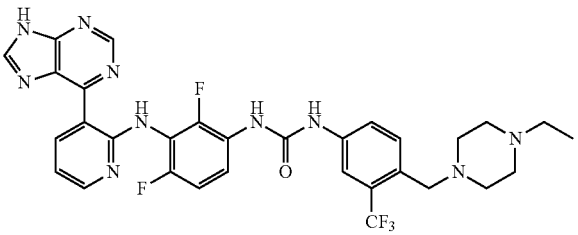 [SMILES: CCN1CCN(Cc2ccc(NC(=O)Nc3ccc(F)c(Nc4ncccc4-c4ncnc5[nH]cnc45)c3F)cc2C(F)(F)F)CC1]

The title compound was synthesized in the same manner as described in Example 2, except that, in step 2 of Example 2, t-butyl 2,6-difluoro-[3-(3-(4-ethylpiperazin-1-ylmethyl)-3-(trifluoromethylphenyl)ureido]phenylcarbamate was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-$d_6$): δ 11.58 (bs, 1H), 9.65 (d, J=7.6 Hz, 1H), 9.61 (s, 1H), 9.04 (s, 1H), 8.75 (s, 1H), 8.73 (s, 1H), 8.22 (d, J=3.6 Hz, 1H), 8.00 (s, 1H), 7.88 (m, 1H), 7.70 (d, J=8.6 Hz, 1H), 7.62 (d, J=8.6 Hz, 1H), 7.16 (m, 1H), 7.06 (m, 1H), 3.79 (s, 2H), 3.11 (m, 6H), 2.50 (m, 4H), 1.22 (t, J=7.2 Hz, 3H).

Example 61. Preparation of 4-Chloro-N-2-Fluoro-5-[3-(9H-Purin-6-Yl)Pyridin-2-Ylamino)Phenyl-3-(Trifluoromethyl)Benzamide

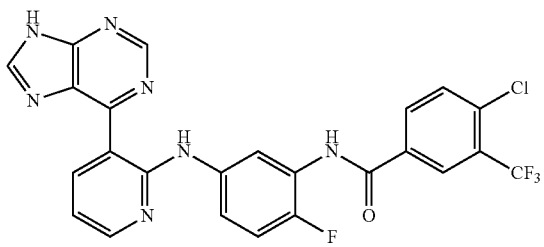

The title compound was synthesized in the same manner as described in Example 2, except that, in step 2 of Example 2, [3-(4-chloro-3-trifluoromethyl-benzoylamino)-4-fluorophenyl]carbamic acid t-butyl ester was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-$d_6$): δ 12.24 (s, 1H), 9.67 (dd, 1H), 9.52 (s, 1H), 9.15 (s, 1H), 8.96 (s, 1H), 8.66 (s, 1H), 8.41 (dd, 1H), 8.33 (dd, 1H), 8.09 (s, 1H), 7.66-7.61 (m, 2H), 7.50-7.46 (m, 1H), 7.22 (q, 1H), 7.03 (q, 1H)

Example 62. Preparation of N-2-Fluoro-5-[3-(9H-Purin-6-Yl)Pyridin-2-Ylamino)Phenyl-3-Nitro-5-(Trifluoromethyl)Benzamide

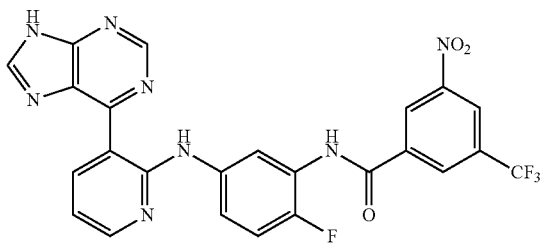 [SMILES: O=C(Nc1cc(Nc2ncccc2-c2ncnc3[nH]cnc23)ccc1F)c1cc([N+](=O)[O-])cc(C(F)(F)F)c1]

The title compound was synthesized in the same manner as described in Example 2, except that, in step 2 of Example 2, [4-fluoro-3-(3-nitro-5-trifluoromethyl-benzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-$d_6$): δ 12.59 (s, 1H), 10.81 (s, 1H), 9.73 (s, 1H), 9.11 (s, 1H), 9.07 (s, 1H), 8.79 (s, 1H), 8.74 (s, 1H), 8.71 (s, 1H), 8.35 (dd, 1H), 8.19 (dd, 2H), 7.73-7.69 (m, 1H), 7.32 (q, 1H), 7.04 (q, 1H)

Example 63. Preparation of N-2-Fluoro-5-[3-(9H-Purin-6-Yl)Pyridin-2-Ylamino)Phenyl-3-Methoxy-5-(Trifluoromethyl)Benzamide

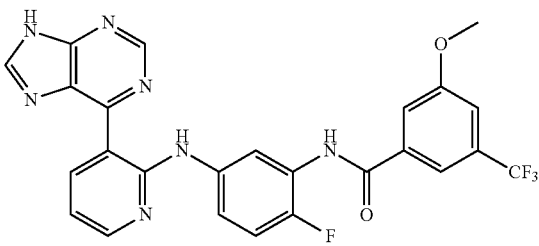 [SMILES: COc1cc(C(=O)Nc2cc(Nc3ncccc3-c3ncnc4[nH]cnc34)ccc2F)cc(C(F)(F)F)c1]

The title compound was synthesized in the same manner as described in Example 2, except that, in step 2 of Example 2, [4-fluoro-3-(3-methoxy-5-trifluoromethyl-benzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.84 (s, 1H), 12.59 (s, 1H), 10.44 (s, 1H), 9.74 (s, 1H), 9.11 (s, 1H), 8.35 (dd, 1H), 8.10 (dd, 1H), 7.92 (s, 1H), 7.84 (s, 1H), 7.73-7.69 (m, 1H), 7.50 (s, 1H), 7.29 (t, 1H), 7.04 (dd, 1H), 3.93 (s, 3H)

Example 64. Preparation of N-2-Fluoro-5-[3-(9H-Purin-6-Yl)Pyridin-2-Ylamino)Phenyl-(6-Methylpyridin-2-Yl)Benzamide

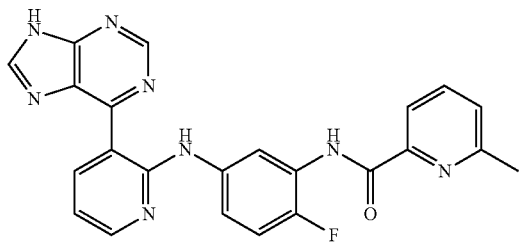 [SMILES: Cc1cccc(C(=O)Nc2cc(Nc3ncccc3-c3ncnc4[nH]cnc34)ccc2F)n1]

The title compound was synthesized in the same manner as described in Example 2, except that, in step 2 of Example 2, 4-fluoro-3-6-methylpyridine-2-carbonyl)amino]phenyl-carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.84 (brs, 1H), 12.48 (s, 1H), 10.38 (s, 1H), 9.11 (s, 1H), 8.72 (s, 1H), 8.64 (dd, 1H), 8.35 (q, 1H), 8.01-7.96 (m, 2H), 7.65-7.61 (m, 1H), 7.57 (dd, 1H), 7.32 (dd, 1H), 7.05 (dd, 1H), 2.63 (s, 3H)

Example 65. Preparation of N-2-Fluoro-5-[3-(9H-Purin-6-Yl)Pyridin-2-Ylamino)Phenyl-3,5-Bis(Trifluoromethyl)Benzamide

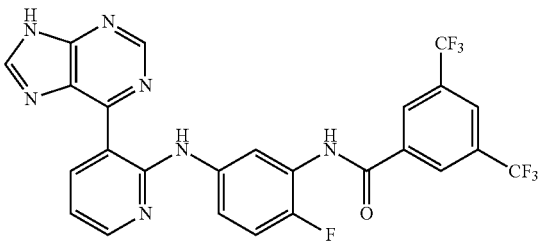

The title compound was synthesized in the same manner as described in Example 2, except that, in step 2 of Example 2, [3-(3,5-bistrifluoromethylbenzoylamino)-4-fluorophenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.83 (s, 1H), 12.51 (s, 1H), 10.71 (s, 1H), 9.68 (dd, 1H), 9.14 (s, 1H), 8.93 (s, 1H), 8.65 (s, 1H), 8.40 (s, 1H), 8.34 (dd, 1H), 8.17 (dd, 1H), 7.73-7.69 (m, 1H), 7.30 (dd, 1H), 7.01 (dd, 1H)

Example 66. Preparation of N-2-Chloro-5-[3-(9H-Purin-6-Yl)Pyridin-2-Ylamino)Phenyl-3-Trifluoromethylbenzamide

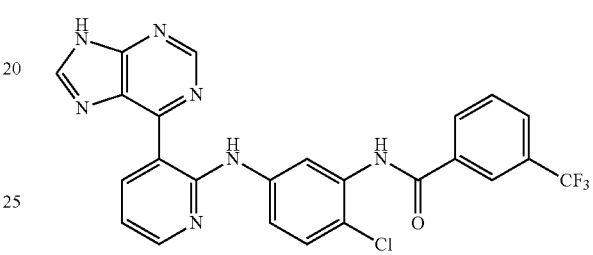

The title compound was synthesized in the same manner as described in Example 2, except that, in step 2 of Example 2, [4-chloro-(3-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.85 (s, 1H), 12.75 (s, 1H), 10.46 (s, 1H), 9.75 (d, 1H), 9.12 (s, 1H), 8.70 (s, 1H), 8.39-8.36 (m, 2H), 8.31 (d, 1H), 8.00 (d, 1H), 7.86-7.80 (m, 2H), 7.50 (d, 1H), 7.08 (dd, 1H)

Example 67. Preparation of N-2-Chloro-5-[3-(9H-Purin-6-Yl)Pyridin-2-Ylamino)Phenyl-3-Fluoro-5-Trifluoromethylbenzamide

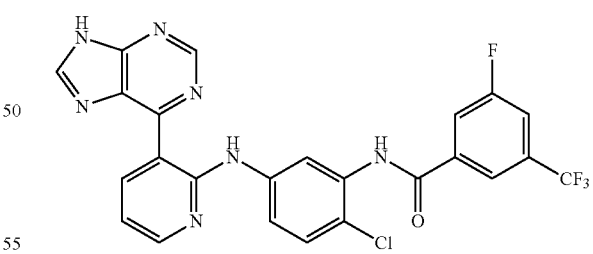

The title compound was synthesized in the same manner as described in Example 2, except that, in step 2 of Example 2, [4-chloro-3-(3-fluoro-5-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.84 (s, 1H), 12.65 (s, 1H), 10.54 (s, 1H), 9.71 (dd, 1H), 9.19 (d, 1H), 8.96 (s, 1H), 8.39 (dd, 1H), 8.29 (s, 1H), 8.24 (s, 1H), 8.16-8.14 (m, 2H), 8.00 (d, 1H), 7.85 (dd, 1H), 7.50 (d, 1H), 7.08 (dd, 1H)

Example 68. Preparation of N-2-Methyl-5-[3-(9H-Purin-6-Yl)Pyridin-2-Ylamino)Phenyl-3-Trifluoromethylbenzamide

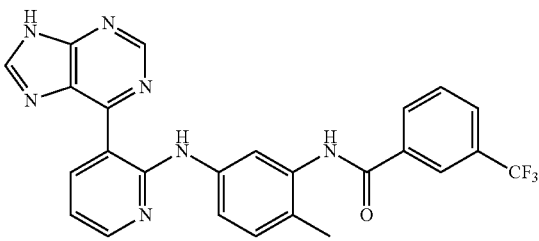 [SMILES: Cc1ccc(Nc2ncccc2-c2ncnc3[nH]cnc23)cc1NC(=O)c1cccc(C(F)(F)F)c1]

The title compound was synthesized in the same manner as described in Example 2, except that, in step 2 of Example 2, [4-methyl-3-(3-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.81 (s, 1H), 12.63 (s, 1H), 10.27 (s, 1H), 9.74 (brs, 1H), 9.11 (s, 1H), 8.36-8.31 (m, 3H), 7.98 (d, 1H), 7.89 (d, 1H), 7.80 (t, 1H), 7.66 (dd, 1H), 7.01 (dd, 1H), 2.19 (s, 1H)

Example 69. Preparation of N-2-Methoxy-5-[3-(9H-Purin-6-Yl)Pyridin-2-Ylamino)Phenyl-3-Trifluoromethylbenzamide

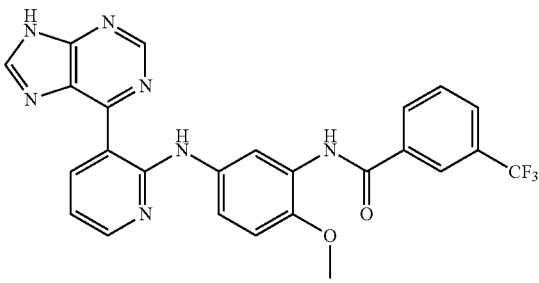 [SMILES: COc1ccc(Nc2ncccc2-c2ncnc3[nH]cnc23)cc1NC(=O)c1cccc(C(F)(F)F)c1]

The title compound was synthesized in the same manner as described in Example 2, except that, in step 2 of Example 2, [4-methoxy-3-(3-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 12.61 (s, 1H), 9.99 (s, 1H), 9.86 (d, 1H), 9.11 (s, 1H), 8.77 (s, 1H), 8.31 (s, 1H), 8.27 (d, 1H), 8.21 (dd, 1H), 8.02 (d, 1H), 7.97 (d, 1H), 7.78 (t, 1H), 7.55 (dd, 1H), 7.18 (d, 1H), 3.87 (s, 3H)

Example 70. Preparation of N-4-Methoxy-5-[3-(9H-Purin-6-Yl)Pyridin-2-Ylamino)Phenyl-3-Trifluoromethylbenzamide

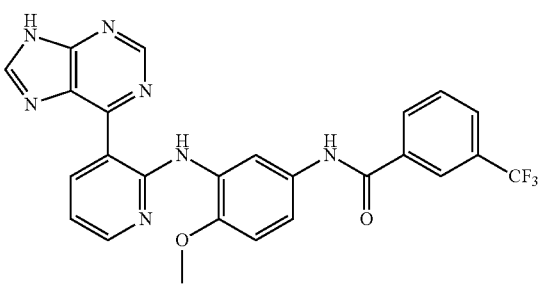 [SMILES: COc1ccc(NC(=O)c2cccc(C(F)(F)F)c2)cc1Nc1ncccc1-c1ncnc2[nH]cnc12]

The title compound was synthesized in the same manner as described in Example 2, except that, in step 2 of Example 2, [2-methoxy-5-(3-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 12.98 (s, 1H), 10.50 (s, 1H), 9.83 (d, 1H), 9.12 (s, 1H), 8.81 (s, 1H), 8.76 (s, 1H), 8.35 (dd, 1H), 8.33 (s, 1H), 8.29 (d, 1H), 7.95 (d, 1H), 7.78 (t, 1H), 7.55 (dd, 1H), 7.14-7.11 (m, 2H), 3.97 (s, 3H)

Example 71. Preparation of N-4-Methyl-5-[3-(9H-Purin-6-Yl)Pyridin-2-Ylamino)Phenyl-3-Trifluoromethylbenzamide

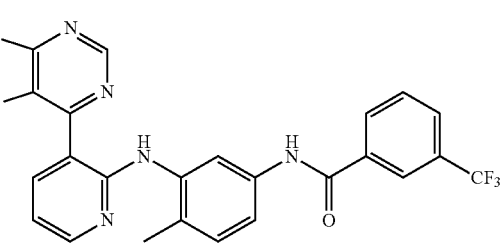

The title compound was synthesized in the same manner as described in Example 2, except that, in step 2 of Example 2, [2-methyl-5-(3-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 12.34 (s, 1H), 10.46 (s, 1H), 9.77 (d, 1H), 9.06 (s, 1H), 8.70-8.65 (m, 2H), 8.34 (dd, 1H), 8.31 (s, 1H), 8.27 (d, 1H), 7.94 (d, 1H), 7.77 (t, 1H), 7.46 (dd, 1H), 7.23 (d, 1H), 7.02 (dd, 1H), 2.44 (s, 3H)

Example 72. Preparation of N-2,6-Difluoro-3-[3-(9H-Purin-6-Yl)Pyridin-2-Ylamino)Phenyl-3-Trifluoromethylbenzamide

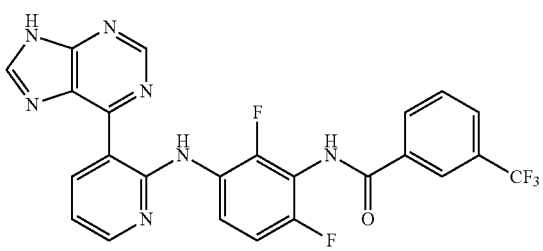 [SMILES: O=C(Nc1c(F)ccc(Nc2ncccc2-c2ncnc3[nH]cnc23)c1F)c1cccc(C(F)(F)F)c1]

The title compound was synthesized in the same manner as described in Example 2, except that, in step 2 of Example 2, [2,4-difluoro-3-(3-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.58 (s, 1H), 10.55 (s, 1H), 10.04 (dd, 1H), 8.72-8.67 (m, 2H), 8.39 (s, 1H), 8.33 (d, 1H), 8.28 (dd, 1H), 8.20 (s, 1H), 8.03 (d, 1H), 7.83 (t, 1H), 7.20 (t, 1H), 7.03 (dd, 1H)

Example 73. Preparation of 2-Fluoro-5-[3-(9H-Purin-6-Yl)Pyridin-2-Ylamino]-N-(3-Trifluoromethylphenyl)Benzamide

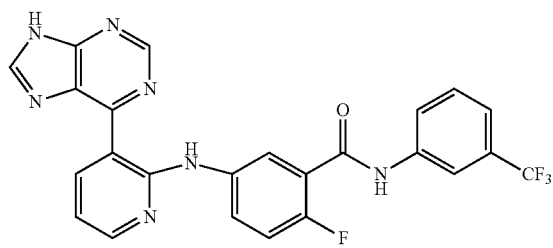 [SMILES: O=C(Nc1cccc(C(F)(F)F)c1)c1cc(Nc2ncccc2-c2ncnc3[nH]cnc23)ccc1F]

Step 1: Preparation of [4-Fluoro-3-(3-Trifluoromethylphenylcarbamoyl)Phenyl]Carbamoic Acid t-Butyl Ester

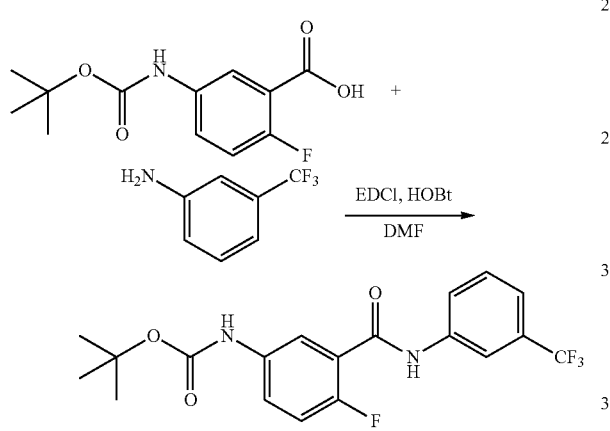

5-(t-butoxycarbonylamino)-2-fluorobenzoic acid (1 g, 4.6 mmol), (3-trifluoromethyl)aniline (0.74 g, 4.6 mmol), 1-ethyl-3-(3-dimethylaminopropyl)carbodiimide (1.3 g, 6.9 mmol), and 1-hydroxybenzotriazole (1.9 g, 6.9 mmol) were added to a DMF solvent, followed by stirring at room temperature for 12 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

$^1$H NMR (400 MHz, DMSO-$d_6$): δ 9.87 (s, 1H), 8.23 (S, 1H), 8.14 (d, 1H), 7.69 (d, 1H), 7.55 (t, 1H), 7.37 (d, 1H), 6.58 (d, 2H), 4.25 (m, 1H), 1.55 (s, 9H)

Step 2: Preparation of 2-Fluoro-5-[3-(9H-Purin-6-Yl)Pyridin-2-Ylamino]-N-(3-Trifluoromethylphenyl)Benzamide

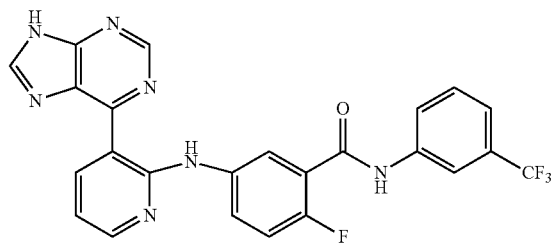 [SMILES: O=C(Nc1cccc(C(F)(F)F)c1)c1cc(Nc2ncccc2-c2ncnc3[nH]cnc23)ccc1F]

The title compound was synthesized in the same manner as described in Example 2, except that, in step 2 of Example 2, [4-fluoro-3-(3-trifluoromethylphenylcarbamoyl)phenyl]carbamic acid t-butyl ester prepared in step 1 was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 12.98 (s, 1H), 10.81 (s, 1H), 9.80 (d, 1H), 8.99 (s, 2H), 8.49 (s, 1H), 8.33-8.31 (m, 1H), 8.25 (s, 1H), 8.15 (dd, 1H), 8.05-8.01 (m, 1H), 7.94 (d, 1H), 7.61 (t, 1H), 7.47 (d, 1H), 7.33 (t, 1H), 7.03 (dd, 1H)

Example 74. Preparation of 1-(4-Chloro-3-Trifluoromethylphenyl)-3-2-Fluoro-5-[3-(9H-Purin-6-Yl)Pyridin-2-Ylamino]Phenylurea

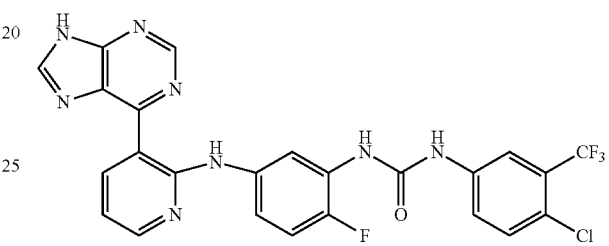

Step 1: Preparation of 3-[3-(4-Chloro-3-Trifluorophenyl)Ureido]-4-Fluorophenylcarbamic Acid t-Butyl Ester

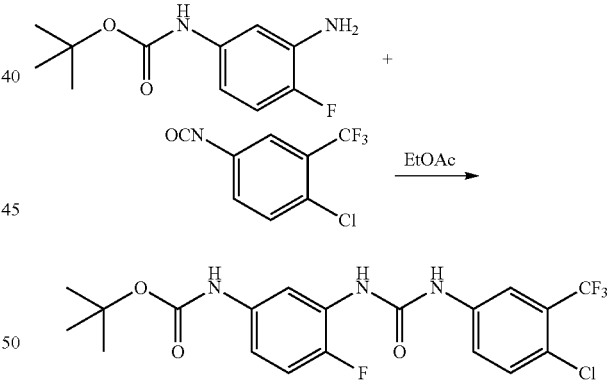

(3-amino-4-fluorophenyl)carbamic acid t-butyl ester (1 g, 4 mmol) and 1-chloro-4-isocyanato-2-trifluoromethylbenzene (1 g, 4.6 mmol) were added to an ethyl acetate solvent, followed by stirring at 40° C. for 2 hours. After completion of the reaction, the reaction solution was washed with water and brine and extracted with dichloromethane. The organic layer was dried with anhydrous magnesium sulfate, concentrated under reduced pressure, and then purified by column chromatography to afford the title compound.

$^1$H NMR (400 MHz, DMSO-$d_6$): δ 9.06 (s, 1H), 8.79 (s, 1H), 8.37 (s, 1H), 8.32 (d, 1H), 7.77 (d, 1H), 7.56 (m, 1H), 7.07 (m, 1H), 6.92 (m, 1H), 4.22 (m, 1H), 1.55 (s, 9H)

Step 2: Preparation of 1-(4-Chloro-3-Trifluoromethylphenyl)-3-2-Fluoro-5-[3-(9H-Purin-6-Yl)Pyridin-2-Ylamino]Phenylurea

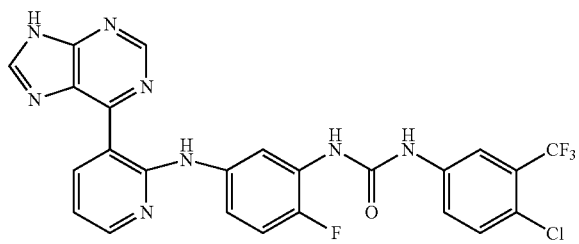 [SMILES: O=C(Nc1ccc(Cl)c(C(F)(F)F)c1)Nc1cc(Nc2ncccc2-c2ncnc3[nH]cnc23)ccc1F]

The title compound was synthesized in the same manner as described in Example 2, except that, in step 2 of Example 2, 3-[3-(4-chloro-3-trifluorophenyl)ureido-4-fluorophenyl]carbamic acid t-butyl ester prepared in step 1 was used instead of t-butyl-2,6-difluoro-3-(3-(4-methyl-1H-imidazol-1-yl)-5-(trifluoromethyl)benzamido)phenylcarbamate.

NMR (400 MHz, DMSO-$d_6$): δ 13.85 (s, 1H), 10.81 (s, 1H), 12.40 (s, 1H), 9.97 (s, 1H), 9.73 (d, 1H), 9.09 (s, 1H), 8.85 (s, 1H), 8.73 (s, 1H), 8.39 (dd, 1H), 8.29 (dd, 1H), 8.09 (d, 1H), 7.67-7.61 (m, 2H), 7.61 (t, 1H), 7.47-7.43 (m, 1H), 7.25 (dd, 1H), 7.05 (dd, 1H)

Example 75. Preparation of 1-3-Fluoro-4-[3-(9H-Purin-6-Yl)Pyridin-2-Ylamino]Phenyl-3-(3-Trifluoromethylphenyl)Urea

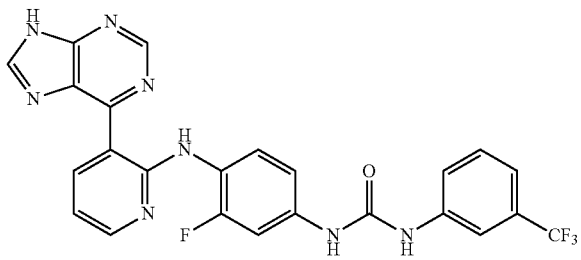 [SMILES: O=C(Nc1cccc(C(F)(F)F)c1)Nc1ccc(Nc2ncccc2-c2ncnc3[nH]cnc23)c(F)c1]

The title compound was synthesized in the same manner as described in Example 2, except that, in step 2 of Example 2, 2-fluoro-4-[3-(3-trifluoromethylphenyl)ureido]phenylcarbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.86 (s, 1H), 12.75 (s, 1H), 9.80 (s, 1H), 9.33 (s, 1H), 9.15 (s, 1H), 8.72 (s, 1H), 8.39 (dd, 1H), 8.12 (dd, 1H), 8.04 (s, 1H), 7.95 (t, 1H), 7.56-7.50 (m, 2H), 7.42 (d, 1H), 7.31 (d, 1H), 7.05 (dd, 1H)

Example 76. Preparation of N-2-Fluoro-5-[3-(9H-Purin-6-Yl)Pyridin-2-Ylamino]Phenyl-2-(3-Trifluoromethylphenyl)Acetamide

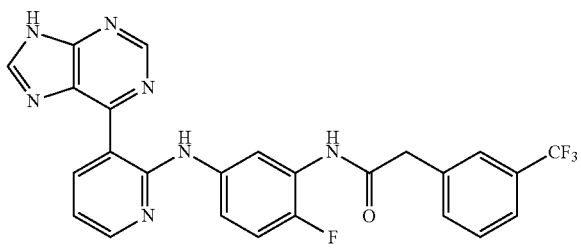 [SMILES: O=C(Cc1cccc(C(F)(F)F)c1)Nc1cc(Nc2ncccc2-c2ncnc3[nH]cnc23)ccc1F]

The title compound was synthesized in the same manner as described in Example 2, except that, in step 2 of Example 2, 4-fluoro-3-[2-(3-trifluoromethylphenyl)acetylamino]phenylcarbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.82 (s, 1H), 12.37 (s, 1H), 10.04 (s, 1H), 9.68 (brs, 1H), 9.06 (s, 1H), 8.70 (s, 1H), 8.31-8.26 (m, 2H), 7.73 (s, 1H), 7.67-7.54 (m, 4H), 7.22 (dd, 1H), 7.01 (dd, 1H). 3.88 (s, 2H)

Example 77. Preparation of N-(3-Cyanomethylphenyl)-4-Fluoro-3-[3-(9H-Purin-6-Yl)Pyridin-2-Ylamino]Benzamide

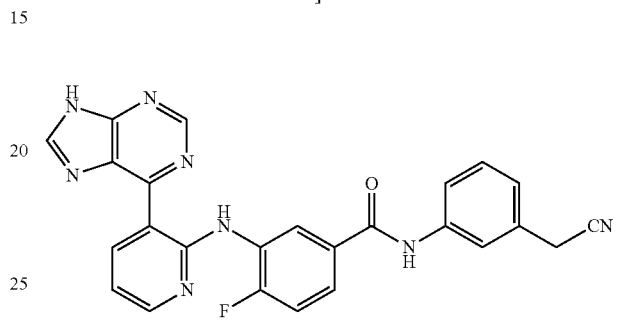

The title compound was synthesized in the same manner as described in Example 2, except that, in step 2 of Example 2, [5-(3-cyanomethylphenylcarbamoyl)-2-fluorophenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 12.97 (s, 1H), 10.38 (s, 1H), 9.68 (brs, 1H), 9.83 (d, 1H), 9.20 (dd, 1H), 9.05 (s, 1H), 8.72 (s, 1H), 8.44 (dd, 2H), 7.87 (s, 1H), 7.72 (d, 1H), 7.66-7.63 (m, 1H), 7.46 (dd, 1H). 7.38 (t, 1H), 7.14 (dd, 1H), 7.08 (d, 1H), 4.07 (s, 2H)

Example 78. Preparation of N-4-[(3-(9H-Purin-6-Yl)Pyridin-2-Yl)Amino]-3-Fluorophenyl-4-(Cyanomethyl)Benzamide

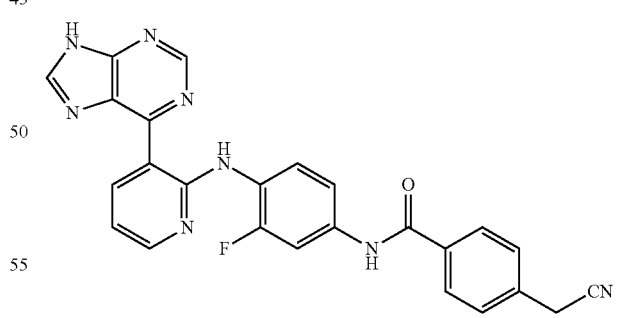

The title compound was synthesized in the same manner as described in Example 2, except that, in step 2 of Example 2, 4-[4-(cyanomethyl)benzamido]-2-fluorophenylcarbamic acid t-butyl ester was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.89 (s, 1H), 13.00 (s, 1H), 10.68 (s, 1H), 10.35 (s, 1H), 9.87 (d, 1H), 9.22 (d, 1H), 9.07 (s, 1H), 8.75 (s, 1H), 8.46-8.44 (m, 2H), 8.02 (d,

1H), 7.91 (d, 1H), 7.79 (d, 2H), 7.68-7.62 (m, 1H). 7.52-7.46 (m, 1H), 7.32 (d, 1H), 7.14 (dd, 1H), 4.01 (s, 2H)

Example 79. Preparation of N-4-[3-(9H-Purin-6-Yl) Pyridin-2-Ylamino]Phenyl-3-Trifluoromethylbenzamide

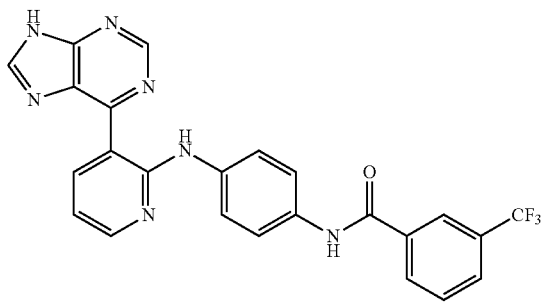 [SMILES: O=C(Nc1ccc(Nc2ncccc2-c2ncnc3[nH]cnc23)cc1)c1cccc(C(F)(F)F)c1]

The title compound was synthesized in the same manner as described in Example 2, except that, in step 2 of Example 2, [4-(3-trifluoromethylbenzoylamino)phenyl]carbamic acid t-butyl ester was used instead of t-butyl-2,6-difluoro-3-(3-(4-methyl-1H-imidazol-1-yl)-5-(trifluoromethyl)benzamido)phenylcarbamate.

¹H NMR (400 MHz, DMSO-d₆): δ 13.86 (s, 1H), 12.66 (s, 1H), 10.45 (s, 1H), 9.78 (s, 1H), 9.13 (s, 1H), 8.71 (s, 1H), 8.36 (dd, 1H), 8.31 (s, 1H), 8.27 (d, 1H), 7.95 (d, 1H), 7.85 (d, 2H), 7.80-7.74 (m, 3H). 7.01 (dd, 1H)

Example 80. Preparation of N-2-Methoxy-4-[3-(9H-Purin-6-Yl)Pyridin-2-Ylamino]Phenyl-3-Trifluoromethylbenzamide

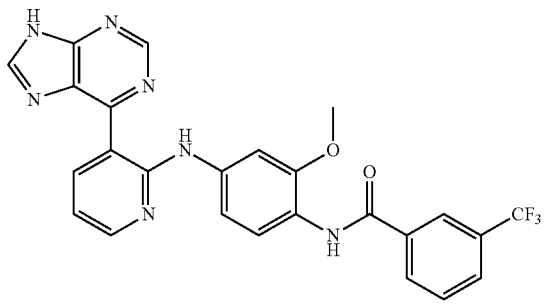 [SMILES: COc1cc(Nc2ncccc2-c2ncnc3[nH]cnc23)ccc1NC(=O)c1cccc(C(F)(F)F)c1]

The title compound was synthesized in the same manner as described in Example 2, except that, in step 2 of Example 2, [3-methoxy-4-(3-trifluoromethylbenzoylamino)phenyl] carbamic acid t-butyl ester was used instead of t-butyl-2,6-difluoro-3-(3-(4-methyl-1H-imidazol-1-yl)-5-(trifluoromethyl)benzamido)phenylcarbamate.

¹H NMR (400 MHz, DMSO-d₆): δ 13.86 (s, 1H), 12.69 (s, 1H), 9.83 (s, 1H), 9.78 (d, 1H), 9.16 (s, 1H), 8.72 (s, 1H), 8.39 (dd, 1H), 8.31 (s, 1H), 8.26 (d, 1H), 7.95 (d, 1H), 7.77 (t, 2H), 7.51 (d, 1H). 7.40 (dd, 1H), 7.04 (dd, 1H)

Example 81. Preparation of N-(3-(3-(9H-purin-6-yl) pyridin-2-ylamino)-2,4-difluorophenyl)-3-(4-fluorophenyl)-2-oxoimidazolidine-1-carboxamide

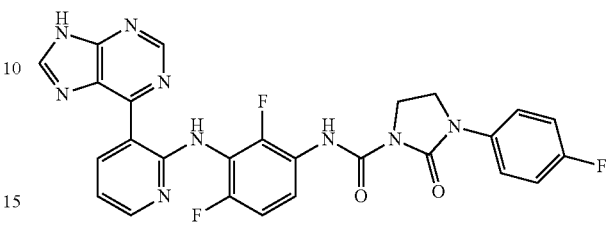

The title compound was synthesized in the same manner as described in Example 2, except that, in step 2 of Example 2, (2,6-difluoro-3-[3-(4-fluorophenyl)-2-oxo-imidazolidine-1-carbonyl]aminophenyl)carbamic acid t-butyl ester was used instead of t-butyl-2,6-difluoro-3-(3-(4-methyl-1H-imidazol-1-yl)-5-(trifluoromethyl)benzamido)phenylcarbamate.

¹H NMR (400 MHz, DMSO-d₆): δ 11.64 (s, 1H), 10.60 (d, J=2.4 Hz, 1H), 9.65 (brs, 1H), 8.72 (s, 1H), 8.24 (m, 1H), 8.01 (m, 1H), 7.63 (m, 2H), 7.28 (m, 3H), 7.25 (m, 1H), 3.96 (s, 4H)

Example 82. Preparation of N-(4-(3-(9H-Purin-6-Yl)Pyridin-2-Ylamino)-3-Fluorophenyl)-3-(2-Cyanopropan-2-Yl)Benzamide

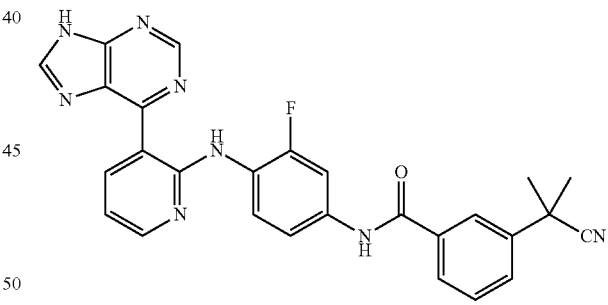

The title compound was synthesized in the same manner as described in Example 2, except that, in step 2 of Example 2, 4-[3-(2-cyanopropan-2-yl)benzamido]-2-fluorophenyl-carbamic acid t-butyl ester was used instead of t-butyl-2,6-difluoro-3-(3-(4-methyl-1H-imidazol-1-yl)-5-(trifluoromethyl)benzamido)phenylcarbamate.

¹H NMR (400 MHz, DMSO-d₆): δ 13.88 (brs, 1H), 12.88 (s, 1H), 10.45 (s, 1H), 9.85 (d, J=7.6 Hz, 1H), 9.02 (s, 1H), 8.67 (s, 1H), 8.62 (t, J=9.2 Hz, 1H), 8.39 (dd, J=2.8, 2.0 Hz, 1H), 8.07 (s, 1H), 7.96 (d, J=7.6 Hz, 1H), 7.88 (dd, J=11.6, 2.0 Hz, 1H), 7.77 (d, J=7.6 Hz, 1H), 7.62 (t, J=8.0 Hz, 1H), 7.52 (d, J=8.8 Hz, 1H), 7.08 (m, 1H), 1.77 (s, 6H). (m, 1H), 7.63 (m, 2H), 7.28 (m, 3H), 7.25 (m, 1H), 3.96 (s, 4H)

Example 83. Preparation of N-(3-(3-(7H-Pyrrolo[2,3-d]Pyrimidin-4-Yl)Pyridin-2-Ylamino)-2,4-Difluorophenyl)-3-(1-Amino-2-Methyl-1-Oxopropan-2-Yl)Benzamide

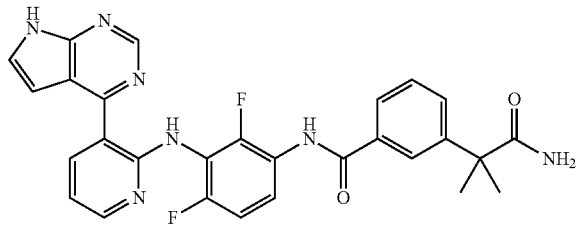 [SMILES: CC(C)(C(N)=O)c1cccc(C(=O)Nc2ccc(F)c(Nc3ncccc3-c3ncnc4[nH]ccc34)c2F)c1]

Step 1: Preparation of 4-(2-Fluoropyridin-3-Yl)-7H-Pyrrolo[2,3-d]Pyrimidine

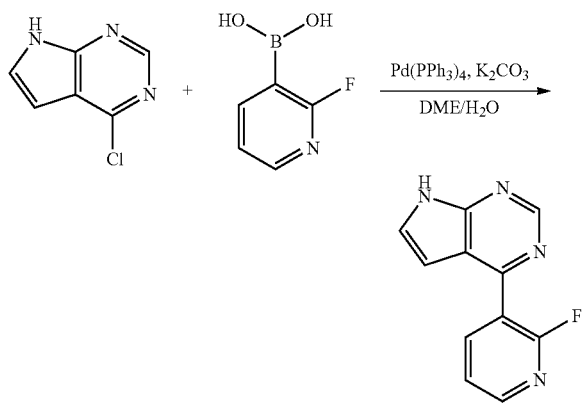

4-chloro-7H-pyrrolo[2,3-d]pyrimidine (100 mg, 0.65 mmol), 2-fluoropyridin-3-ylboronic acid (119 mg, 0.846 mmol), tetrakis(triphenylphosphine)palladium(0) (30 mg, 0.026 mmol) and calcium carbonate (179 mg, 1.3 mmol) were added to a mixed solvent of dimethoxyethane and water. The solution was stirred under reflux at 100° C. for 6 hours. After completion of the reaction, the reaction solution was concentrated under reduced pressure, and the residue was aqueous sodium hydrogen carbonate solution and brine and extracted with ethyl acetate. After drying with anhydrous magnesium sulfate, and then the purification by column chromatography was performed to afford 33 mg (yield: 23.9%) of the title compound.

$^1$H NMR (400 MHz, DMSO-d$_6$): δ 12.33 (brs, 1H), 8.87 (s, 1H), 8.43 (d, J=3.6 Hz, 1H), 8.38 (t, J=8.8 Hz, 1H), 7.65 (d, J=4.6 Hz, 1H), 7.58 (t, J=5.5 Hz, 1H), 6.55 (t, J=3 Hz, 1H)

Step 2: Preparation of 4-(2-Fluoropyridin-3-Yl)-7-(Methoxymethyl)-7H-Pyrrolo[2,3-d]Pyrimidine

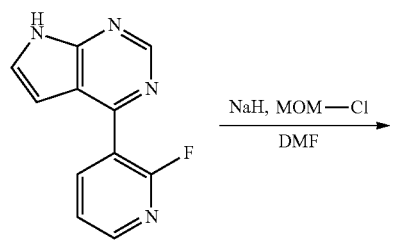

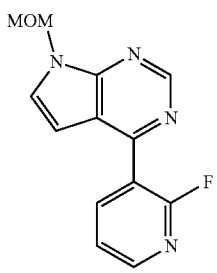

4-(2-fluoropyridin-3-yl)-7H-pyrrolo[2,3-d]pyrimidine (50 mg, 0.233 mmol) prepared in step 1 was dissolved in an N,N-dimethylformamide solvent. The solution was cooled to 0° C., and sodium hydride (60% dispersion in mineral oil, 14 mg, 0.3495 mmol) was slowly added in portions thereto. Next, the solution was stirred at 0° C. for 30 minutes, and then chloromethylether (0.02 mL, 0.2563 mmol) was added thereto, followed by stirring at room temperature for 3 hours. After completion of the reaction, the reaction solution was added to water and extracted with ethyl acetate. The organic layer was dried with anhydrous magnesium sulfate, concentrated under reduced pressure, and then purified by column chromatography to afford 46 mg (yield: 73.7%) of the title compound.

$^1$H NMR (400 MHz, CDCl$_3$): δ 9.02 (s, 1H), 8.40-8.36 (m, 2H), 7.44-7.40 (m, 2H), 6.72 (t, J=4.1 Hz, 1H), 5.68 (s, 2H), 3.35 (s, 3H)

Step 3: Preparation of 3-(2-cyanopropan-2-yl)-N-(2,4-difluoro-3-(3-(7-(methoxymethyl)-7H-pyrrolo[2,3-d]pyrimidin-4-yl)pyridin-2-ylamino)phenyl)benzamide

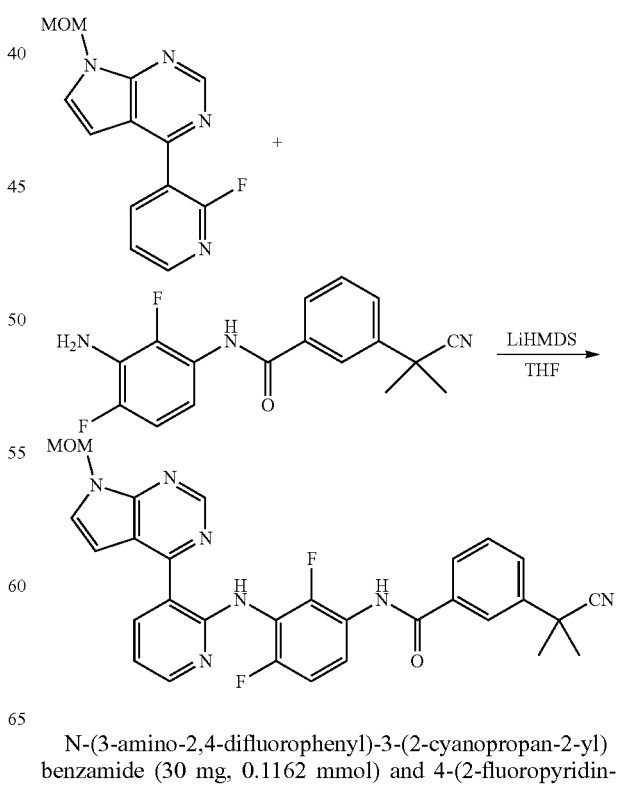

N-(3-amino-2,4-difluorophenyl)-3-(2-cyanopropan-2-yl)benzamide (30 mg, 0.1162 mmol) and 4-(2-fluoropyridin- 3-yl)-7-(methoxymethyl)-7H-pyrrolo[2,3-d]pyrimidine (40 mg, 0.1278 mmol) prepared in step 2 were dissolved in a tetrahydrofuran solvent. The solution was cooled to 0° C., and lithium(bistrimethylsilyl)amide (1.0 M solution in THF, 0.581 mL, 0.3495 mmol) was slowly added in portions thereto. Next, the solution was stirred at 0° C. for 20 minutes, and then stirred at room temperature for 5 hours. After completion of the reaction, the remaining lithium (bistrimethylsilyl)amide was removed by adding a small amount of 1M hydrochloric acid aqueous solution, and then aqueous sodium hydrogen carbonate solution was added to the reaction solution, followed by extraction with ethyl acetate. The organic layer was dried with anhydrous magnesium sulfate, concentrated under reduced pressure, and then purified by column chromatography to afford 57 mg (yield: 89%) of the title compound.

$^1$H NMR (400 MHz, CDCl$_3$): δ 10.86 (brs, 1H), 8.99 (s, 1H), 8.31-8.28 (m, 2H), 8.24-8.19 (m, 1H), 8.00 (brs, 2H), 7.79-7.73 (m, 2H), 7.53 (t, J=7.8 Hz, 1H), 7.48 (d, J=3.5 Hz, 1H), 7.05 (t, J=9.4 Hz, 1H), 6.95-6.91 (m, 2H), 5.07 (s, 2H), 3.35 (s, 3H), 1.78 (s, 6H)

Step 4: Preparation of N-(3-(3-(7H-Pyrrolo[2,3-d]Pyrimidin-4-Yl)Pyridin-2-Ylamino)-2,4-Difluorophenyl)-3-(1-Amino-2-Methyl-1-Oxopropan-2-Yl)Benzamide

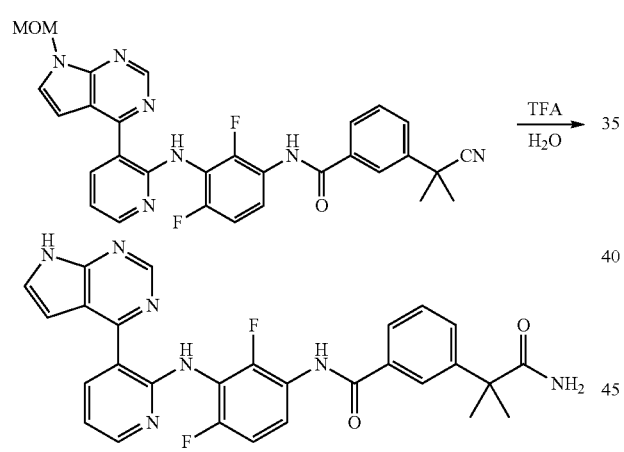

3-(2-cyanopropan-2-yl)-N-(2,4-difluoro-3-(3-(7-(methoxymethyl)-7H-pyrrolo[2,3-d]pyrimidin-4-yl)pyridin-2-ylamino)phenyl)benzamide (50 mg, 0.0975 mmol) prepared in step 3 was dissolved in a mixed solution of trifluoroacetic acid (1.8 mL) and water (0.2 mL). The solution was stirred under reflux at 80° C. for 24 hours. The reaction solution was washed with sodium hydrogen carbonate solution and brine and extracted with ethyl acetate. The organic layer was dried with anhydrous magnesium sulfate, concentrated under reduced pressure, and then purified by column chromatography to afford 5 mg (yield: 9.7%) of the title compound.

$^1$H NMR (400 MHz, CDCl$_3$): δ 10.88 (s, 1H), 9.80 (brs, 1H), 8.94 (s, 1H), 8.32 (d, J=7.5 Hz, 1H), 8.28 (d, J=4.3 Hz, 1H), 8.19 (brs, 1H), 8.02 (s, 1H), 7.96 (s, 1H), 7.73 (d, J=7.9 Hz, 1H), 7.61 (d, J=7.9 Hz, 1H), 7.50-7.45 (m, 2H), 7.04 (t, J=9 Hz, 1H), 6.95-6.92 (m, 1H), 6.89 (brs, 1H), 5.57 (brs, 1H), 5.27 (brs, 1H), 1.64 (s, 6H)

Example 84. Preparation of N-(5-(3-(7H-Pyrrolo[2,3-d]Pyrimidin-4-Yl)Pyridin-2-Ylamino)-2,4-Difluorophenyl)-3-(2-Cyanopropan-2-Yl)Benzamide

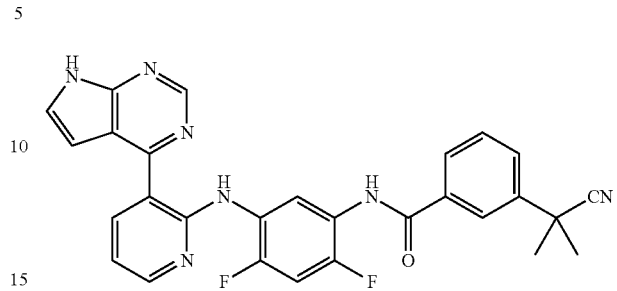

Step 1: Preparation of 4-(2-Fluoropyridin-3-Yl)-7H-Pyrrolo[2,3-d]Pyrimidine

The title compound was obtained in the same manner as described in step 1 of Example 83.

Step 2: Preparation of N-(5-(3-(7H-Pyrrolo[2,3-d]Pyrimidin-4-Yl)Pyridin-2-Ylamino)-2,4-Difluorophenyl)-3-(2-Cyanopropan-2-Yl)Benzamide

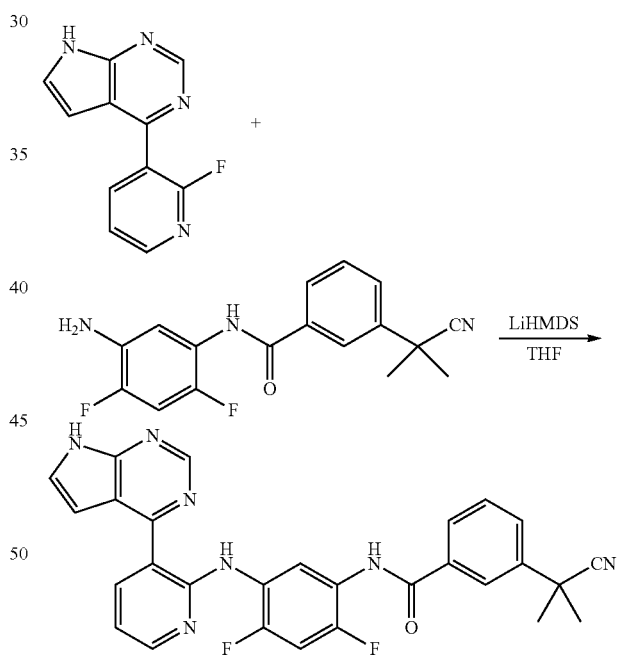

4-(2-fluoropyridin-3-yl)-7H-pyrrolo[2,3-d]pyrimidine (20 mg, 0.0934 mmol), prepared in step 1, and N-(5-amino-2,4-difluorophenyl)-3-(2-cyanopropan-2-yl)benzamide (32 mg, 0.1027 mmol) were dissolved in a tetrahydrofuran solvent. The solution was cooled to 0° C., and lithium (bistrimethylsilyl)amide (1.0 M solution in THF, 0.467 mL, 0.467 mmol) was added slowly in small portions thereto. Next, the solution was stirred at 0° C. for 20 minutes, and then stirred at room temperature for 5 hours. After completion of the reaction, the remaining lithium(bistrimethylsilyl) amide was removed by adding a small amount of 1M hydrochloric acid aqueous solution, and then aqueous sodium hydrogen carbonate solution was added to the reaction solution, followed by extraction with ethyl acetate. The organic layer was dried with anhydrous magnesium sulfate and concentrated under reduced pressure, and the obtained solid was washed with a mixed solution of methanol and dichloromethane, thereby obtaining 18 mg (yield: 37.8%) of the title compound.

$^1$H NMR (400 MHz, DMSO-d$_6$): δ 12.48 (brs, 1H), 11.98 (s, 1H), 10.24 (s, 1H), 8.92 (s, 1H), 8.66 (t, J=8.4 Hz, 1H), 8.49 (d, J=7.8 Hz, 1H), 8.35-8.33 (m, 1H), 8.10 (s, 1H), 7.96 (d, J=7.8 Hz, 1H), 7.77-7.74 (m, 2H), 7.60 (t, J=7.9 Hz, 1H), 7.46 (t, J=10.6 Hz, 1H), 7.09-7.05 (m, 1H), 6.94 (d, J=3.6 Hz, 1H), 1.74 (s, 6H)

Example 85. Preparation of N-(3-(3-(7H-Pyrrolo[2,3-d]Pyrimidin-4-Yl)Pyridin-2-Ylamino)-2,4-Difluorophenyl)-3-(2-Cyanopropan-2-Yl)Benzamide

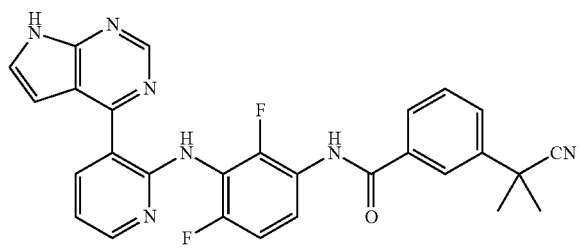 [SMILES: CC(C)(C#N)c1cccc(C(=O)Nc2ccc(F)c(Nc3ncccc3-c3ncnc4[nH]ccc34)c2F)c1]

The title compound was synthesized in the same manner as described in Example 84, except that, in step 2 of Example 84, N-(3-amino-2,4-difluorophenyl)-3-(2-cyanopropan-2-yl)benzamide was used instead of N-(5-amino-2,4-difluorophenyl)-3-(2-cyanopropan-2-yl)benzamide.

$^1$H NMR (400 MHz, CDCl$_3$): δ 10.91 (brs, 1H), 9.33 (brs, 1H), 8.97 (s, 1H), 8.33-8.28 (m, 2H), 8.25-8.19 (m, 1H), 8.00 (brs, 2H), 7.79-7.73 (m, 2H), 7.54 (t, J=7.8 Hz, 1H), 7.46-7.45 (m, 1H), 7.08-7.03 (m, 1H), 6.96-6.93 (m, 1H), 6.91-6.90 (m, 1H), 1.78 (s, 6H)

Example 86. Preparation of N-(3-(3-(7H-Pyrrolo[2,3-d]Pyrimidin-4-Yl)Pyridin-2-Ylamino)-2-Fluorophenyl)-3-(2-Cyanopopan-2-Yl)Benzamide

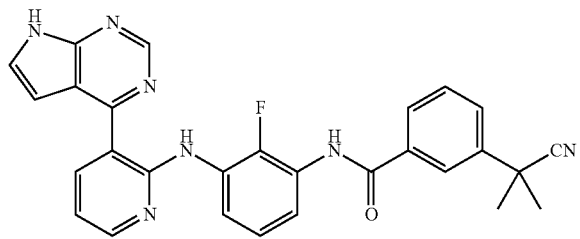 [SMILES: CC(C)(C#N)c1cccc(C(=O)Nc2cccc(Nc3ncccc3-c3ncnc4[nH]ccc34)c2F)c1]

The title compound was synthesized in the same manner as described in Example 84, except that, in step 2 of Example 84, N-(3-amino-2-fluorophenyl)-3-(2-cyanopropan-2-yl)benzamide was used instead of N-(5-amino-2,4-difluorophenyl)-3-(2-cyanopropan-2-yl)benzamide.

$^1$H NMR (400 MHz, DMSO-d$_6$): δ 12.41 (brs, 1H), 12.01 (s, 1H), 10.26 (brs, 1H), 8.89 (s, 1H), 8.49-8.47 (m, 2H), 8.40-8.38 (m, 1H), 8.11 (s, 1H), 7.97 (d, J=7.8 Hz, 1H), 7.77-7.74 (m, 2H), 7.60 (t, 1H), 7.19-7.13 (m, 2H), 7.11-7.08 (m, 1H), 6.93 (d, J=3.6 Hz, 1H)

Example 87. Preparation of N-2-Fluoro-5-[3-(7H-Pyrrolo[2,3-d]Pyrimidin-4-Yl)Pyridin-2-Ylamino] Phenyl-3-Trifluoromethyl Benzamide

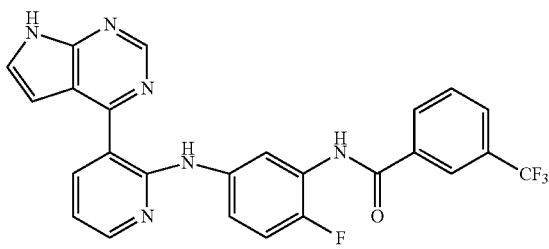 [SMILES: O=C(Nc1cc(Nc2ncccc2-c2ncnc3[nH]ccc23)ccc1F)c1cccc(C(F)(F)F)c1]

The title compound was synthesized in the same manner as described in Example 84, except that, in step 2 of Example 84, N-(5-amino-2-fluorophenyl)-3-trifluoromethylbenzamide was used instead of N-(5-amino-2,4-difluorophenyl)-3-(2-cyanopropan-2-yl)benzamide.

$^1$H NMR (400 MHz, DMSO-d$_6$): δ $^1$H NMR (400 MHz, DMSO-d$_6$): δ 11.49 (s, 1H), 8.96 (s, 1H), 8.38 (dd, 1H), 8.26-8.34 (m, 3H), 7.98-8.03 (m, 2H), 7.77-7.82 (m, 1H), 7.72 (d, 1H), 7.61-7.65 (m, 1H), 7.23-7.27 (q, 1H), 7.01-7.04 (q, 1H), 6.87 (d, 1H)

Example 88. Preparation of 3-Fluoro-N-2-Fluoro-5-[3-(7H-Pyrrolo[2,3-d]Pyrimidin-4-Yl)Pyridin-2-Ylamino]Phenyl-5-Trifluoromethyl Benzamide

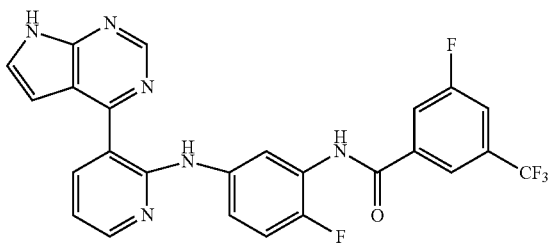 [SMILES: O=C(Nc1cc(Nc2ncccc2-c2ncnc3[nH]ccc23)ccc1F)c1cc(F)cc(C(F)(F)F)c1]

The title compound was synthesized in the same manner as described in Example 84, except that, in step 2 of Example 84, N-(5-amino-2-fluorophenyl)-3-fluoro-5-trifluoromethylbenzamide was used instead of N-(5-amino-2,4-difluorophenyl)-3-(2-cyanopropan-2-yl)benzamide.

$^1$H NMR (400 MHz, DMSO-d$_6$): δ 11.50 (s, 1H), 8.96 (s, 1H), 8.38 (dd, 1H), 8.32 (dd, 1H), 8.22 (s, 1H), 8.11 (d, 1H), 8.03 (dd, 1H), 7.98 (d, 1H), 7.72 (d, 1H), 7.25 (t, 1H), 7.03 (q, 1H), 6.87 (d, 1H)

Example 89. Preparation of 4-Chloro-N-2-Fluoro-5-[3-(7H-Pyrrolo[2,3-d]Pyrimidin-4-Yl)Pyridin-2-Ylamino]Phenyl-5-Trifluoromethyl Benzamide

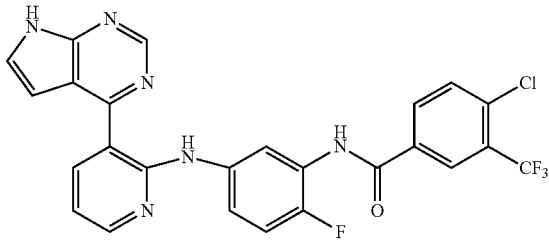 [SMILES: O=C(Nc1cc(Nc2ncccc2-c2ncnc3[nH]ccc23)ccc1F)c1ccc(Cl)c(C(F)(F)F)c1]

The title compound was synthesized in the same manner as described in Example 84, except that, in step 2 of Example 84, N-(5-amino-2-fluorophenyl)-4-chloro-3-trifluoromethylbenzamide was used instead of N-(5-amino-2,4-difluorophenyl)-3-(2-cyanopropan-2-yl)benzamide.

Example 90. Preparation of N-2-Fluoro-5-[3-(7H-Pyrrolo[2,3-d]Pyrimidin-4-Yl)Pyridin-2-Ylamino]Phenyl-3,5-Bistrifluoromethyl Benzamide

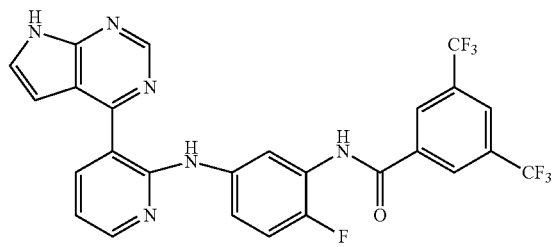 [SMILES: O=C(Nc1cc(Nc2ncccc2-c2ncnc3[nH]ccc23)ccc1F)c1cc(C(F)(F)F)cc(C(F)(F)F)c1]

The title compound was synthesized in the same manner as described in Example 84, except that, in step 2 of Example 84, N-(5-amino-2-fluorophenyl)-3,5-bistrifluoromethylbenzamide was used instead of N-(5-amino-2,4-difluorophenyl)-3-(2-cyanopropan-2-yl)benzamide.

Example 91. Preparation of 3-(2-Cyanopropan-2-Yl)-N-2-Fluoro-5-[3-(7H-Pyrrolo[2,3-d]Pyrimidin-4-Yl)Pyridin-2-Ylamino]Phenyl Benzamide

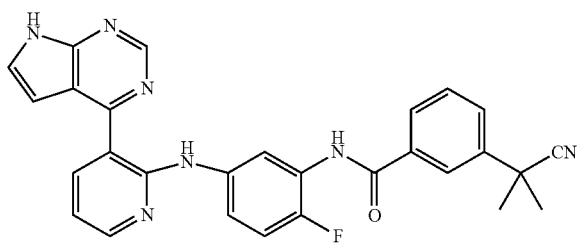 [SMILES: CC(C)(C#N)c1cccc(C(=O)Nc2cc(Nc3ncccc3-c3ncnc4[nH]ccc34)ccc2F)c1]

The title compound was synthesized in the same manner as described in Example 84, except that, in step 2 of Example 84, N-(5-amino-2-fluorophenyl)-3-(2-cyanopropan-2-yl)benzamide was used instead of N-(5-amino-2,4-difluorophenyl)-3-(2-cyanopropan-2-yl)benzamide.

$^1$H NMR (400 MHz, DMSO-$d_6$): δ 12.44 (s, 1H), 11.49 (s, 1H), 10.25 (s, 1H), 8.96 (s, 1H), 8.38 (dd, 1H), 8.11 (s, 1H), 7.93-8.00 (m, 2H), 7.73-7.78 (m, 1H), 7.72 (d, 1H), 7.64-7.58 (m, 2H), 7.20-7.27 (m, 1H), 7.02 (q, 1H), 6.87 (d, 1H), 1.75 (6H, s).

Example 92. Preparation of 3-(2-Cyanopropan-2-Yl)-5-Fluoro-N-2-Fluoro-5-[3-(7H-Pyrrolo[2,3-d]Pyrimidin-4-Yl)Pyridin-2-Ylamino]Phenyl Benzamide

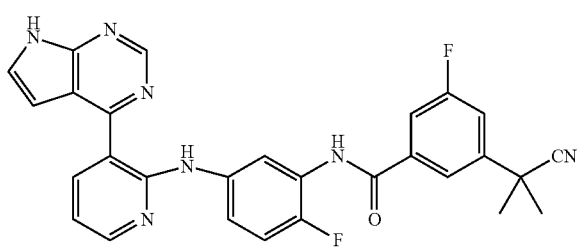 [SMILES: CC(C)(C#N)c1cc(F)cc(C(=O)Nc2cc(Nc3ncccc3-c3ncnc4[nH]ccc34)ccc2F)c1]

The title compound was synthesized in the same manner as described in Example 84, except that, in step 2 of Example 84, N-(5-amino-2-fluorophenyl)-3-(2-cyanopropan-2-yl)-5-fluorobenzamide was used instead of N-(5-amino-2,4-difluorophenyl)-3-(2-cyanopropan-2-yl)benzamide.

$^1$H NMR (400 MHz, DMSO-$d_6$): δ 12.44 (brs, 1H), 11.50 (s, 1H), 10.25 (brs, 1H), 8.97 (s, 1H), 8.38 (dd, 1H), 8.32 (dd, 1H), 7.99-8.03 (m, 2H), 7.78-7.81 (m, 1H), 7.72 (d, 1H), 7.61-7.67 (m, 2H), 7.25 (q, 1H), 7.02 (q, 1H), 6.87 (d, 1H), 1.75 (6H, s)

Example 93. Preparation of 4-Chloro-3-(2-Cyanopropan-2-Yl)-N-2-Fluoro-5-[3-(7H-Pyrrolo[2,3-d]Pyrimidin-4-Yl)Pyridin-2-Ylamino]Phenyl Benzamide

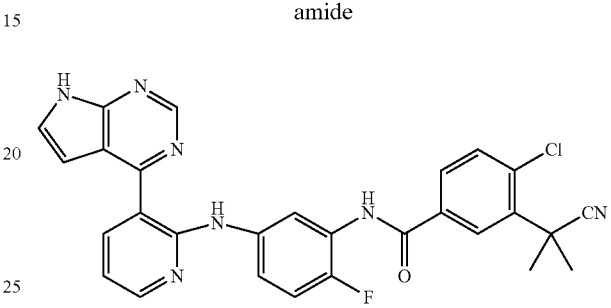

The title compound was synthesized in the same manner as described in Example 84, except that, in step 2 of Example 84, N-(5-amino-2-fluorophenyl)-4-chloro-3-(2-cyanopropan-2-yl)-5-fluorobenzamide was used instead of N-(5-amino-2,4-difluorophenyl)-3-(2-cyanopropan-2-yl)benzamide.

Example 94. Preparation of 3-(2-Cyanopropan-2-Yl)-N-3-[3-(7H-Pyrrolo[2,3-d]Pyrimidin-4-Yl)Pyridin-2-Ylamino]Phenyl Benzamide

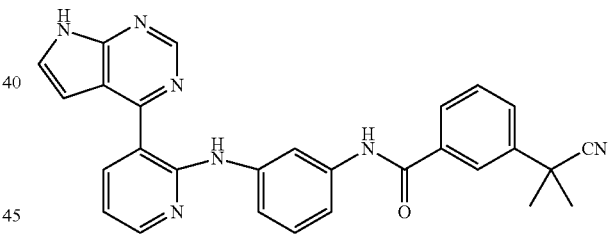

The title compound was synthesized in the same manner as described in Example 84, except that, in step 2 of Example 84, N-(3-aminophenyl)-3-(2-cyanopropan-2-yl)benzamide was used instead of N-(5-amino-2,4-difluorophenyl)-3-(2-cyanopropan-2-yl)benzamide.

Example 95. Preparation of 3-(2-Cyanopropan-2-Yl)-N-4-Fluoro-3-[3-(7H-Pyrrolo[2,3-d]Pyrimidin-4-Yl)Pyridin-2-Ylamino]Phenyl Benzamide

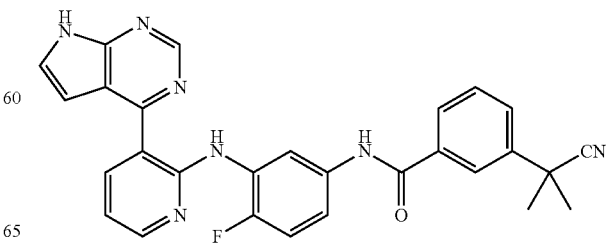

The title compound was synthesized in the same manner as described in Example 84, except that, in step 2 of Example 84, N-(3-amino-4-fluorophenyl)-3-(2-cyanopropan-2-yl)benzamide was used instead of N-(5-amino-2,4-difluorophenyl)-3-(2-cyanopropan-2-yl)benzamide.

Example 96. Preparation of 3-(2-Cyanopropan-2-Yl)-N-2,6-Difluoro-3-[3-(7H-Pyrrolo[2,3-d]Pyrimidin-4-Yl)Pyridin-2-Ylamino]Phenyl Benzamide

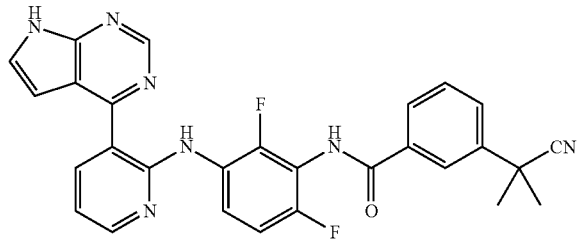 [SMILES: CC(C)(C#N)c1cccc(C(=O)Nc2c(F)ccc(Nc3ncccc3-c3ncnc4[nH]ccc34)c2F)c1]

The title compound was synthesized in the same manner as described in Example 84, except that, in step 2 of Example 84, N-(3-amino-2,6-difluorophenyl)-3-(2-cyanopropan-2-yl)benzamide was used instead of N-(5-amino-2,4-difluorophenyl)-3-(2-cyanopropan-2-yl)benzamide.

Example 97. Preparation of N-2-Chloro-5-[3-(7H-Pyrrolo[2,3-d]Pyrimidin-4-Yl)Pyridin-2-Ylamino]Phenyl-3-(2-Cyanopropan-2-Yl)Benzamide

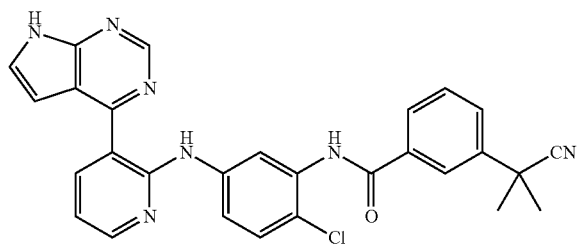 [SMILES: CC(C)(C#N)c1cccc(C(=O)Nc2cc(Nc3ncccc3-c3ncnc4[nH]ccc34)ccc2Cl)c1]

The title compound was synthesized in the same manner as described in Example 84, except that, in step 2 of Example 84, N-(5-amino-2-chlorophenyl)-3-(2-cyanopropan-2-yl)benzamide was used instead of N-(5-amino-2,4-difluorophenyl)-3-(2-cyanopropan-2-yl)benzamide.

Example 98. Preparation of 3-(2-Cyanopropan-2-Yl)-N-3-Fluoro-5-[3-(7H-Pyrrolo[2,3-d]Pyrimidin-4-Yl)Pyridin-2-Ylamino]Phenylbenzamide

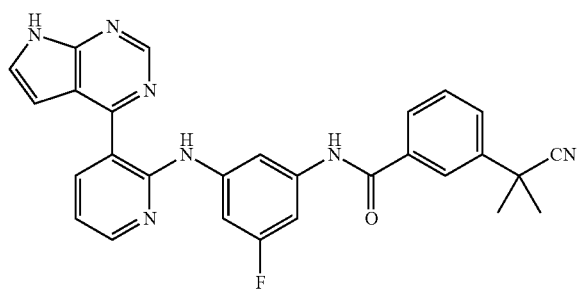 [SMILES: CC(C)(C#N)c1cccc(C(=O)Nc2cc(F)cc(Nc3ncccc3-c3ncnc4[nH]ccc34)c2)c1]

The title compound was synthesized in the same manner as described in Example 84, except that, in step 2 of Example 84, N-(3-amino-5-fluorophenyl)-3-(2-cyanopropan-2-yl)benzamide was used instead of N-(5-amino-2,4-difluorophenyl)-3-(2-cyanopropan-2-yl)benzamide.

Example 99. Preparation of 3-(2-Cyanopropan-2-Yl)-N-4-Methyl-3-[3-(7H-Pyrrolo[2,3-d]Pyrimidin-4-Yl)Pyridin-2-Ylamino]Phenylbenzamide

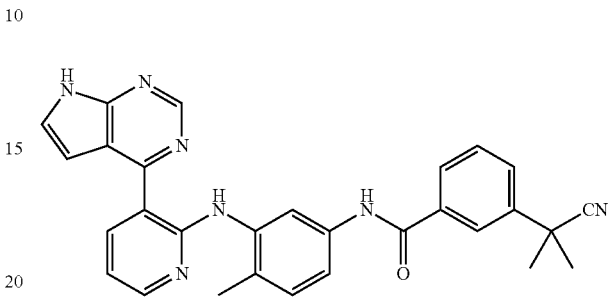

The title compound was synthesized in the same manner as described in Example 84, except that, in step 2 of Example 84, N-(3-amino-4-methylphenyl)-3-(2-cyanopropan-2-yl)benzamide was used instead of N-(5-amino-2,4-difluorophenyl)-3-(2-cyanopropan-2-yl)benzamide.

Example 100. Preparation of 3-(2-Cyanopropan-2-Yl)-N-4-Methoxy-3-[3-(7H-Pyrrolo[2,3-d]Pyrimidin-4-Yl)Pyridin-2-Ylamino]Phenylbenzamide

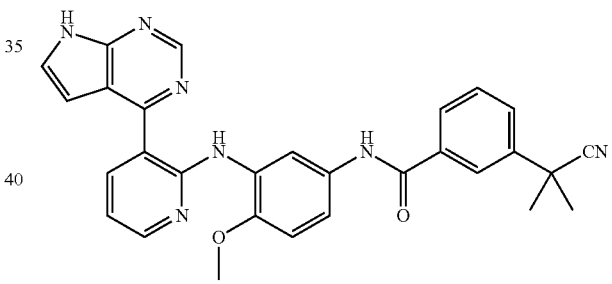

The title compound was synthesized in the same manner as described in Example 84, except that, in step 2 of Example 84, N-(3-amino-4-methoxyphenyl)-3-(2-cyanopropan-2-yl)benzamide was used instead of N-(5-amino-2,4-difluorophenyl)-3-(2-cyanopropan-2-yl)benzamide.

Example 101. Preparation of N-3-[3-(7H-Pyrrolo[2,3-d]Pyrimidin-4-Yl)Pyridin-2-Ylamino]Phenyl-3-Trifluoromethylbenzamide

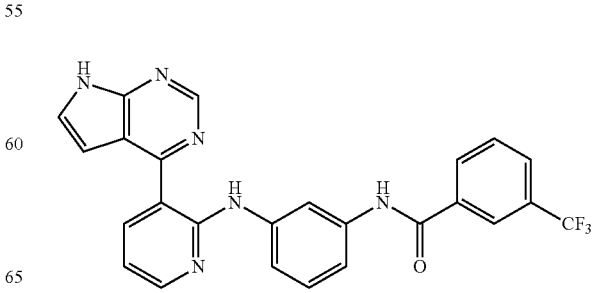

The title compound was synthesized in the same manner as described in Example 84, except that, in step 2 of Example 84, N-(3-aminophenyl)-3-trifluoromethylbenzamide was used instead of N-(5-amino-2,4-difluorophenyl)-3-(2-cyanopropan-2-yl)benzamide.

Example 102. Preparation of N-2-Fluoro-3-[3-(7H-Pyrrolo[2,3-d]Pyrimidin-4-Yl)Pyridin-2-Ylamino]Phenyl-3-Trifluoromethylbenzamide

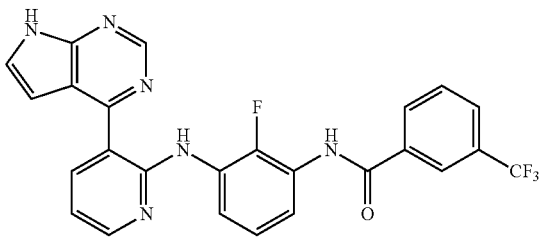 [SMILES: O=C(Nc1cccc(Nc2ncccc2-c2ncnc3[nH]ccc23)c1F)c1cccc(C(F)(F)F)c1]

The title compound was synthesized in the same manner as described in Example 84, except that, in step 2 of Example 84, N-(3-amino-2-fluorophenyl)-3-trifluoromethylbenzamide was used instead of N-(5-amino-2,4-difluorophenyl)-3-(2-cyanopropan-2-yl)benzamide.

Example 103. Preparation of N-4-Fluoro-3-[3-(7H-Pyrrolo[2,3-d]Pyrimidin-4-Yl)Pyridin-2-Ylamino]Phenyl-3-Trifluoromethylbenzamide

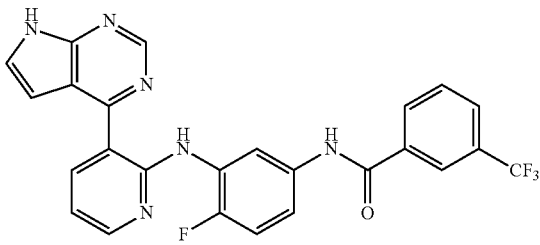 [SMILES: O=C(Nc1ccc(F)c(Nc2ncccc2-c2ncnc3[nH]ccc23)c1)c1cccc(C(F)(F)F)c1]

The title compound was synthesized in the same manner as described in Example 84, except that, in step 2 of Example 84, N-(3-amino-4-fluorophenyl)-3-trifluoromethylbenzamide was used instead of N-(5-amino-2,4-difluorophenyl)-3-(2-cyanopropan-2-yl)benzamide.

Example 104. Preparation of N-2,4-Difluoro-3-[3-(7H-Pyrrolo[2,3-d]Pyrimidin-4-Yl)Pyridin-2-Ylamino]Phenyl-3-Trifluoromethylbenzamide

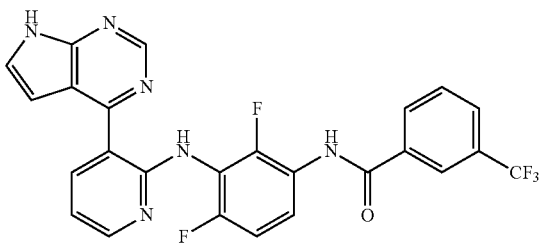 [SMILES: O=C(Nc1ccc(F)c(Nc2ncccc2-c2ncnc3[nH]ccc23)c1F)c1cccc(C(F)(F)F)c1]

The title compound was synthesized in the same manner as described in Example 84, except that, in step 2 of Example 84, N-(3-amino-2,4-difluorophenyl)-3-trifluoromethylbenzamide was used instead of N-(5-amino-2,4-difluorophenyl)-3-(2-cyanopropan-2-yl)benzamide.

Example 105. Preparation of N-2,6-Difluoro-3-[3-(7H-Pyrrolo[2,3-d]Pyrimidin-4-Yl)Pyridin-2-Ylamino]Phenyl-3-Trifluoromethylbenzamide

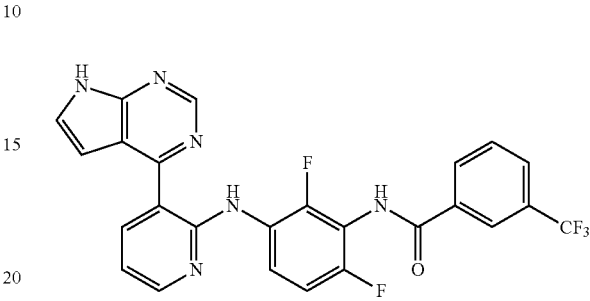

The title compound was synthesized in the same manner as described in Example 84, except that, in step 2 of Example 84, N-(3-amino-2,6-difluorophenyl)-3-trifluoromethylbenzamide was used instead of N-(5-amino-2,4-difluorophenyl)-3-(2-cyanopropan-2-yl)benzamide.

Example 106. Preparation of N-2,4-Difluoro-5-[3-(7H-Pyrrolo[2,3-d]Pyrimidin-2-Yl)Pyridin-2-Ylamino]Phenyl-3-Trifluoromethylbenzamide

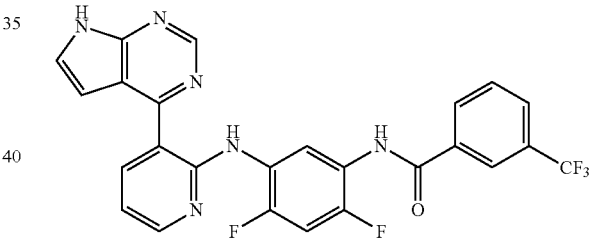

The title compound was synthesized in the same manner as described in Example 84, except that, in step 2 of Example 84, N-(5-amino-2,4-difluorophenyl)-3-trifluoromethylbenzamide was used instead of N-(5-amino-2,4-difluorophenyl)-3-(2-cyanopropan-2-yl)benzamide.

Example 107. Preparation of N-2-Chloro-5-[3-(7H-Pyrrolo[2,3-d]Pyrimidin-4-Yl)Pyridin-2-Ylamino]Phenyl-3-Trifluoromethylbenzamide

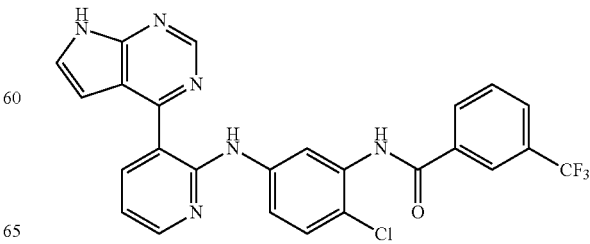

The title compound was synthesized in the same manner as described in Example 84, except that, in step 2 of Example 84, N-(5-amino-2-chlorophenyl)-3-trifluoromethylbenzamide was used instead of N-(5-amino-2,4-difluorophenyl)-3-(2-cyanopropan-2-yl)benzamide.

Example 108. Preparation of N-4-Methyl-3-[3-(7H-Pyrrolo[2,3-d]Pyrimidin-4-Yl)Pyridin-2-Ylamino]Phenyl-3-Trifluoromethylbenzamide

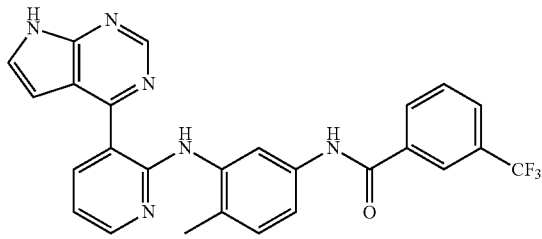 [SMILES: Cc1ccc(NC(=O)c2cccc(C(F)(F)F)c2)cc1Nc1ncccc1-c1ncnc2[nH]ccc12]

The title compound was synthesized in the same manner as described in Example 84, except that, in step 2 of Example 84, N-(3-amino-4-methylphenyl)-3-trifluoromethylbenzamide was used instead of N-(5-amino-2,4-difluorophenyl)-3-(2-cyanopropan-2-yl)benzamide.

Example 109. Preparation of N-4-Methoxy-3-[3-(7H-Pyrrolo[2,3-d]Pyrimidin-4-Yl)Pyridin-2-Ylamino]Phenyl-3-Trifluoromethylbenzamide

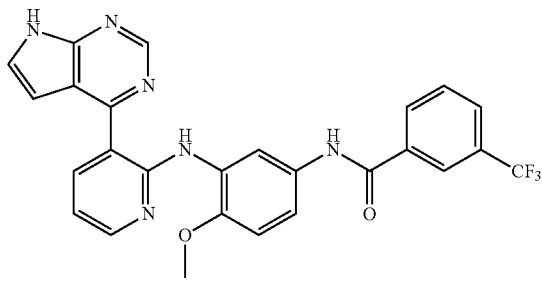 [SMILES: COc1ccc(NC(=O)c2cccc(C(F)(F)F)c2)cc1Nc1ncccc1-c1ncnc2[nH]ccc12]

The title compound was synthesized in the same manner as described in Example 84, except that, in step 2 of Example 84, N-(3-amino-4-methoxyphenyl)-3-trifluoromethylbenzamide was used instead of N-(5-amino-2,4-difluorophenyl)-3-(2-cyanopropan-2-yl)benzamide.

Example 110. Preparation of N-3-Fluoro-5-[3-(7H-Pyrrolo[2,3-d]Pyrimidin-4-Yl)Pyridin-2-Ylamino]Phenyl-3-Trifluoromethylbenzamide

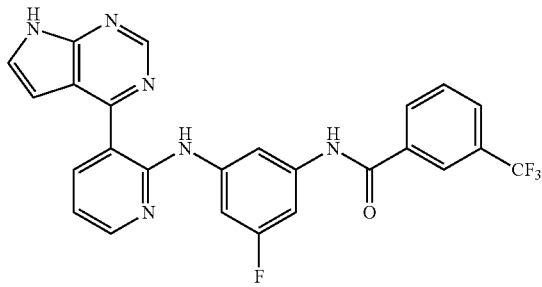 [SMILES: O=C(Nc1cc(F)cc(Nc2ncccc2-c2ncnc3[nH]ccc23)c1)c1cccc(C(F)(F)F)c1]

The title compound was synthesized in the same manner as described in Example 84, except that, in step 2 of Example 84, N-(3-amino-5-fluorophenyl)-3-trifluoromethylbenzamide was used instead of N-(5-amino-2,4-difluorophenyl)-3-(2-cyanopropan-2-yl)benzamide.

Example 111. Preparation of N-5-[(3-(9H-Purin-6-Yl)Pyridin-2-Yl)Amino]-2-Fluorophenyl-4-Fluoro-3-(Trifluoromethyl)Benzamide

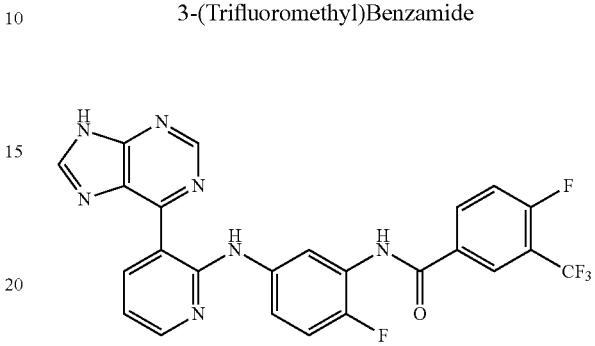

The title compound was synthesized in the same manner as described in Example 2, except that, in step 2 of Example 2, t-butyl[4-fluoro-3-(4-fluoro-3-(trifluoromethyl)benzamido)phenyl]carbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 12.50 (s, 1H), 10.48 (s, 1H), 9.69 (dd, 1H), 9.16 (s, 1H), 8.95 (s, 1H), 8.43-8.32 (m, 3H), 8.11 (dd, 1H), 7.74-7.66 (m, 2H), 7.27 (dd, 1H), 7.02 (q, 1H)

Example 112. Preparation of 5-[3-(9H-Purin-6-Yl)Amino]-N-[3-(2-Cyanopropan-2-Yl)Phenyl]-2-Fluorobenzamide

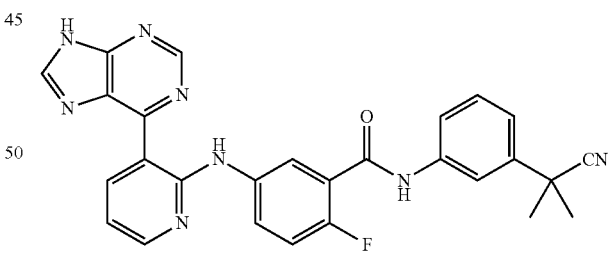

The title compound was synthesized in the same manner as described in Example 73, except that, in step 2 of Example 73, t-butyl 3-[(3-(2-cyanopropan-2-yl)phenyl)carbamoyl]-4-fluorophenylcarbamate was used instead of t-butyl[4-fluoro-3-(3-trifluoromethylphenylcarbamoyl)phenyl]carbamate.

$^1$H NMR (400 MHz, DMSO-d$_6$): δ 13.84 (s, 1H), 12.59 (s, 1H), 9.77 (d, 1H), 9.12 (s, 1H), 8.71 (s, 1H), 8.34 (d, 3H), 7.89 (s, 1H), 7.73 (s, 1H), 7.28 (m, 4H), 7.03 (q, 1H), 6.95 (m, 1H), 1.44 (s, 6H).

Example 113. Preparation of N-5-[(3-(9H-Purin-6-Yl)Pyridin-2-Yl)Amino]-2-Fluorophenyl-3-Fluorobenzamide

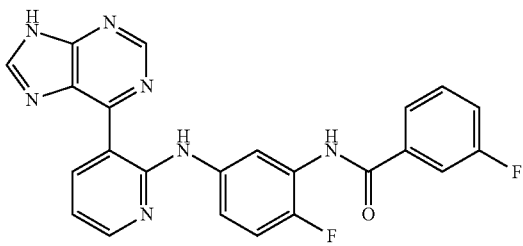 [SMILES: O=C(Nc1cc(Nc2ncccc2-c2ncnc3[nH]cnc23)ccc1F)c1cccc(F)c1]

The title compound was synthesized in the same manner as described in Example 2, except that, in step 2 of Example 2, t-butyl [4-fluoro-3-(3-fluorobenzamido)phenyl]carbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (s, 1H), 12.50 (s, 1H), 10.27 (s, 1H), 9.75 (s, 1H), 9.10 (s, 1H), 8.69 (s, 1H), 8.34 (q, 1H), 8.08 (dd, 1H), 7.86 (d, 1H), 7.80 (dd, 1H), 7.69 (m, 1H), 7.58 (m, 1H), 7.47 (m, 1H), 7.28 (t, 1H), 7.02 (q, 1H)

Example 114. Preparation of 5-[3-(9H-Purin-6-Yl)Pyridin-2-Yl]Amino-N-(3,4-Difluorophenyl)-2-Fluorobenzamide

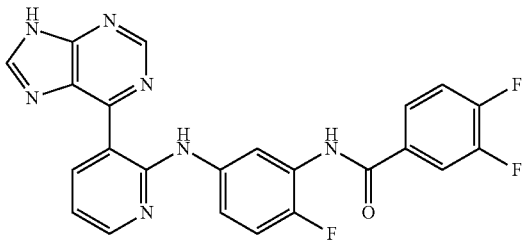

The title compound was synthesized in the same manner as described in Example 2, except that, in step 2 of Example 2, t-butyl [4-fluoro-3-(3,4-difluorobenzamido)phenyl]carbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (s, 1H), 12.59 (s, 1H), 10.28 (s, 1H), 9.73 (d, 1H), 9.09 (s, 1H), 8.68 (s, 1H), 8.33 (q, 1H), 8.03 (m, 2H), 7.89 (q, 1H), 7.72-7.62 (m, 2H), 7.25 (t, 1H), 7.02 (q, 1H)

Example 115. Preparation of 5-[3-(9H-purin-6-yl)pyridin-2-yl]amino-N-(3,5-difluorophenyl)-2-fluorobenzamide

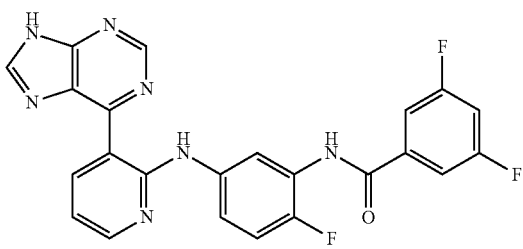 [SMILES: O=C(Nc1cc(Nc2ncccc2-c2ncnc3[nH]cnc23)ccc1F)c1cc(F)cc(F)c1]

The title compound was synthesized in the same manner as described in Example 2, except that, in step 2 of Example 2, t-butyl [4-fluoro-3-(3,5-difluorobenzamido)phenyl]carbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.85 (s, 1H), 12.60 (s, 1H), 10.36 (s, 1H), 9.76 (s, 1H), 9.11 (s, 1H), 8.34 (q, 1H), 8.09 (q, 1H), 7.69 (m, 3H), 7.53 (m, 1H), 7.26 (t, 1H), 7.03 (q, 1H)

Example 116. Preparation of N-5-[(3-(9H-purin-6-yl)pyridin-2-yl)amino]-2-fluoropheny-3-(2-cyanopropan-2-yl)-4-fluorobenzamide

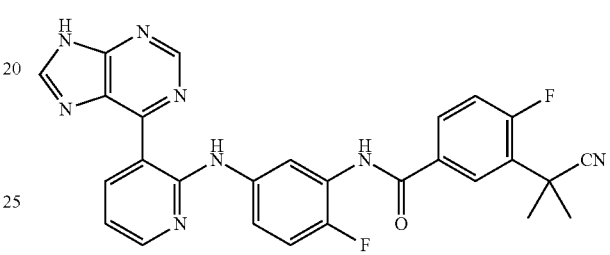

The title compound was synthesized in the same manner as described in Example 2, except that, in step 2 of Example 2, t-butyl 3-[3-(2-cyanopropan-2-yl)-4-fluorobenzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.85 (s, 1H), 12.62 (s, 1H), 10.32 (s, 1H), 9.77 (d, 1H), 9.11 (s, 1H), 8.71 (s, 1H), 8.34 (q, 1H), 8.12-8.07 (m, 3H), 7.68 (t, 1H), 7.48 (m, 1H), 7.26 (t, 1H), 7.02 (q, 1H), 1.81 (s, 6H).

Example 117. Preparation of N-5-[(3-(9H-purin-6-yl)pyridin-2-yl)amino]-2-fluorophenyl-4-chloro-3-(2-cyanopropan-2-yl)benzamide

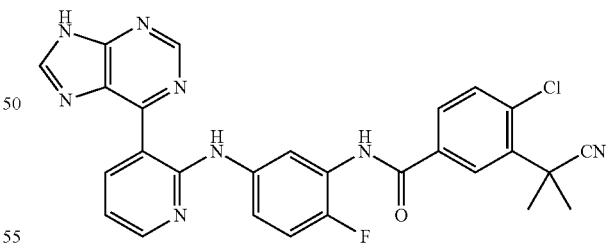

The title compound was synthesized in the same manner as described in Example 2, except that, in step 2 of Example 2, t-butyl 3-[3-(2-cyanopropan-2-yl)-4-chlorobenzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 12.55 (s, 1H), 10.38 (s, 1H), 9.73 (d, 1H), 9.12 (s, 1H), 8.71 (s, 1H), 8.34 (q, 1H), 8.13-8.10 (m, 2H), 8.01 (dd, 1H), 7.74 (d, 1H), 7.68 (t, 1H), 7.27 (t, 1H), 7.03 (q, 1H), 1.88 (s, 6H)

Example 118. Preparation of 1-5-[(3-(9H-purin-6-yl)pyridin-2-yl)amino]-2-fluorophenyl-3-[3-(trifluoromethyl)phenyl]urea

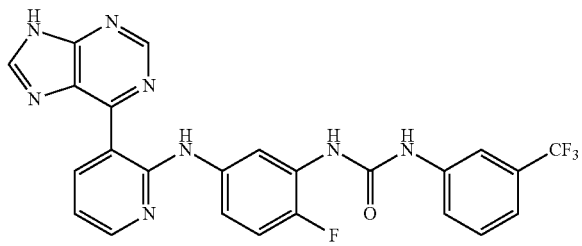

The title compound was synthesized in the same manner as described in Example 2, except that, in step 2 of Example 2, t-butyl 4-fluoro-3-[3-(3-(trifluoromethyl)phenyl)ureido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.84 (s, 1H), 12.36 (s, 1H), 9.74 (d, 1H), 9.43 (s, 1H), 9.09 (s, 1H), 8.70 (s, 1H), 8.62 (s, 1H), 8.43 n (d, 1H), 8.32 (dd, 1H), 8.01 (s, 1H), 7.60-7.48 (m, 3H), 7.32 (d, 1H), 7.20 (q, 1H), 7.00 (q, 1H)

Example 119. Preparation of N-5-[(3-(9H-purin-6-yl)pyridin-2-yl)amino]-2-fluorophenyl-6-(2-cyanopropan-2-yl)picolinamide

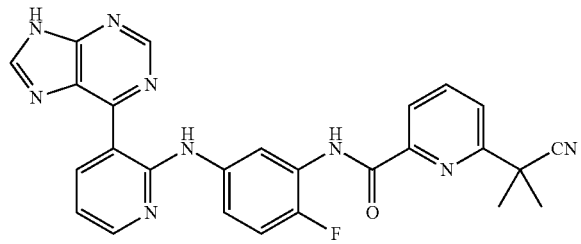 [SMILES: CC(C)(C#N)c1cccc(C(=O)Nc2cc(Nc3ncccc3-c3ncnc4[nH]cnc34)ccc2F)n1]

The title compound was synthesized in the same manner as described in Example 2, except that, in step 2 of Example 2, t-butyl 3-[6-(2-cyanopropan-2-yl)picolinamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.78 (t, 1H), 12.53 (s, 1H), 10.40 (s, 1H), 9.73 (s, 1H), 9.10 (s, 1H), 8.69 (s, 1H), 8.67 (s, 1H), 8.64 (t, 1H), 8.35 (q, 1H), 8.22-8.15 (m, 2H), 7.93 (q, 1H), 7.67-7.63 (m, 1H), 7.30 (dd, 1H), 7.03 (q, 1H), 1.82 (s, 6H)

Example 120. Preparation of N-5-[(3-(9H-purin-6-yl)pyridin-2-yl)amino]-2-fluorophenyl-2-fluoro-5-(trifluoromethyl)benzamide

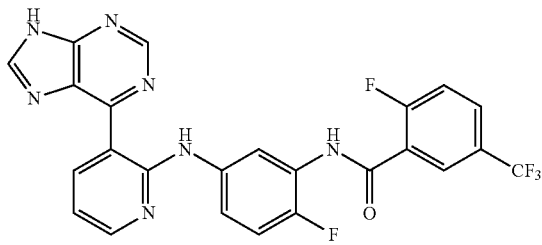 [SMILES: O=C(Nc1cc(Nc2ncccc2-c2ncnc3[nH]cnc23)ccc1F)c1cc(C(F)(F)F)ccc1F]

The title compound was synthesized in the same manner as described in Example 2, except that, in step 2 of Example 2, t-butyl [4-fluoro-3-(2-fluoro-5-(trifluoromethyl)benzamido)phenyl]carbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.80 (s, 1H), 12.55 (s, 1H), 10.41 (s, 1H), 9.72 (s, 1H), 9.08 (s, 1H), 8.67 (s, 1H), 8.33 (q, 1H), 8.29 (d, 1H), 8.09 (d, 1H), 8.01 (m, 1H), 7.70-7.61 (m, 2H), 7.26 (t, 1H), 7.02 (q, 1H)

Example 121. Preparation of N-5-[(3-(9H-purin-6-yl)pyridin-2-yl)amino]-2-fluorophenyl-2-fluoro-3-(trifluoromethyl)benzamide

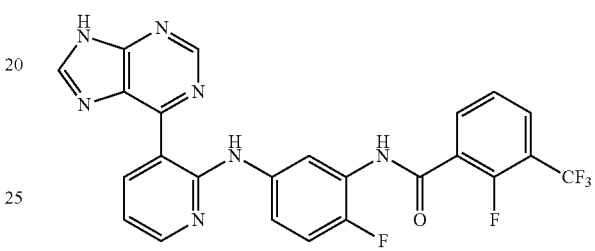

The title compound was synthesized in the same manner as described in Example 2, except that, in step 2 of Example 2, t-butyl [4-fluoro-3-(2-fluoro-3-(trifluoromethyl)benzamido)phenyl]carbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (d, 1H), 12.52 (s, 1H), 10.47 (s, 1H), 9.72 (s, 1H), 9.10 (s, 1H), 8.69 (s, 1H), 8.34 (q, 1H), 8.27 (d, 1H), 8.02 (t, 1H), 7.96 (t, 1H), 7.66 (m, 1H), 7.53 (t, 1H), 7.26 (t, 1H), 7.04 (q, 1H)

Example 122: Preparation of N-3-[(3-(9H-purin-6-yl)pyridin-2-yl)amino]-2-fluorophenyl-3-(trifluoromethyl)benzamide

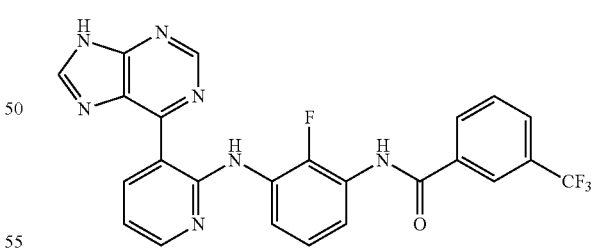

The title compound was synthesized in the same manner as described in Example 2, except that, in step 2 of Example 2, t-butyl 2-fluoro-3-[3-(trifluoromethyl)benzamido]phenylcarbamate was used instead of t-butyl-2,6-difluoro-3-(3-(4-methyl-1H-imidazol-1-yl)-5-(trifluoromethyl)benzamido) phenylcarbamate.

$^1$H NMR (400 MHz, DMSO-d$_6$): δ 13.83 (d, 1H), 12.89 (s, 1H), 10.48 (s, 1H), 9.83 (s, 1H), 9.01 (s, 1H), 8.71 (s, 1H), 8.58 (m, 1H), 8.42 (q, 1H), 8.36 (s, 1H), 8.31 (d, 1H), 8.00 (d, 1H), 7.79 (t, 1H), 7.18 (m, 2H), 7.11 (q, 1H)

Example 123. Preparation of 1-5-[(3-(9H-purin-6-yl)pyridin-2-yl)amino]-2-fluorophenyl-3-[4-(trifluoromethyl)phenyl]urea

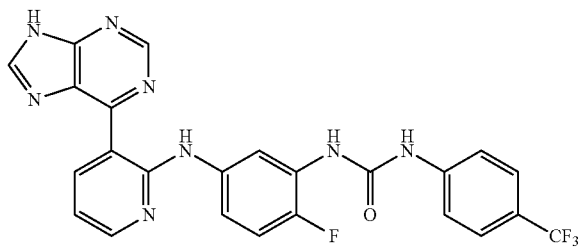 [SMILES: O=C(Nc1ccc(C(F)(F)F)cc1)Nc1cc(Nc2ncccc2-c2ncnc3[nH]cnc23)ccc1F]

The title compound was synthesized in the same manner as described in Example 2, except that, in step 2 of Example 2, t-butyl 4-fluoro-3-[3-(3-(trifluoromethyl)phenyl)ureido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.84 (s, 1H), 12.36 (s, 1H), 9.74 (d, 1H), 9.43 (s, 1H), 9.09 (s, 1H), 8.70 (s, 1H), 8.62 (s, 1H), 8.43 (d, 1H), 8.32 (dd, 1H), 8.01 (s, 1H), 7.60-7.48 (m, 3H), 7.20 (m, 2H), 7.00 (q, 1H)

Example 124. Preparation of N-5-[(3-(9H-purin-6-yl)pyridin-2-yl)amino]-2-chlorophenyl-3,5-bis(trifluoromethyl)benzamide

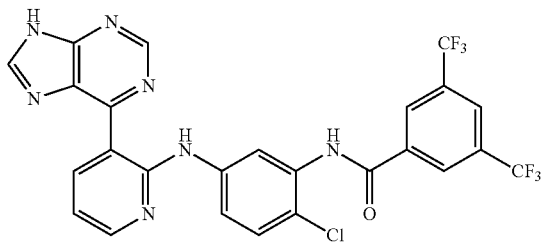

The title compound was synthesized in the same manner as described in Example 2, except that, in step 2 of Example 2, t-butyl 4-chloro-3-[3,5-bis(trifluoromethyl)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.83 (d, 1H), 12.73 (s, 1H), 10.70 (s, 1H), 9.73 (s, 1H), 9.12 (s, 1H), 8.71 (s, 1H), 8.66 (s, 2H), 8.42 (s, 1H), 8.38 (q, 1H), 8.17 (d, 1H), 7.84 (q, 1H), 7.51 (d, 1H), 7.07 (q, 1H)

Example 125. Preparation of N-5-[(3-(9H-purin-6-yl)pyridin-2-yl)amino]-2-fluorophenyl-3-(methylthio)benzamide

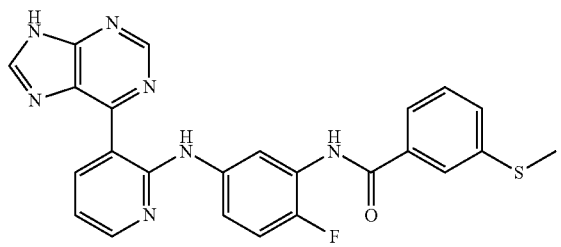 [SMILES: CSc1cccc(C(=O)Nc2cc(Nc3ncccc3-c3ncnc4[nH]cnc34)ccc2F)c1]

The title compound was synthesized in the same manner as described in Example 2, except that, in step 2 of Example 2, t-butyl 4-fluoro-3-[3-(methylthio)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.82 (s, 1H), 12.56 (s, 1H), 10.19 (s, 1H), 9.73 (s, 1H), 9.10 (s, 1H), 8.68 (s, 1H), 8.34 (q, 2H), 8.07 (t, 1H), 7.86 (s, 1H), 7.75 (d, 1H), 7.68 (t, 1H), 7.45 (m, 2H), 7.24 (t, 1H), 7.02 (q, 1H), 2.60 (s, 3H)

Example 126. Preparation of N-5-[(3-(9H-purin-6-yl)pyridin-2-yl)amino]-2-fluorophenyl-3-(methylsulfonyl)benzamide

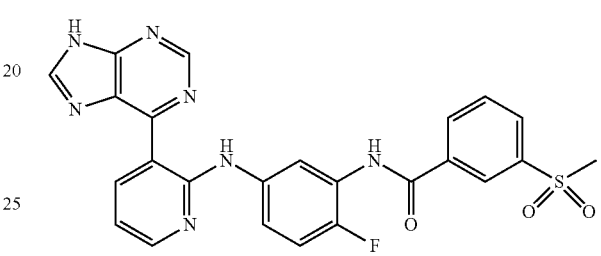

The title compound was synthesized in the same manner as described in Example 2, except that, in step 2 of Example 2, t-butyl 4-fluoro-3-[3-(methylsulfonyl)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.82 (s, 1H), 12.56 (s, 1H), 10.50 (s, 1H), 9.75 (s, 1H), 9.10 (s, 1H), 8.68 (s, 1H), 8.54 (q, 2H), 8.32 (m, 2H), 8.17-8.12 (m, 2H), 7.83 (t, 1H), 7.70 (m, 1H), 7.27 (t, 2H), 7.03 (q, 1H), 1.35 (s, 3H)

Example 127. Preparation of N-5-[(3-(9H-purin-6-yl)pyridin-2-yl)amino]-2-chlorophenyl-3-(2-cyanopropan-2-yl)-5-fluorobenzamide

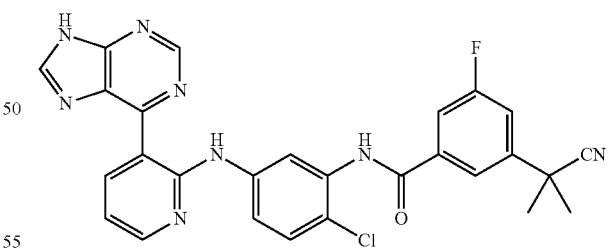

The title compound was synthesized in the same manner as described in Example 2, except that, in step 2 of Example 2, t-butyl 3-[3-(2-cyanopropan-2-yl)-5-fluorobenzamido]-4-chlorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-$d_6$): δ 13.85 (s, 1H), 12.70 (s, 1H), 10.39 (s, 1H), 9.73 (d, 1H), 9.14 (s, 1H), 8.72 (s, 1H), 8.38 (q, 1H), 8.13 (d, 1H), 8.04 (s, 1H), 7.86-7.83 (m, 2H), 7.65 (d, 1H), 7.50 (d, 1H), 7.07 (q, 1H), 1.77 (s, 6H)

Example 128. Preparation of N-5-[(3-(9H-purin-6-yl)pyridin-2-yl)amino]-2-fluorophenyl-2,4-bis(trifluoromethyl)benzamide

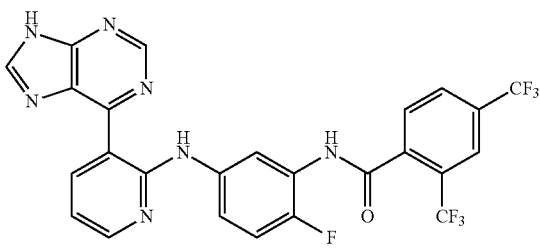 [SMILES: O=C(Nc1cc(Nc2ncccc2-c2ncnc3[nH]cnc23)ccc1F)c1ccc(C(F)(F)F)cc1C(F)(F)F]

The title compound was synthesized in the same manner as described in Example 2, except that, in step 2 of Example 2, t-butyl 3-[2,4-bis(trifluoromethyl)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (d, 1H), 12.43 (s, 1H), 10.56 (s, 1H), 9.71 (s, 1H), 9.10 (s, 1H), 8.70 (s, 1H), 8.33 (q, 1H), 8.28 (dd, 1H), 8.22 (d, 1H), 8.20 (s, 1H), 7.99 (d, 1H), 7.85 (m, 1H), 7.26 (t, 1H), 7.03 (q, 1H)

Example 129. Preparation of N-5-[(3-(9H-purin-6-yl)pyridin-2-yl)amino]-2-fluorophenyl-3,4-bis(trifluoromethyl)benzamide

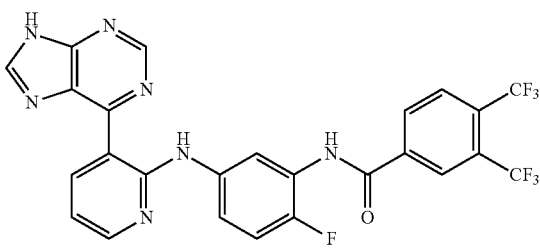

The title compound was synthesized in the same manner as described in Example 2, except that, in step 2 of Example 2, t-butyl 3-[3,4-bis(trifluoromethyl)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.81 (d, 1H), 12.57 (s, 1H), 10.69 (s, 1H), 9.75 (s, 1H), 9.11 (s, 1H), 8.70 (s, 1H), 8.45 (d, 1H), 8.34 (dd, 1H), 8.26 (d, 1H), 8.16 (dd, 1H), 7.70 (m, 1H), 7.28 (t, 1H), 7.03 (q, 1H)

Example 130. Preparation of N-5-[(3-(9H-purin-6-yl)pyridin-2-yl)amino]-2-fluorophenyl-2,5-bis(trifluoromethyl)benzamide

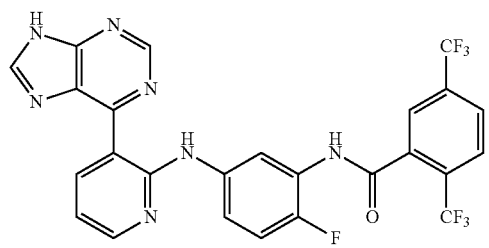 [SMILES: O=C(Nc1cc(Nc2ncccc2-c2ncnc3[nH]cnc23)ccc1F)c1cc(C(F)(F)F)ccc1C(F)(F)F]

The title compound was synthesized in the same manner as described in Example 2, except that, in step 2 of Example 2, t-butyl 3-[2,5-bis(trifluoromethyl)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.84 (d, 1H), 12.45 (s, 1H), 10.58 (s, 1H), 9.72 (s, 1H), 9.10 (s, 1H), 8.71 (s, 1H), 8.33 (dd, 1H), 8.28 (d, 1H), 8.17 (s, 1H), 8.12 (s, 2H), 7.67 (m, 1H), 7.26 (t, 1H), 7.03 (q, 1H)

Example 131. Preparation of N-5-[(3-(9H-purin-6-yl)pyridin-2-yl)amino]-2-fluorophenyl-3-(trifluoromethoxy)benzamide

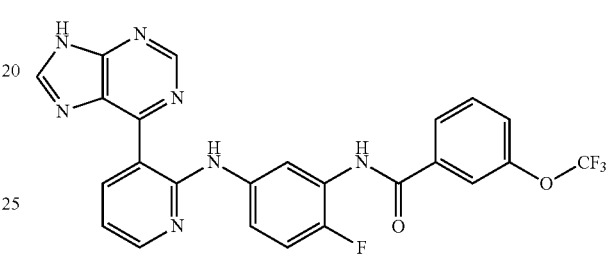

The title compound was synthesized in the same manner as described in Example 2, except that, in step 2 of Example 2, t-butyl 4-fluoro-3-[3-(trifluoromethoxy)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (d, 1H), 12.55 (s, 1H), 10.36 (s, 1H), 9.72 (s, 1H), 9.11 (d, 1H), 8.70 (s, 1H), 8.35 (dd, 1H), 8.09 (dd, 1H), 8.06 (d, 1H), 7.96 (s, 1H), 7.68 (t, 2H), 7.63 (d, 1H), 7.26 (t, 1H), 7.02 (q, 1H)

Example 132. Preparation of N-5-[(3-(9H-purin-6-yl)pyridin-2-yl)amino]-2-fluorophenyl-3,5-dimethoxybenzamide

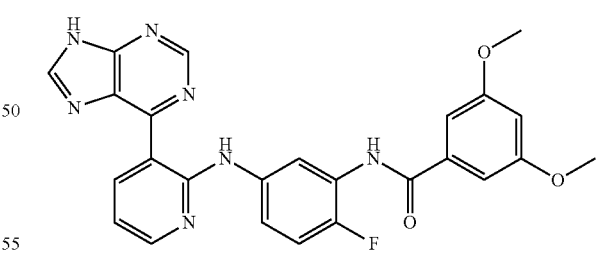

The title compound was synthesized in the same manner as described in Example 2, except that, in step 2 of Example 2, t-butyl [3-(3,5-dimethoxybenzamido)-4-fluorophenyl]carbamate was used instead of t-butyl-2,6-difluoro-3-(3-(4-methyl-1H-imidazol-1-yl)-5-(trifluoromethyl)benzamido) phenylcarbamate.

$^1$H NMR (400 MHz, DMSO-d$_6$): δ 13.82 (d, 1H), 12.54 (s, 1H), 10.12 (s, 1H), 9.73 (s, 1H), 9.12 (d, 1H), 8.72 (s, 1H), 8.34 (dd, 1H), 8.04 (dd, 1H), 7.67 (m, 1H), 7.26 (t, 1H), 7.17 (d, 2H), 7.04 (q, 1H), 6.72 (t, 1H), 3.83 (s, 6H).

Example 133. Preparation of N-5-[(3-(9H-purin-6-yl)pyridin-2-yl)amino]-2-fluorophenyl-3-fluoro-4-(trifluoromethyl)benzamide

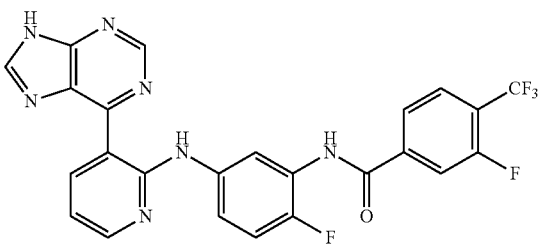 [SMILES: O=C(Nc1cc(Nc2ncccc2-c2ncnc3[nH]cnc23)ccc1F)c1ccc(C(F)(F)F)c(F)c1]

The title compound was synthesized in the same manner as described in Example 2, except that, in step 2 of Example 2, t-butyl 4-fluoro-3-[3-fluoro-4-(trifluoromethyl)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (s, 1H), 12.55 (s, 1H), 10.51 (s, 1H), 9.73 (s, 1H), 9.12 (d, 1H), 8.72 (s, 1H), 8.34 (dd, 1H), 8.12 (dd, 1H), 8.07 (d, 1H), 8.00 (m, 2H), 7.69 (m, 1H), 7.28 (t, 1H), 7.04 (q, 1H)

Example 134. Preparation of N-5-[(3-(9H-purin-6-yl)pyridin-2-yl)amino]-2-fluorophenyl-4-methoxy-3-(trifluoromethyl)benzamide

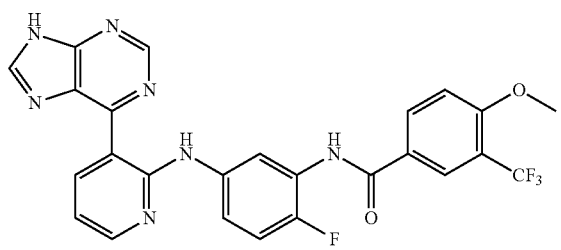 [SMILES: COc1ccc(C(=O)Nc2cc(Nc3ncccc3-c3ncnc4[nH]cnc34)ccc2F)cc1C(F)(F)F]

The title compound was synthesized in the same manner as described in Example 2, except that, in step 2 of Example 2, t-butyl 4-fluoro-3-[4-methoxy-3-(trifluoromethyl)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.84 (s, 1H), 12.55 (s, 1H), 10.28 (s, 1H), 9.74 (s, 1H), 9.11 (d, 1H), 8.70 (s, 1H), 8.34 (dd, 1H), 8.30 (d, 2H), 8.08 (dd, 1H), 7.67 (m, 1H), 7.43 (d, 1H), 7.25 (t, 1H), 7.04 (q, 1H)

Example 135. Preparation of N-5-[(3-(9H-purin-6-yl)pyridin-2-yl)amino]-2-fluorophenyl-3-chloro-5-(trifluoromethyl)benzamide

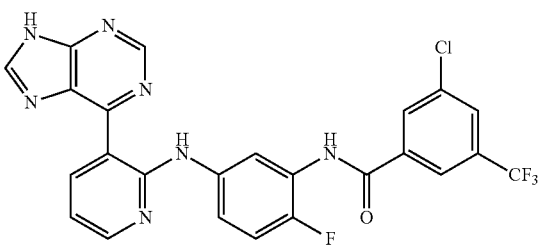

The title compound was synthesized in the same manner as described in Example 2, except that, in step 2 of Example 2, t-butyl 3-[3-chloro-5-(trifluoromethyl)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.83 (s, 1H), 12.58 (s, 1H), 10.56 (s, 1H), 9.73 (s, 1H), 9.11 (s, 1H), 8.70 (s, 1H), 8.36-8.34 (m, 2H), 8.31 (s, 2H), 8.13-8.17 (m, 2H), 7.69 (m, 1H), 7.27 (t, 1H), 7.03 (q, 1H)

Example 136. Preparation of N-5-[(3-(9H-purin-6-yl)pyridin-2-yl)amino]-2-fluorophenyl-6-(trifluoromethyl) picolinamide

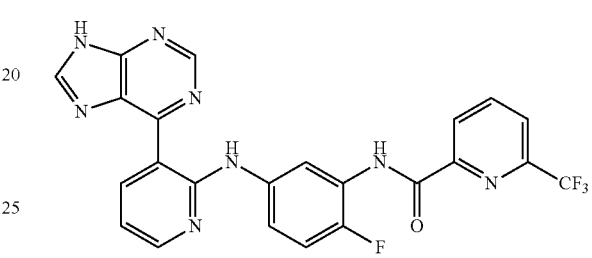

The title compound was synthesized in the same manner as described in Example 2, except that, in step 2 of Example 2, t-butyl 4-fluoro-3-[6-(trifluoromethyl)picolinamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.83 (s, 1H), 12.53 (s, 1H), 10.30 (s, 1H), 9.72 (s, 1H), 9.11 (s, 1H), 8.70 (s, 1H), 8.46 (q, 1H), 8.44 (d, 1H), 8.40 (d, 1H), 8.38-8.35 (m, 1H), 8.22 (d, 1H), 7.66 (m, 1H), 7.30 (t, 1H), 7.03 (q, 1H)

Example 137. Preparation of N-5-[(3-(9H-purin-6-yl)pyridin-2-yl)amino]-2-fluorophenyl-4-fluoro-3-methylbenzamide

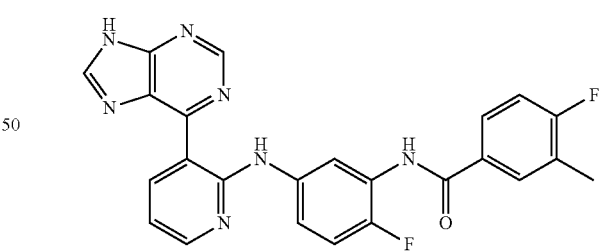

The title compound was synthesized in the same manner as described in Example 2, except that, in step 2 of Example 2, t-butyl [4-fluoro-3-(4-fluoro-3-methylbenzamido)phenyl]carbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (s, 1H), 12.53 (s, 1H), 10.13 (s, 1H), 9.72 (s, 1H), 9.11 (d, 1H), 8.70 (s, 1H), 8.34 (dd, 1H), 8.07 (dd, 1H), 7.96 (d, 1H), 7.88 (m, 1H), 7.67 (m, 1H), 7.33-7.24 (m, 2H), 7.02 (q, 1H), 2.32 (s, 3H)

Example 138. Preparation of N-5-[(3-(9H-purin-6-yl)pyridin-2-yl)amino]-2-fluorophenyl-4-methyl-3-(trifluoromethyl)benzamide

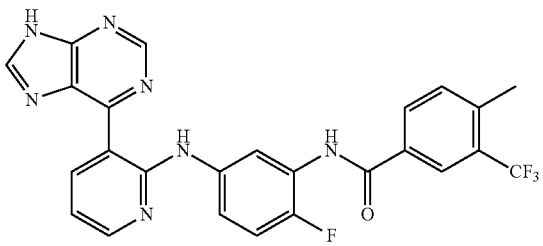 [SMILES: Cc1ccc(C(=O)Nc2cc(Nc3ncccc3-c3ncnc4[nH]cnc34)ccc2F)cc1C(F)(F)F]

The title compound was synthesized in the same manner as described in Example 2, except that, in step 2 of Example 2, t-butyl 4-fluoro-3-[4-methyl-3-(trifluoromethyl)benzamido]phenylcarbamate was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-d$_6$): δ 12.56 (s, 1H), 10.40 (s, 1H), 9.74 (d, 1H), 9.12 (d, 1H), 8.72 (s, 1H), 8.33 (dd, 1H), 8.30 (s, 1H), 8.18 (d, 1H), 8.08 (dd, 1H), 7.67 (m, 1H), 7.63 (d, 1H), 7.28 (t, 1H), 7.05 (q, 1H), 2.50 (s, 3H)

Example 139. Preparation of N-5-[(3-(9H-purin-6-yl)pyridin-2-yl)amino]-2-fluorophenyl-3-methyl-5-(trifluoromethyl)benzamide

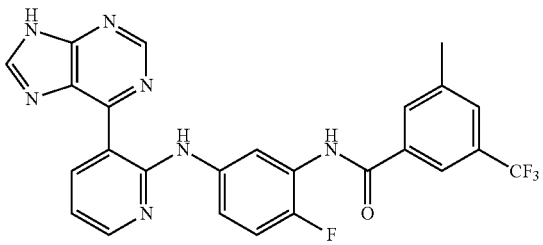 [SMILES: Cc1cc(C(=O)Nc2cc(Nc3ncccc3-c3ncnc4[nH]cnc34)ccc2F)cc(C(F)(F)F)c1]

The title compound was synthesized in the same manner as described in Example 2, except that, in step 2 of Example 2, t-butyl 4-fluoro-3-[3-methyl-5-(trifluoromethyl)benzamido]phenylcarbamate was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-d$_6$): δ 13.81 (s, 1H), 12.57 (s, 1H), 10.39 (s, 1H), 9.74 (s, 1H), 9.11 (s, 1H), 8.70 (s, 1H), 8.34 (q, 1H), 8.13-8.10 (m, 3H), 7.82 (s, 1H), 7.69 (m, 1H), 7.26 (t, 1H), 7.03 (q, 1H), 2.49 (s, 3H)

Example 140. Preparation of N-5-[(3-(9H-purin-6-yl)pyridin-2-yl)amino]-2-fluorophenyl-3-methoxy-5-(trifluoromethoxy)benzamide

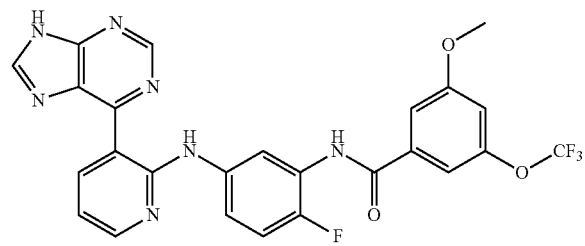 [SMILES: COc1cc(OC(F)(F)F)cc(C(=O)Nc2cc(Nc3ncccc3-c3ncnc4[nH]cnc34)ccc2F)c1]

The title compound was synthesized in the same manner as described in Example 2, except that, in step 2 of Example 2, t-butyl 4-fluoro-3-[3-methoxy-5-(trifluoromethoxy)benzamido]phenylcarbamate was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-d$_6$): δ 12.58 (s, 1H), 10.37 (s, 1H), 9.75 (d, 1H), 9.12 (s, 1H), 8.73 (s, 1H), 8.32 (q, 1H), 8.05 (t, 1H), 7.68 (t, 1H), 7.64 (s, 1H), 7.54 (s, 1H), 7.29 (t, 1H), 7.21 (s, 1H), 7.06 (q, 1H), 3.90 (s, 3H)

Example 141. Preparation of N-5-[(3-(9H-purin-6-yl)pyridin-2-yl)amino]-2-fluorophenyl-3-cyclopropylbenzamide

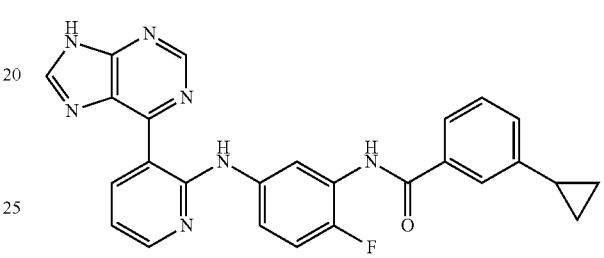

The title compound was synthesized in the same manner as described in Example 2, except that, in step 2 of Example 2, t-butyl [3-(3-cyclopropyl benzamido)-4-fluorophenyl] carbamate was used instead of t-butyl-2,6-difluoro-3-(3-(4-methyl-1H-imidazol-1-yl)-5-(trifluoromethyl)benzamido) phenylcarbamate.
$^1$H NMR (400 MHz, DMSO-d$_6$): δ 12.56 (s, 1H), 10.13 (s, 1H), 9.74 (d, 1H), 9.12 (s, 1H), 8.73 (s, 1H), 8.32 (q, 1H), 8.04 (dd, 1H), 7.75 (d, 1H), 7.68-7.65 (m, 2H), 7.33 (d, 1H), 7.27 (t, 1H), 7.05 (q, 1H), 2.06-1.99 (m, 3H), 1.03-0.98 (m, 2H), 0.810-0.76 (m, 1H)

Example 142. Preparation of N-5-[(3-(9H-purin-6-yl)pyridin-2-yl)amino]-2-fluorophenyl-3-chloro-5-(trifluoromethoxy)benzamide

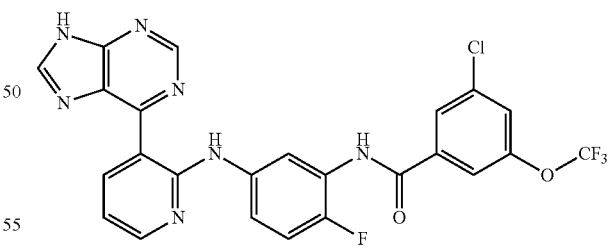

The title compound was synthesized in the same manner as described in Example 2, except that, in step 2 of Example 2, t-butyl 3-[3-chloro-5-(trifluoromethoxy)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.
$^1$H NMR (400 MHz, DMSO-d$_6$): δ 13.83 (s, 1H), 12.57 (s, 1H), 10.48 (s, 1H), 9.73 (s, 1H), 9.11 (s, 1H), 8.71 (s, 1H), 8.34 (q, 1H), 8.14 (s, 1H), 8.11 (dd, 1H), 7.94 (s, 1H), 7.88 (s, 1H), 7.69 (m, 1H), 7.27 (t, 1H), 7.03 (q, 1H)

Example 143. Preparation of N-5-[(3-(9H-purin-6-yl)pyridin-2-yl)amino]-2-fluorophenyl-4-fluoro-3-(trifluoromethoxy)benzamide

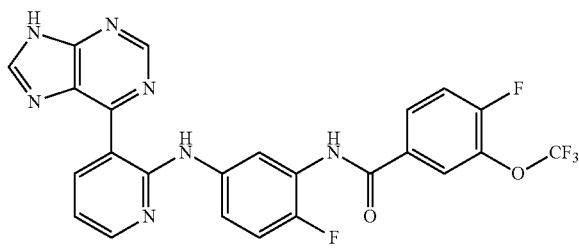 [SMILES: O=C(Nc1cc(Nc2ncccc2-c2ncnc3[nH]cnc23)ccc1F)c1ccc(F)c(OC(F)(F)F)c1]

The title compound was synthesized in the same manner as described in Example 2, except that, in step 2 of Example 2, t-butyl 4-fluoro-3-[4-fluoro-3-(trifluoromethoxy)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.83 (s, 1H), 12.57 (s, 1H), 10.40 (s, 1H), 9.74 (s, 1H), 9.11 (s, 1H), 8.71 (s, 1H), 8.34 (q, 1H), 8.19-8.10 (m, 4H), 7.75-7.69 (m, 2H), 7.27 (t, 1H), 7.03 (q, 1H)

Example 144. Preparation of N-5-[(3-(9H-purin-6-yl)pyridin-2-yl)amino]-2-fluorophenyl-4-(trifluoromethyl) picolinamide

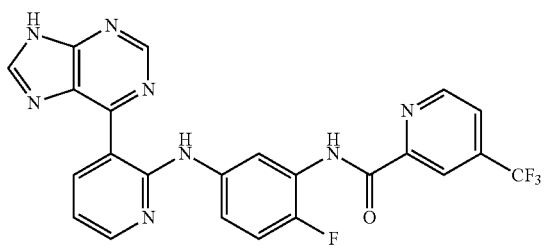 [SMILES: O=C(Nc1cc(Nc2ncccc2-c2ncnc3[nH]cnc23)ccc1F)c1cc(C(F)(F)F)ccn1]

The title compound was synthesized in the same manner as described in Example 2, except that, in step 2 of Example 2, t-butyl 4-fluoro-3-[4-(trifluoromethyl)picolinamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.83 (s, 1H), 12.53 (s, 1H), 10.50 (s, 1H), 9.72 (s, 1H), 9.10 (s, 1H), 9.06 (d, 1H), 8.70 (s, 1H), 8.52 (d, 1H), 8.39 (s, 1H), 8.35 (d, 1H), 8.13 (d, 1H), 7.66 (m, 1H), 7.30 (t, 1H), 7.03 (q, 1H)

Example 145. Preparation of N-5-[(3-(9H-purin-6-yl)pyridin-2-yl)amino]-2-fluorophenyl-3-methylbenzamide

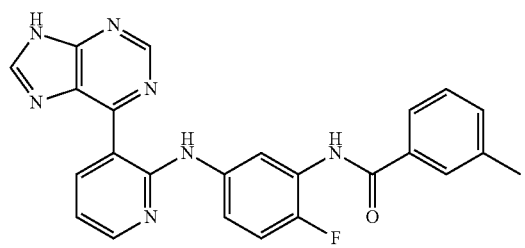 [SMILES: Cc1cccc(C(=O)Nc2cc(Nc3ncccc3-c3ncnc4[nH]cnc34)ccc2F)c1]

The title compound was synthesized in the same manner as described in Example 2, except that, in step 2 of Example 2, t-butyl [4-fluoro-3-(3-methylbenzamido)phenyl]carbamate was used instead of t-butyl-2,6-difluoro-3-(3-(4-methyl-1H-imidazol-1-yl)-5-(trifluoromethyl)benzamido)phenyl-carbamate.

$^1$H NMR (400 MHz, DMSO-d$_6$): δ 13.83 (s, 1H), 12.53 (s, 1H), 10.10 (s, 1H), 9.72 (s, 1H), 9.11 (s, 1H), 8.70 (s, 1H), 8.34 (q, 1H), 8.07 (dd, 1H), 7.83 (s, 1H), 7.79 (t, 1H), 7.67 (m, 1H), 7.42 (d, 2H), 7.24 (t, 1H), 7.02 (q, 1H), 2.41 (s, 3H).

Example 146. Preparation of N-5-[(3-(9H-purin-6-yl)pyridin-2-yl)amino]-2-fluorophenyl-3-chlorobenzamide

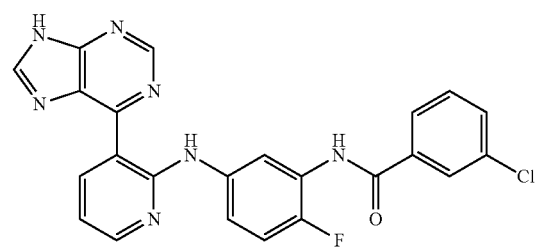 [SMILES: O=C(Nc1cc(Nc2ncccc2-c2ncnc3[nH]cnc23)ccc1F)c1cccc(Cl)c1]

The title compound was synthesized in the same manner as described in Example 2, except that, in step 2 of Example 2, t-butyl [3-(3-chlorobenzamido)-4-fluorophenyl]carbamate was used instead of t-butyl-2,6-difluoro-3-(3-(4-methyl-1H-imidazol-1-yl)-5-(trifluoromethyl)benzamido)phenyl-carbamate.

$^1$H NMR (400 MHz, DMSO-d$_6$): δ 12.54 (s, 1H), 10.38 (s, 1H), 9.74 (s, 1H), 9.11 (s, 1H), 8.71 (s, 1H), 8.34 (q, 1H), 8.09-8.06 (m, 2H), 7.97 (d, 1H), 7.72-7.68 (m, 2H), 7.56 (t, 1H), 7.26 (t, 1H), 7.03 (q, 1H)

Example 147. Preparation of N-5-[(3-(9H-purin-6-yl)pyridin-2-yl)amino]-2-fluorophenyl-4-chloro-3-(trifluoromethoxy)benzamide

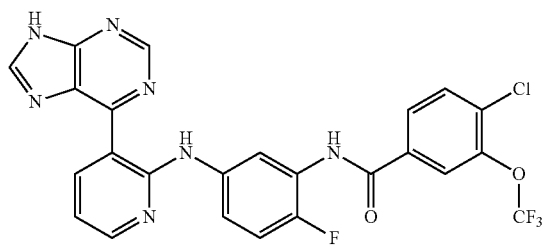 [SMILES: O=C(Nc1cc(Nc2ncccc2-c2ncnc3[nH]cnc23)ccc1F)c1ccc(Cl)c(OC(F)(F)F)c1]

The title compound was synthesized in the same manner as described in Example 2, except that, in step 2 of Example 2, t-butyl 3-[4-chloro-3-(trifluoromethoxy)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 12.57 (s, 1H), 10.46 (s, 1H), 9.72 (s, 1H), 9.11 (s, 1H), 8.70 (s, 1H), 8.34 (q, 1H), 8.14-8.08 (m, 3H), 7.91 (d, 1H), 7.69 (m, 1H), 7.27 (t, 1H), 7.03 (q, 1H)

Example 148. Preparation of N-5-[(3-(9H-purin-6-yl)pyridin-2-yl)amino]-2-fluorophenyl-3-fluoro-2-(trifluoromethyl)isonicotinamide

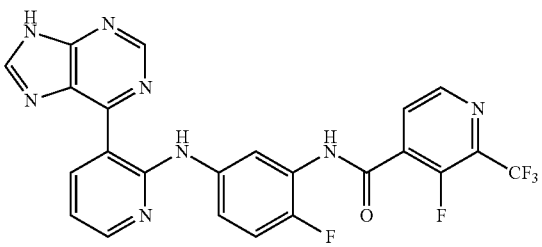 [SMILES: O=C(Nc1cc(Nc2ncccc2-c2ncnc3[nH]cnc23)ccc1F)c1ccnc(C(F)(F)F)c1F]

The title compound was synthesized in the same manner as described in Example 2, except that, in step 2 of Example 2, t-butyl 4-fluoro-3-[3-fluoro-2-(trifluoromethyl)isonicotinamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.86 (s, 1H), 12.54 (s, 1H), 10.72 (s, 1H), 9.76 (s, 1H), 9.11 (s, 1H), 8.75 (d, 1H), 8.72 (s, 1H), 8.36 (q, 1H), 8.34 (t, 1H), 8.11 (t, 1H), 7.65 (m, 1H), 7.29 (t, 1H), 7.04 (q, 1H)

Example 149. Preparation of N-5-[(3-(9H-purin-6-yl)pyridin-2-yl)amino]-2-fluorophenyl-5-(trifluoromethyl)nicotinamide

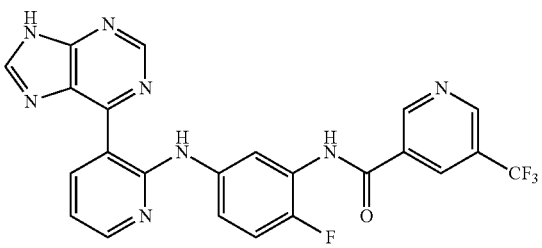 [SMILES: O=C(Nc1cc(Nc2ncccc2-c2ncnc3[nH]cnc23)ccc1F)c1cncc(C(F)(F)F)c1]

The title compound was synthesized in the same manner as described in Example 2, except that, in step 2 of Example 2, t-butyl 4-fluoro-3-[5-(trifluoromethyl)nicotinamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 12.57 (s, 1H), 10.70 (s, 1H), 9.74 (s, 1H), 9.42 (s, 1H), 9.21 (s, 1H), 9.11 (s, 1H), 8.75 (s, 1H), 8.71 (s, 1H), 8.34 (q, 1H), 8.17 (dd, 1H), 7.69 (m, 1H), 7.28 (t, 1H), 7.03 (q, 1H)

Example 150. Preparation of N-5-[(3-(9H-purin-6-yl)pyridin-2-yl)amino]-2-fluorophenyl-4-methoxy-3-(trifluoromethoxy)benzamide

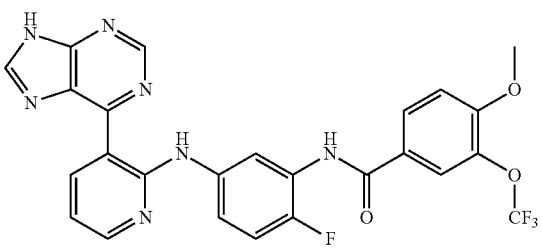

The title compound was synthesized in the same manner as described in Example 2, except that, in step 2 of Example 2, t-butyl 4-fluoro-3-[4-methoxy-3-(trifluoromethoxy)benzamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.85 (s, 1H), 12.60 (s, 1H), 10.21 (s, 1H), 9.77 (s, 1H), 9.12 (s, 1H), 8.71 (s, 1H), 8.35 (q, 1H), 8.12-8.06 (m, 2H), 8.01 (s, 1H), 7.68 (m, 1H), 7.40 (d, 1H), 7.25 (t, 1H), 7.03 (q, 1H), 3.96 (s, 3H)

Example 151. Preparation of N-5-[(3-(9H-purin-6-yl)pyridin-2-yl)amino]-2-fluorophenyl-2-(trifluoromethyl)isonicotinamide

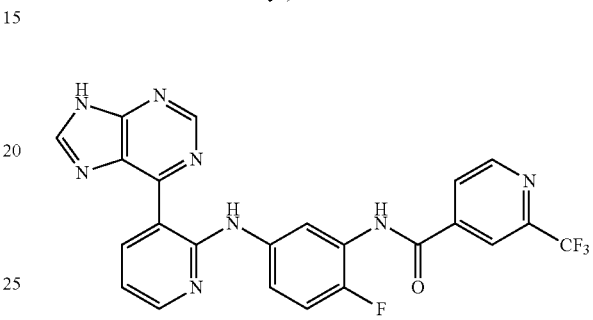

The title compound was synthesized in the same manner as described in Example 2, except that, in step 2 of Example 2, t-butyl 4-fluoro-3-[2-(trifluoromethyl)isonicotinamido]phenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.83 (s, 1H), 12.58 (s, 1H), 10.72 (s, 1H), 9.72 (s, 1H), 9.11 (d, 1H), 9.01 (d, 1H), 8.70 (s, 1H), 8.41 (s, 1H), 8.34 (q, 1H), 8.23 (d, 1H), 8.18 (q, 1H), 7.70 (m, 1H), 7.29 (t, 1H), 7.03 (q, 1H)

Example 152. Preparation of N-3-[(3-(9H-purin-6-yl)pyridin-2-yl)amino]-4-methoxyphenyl-3-(2-cyanopropan-2-yl)benzamide

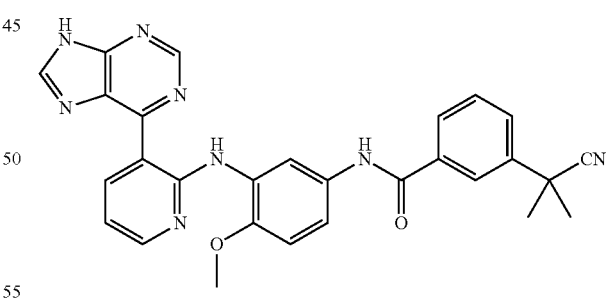

The title compound was synthesized in the same manner as described in Example 2, except that, in step 2 of Example 2, t-butyl 5-[3-(2-cyanopropan-2-yl)benzamido]-2-methoxyphenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.85 (s, 1H), 12.89 (s, 1H), 10.22 (s, 1H), 9.72 (s, 1H), 9.10 (s, 1H), 9.03 (s, 1H), 8.69 (s, 1H), 8.40 (s, 1H), 8.60 (s, 1H), 7.94 (d, 1H), 7.73 (d, 1H), 7.55 (t, 1H), 7.37 (d, 1H), 7.03 (d, 2H), 4.01 (s, 3H), 1.74 (s, 6H)

Example 153. Preparation of N-3-[(3-(9H-purin-6-yl)pyridin-2-yl)amino]-4-methylphenyl-3-(2-cyanopropan-2-yl)benzamide

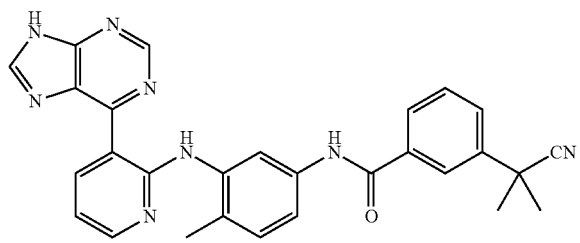 [SMILES: Cc1ccc(NC(=O)c2cccc(C(C)(C)C#N)c2)cc1Nc1ncccc1-c1ncnc2[nH]cnc12]

The title compound was synthesized in the same manner as described in Example 2, except that, in step 2 of Example 2, t-butyl 5-[3-(2-cyanopropan-2-yl)benzamido]-2-methylphenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.85 (s, 1H), 12.31 (s, 1H), 10.27 (s, 1H), 9.81 (s, 1H), 9.08 (s, 1H), 9.03 (s, 1H), 8.72 (s, 1H), 8.63 (d, 1H), 8.33 (q, 1H), 8.04 (d, 1H), 7.94 (d, 1H), 7.73 (dd, 1H), 7.57 (t, 1H), 7.43 (dd, 1H), 7.23 (d, 1H), 7.03 (d, 2H), 2.49 (s, 3H), 1.75 (s, 6H)

Example 154. Preparation of N-5-[(3-(9H-purin-6-yl)pyridin-2-yl)amino]-2-fluorophenyl-3-(2-cyanopropan-2-yl)-5-(trifluoromethyl)benzamide

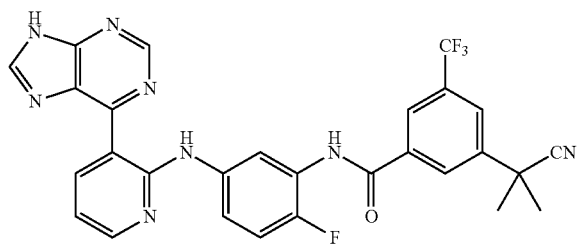 [SMILES: CC(C)(C#N)c1cc(C(=O)Nc2cc(Nc3ncccc3-c3ncnc4[nH]cnc34)ccc2F)cc(C(F)(F)F)c1]

The title compound was synthesized in the same manner as described in Example 2, except that, in step 2 of Example 2, t-butyl 3-[3-(2-cyanopropan-2-yl)-5-(trifluoromethyl)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 12.58 (s, 1H), 10.57 (s, 1H), 9.74 (s, 1H), 9.12 (s, 1H), 8.71 (s, 1H), 8.44 (s, 1H), 8.36-8.35 (m, 2H), 8.13 (dd, 1H), 8.08 (s, 1H), 7.69 (m, 1H), 7.28 (t, 1H), 7.03 (q, 2H)

Example 155. Preparation of N-5-[(3-(9H-purin-6-yl)pyridin-2-yl)amino]-2-fluorophenyl-3-(2-cyanopropan-2-yl)-5-methylbenzamide

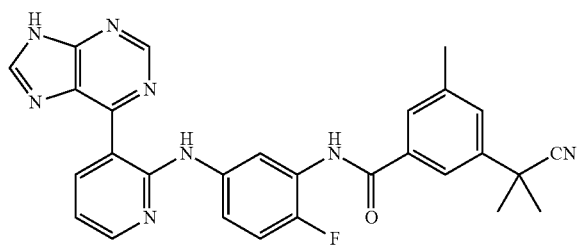 [SMILES: Cc1cc(C(=O)Nc2cc(Nc3ncccc3-c3ncnc4[nH]cnc34)ccc2F)cc(C(C)(C)C#N)c1]

The title compound was synthesized in the same manner as described in Example 2, except that, in step 2 of Example 2, t-butyl 3-[3-(2-cyanopropan-2-yl)-5-methylbenzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.82 (s, 1H), 12.55 (s, 1H), 10.22 (s, 1H), 9.72 (s, 1H), 9.12 (s, 1H), 8.71 (s, 1H), 8.35 (dd, 1H), 8.09 (dd, 1H), 7.92 (s, 1H), 7.82 (s, 1H), 7.69 (m, 1H), 7.59 (s, 1H), 7.25 (t, 1H), 7.02 (q, 2H), 2.45 (s, 3H), 1.87 (s, 6H)

Example 156. Preparation of N-5-[(3-(9H-purin-6-yl)pyridin-2-yl)amino]-2-fluorophenyl-2-bromo-3-(2-cyanopropan-2-yl)-5-methoxybenzamide

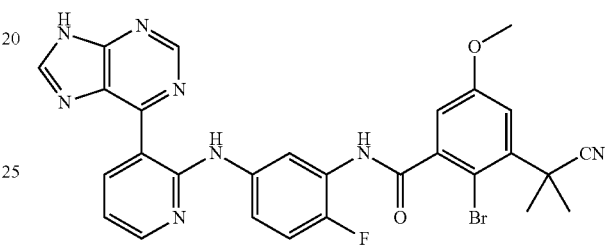

The title compound was synthesized in the same manner as described in Example 2, except that, in step 2 of Example 2, t-butyl 3-[2-bromo-3-(2-cyanopropan-2-yl)-5-methoxybenzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.83 (s, 1H), 12.42 (s, 1H), 10.38 (s, 1H), 9.70 (s, 1H), 9.09 (d, 1H), 8.70 (s, 1H), 8.34 (dd, 1H), 8.27 (dd, 1H), 7.66 (m, 1H), 7.24 (t, 1H), 7.16 (d, 1H), 7.13 (d, 1H), 7.03 (q, 2H), 3.87 (s, 3H)

Example 157. Preparation of N-5-[(3-(9H-purin-6-yl)pyridin-2-yl)amino]-2-fluorophenyl-3-cyano-5-(trifluoromethyl)benzamide

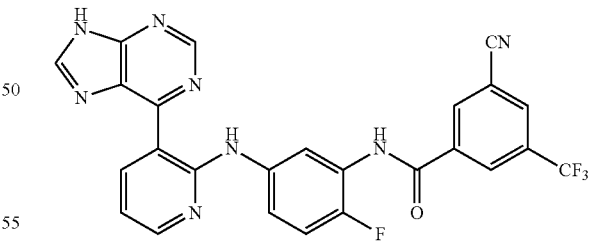

The title compound was synthesized in the same manner as described in Example 2, except that, in step 2 of Example 2, t-butyl 3-[3-cyano-5-(trifluoromethyl)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.83 (s, 1H), 12.58 (s, 1H), 10.56 (s, 1H), 9.73 (s, 1H), 9.11 (s, 1H), 8.70 (s, 1H), 8.36-8.34 (m, 2H), 8.31 (s, 2H), 8.13-8.17 (m, 2H), 7.69 (m, 1H), 7.27 (t, 1H), 7.03 (q, 1H)

Example 158. Preparation of N-5-[(3-(9H-purin-6-yl)pyridin-2-yl)amino]-2-fluorophenyl-3-bromo-5-(trifluoromethyl)benzamide

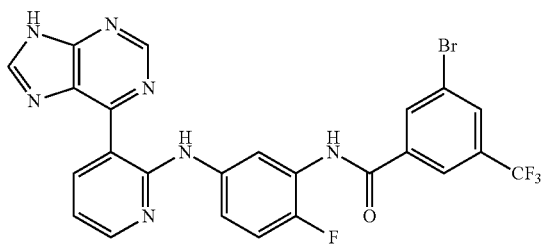

The title compound was synthesized in the same manner as described in Example 2, except that, in step 2 of Example 2, t-butyl 3-[3-bromo-5-(trifluoromethyl)benzamido]-4-fluorophenylcarbamate was used instead of t-butyl-2,6-difluoro-3-(3-(4-methyl-1H-imidazol-1-yl)-5-(trifluoromethyl)benzamido)phenylcarbamate.

$^1$H NMR (400 MHz, DMSO-d$_6$): δ 13.84 (s, 1H), 12.59 (s, 1H), 10.57 (s, 1H), 9.74 (s, 1H), 9.10 (s, 1H), 8.68 (s, 1H), 8.36-8.34 (m, 2H), 8.30 (s, 2H), 8.13-8.17 (m, 2H), 7.68 (m, 1H), 7.27 (t, 1H), 7.02 (q, 1H)

Table 1 below summarizes the structures of the compounds prepared in Examples 1 to 158.

TABLE 1

| Example No. | Structure |
|---|---|
| 1 | 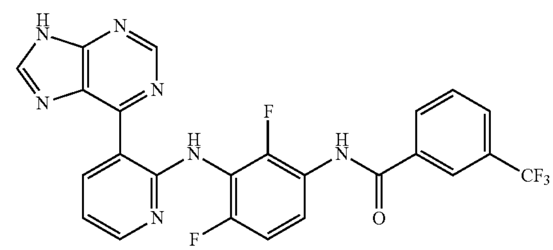 |
| 2 | 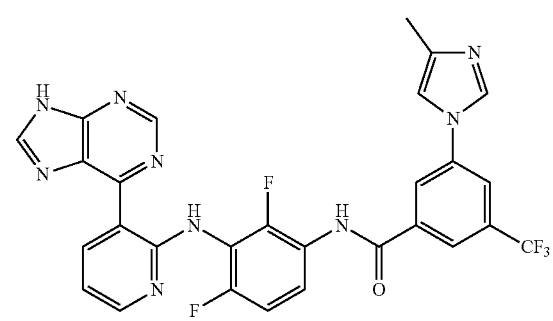 [SMILES: Cc1cn(-c2cc(C(=O)Nc3ccc(F)c(Nc4ncccc4-c4ncnc5[nH]cnc45)c3F)cc(C(F)(F)F)c2)cn1] |
| 3 | 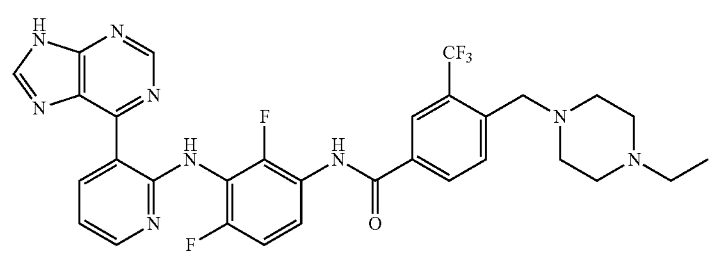 [SMILES: CCN1CCN(Cc2ccc(C(=O)Nc3ccc(F)c(Nc4ncccc4-c4ncnc5[nH]cnc45)c3F)cc2C(F)(F)F)CC1] |
| 4 | 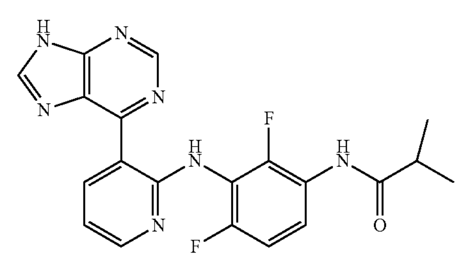 [SMILES: CC(C)C(=O)Nc1ccc(F)c(Nc2ncccc2-c2ncnc3[nH]cnc23)c1F] |

TABLE 1-continued
| Example No. | Structure |
|---|---|
| 5 | 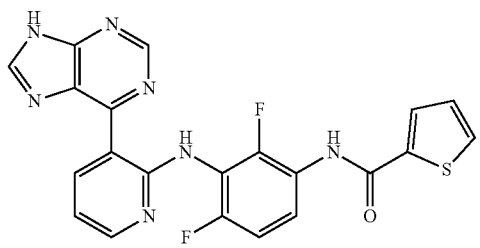 [SMILES: O=C(Nc1ccc(F)c(Nc2ncccc2-c2ncnc3[nH]cnc23)c1F)c1cccs1] |
| 6 | 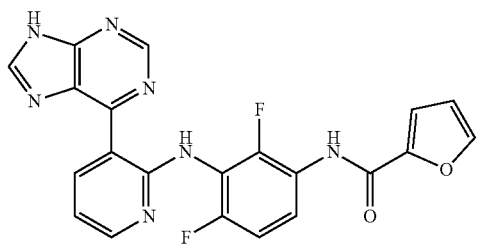 |
| 7 | 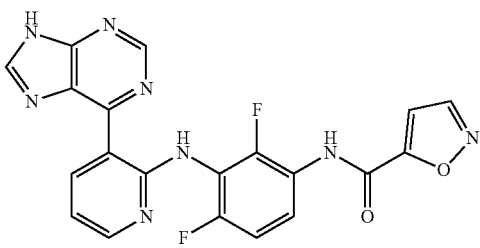 [SMILES: O=C(Nc1ccc(F)c(Nc2ncccc2-c2ncnc3[nH]cnc23)c1F)c1ccno1] |
| 8 | 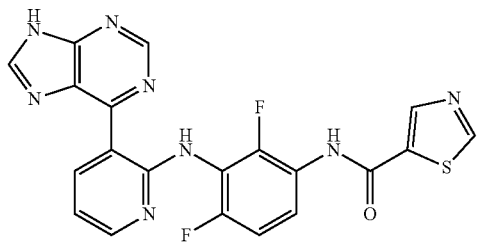 [SMILES: O=C(Nc1ccc(F)c(Nc2ncccc2-c2ncnc3[nH]cnc23)c1F)c1cncs1] |
| 9 | 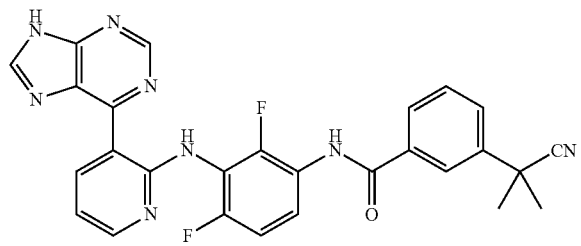 |
| 10 | 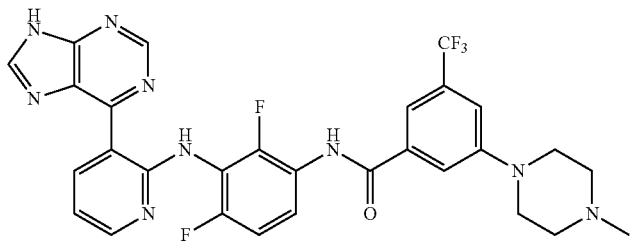 [SMILES: CN1CCN(c2cc(C(=O)Nc3ccc(F)c(Nc4ncccc4-c4ncnc5[nH]cnc45)c3F)cc(C(F)(F)F)c2)CC1] |

TABLE 1-continued
| Example No. | Structure |
|---|---|
| 11 | 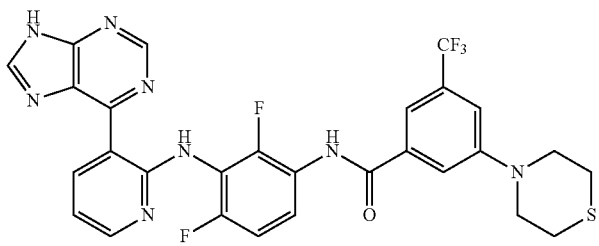 [SMILES: O=C(Nc1ccc(F)c(Nc2ncccc2-c2ncnc3[nH]cnc23)c1F)c1cc(N2CCSCC2)cc(C(F)(F)F)c1] |
| 12 | 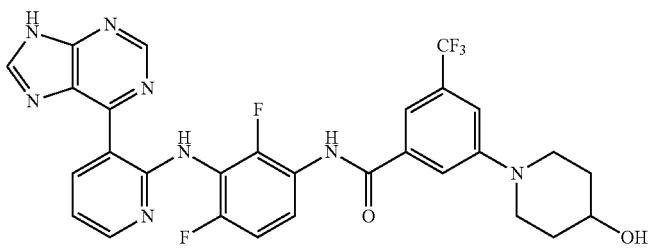 [SMILES: O=C(Nc1ccc(F)c(Nc2ncccc2-c2ncnc3[nH]cnc23)c1F)c1cc(N2CCC(O)CC2)cc(C(F)(F)F)c1] |
| 13 | 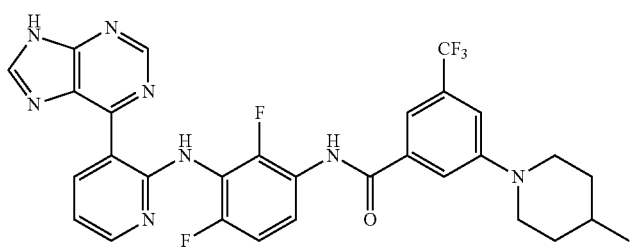 [SMILES: CC1CCN(c2cc(C(=O)Nc3ccc(F)c(Nc4ncccc4-c4ncnc5[nH]cnc45)c3F)cc(C(F)(F)F)c2)CC1] |
| 14 | 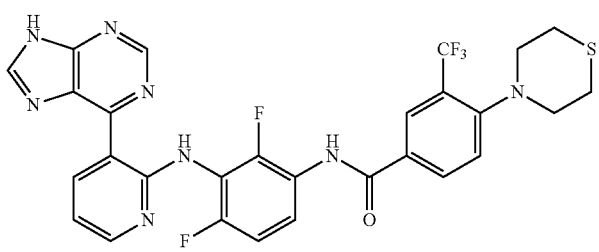 [SMILES: O=C(Nc1ccc(F)c(Nc2ncccc2-c2ncnc3[nH]cnc23)c1F)c1ccc(N2CCSCC2)c(C(F)(F)F)c1] |
| 15 | 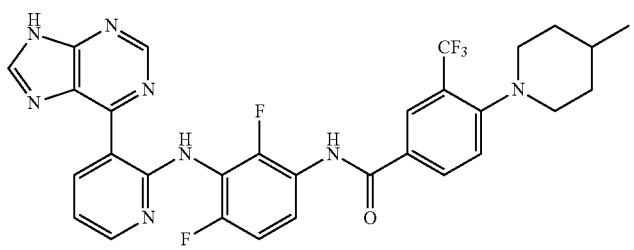 [SMILES: CC1CCN(c2ccc(C(=O)Nc3ccc(F)c(Nc4ncccc4-c4ncnc5[nH]cnc45)c3F)cc2C(F)(F)F)CC1] |
| 16 | 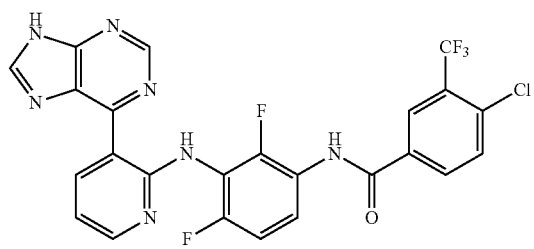 [SMILES: O=C(Nc1ccc(F)c(Nc2ncccc2-c2ncnc3[nH]cnc23)c1F)c1ccc(Cl)c(C(F)(F)F)c1] |

TABLE 1-continued
| Example No. | Structure |
|---|---|
| 17 | 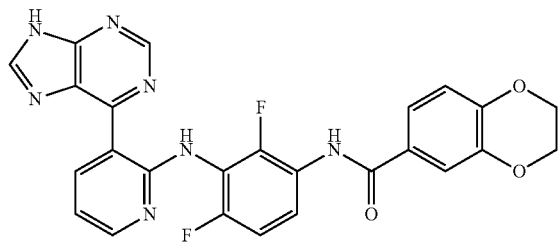 [SMILES: O=C(Nc1ccc(F)c(Nc2ncccc2-c2ncnc3[nH]cnc23)c1F)c1ccc2c(c1)OCCO2] |
| 18 | 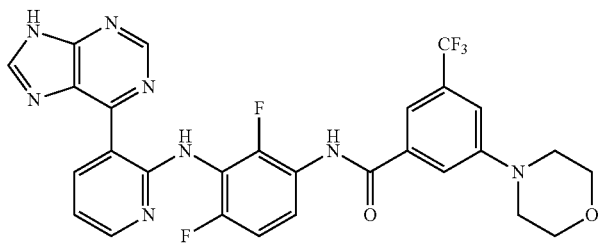 [SMILES: O=C(Nc1ccc(F)c(Nc2ncccc2-c2ncnc3[nH]cnc23)c1F)c1cc(N2CCOCC2)cc(C(F)(F)F)c1] |
| 19 | 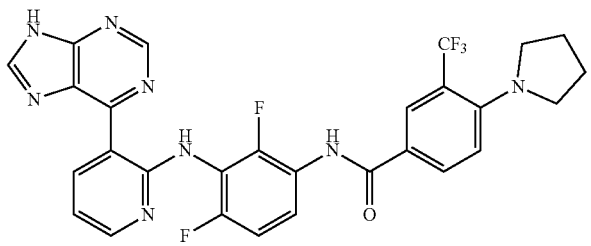 [SMILES: O=C(Nc1ccc(F)c(Nc2ncccc2-c2ncnc3[nH]cnc23)c1F)c1ccc(N2CCCC2)c(C(F)(F)F)c1] |
| 20 | 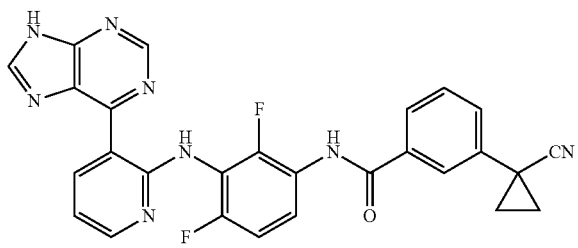 [SMILES: N#CC1(c2cccc(C(=O)Nc3ccc(F)c(Nc4ncccc4-c4ncnc5[nH]cnc45)c3F)c2)CC1] |
| 21 | 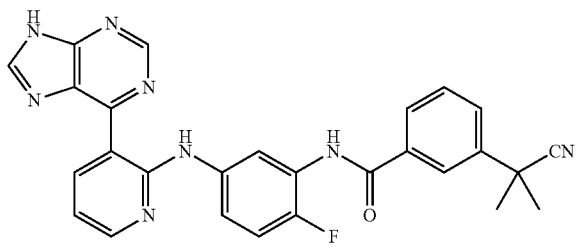 |
| 22 | 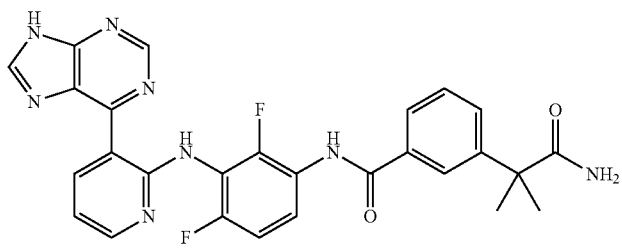 [SMILES: CC(C)(C(N)=O)c1cccc(C(=O)Nc2ccc(F)c(Nc3ncccc3-c3ncnc4[nH]cnc34)c2F)c1] |

TABLE 1-continued

| Example No. | Structure |
|---|---|
| 23 | 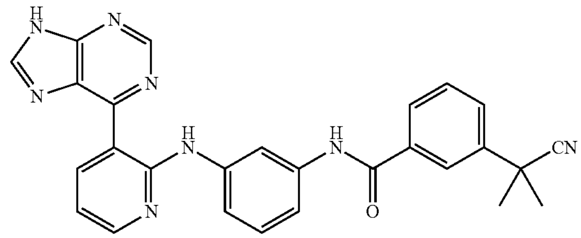 [SMILES: CC(C)(C#N)c1cccc(C(=O)Nc2cccc(Nc3ncccc3-c3ncnc4[nH]cnc34)c2)c1] |
| 24 | 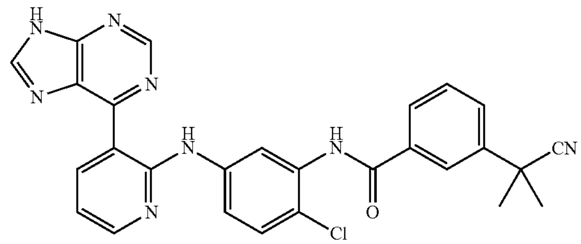 |
| 25 | 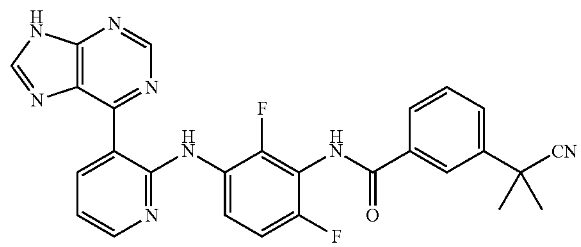 |
| 26 | 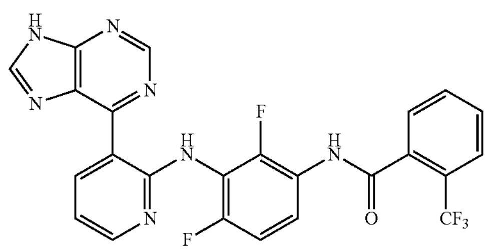 [SMILES: O=C(Nc1ccc(F)c(Nc2ncccc2-c2ncnc3[nH]cnc23)c1F)c1ccccc1C(F)(F)F] |
| 27 | 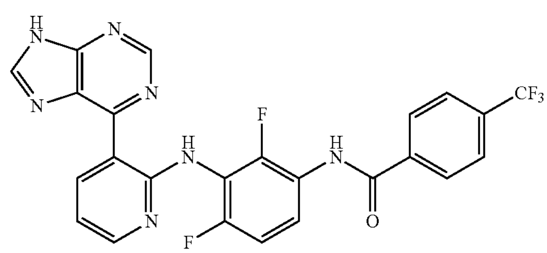 [SMILES: O=C(Nc1ccc(F)c(Nc2ncccc2-c2ncnc3[nH]cnc23)c1F)c1ccc(C(F)(F)F)cc1] |
| 28 | 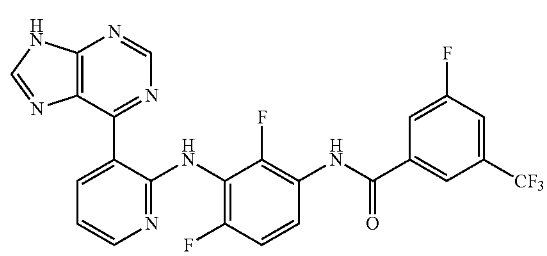 |

TABLE 1-continued
| Example No. | Structure |
|---|---|
| 29 | 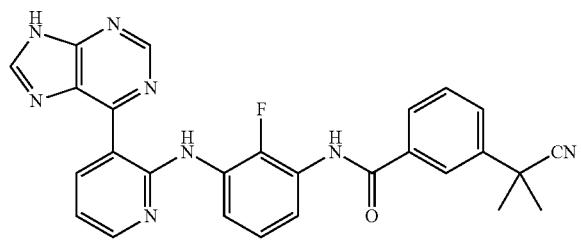 |
| 30 | 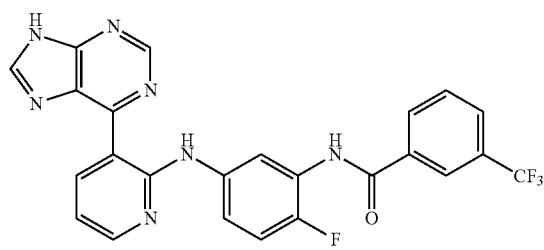 |
| 31 | 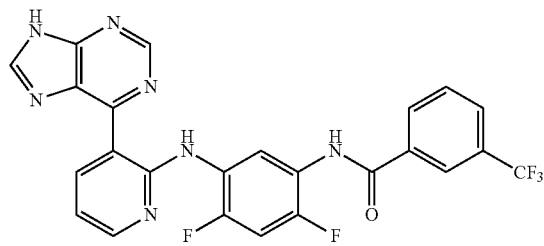 [SMILES: O=C(Nc1cc(Nc2ncccc2-c2ncnc3[nH]cnc23)c(F)cc1F)c1cccc(C(F)(F)F)c1] |
| 32 | 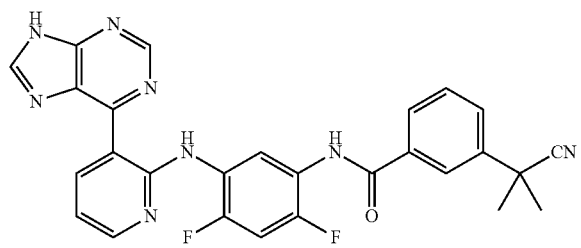 [SMILES: CC(C)(C#N)c1cccc(C(=O)Nc2cc(Nc3ncccc3-c3ncnc4[nH]cnc34)c(F)cc2F)c1] |
| 33 | 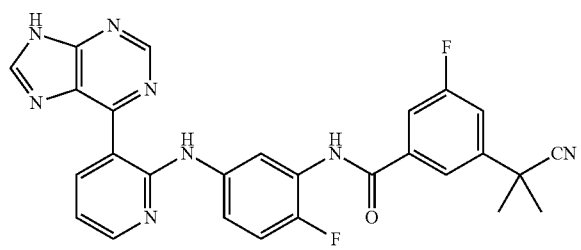 |
| 34 | 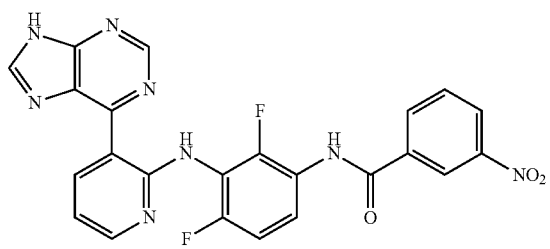 |

TABLE 1-continued

| Example No. | Structure |
|---|---|
| 35 | 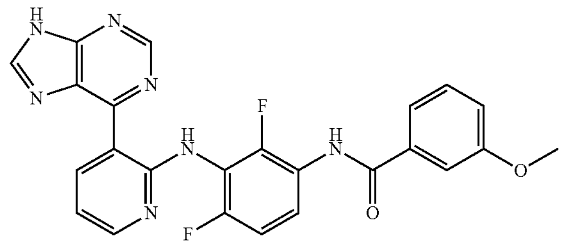 [SMILES: COc1cccc(C(=O)Nc2ccc(F)c(Nc3ncccc3-c3ncnc4[nH]cnc34)c2F)c1] |
| 36 | 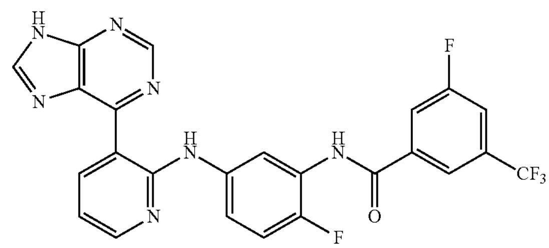 |
| 37 | 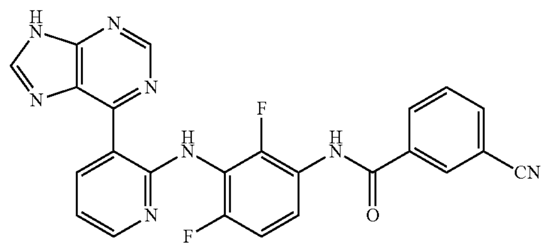 [SMILES: N#Cc1cccc(C(=O)Nc2ccc(F)c(Nc3ncccc3-c3ncnc4[nH]cnc34)c2F)c1] |
| 38 | 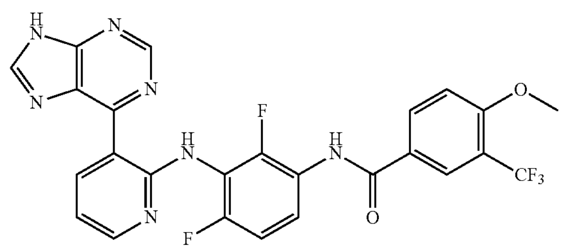 [SMILES: COc1ccc(C(=O)Nc2ccc(F)c(Nc3ncccc3-c3ncnc4[nH]cnc34)c2F)cc1C(F)(F)F] |
| 39 | 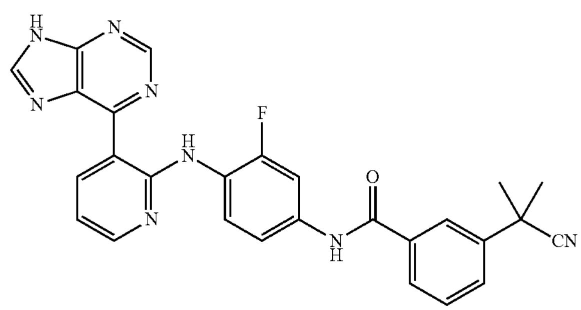 [SMILES: CC(C)(C#N)c1cccc(C(=O)Nc2ccc(Nc3ncccc3-c3ncnc4[nH]cnc34)c(F)c2)c1] |
| 40 | 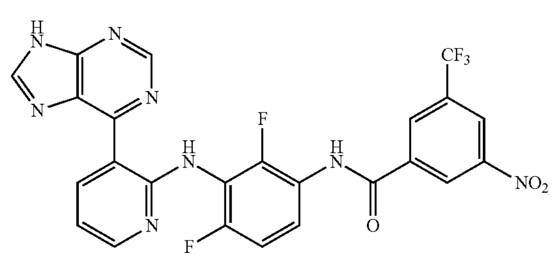 [SMILES: O=C(Nc1ccc(F)c(Nc2ncccc2-c2ncnc3[nH]cnc23)c1F)c1cc([N+](=O)[O-])cc(C(F)(F)F)c1] |

TABLE 1-continued
| Example No. | Structure |
|---|---|
| 41 | 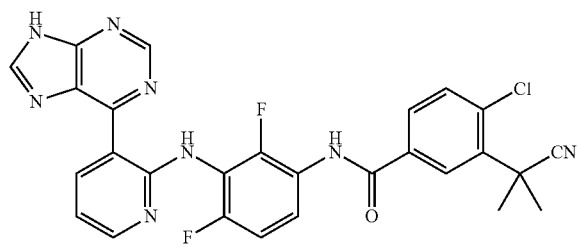 |
| 42 | 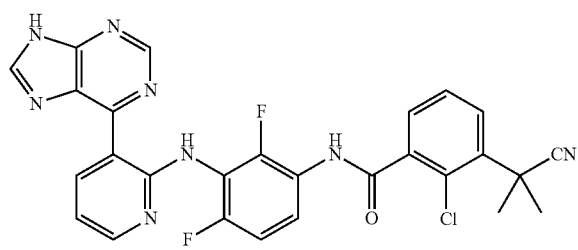 |
| 43 | 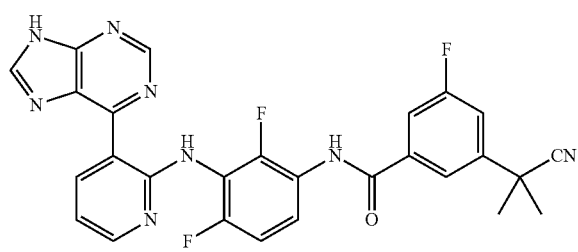 |
| 44 | 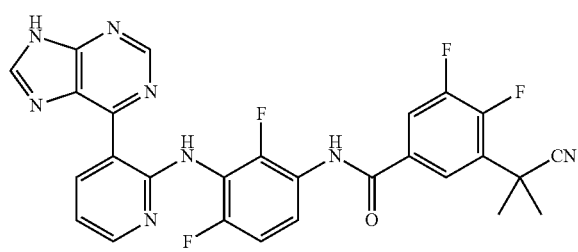 |
| 45 | 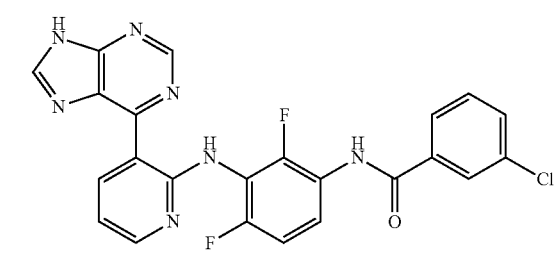 [SMILES: O=C(Nc1ccc(F)c(Nc2ncccc2-c2ncnc3[nH]cnc23)c1F)c1cccc(Cl)c1] |
| 46 | 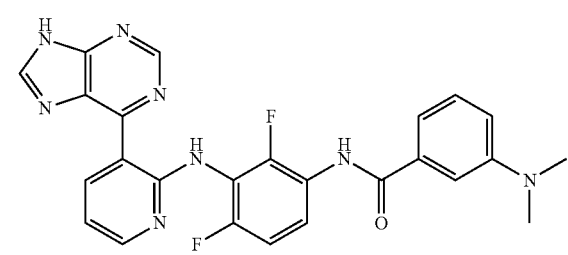 |

TABLE 1-continued
| Example No. | Structure |
|---|---|
| 47 | 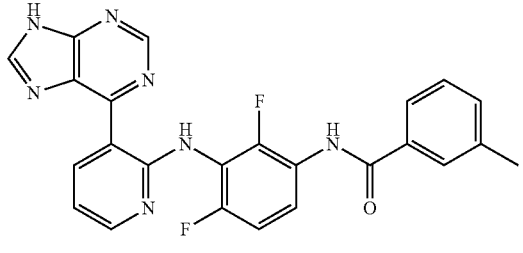 [SMILES: Cc1cccc(C(=O)Nc2ccc(F)c(Nc3ncccc3-c3ncnc4[nH]cnc34)c2F)c1] |
| 48 | 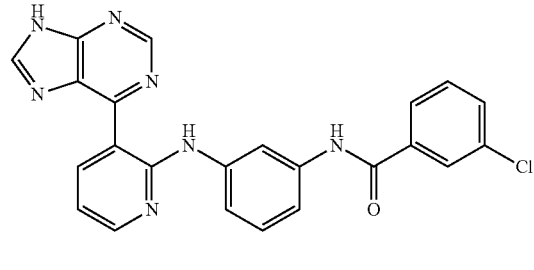 [SMILES: O=C(Nc1cccc(Nc2ncccc2-c2ncnc3[nH]cnc23)c1)c1cccc(Cl)c1] |
| 49 | 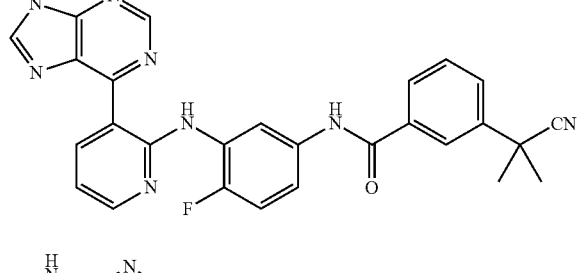 |
| 50 | 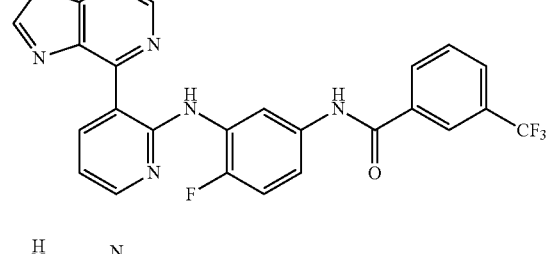 |
| 51 | 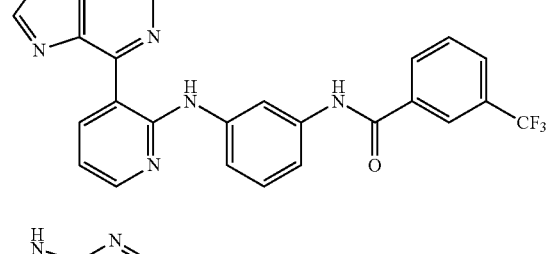 |
| 52 | 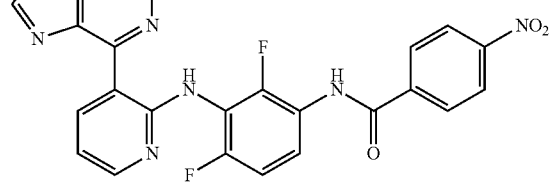 |

TABLE 1-continued
| Example No. | Structure |
|---|---|
| 53 | 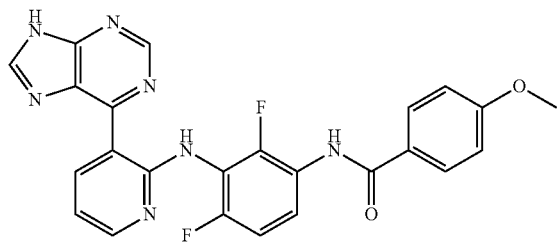 [SMILES: COc1ccc(C(=O)Nc2ccc(F)c(Nc3ncccc3-c3ncnc4[nH]cnc34)c2F)cc1] |
| 54 | 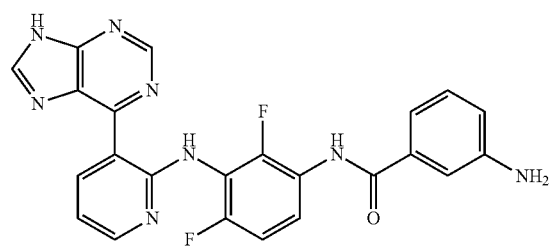 |
| 55 | 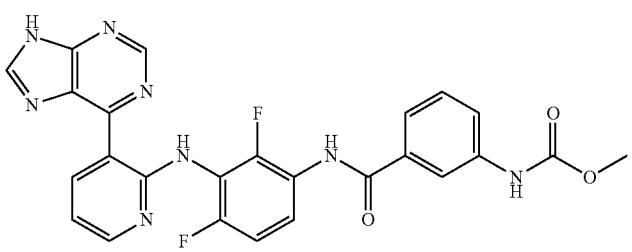 [SMILES: COC(=O)Nc1cccc(C(=O)Nc2ccc(F)c(Nc3ncccc3-c3ncnc4[nH]cnc34)c2F)c1] |
| 56 | 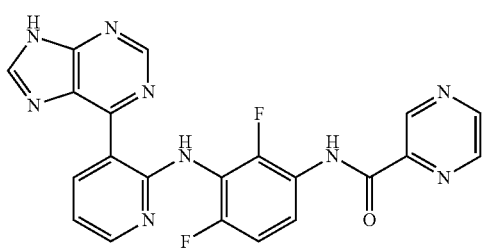 |
| 57 | 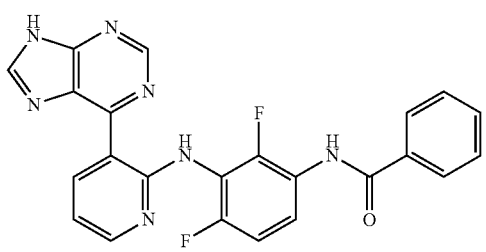 |
| 58 | 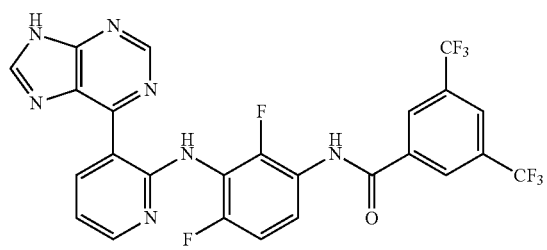 |

TABLE 1-continued

| Example No. | Structure |
|---|---|
| 59 | 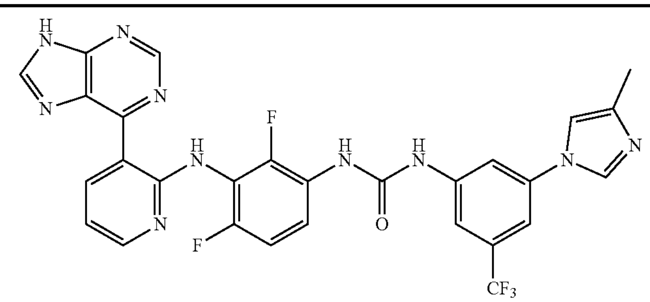 |
| 60 | 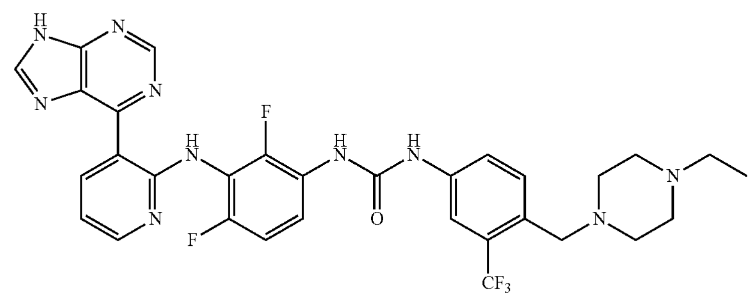 [SMILES: CCN1CCN(Cc2ccc(NC(=O)Nc3ccc(F)c(Nc4ncccc4-c4ncnc5[nH]cnc45)c3F)cc2C(F)(F)F)CC1] |
| 61 | 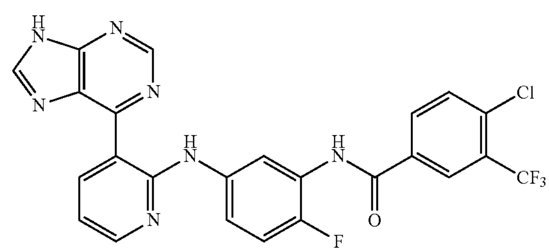 |
| 62 | 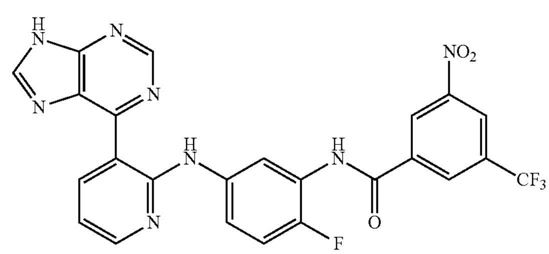 |
| 63 | 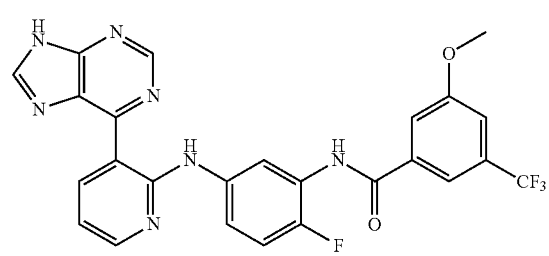 |
| 64 | 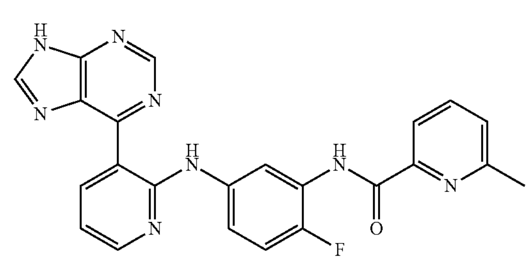 [SMILES: Cc1cccc(C(=O)Nc2cc(Nc3ncccc3-c3ncnc4[nH]cnc34)ccc2F)n1] |

TABLE 1-continued

| Example No. | Structure |
|---|---|
| 65 | 7H-purin-6-yl-pyridin-3-yl linked via NH to 4-fluoro-phenyl with N-(3,5-bis(trifluoromethyl)benzoyl)amide |
| 66 | 7H-purin-6-yl-pyridin-3-yl linked via NH to 4-chloro-phenyl with N-(3-(trifluoromethyl)benzoyl)amide |
| 67 | 7H-purin-6-yl-pyridin-3-yl linked via NH to 4-chloro-phenyl with N-(3-fluoro-5-(trifluoromethyl)benzoyl)amide |
| 68 | 7H-purin-6-yl-pyridin-3-yl linked via NH to 4-methyl-phenyl with N-(3-(trifluoromethyl)benzoyl)amide |
| 69 | 7H-purin-6-yl-pyridin-3-yl linked via NH to 4-methoxy-phenyl with N-(3-(trifluoromethyl)benzoyl)amide |
| 70 | 7H-purin-6-yl-pyridin-3-yl linked via NH to 4-methoxy-phenyl (NH at ortho to OMe) with N-(3-(trifluoromethyl)benzoyl)amide |

TABLE 1-continued
| Example No. | Structure |
|---|---|
| 71 | 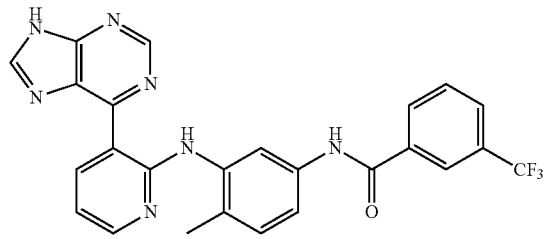 |
| 72 | 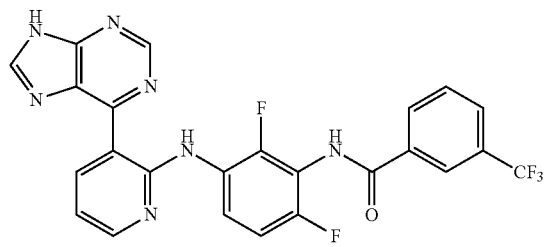 |
| 73 | 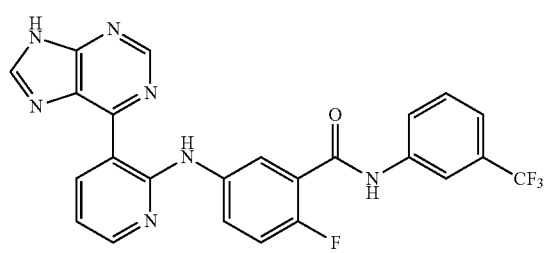 [SMILES: O=C(Nc1cccc(C(F)(F)F)c1)c1cc(Nc2ncccc2-c2ncnc3[nH]cnc23)ccc1F] |
| 74 | 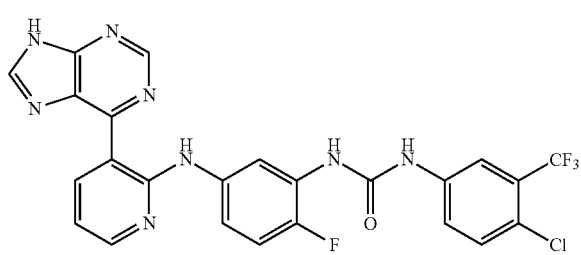 [SMILES: O=C(Nc1ccc(Cl)c(C(F)(F)F)c1)Nc1cc(Nc2ncccc2-c2ncnc3[nH]cnc23)ccc1F] |
| 75 | 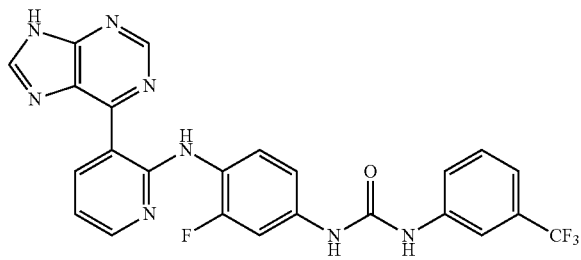 [SMILES: O=C(Nc1cccc(C(F)(F)F)c1)Nc1ccc(Nc2ncccc2-c2ncnc3[nH]cnc23)c(F)c1] |
| 76 | 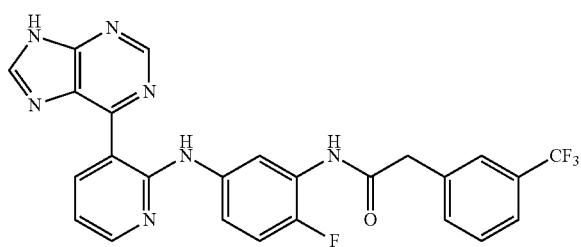 [SMILES: O=C(Cc1cccc(C(F)(F)F)c1)Nc1cc(Nc2ncccc2-c2ncnc3[nH]cnc23)ccc1F] |

TABLE 1-continued
| Example No. | Structure |
|---|---|
| 77 | 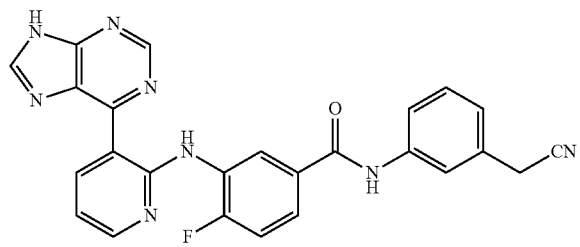 [SMILES: N#CCc1cccc(NC(=O)c2ccc(F)c(Nc3ncccc3-c3ncnc4[nH]cnc34)c2)c1] |
| 78 | 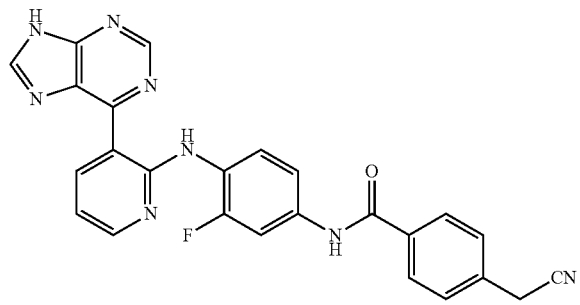 [SMILES: N#CCc1ccc(C(=O)Nc2ccc(Nc3ncccc3-c3ncnc4[nH]cnc34)c(F)c2)cc1] |
| 79 | 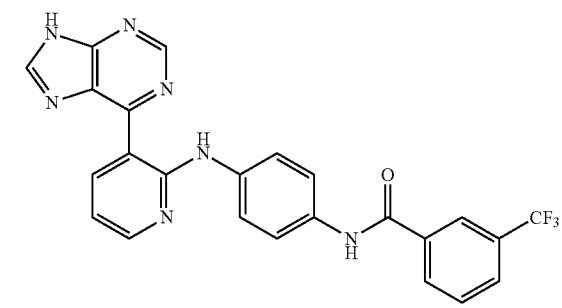 [SMILES: O=C(Nc1ccc(Nc2ncccc2-c2ncnc3[nH]cnc23)cc1)c1cccc(C(F)(F)F)c1] |
| 80 | 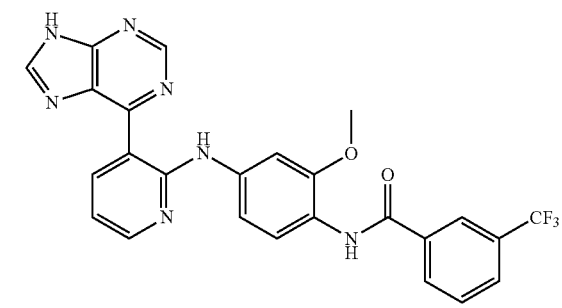 [SMILES: COc1cc(Nc2ncccc2-c2ncnc3[nH]cnc23)ccc1NC(=O)c1cccc(C(F)(F)F)c1] |
| 81 | 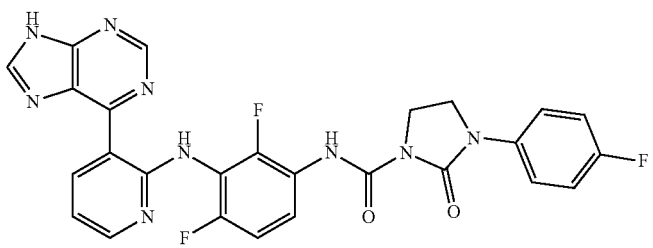 [SMILES: O=C(Nc1ccc(F)c(Nc2ncccc2-c2ncnc3[nH]cnc23)c1F)N1CCN(c2ccc(F)cc2)C1=O] |

TABLE 1-continued
| Example No. | Structure |
|---|---|
| 82 | 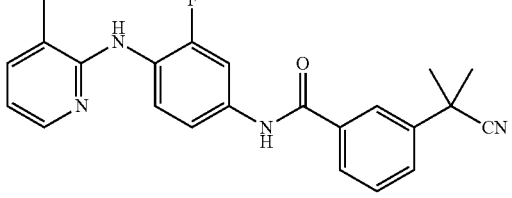 |
| 83 | 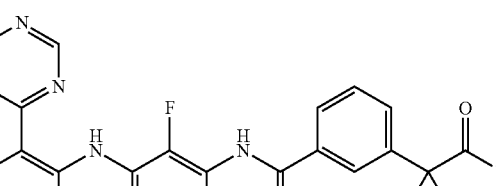 |
| 84 | 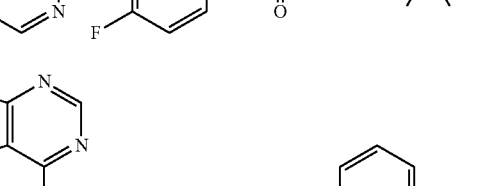 |
| 85 | 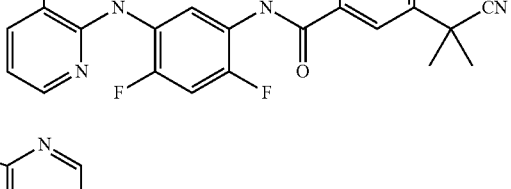 |
| 86 | 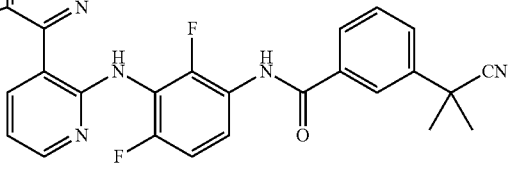 |
| 87 | 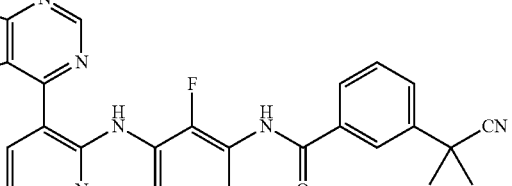 |

TABLE 1-continued
| Example No. | Structure |
|---|---|
| 88 | 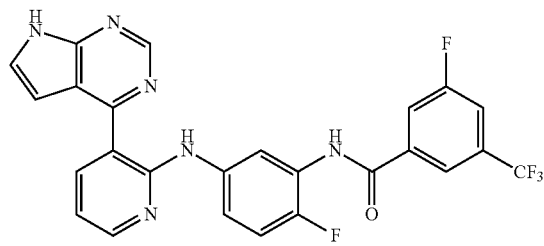 [SMILES: O=C(Nc1cc(Nc2ncccc2-c2ncnc3[nH]ccc23)ccc1F)c1cc(F)cc(C(F)(F)F)c1] |
| 89 | 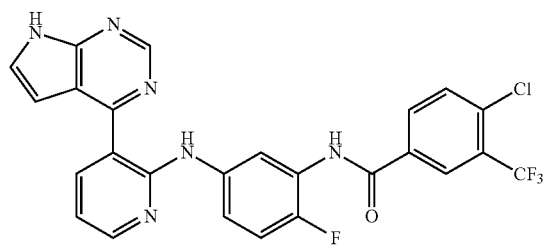 [SMILES: O=C(Nc1cc(Nc2ncccc2-c2ncnc3[nH]ccc23)ccc1F)c1ccc(Cl)c(C(F)(F)F)c1] |
| 90 | 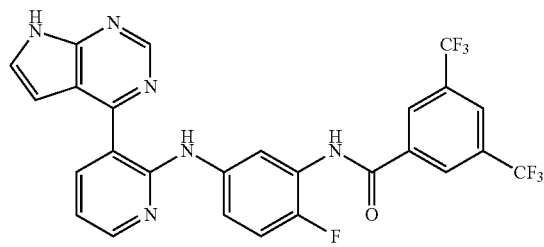 |
| 91 | 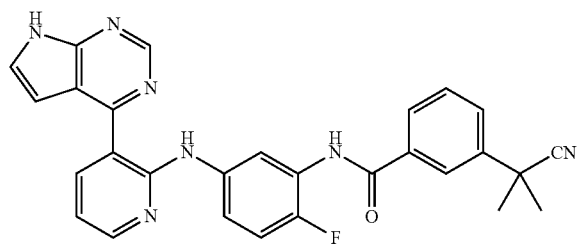 |
| 92 | 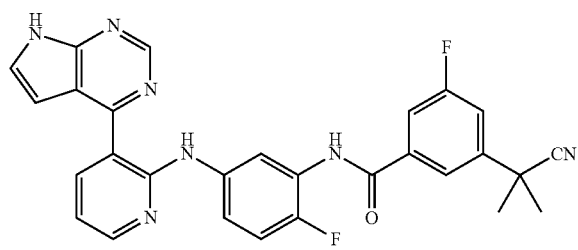 |
| 93 | 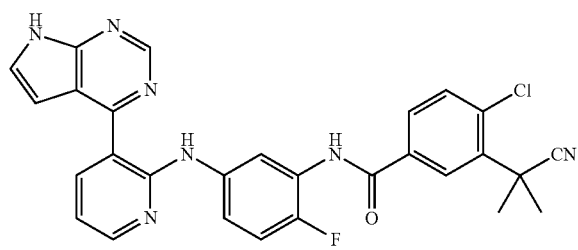 [SMILES: CC(C)(C#N)c1cc(C(=O)Nc2cc(Nc3ncccc3-c3ncnc4[nH]ccc34)ccc2F)ccc1Cl] |

TABLE 1-continued

| Example No. | Structure |
|---|---|
| 94 | (structure) |
| 95 | (structure) |
| 96 | (structure) |
| 97 | (structure) |
| 98 | (structure) |
| 99 | (structure) |

TABLE 1-continued

| Example No. | Structure |
|---|---|
| 100 | *(7H-pyrrolo[2,3-d]pyrimidin-4-yl)pyridin-2-yl amino - 4-methoxyphenyl - NHC(O) - 3-(2-cyanopropan-2-yl)phenyl)* |
| 101 | *(7H-pyrrolo[2,3-d]pyrimidin-4-yl)pyridin-2-yl amino - phenyl - NHC(O) - 3-(CF₃)phenyl)* |
| 102 | *(7H-pyrrolo[2,3-d]pyrimidin-4-yl)pyridin-2-yl amino - 2-fluorophenyl - NHC(O) - 3-(CF₃)phenyl)* |
| 103 | *(7H-pyrrolo[2,3-d]pyrimidin-4-yl)pyridin-2-yl amino - 4-fluorophenyl - NHC(O) - 3-(CF₃)phenyl)* |
| 104 | *(7H-pyrrolo[2,3-d]pyrimidin-4-yl)pyridin-2-yl amino - 2,4-difluorophenyl - NHC(O) - 3-(CF₃)phenyl)* |
| 105 | *(7H-pyrrolo[2,3-d]pyrimidin-4-yl)pyridin-2-yl amino - 2,6-difluorophenyl - NHC(O) - 3-(CF₃)phenyl)* |

TABLE 1-continued

| Example No. | Structure |
| --- | --- |
| 106 | (7H-pyrrolo[2,3-d]pyrimidin-4-yl)pyridin-3-yl linked via NH to 2,5-difluorophenyl, with NHC(O)-(3-CF₃-phenyl) amide |
| 107 | (7H-pyrrolo[2,3-d]pyrimidin-4-yl)pyridin-3-yl linked via NH to 4-chlorophenyl, with NHC(O)-(3-CF₃-phenyl) amide |
| 108 | (7H-pyrrolo[2,3-d]pyrimidin-4-yl)pyridin-3-yl linked via NH to 4-methylphenyl, with NHC(O)-(3-CF₃-phenyl) amide |
| 109 | (7H-pyrrolo[2,3-d]pyrimidin-4-yl)pyridin-3-yl linked via NH to 4-methoxyphenyl, with NHC(O)-(3-CF₃-phenyl) amide |
| 110 | (7H-pyrrolo[2,3-d]pyrimidin-4-yl)pyridin-3-yl linked via NH to 3-fluorophenyl, with NHC(O)-(3-CF₃-phenyl) amide |
| 111 | (9H-purin-6-yl)pyridin-3-yl linked via NH to 4-fluorophenyl, with NHC(O)-(3-CF₃-4-F-phenyl) amide |

TABLE 1-continued

| Example No. | Structure |
|---|---|
| 112 | 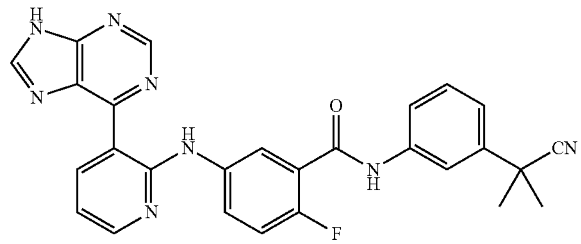 [SMILES: CC(C)(C#N)c1cccc(NC(=O)c2cc(Nc3ncccc3-c3ncnc4[nH]cnc34)ccc2F)c1] |
| 113 | 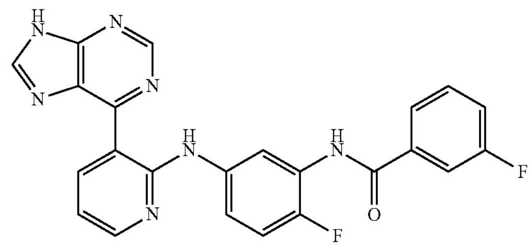 [SMILES: O=C(Nc1cc(Nc2ncccc2-c2ncnc3[nH]cnc23)ccc1F)c1cccc(F)c1] |
| 114 | 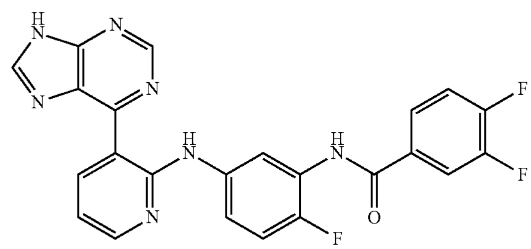 |
| 115 | 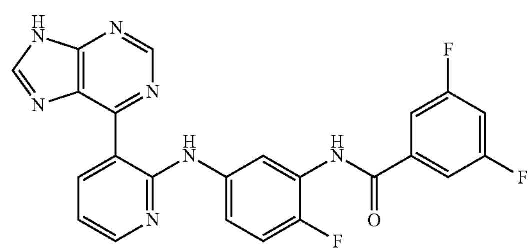 |
| 116 | 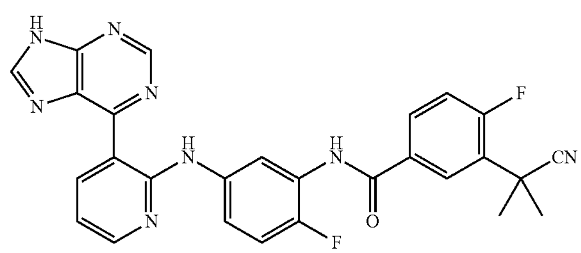 |
| 117 | 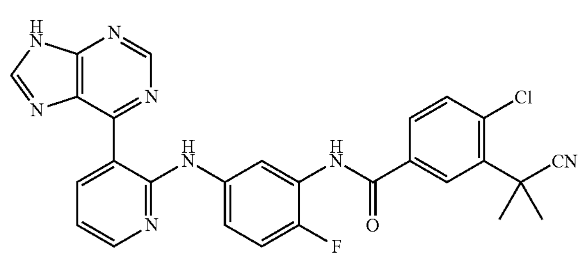 |

TABLE 1-continued
| Example No. | Structure |
|---|---|
| 118 | 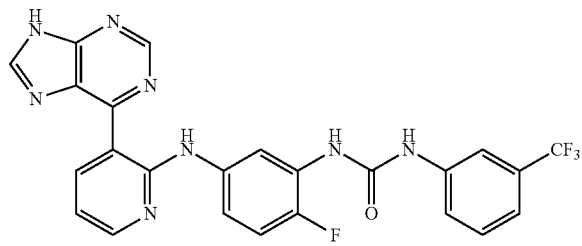 [SMILES: O=C(Nc1cccc(C(F)(F)F)c1)Nc1cc(Nc2ncccc2-c2ncnc3[nH]cnc23)ccc1F] |
| 119 | 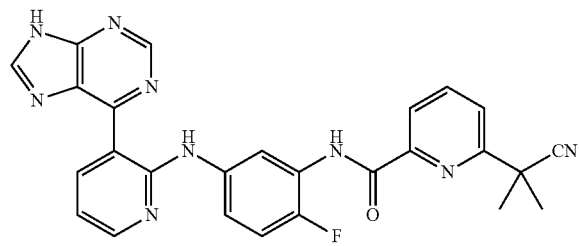 |
| 120 | 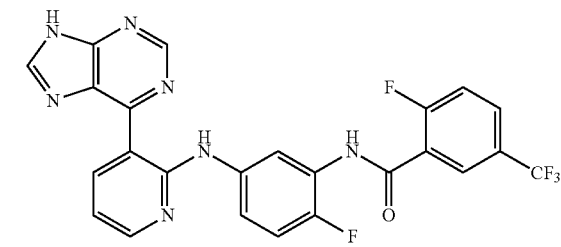 [SMILES: O=C(Nc1cc(Nc2ncccc2-c2ncnc3[nH]cnc23)ccc1F)c1cc(C(F)(F)F)ccc1F] |
| 121 | 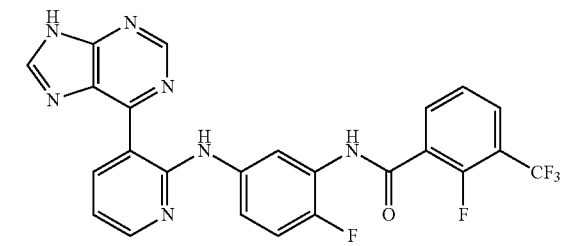 |
| 122 | 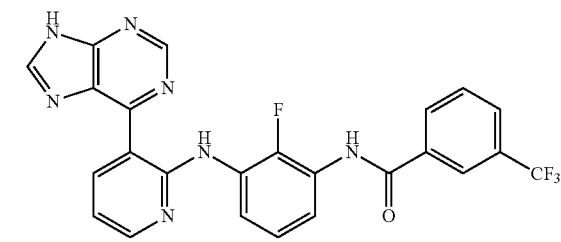 |
| 123 | 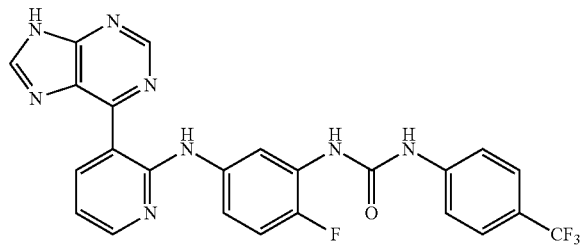 [SMILES: O=C(Nc1ccc(C(F)(F)F)cc1)Nc1cc(Nc2ncccc2-c2ncnc3[nH]cnc23)ccc1F] |

TABLE 1-continued
| Example No. | Structure |
|---|---|
| 124 | 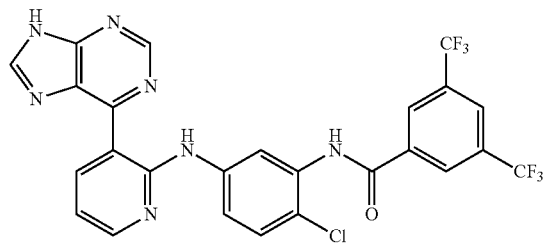 |
| 125 | 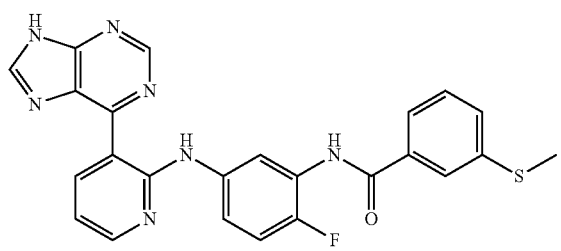 [SMILES: CSc1cccc(C(=O)Nc2cc(Nc3ncccc3-c3ncnc4[nH]cnc34)ccc2F)c1] |
| 126 | 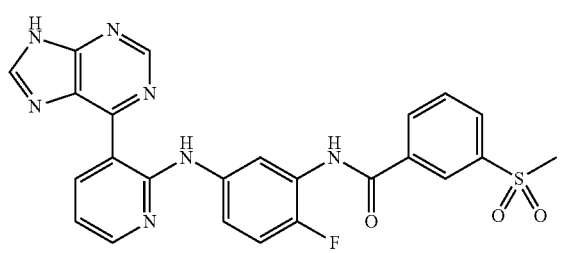 [SMILES: CS(=O)(=O)c1cccc(C(=O)Nc2cc(Nc3ncccc3-c3ncnc4[nH]cnc34)ccc2F)c1] |
| 127 | 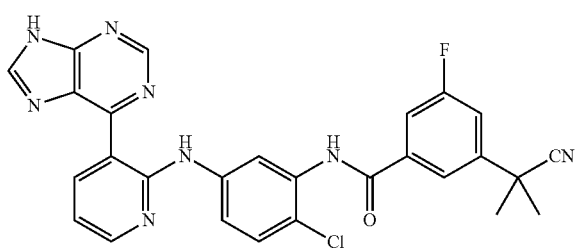 [SMILES: CC(C)(C#N)c1cc(F)cc(C(=O)Nc2cc(Nc3ncccc3-c3ncnc4[nH]cnc34)ccc2Cl)c1] |
| 128 | 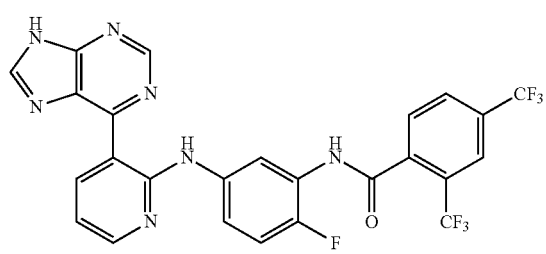 [SMILES: O=C(Nc1cc(Nc2ncccc2-c2ncnc3[nH]cnc23)ccc1F)c1ccc(C(F)(F)F)cc1C(F)(F)F] |
| 129 | 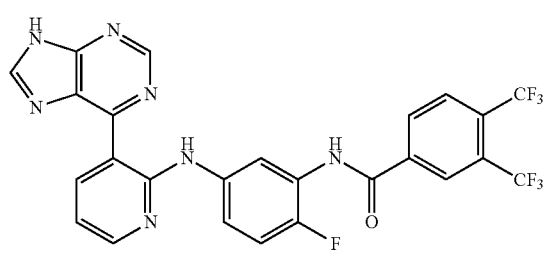 |

TABLE 1-continued
| Example No. | Structure |
|---|---|
| 130 | 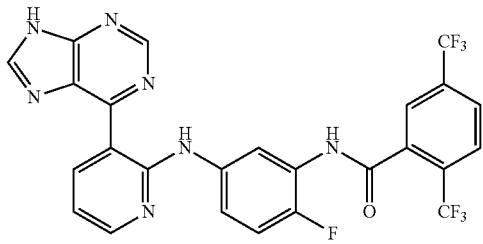 [SMILES: O=C(Nc1cc(Nc2ncccc2-c2ncnc3[nH]cnc23)ccc1F)c1cc(C(F)(F)F)ccc1C(F)(F)F] |
| 131 | 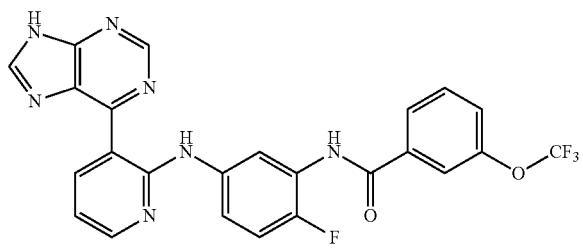 [SMILES: O=C(Nc1cc(Nc2ncccc2-c2ncnc3[nH]cnc23)ccc1F)c1cccc(OC(F)(F)F)c1] |
| 132 | 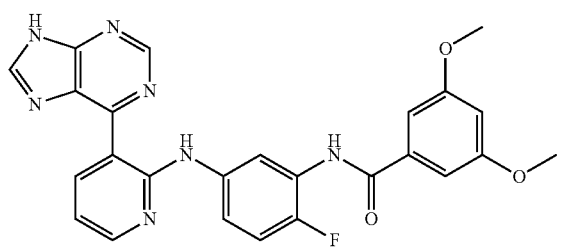 [SMILES: COc1cc(OC)cc(C(=O)Nc2cc(Nc3ncccc3-c3ncnc4[nH]cnc34)ccc2F)c1] |
| 133 | 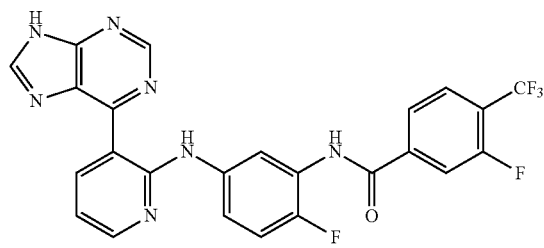 |
| 134 | 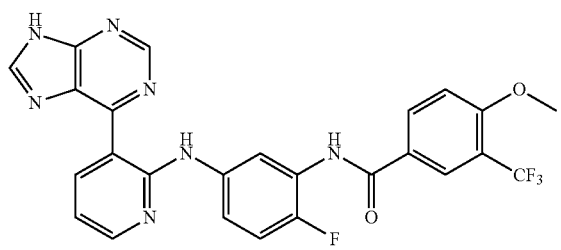 [SMILES: COc1ccc(C(=O)Nc2cc(Nc3ncccc3-c3ncnc4[nH]cnc34)ccc2F)cc1C(F)(F)F] |
| 135 | 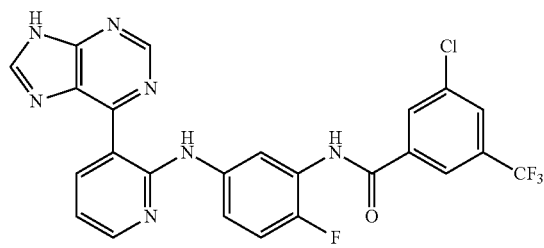 |

TABLE 1-continued
| Example No. | Structure |
|---|---|
| 136 | 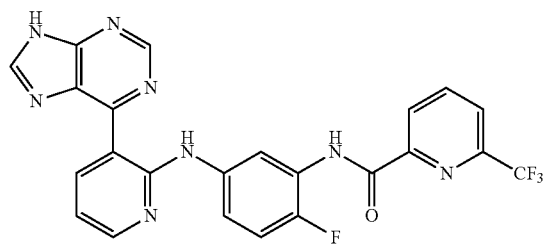 [SMILES: O=C(Nc1cc(Nc2ncccc2-c2ncnc3[nH]cnc23)ccc1F)c1cccc(C(F)(F)F)n1] |
| 137 | 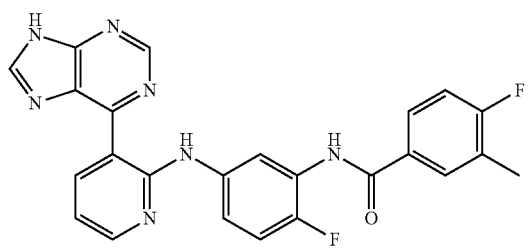 |
| 138 | 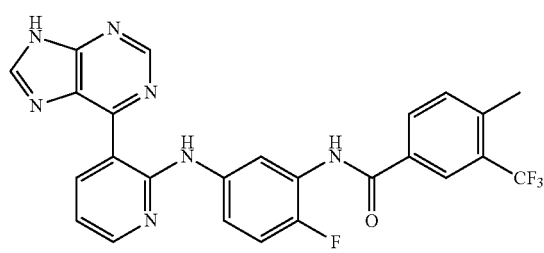 |
| 139 | 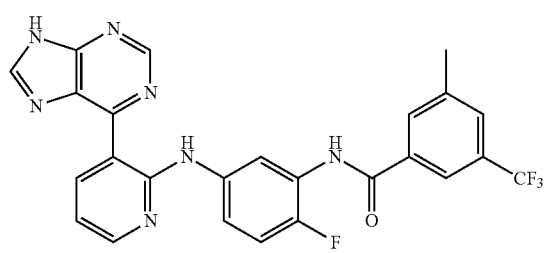 |
| 140 | 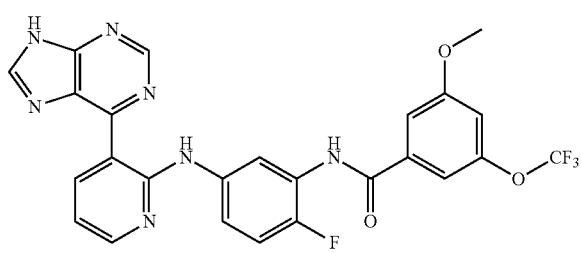 [SMILES: COc1cc(OC(F)(F)F)cc(C(=O)Nc2cc(Nc3ncccc3-c3ncnc4[nH]cnc34)ccc2F)c1] |
| 141 | 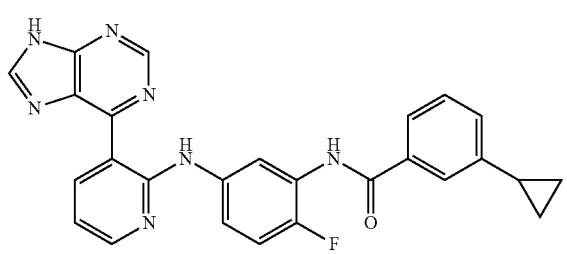 [SMILES: O=C(Nc1cc(Nc2ncccc2-c2ncnc3[nH]cnc23)ccc1F)c1cccc(C2CC2)c1] |

TABLE 1-continued
| Example No. | Structure |
|---|---|
| 142 | 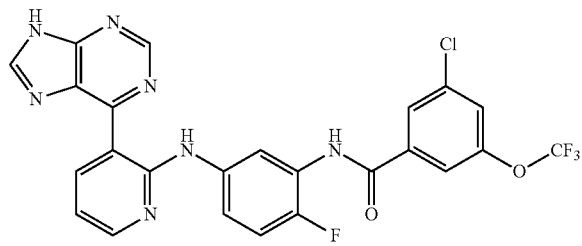 [SMILES: O=C(Nc1cc(Nc2ncccc2-c2ncnc3[nH]cnc23)ccc1F)c1cc(Cl)cc(OC(F)(F)F)c1] |
| 143 | 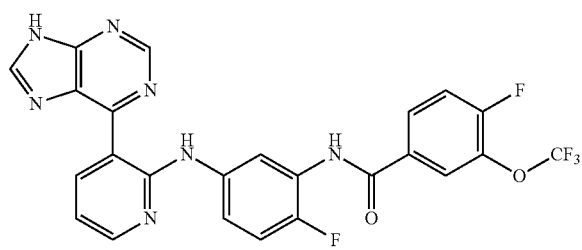 |
| 144 | 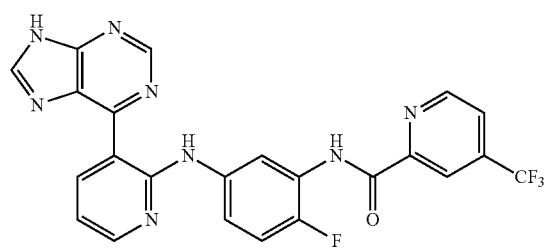 |
| 145 | 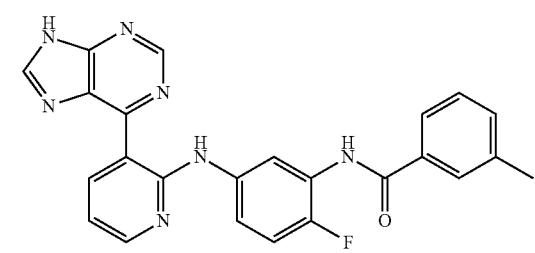 |
| 146 | 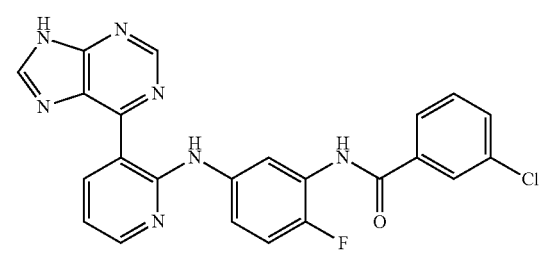 [SMILES: O=C(Nc1cc(Nc2ncccc2-c2ncnc3[nH]cnc23)ccc1F)c1cccc(Cl)c1] |
| 147 | 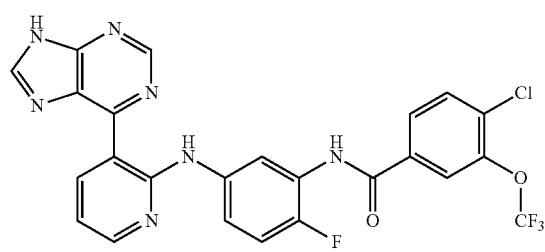 [SMILES: O=C(Nc1cc(Nc2ncccc2-c2ncnc3[nH]cnc23)ccc1F)c1ccc(Cl)c(OC(F)(F)F)c1] |

TABLE 1-continued
| Example No. | Structure |
|---|---|
| 148 | 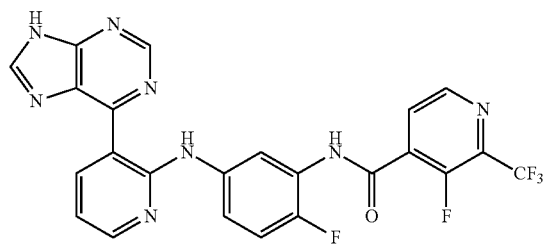 [SMILES: O=C(Nc1cc(Nc2ncccc2-c2ncnc3[nH]cnc23)ccc1F)c1ccnc(C(F)(F)F)c1F] |
| 149 | 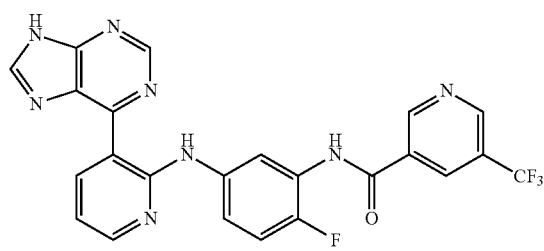 [SMILES: O=C(Nc1cc(Nc2ncccc2-c2ncnc3[nH]cnc23)ccc1F)c1cncc(C(F)(F)F)c1] |
| 150 | 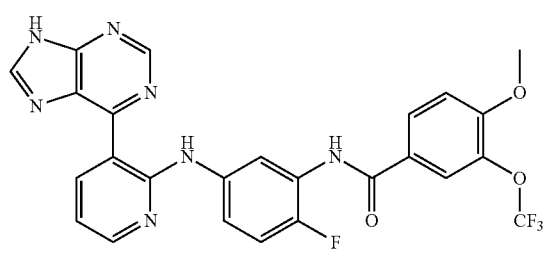 [SMILES: COc1ccc(C(=O)Nc2cc(Nc3ncccc3-c3ncnc4[nH]cnc34)ccc2F)cc1OC(F)(F)F] |
| 151 | 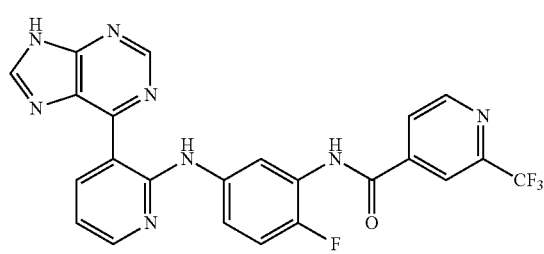 |
| 152 | 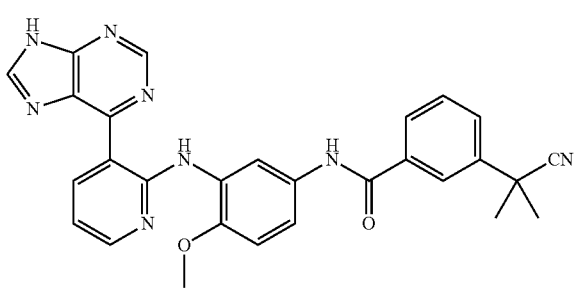 [SMILES: COc1ccc(NC(=O)c2cccc(C(C)(C)C#N)c2)cc1Nc1ncccc1-c1ncnc2[nH]cnc12] |
| 153 | 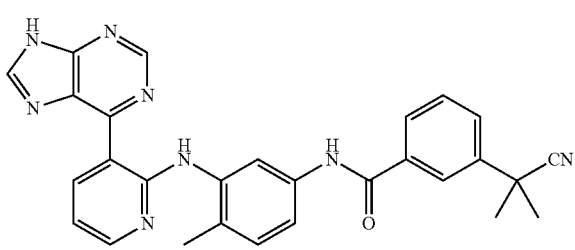 |

TABLE 1-continued

| Example No. | Structure |
|---|---|
| 154 | 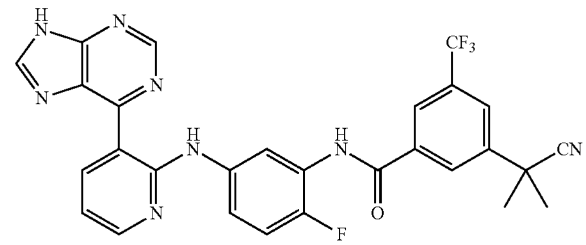 |
| 155 | 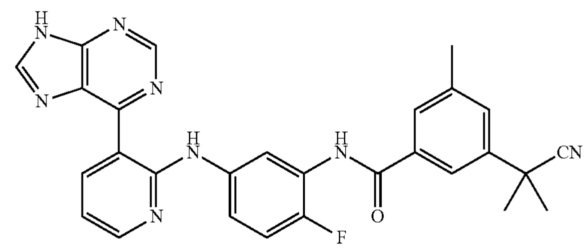 |
| 156 | 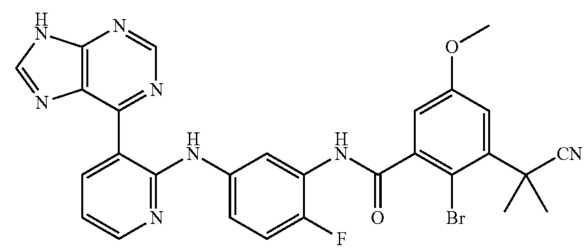 [SMILES: COc1cc(C(=O)Nc2cc(Nc3ncccc3-c3ncnc4[nH]cnc34)ccc2F)c(Br)c(C(C)(C)C#N)c1] |
| 157 | 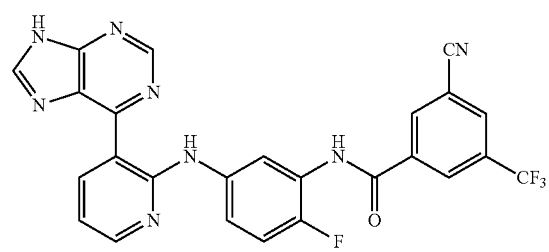 [SMILES: N#Cc1cc(C(=O)Nc2cc(Nc3ncccc3-c3ncnc4[nH]cnc34)ccc2F)cc(C(F)(F)F)c1] |
| 158 | 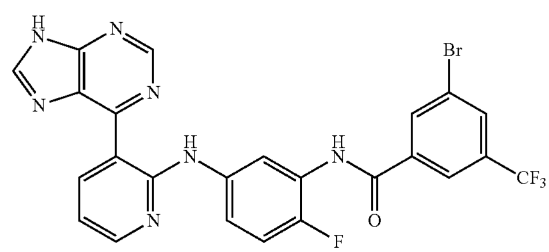 |

Experimental Example 1. Experiment on VEGFR-2 Tyrosine Kinase Inhibitory Activity The inhibitory activities of the compounds of the present invention against VEGFR-2 tyrosine kinase were analyzed using ADP-Glo™ kinase assay kit commercially available from Promega. In the principle of the analysis, kinase, a substrate and ATP are reacted with one another, and then ADP-Glo™ solution is added thereto. The ATP is removed while leaving the produced ADP, and the remaining ADP is converted to ATP by use of a kinase detection reagent, and the ATP is reacted with a luciferin substrate, and the emitted luminescence is measured. Specifically, 5 μl of each compound (5×) was added to each well, and 10 μl of kinase enzyme was added to each well, and then 10 μl of a 1:1 mixture of a kinase substrate and an ATP solution was added to each well (substrate: 5 μg/5 μl; ATP: 20 μM/5 μl). These substances were allowed to react (30° C. and 800 rpm) in a reactor under a light-shielded condition for 30 minutes, and 25 μl of ADP-Glo™ solution was added to each well and allowed to react under a light-shielded condition for 40 minutes (RT; 150 to 170 rpm). 50 μl of a kinase detection reagent was added to each well and allowed to react under a light-shielded condition for 30 minutes (RT; 150 to 170 rpm), and then the luminescence of each well was measured with a luminometer (Molecular Devices, LMax II 384) and converted to $IC_{50}$ values.

VEGFR-2 analysis

KDR: 50 ng;
Substrate: 5 μg;
ATP: 20 mM;
Tris-HCl: 40 mM;
$MgCl_2$: 20 mM;
DTT: 50 μM;
BSA: 0.1 mg/ml;
Reaction time: 30 min (30° C.)/40 min/30 min;
Detection: LMaxII-384.

The solvents used in the experiment were dispensed and used as follows.

2× buffer: 400 μl of 5× buffer included in the kit, 1 μl of DTT (0.1 M), and 599 μl of DIW were mixed to make a volume of 1 ml.

1× buffer: 2× buffer was mixed with DIW at a ratio of 1:1.

Enzyme: Enzyme contained in a 10 μg/100 μl vial included in the kit was dispensed in an amount of 4 μl (400 ng) and stored at −70° C. For use, 76 μl of 1× buffer was added to the stored enzyme, and then 10 μl was added to each well.

ATP solution: 10 mM ATP included in the kit was dispensed in an amount of 25 μl and stored at −70° C. For use, the stored ATP was diluted with 2× buffer to a concentration of 250 μM (5×).

Substrate: a substrate contained in a 1 mg/1 ml vial included in the kit was dispensed in an amount of 40 μl (40 μg) and stored at −70° C. For use, the stored substrate was mixed with the ATP solution at a ratio of 1:1, and 10 μl of the mixture was added to well.

A compound disclosed in Example 18 of Korean Patent Application Publication No. 2012-0060744 was synthesized and used as a control, and an experimental result value obtained for the compound was indicated as Comparative Example 1. The VEGFR inhibitory activities of the compounds of the present invention and Comparative Example 1 are shown in Table 2 below.

TABLE 2

| Example No. | VEGFR $IC_{50}$ (nM) | Example No. | VEGFR $IC_{50}$ (nM) | Example No. | VEGFR $IC_{50}$ (nM) |
|---|---|---|---|---|---|
| 1 | 11 | 2 | 4,700 | 3 | 5,380 |
| 4 | 2,720 | 5 | 3,080 | 6 | 2,550 |
| 7 | 2,070 | 8 | 2,360 | 9 | 12 |
| 10 | 4,710 | 11 | 4,980 | 12 | 3,440 |
| 13 | 6,050 | 14 | 4,980 | 15 | 6,050 |
| 16 | 5,060 | 17 | 3,370 | 18 | 4,150 |
| 19 | 4,970 | 20 | 335 | 21 | 4.1 |
| 22 | 925 | 23 | 14 | 24 | 191 |
| 25 | 8,500 | 26 | 5,900 | 27 | 229 |
| 28 | 74 | 29 | 12 | 30 | 11 |
| 31 | 4,100 | 32 | 29 | 33 | 126 |
| 34 | 646 | 35 | 846 | 36 | 12 |
| 37 | 526 | 38 | 760 | 39 | 5,031 |
| 40 | 96 | 41 | 82 | 42 | 1,300 |
| 43 | 127 | 44 | 340 | 45 | 147 |
| 46 | 347 | 47 | 118 | 48 | 590 |
| 49 | 10 | 50 | 90 | 51 | 182 |
| 52 | 887 | 53 | 2,500 | 54 | 887 |
| 55 | 14,800 | 56 | 10,000 | 57 | 969 |
| 58 | 11,000 | 59 | 5,400 | 60 | 6,060 |
| 61 | 45,000 | 62 | 1,000 | 63 | 1,100 |
| 64 | 394 | 65 | 21 | 66 | 89 |
| 67 | 40 | 68 | 800 | 69 | 950 |
| 70 | 1,548 | 71 | 1,600 | 72 | 300 |
| 73 | 52 | 74 | 43 | 75 | 982 |
| 76 | 11 | 77 | 35 | 78 | 28 |
| 79 | 982 | 80 | 1,495 | 81 | 121 |
| 82 | 1,425 | 83 | 394 | 84 | 21 |
| 85 | 89 | 86 | 1,548 | 87 | 210 |
| 88 | 109 | 91 | 76 | 92 | 87 |
| 135 | 184 | 139 | 126 | 154 | 253 |
| Comparative Example 1 | 1,600 | | | | |

Experimental Example 2. Experiment on Raf Kinase Inhibitory Activity

In order to examine the inhibitory activities of the compounds of the present invention against Raf kinases (B-Raf, C-Raf, B-Raf$^{V600E}$), the following experiment was performed.

(1) Consecutive Signal Transduction Reaction

To a centrifugation tube, 20 μl of a dilution solvent (20 mM MOPS, pH 7.2, 25 mM (3-glycerol phosphate, 5 mM EGTA, 1 mM sodium orthovanadate, 1 mM dithiothreitol) and 20 μl of a Mg/ATP mixture (500 μM ATP and 75 mM magnesium chloride) were added. Then, each of the derivative compounds of formula 1 was added. As a control, 1 ng of activated raf, 0.4 ng of inactivated MEK1 and 1 μg of inactivated MAPK2 were added without adding Example compounds. The solutions in the tube were concentrated at the bottom of the tube by centrifugation, and then allowed to react at 30° C. for 30 minutes, and 4 μl of the mixture solution was taken and used in the next experimental step.

(2) Phosphorylation of Substrate Protein MBP by MAPK2

To 4 μl of the mixture solution taken in (1), 10 μl of a dilution solvent, 20 μg of MBP as a substrate, and 10 μl of diluted [γ-32P]ATP (1 μCi/μL) were added. The solutions in the tube were concentrated at the bottom of the tube by centrifugation, and then allowed to react at 30° C. for 30 minutes. 25 μl of the reaction solution was carefully placed on the center of 2 cm×2 cm P81 filter paper for 30 seconds. Next, the filter paper was washed three times with 0.75% phosphoric acid solution for 10 minutes each time and washed once with acetone for 5 minutes. Next, the filter paper was transferred into a scintillation vial, and 5 ml of a scintillation cocktail was added thereto. Raf activity inhibition rate ($IC_{50}$) was measured by reading the radioactivity with a scintillation counter in comparison with the control. The results of the measurement are shown in Table 3 below.

TABLE 3

| Example | $IC_{50}$(nM) | | |
|---|---|---|---|
| | B-Raf | B-Raf$^{V600E}$ | C-Raf |
| 1 | 34 | 16 | 23 |
| 9 | 2 | 0.2 | 0.6 |
| 21 | 21 | 10 | 10 |
| 23 | 17 | 7 | 8 |
| 30 | 2.7 | 5.2 | 0.7 |
| 33 | 94 | 33 | 24 |
| 36 | 71 | 30 | 41 |
| 53 | 14 | 6 | 7 |
| 65 | 331 | 187 | 257 |
| 135 | 161 | 86 | 34 |

Experimental Example 3. MTT Assay

MTT assay is frequently used for the purpose of primary screening for the sensitivity of anticancer agents and to examine cytotoxicity. When cancer cells are treated with varying concentrations of any anticancer agent for a predetermined time to induce death of the cells and are then treated with MTT, and when the formation of formazan is measured, the concentration of the anticancer agent, at which about 50% of the cells survive, can be determined. This concentration value is called $IC_{50}$. $IC_{50}$ values differ between drugs, and thus can be characteristic of the drugs. Using this method, the effects of anticancer agents against cell proliferation can be quantitatively compared. Thus, in order to measure the cytotoxicity of samples, MTT assay was performed using CellTiter 96 Non-radioactive Cell Proliferation Assay Kit (Promega).

Cells in a cell suspension were counted with a hematocytometer, and then 200 μL of the cell suspension was added to each well of a 96 well plate at a desired concentration (cell amount determined depending on a cell line). After cell seeding, the cells were incubated in a $CO_2$ incubator at 37° C. overnight. After one day of cell stabilization, the cells were treated with desired concentrations of the compounds. The cells were incubated in a $CO_2$ incubator at 37° C. for 3 days, and then the sample was removed, and 200 μL of MTT solution was added to each well. After 2 hours of incubation, the MTT dilution was carefully shaken, and 200 μL of DMSO was added to each well, followed by shaking with a plate shaker for 60 minutes. The absorbance at a wavelength of 570 nm was measured using an ELISA reader, thereby determining the $IC_{50}$ value of each compound (the absorbance indicates the amount of MTT reduced by the cells and is proportional to the number of viable cells present in each well).

A compound disclosed in Example 18 of Korean Patent Application Publication No. 2012-0060744 was synthesized and used as a control, and an experimental result value obtained for the compound was indicated as Comparative Example 1. The results are shown in Tables 4 and 5 below.

TABLE 4

| Example No. | MTT assay $IC_{50}$ (nM) KRAS mutant (Colon) LS513 $KRAS^{G12V}$ |
|---|---|
| Comparative Example 1 | >50,000 |
| 1 | 1,177 |
| 2 | >10,000 |
| 3 | 4,033 |
| 4 | >10,000 |
| 5 | >10,000 |
| 6 | >10,000 |
| 7 | >10,000 |
| 8 | >10,000 |
| 9 | 656 |
| 10 | 1,172 |
| 11 | 996 |
| 12 | 1,021 |
| 13 | 1,152 |
| 14 | 851 |
| 15 | 1,671 |
| 16 | 2,784 |
| 17 | 1,159 |
| 18 | 3,024 |
| 19 | 939 |
| 20 | 2,603 |
| 21 | 333 |
| 22 | >10,000 |
| 23 | 687 |
| 24 | 476 |
| 25 | >10,000 |
| 26 | >10,000 |
| 27 | >10,000 |
| 28 | 958 |
| 29 | 978 |
| 30 | 143 |
| 31 | >10,000 |
| 32 | 173 |
| 33 | 199 |
| 34 | >10,000 |
| 35 | >10,000 |
| 36 | 250 |
| 37 | >10,000 |
| 38 | 1,857 |
| 39 | >10,000 |
| 40 | 163 |
| 41 | 475 |
| 42 | 1,331 |
| 43 | 402 |
| 44 | 1,322 |
| 45 | >10,000 |
| 46 | 7,091 |
| 47 | >10,000 |
| 48 | 2,485 |
| 49 | 192 |
| 50 | 221 |
| 51 | 5,670 |
| 52 | >10,000 |
| 53 | >10,000 |
| 54 | >10,000 |
| 55 | >10,000 |
| 56 | >10,000 |
| 57 | >10,000 |
| 58 | 407 |
| 59 | 2,140 |
| 60 | >10,000 |
| 61 | 439 |
| 62 | 702 |
| 63 | 690 |
| 64 | 300 |
| 65 | 100 |
| 66 | 135 |
| 67 | 6,586 |
| 68 | 6,586 |
| 69 | 7,105 |
| 70 | 757 |
| 71 | 565 |
| 72 | 1,272 |
| 73 | 80 |
| 74 | 68 |
| 75 | >10,000 |
| 76 | 426 |
| 77 | 145137 |
| 78 | 137 |
| 79 | >10,000 |
| 80 | >10,000 |
| 81 | 388 |
| 82 | >10,000 |
| 83 | 394 |
| 84 | 118 |
| 85 | 676 |
| 86 | >10,000 |
| 87 | 2,183 |
| 88 | 609 |
| 91 | 1,123 |
| 92 | 1,513 |
| Comparative Example 1 | >50,000 |
| 110 | |
| 111 | 300 |

TABLE 4-continued

| Example No. | MTT assay IC$_{50}$ (nM) KRAS mutant (Colon) LS513 KRAS$^{G12V}$ |
|---|---|
| 112 | >10,000 |
| 113 | 1,477 |
| 114 | 3,458 |
| 115 | 4,281 |
| 116 | 587 |
| 117 | 868 |
| 118 | 153 |
| 119 | >10,000 |
| 120 | 3,375 |
| 121 | 304 |
| 122 | 6,583 |
| 123 | 392 |
| 124 | 888 |
| 125 | 767 |
| 126 | 1,114 |
| 127 | 591 |
| 128 | 1,205 |
| 129 | 652 |
| 130 | 1,049 |
| 131 | 102 |
| 132 | 585 |
| 133 | 5,597 |
| 134 | 72 |
| 135 | 80 |
| 136 | 2,297 |
| 137 | 1,059 |
| 138 | 403 |
| 139 | 99 |
| 140 | 294 |
| 141 | 445 |
| 142 | 128 |
| 143 | 559 |
| 144 | 444 |
| 145 | 1,033 |
| 146 | 1,705 |
| 147 | 502 |
| 148 | 529 |
| 149 | 890 |
| 150 | 250 |
| 151 | 350 |
| 152 | 2,958 |
| 153 | 447 |
| 154 | 326 |
| 155 | 145 |
| 156 | 517 |
| 157 | 464 |
| 158 | 283 |

Experimental Example 4. Antitumor Effect on Human Colorectal Cancer LS513 Cell Line Xenograft The LS513 human colorectal cancer cell line was purchased from the ATCC and incubated in a 5% $CO_2$ incubator with RPMI-1640b medium containing 10% fetal bovine serum and 1% penicillin-streptomycin at 37° C.

In this experiment, 5 to 6-week-old female Balb/c nu/nu nude mice (weighed 18 to 20 g) were used. The mice were provided from Nara Biotech Co., Ltd. During the experiment, all the animals were housed on a mouse constant temperature/constant humidity shelf (Individually Ventilated Cages System, LAB & BIO).

Each cage (37.2 cm length×19.2 cm width×13.1 cm height) was sterilized with a sterilizer, and eight mice were received in each cage. The mice were maintained in a hygienic environment controlled to a temperature of 20 to 24° C. and a humidity of 40 to 70% with a 12-hr light/12-hr dark cycle. The mice were allowed to access sterilized feed and drinking water ad libitum. The care and treatment of these animals were carried out according to the Laboratory Animal Care Guidelines of Samjin Pharmaceutical Co., Ltd.

The mice were acclimated to the housing facility for 1 week, and then 0.1 mL of a cell suspension containing $1\times10^7$ cells was injected subcutaneously into the right flank of each mouse. After cell transplantation, the volume of the formed tumor was measured, and mice with formed tumors having a volume of 150 mm$^3$ or more were randomly divided into groups (each consisting of 7 to 8 animals) for treatment with the test compounds and a control. Vehicle (cremophor ELP/dimetylacetamide/hydroxypropyl-β-cyclodextrin/DW, 19.2/6.4/16/58.8%, w/w, pH 3) was orally administered to the control group twice a day, and the test compounds were orally administered to the test groups twice a day at a dose of 60 mg/kg or 30 mg/kg. Administration of the drugs was continued for 14 days. Among the test groups, the test compounds of Example 65, 135, 139 and 154 were orally administered to the test groups once a day at a dose of 50 mg/kg, and administration of the drugs was continued for 13 days. In addition, the test compound of Example 135 was orally administered once at a concentration of 12.5 mg/kg, 25 mg/kg and 50 mg/kg, respectively, and and administration of the drugs was continued for 21 days. At 3-day

TABLE 5

| | MTT assay IC$_{50}$ (nM) | | | | | | |
|---|---|---|---|---|---|---|---|
| | Melanoma | | KRAS mutant (Colon) | | | BRAF mutant (Colon) | |
| Example No. | A-375P BRAF$^{V600E}$ | SK-MEL2 NRAS$^{Q61R}$ | HCT-116 KRAS$^{G13D}$ | LS513 KRAS$^{G12V}$ | SW620 KRAS$^{G12V}$ | WiDR BRAF$^{V600E}$ | HUVEC (VEGF) |
| 1 | 95 | — | 101 | 278 | 849 | 115 | 22 |
| 9 | 40 | 106 | 75 | 138 | 643 | 58 | 44 |
| 21 | 24 | 129 | 63 | 160 | 249 | 28 | 40 |
| 23 | 12 | 58 | 50 | 95 | 321 | 62 | 28 |
| 30 | 246 | 122 | 145 | 79 | 864 | 636 | 13 |
| 36 | 271 | 388 | 117 | 126 | 675 | 644 | 15 |
| 53 | 4 | 35 | 17 | 29 | 180 | 391 | 5.8 |
| 65 | — | — | 208 | 322 | 700 | 247 | 850 |
| 135 | — | — | 74 | 88 | 317 | 68 | 733 |
| 139 | — | — | — | 96 | — | 116 | — |
| 154 | — | — | — | 326 | — | 97 | — |
| Comparative Example 1 | 2 | 4,338 | 15,500 | 55,300 | 50,000 | 335 | 15,000 | intervals from the starting day of the administration, the long axis and short axis of the tumor were measured with digital vernier calipers, and the tumor volume was calculated using the following equation and recorded:

Tumor volume (TV)=Long axis×short axis$^2$/2.

Tumor growth inhibition for absolute tumor volume was calculated using the following equation. In the following equation, $V_0$ is the tumor volume on the first day of drug administration (day 0), and $V_t$ is the tumor volume after last drug administration.

Tumor growth inhibition (TGI)=[1−($V_t$−$V_0$)$_{compound\text{-}treated\ group}$/($V_t$−$V_0$)$_{vehicle\ control\ group}$]×100%.

The results of observation of the in vivo antitumor effects of the compounds of Examples 21 and 30 indicated that the two compounds all showed higher antitumor effects than the control, and the antitumor effects were proportional to the concentrations of the compounds. For the compound of Example 21, an antitumor effect of about 66.7% (P<0.01) compared to the control group was observed in the group treated with 30 mg/kg of the compound, and an antitumor effect of 90.3% (P<0.01) was observed in the group treated with 60 mg/kg of the compound. Similarly, for the compound of Example 30, an antitumor effect of 76.9% (P<0.01) was observed in the group treated with 30 mg/kg of the compound, and an antitumor effect of 88.7% (P<0.01) was observed in the group treated with 60 mg/kg of the compound (FIG. 1).

The compounds of Examples 33, 36 and 63 also showed excellent antitumor effects compared to the vehicle control. The antitumor effects were 96.0% (P<0.01) for the compound of Example 33, 78.5% (P<0.01) for the compound of Example 36, and 57.9% (P<0.01) for the compound of Example 63 (FIG. 2).

The in vivo antitumor effects of the compounds of Example 59 and 60 and Comparative Example 1 (the compound of Example 18 of Korean Patent Application Publication No. 2012-0060744) were comparatively observed, and as a result, it was observed that the compound of Comparative Example 1 showed an antitumor effect of 3.82% (P>0.05) compared to the vehicle control, and the compound of Example 59 showed an antitumor effect of 83.51% (P<0.01), and the compound of Example 60 showed an antitumor effect of 69.06% (P<0.01) (FIG. 3).

The in vivo antitumor effects of the compounds of Example 65, 135, 139 and 154 were comparatively observed, and as a result, it was observed that the compound of Example 65, 135, 139 and 154 showed an antitumor effect of 95.42% (P<0.01), 92.66% (P<0.01), 91.04% (P<0.01), and 83.19% (P<0.01), respectively (FIG. 4)

The in vivo antitumor effects according to the concentration of Example 135, it was observed that an antitumor effect in 12.5 mg/kg of Example 135 was 52.36%, an antitumor effect in 25 mg/kg of Example 135 was 74.73%, and an antitumor effect in 50 mg/kg of Example 135 was 86.85% (FIG. 5).

The invention claimed is:

1. A pyridine derivative represented by the following formula I and a pharmaceutically acceptable salt thereof:

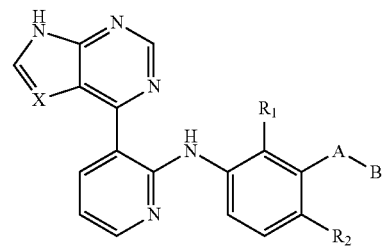

[Formula I]

wherein
X is N;
$R_1$ is hydrogen;
$R_2$ is fluoro;
A is

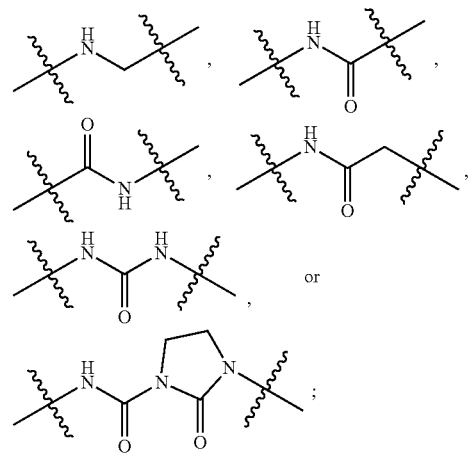

and
B is $C_{1-8}$ alkyl, aryl, or heteroaryl,
wherein one or more hydrogen atoms in the aryl or heteroaryl can be each independently substituted with a substituent selected from the group consisting of halogen, —$CF_3$, —$NO_2$, —OH, —SH, —CN, —$NR_3R_4$, —NHC(O)$OR_5$, —$SO_2R_6$, $C_{1-8}$ alkoxy, $C_{1-8}$ thioalkoxy, $C_{1-8}$ alkyl, $C_{3-6}$ cycloalkyl, 3- to 6-membered heterocycloalkyl, $C_{5-8}$ aryl, and 5- to 8-membered heteroaryl;
wherein one or more hydrogen atoms in the $C_{1-8}$ alkoxy among the substituents can be each independently substituted with halogen,
one or more hydrogen atoms in the $C_{1-8}$ alkyl or $C_{3-6}$ cycloalkyl among the substituents can be each independently substituted with 3- to 6-membered heterocycloalkyl which is unsubstituted or substituted with $C_{1-8}$ alkyl, —CN, or —C(O)$NH_2$,
one or more hydrogen atoms in the 3- to 6-membered heterocycloalkyl among the substituents can be each independently substituted with $C_{1-8}$ alkyl or —OH,
one or more hydrogen atoms in the $C_{5-8}$ aryl or 5- to 8-membered heteroaryl among the substituents can be each independently substituted with halogen, —$CF_3$, —$NO_2$, —OH, —SH, —CN, —$NR_3R_4$, —NHC(O)$OR_5$, —C(O)$NR_3R_4$, $C_{1-8}$ alkoxy, $C_{1-8}$ thioalkoxy, or $C_{1-8}$ alkyl, wherein $R_3$, $R_4$, $R_5$, and $R_6$ are each independently hydrogen or $C_{1-6}$ alkyl, wherein one or more atoms in the $C_{1-6}$ alkyl can be substituted with halogen.

2. The pyridine derivative or pharmaceutically acceptable salt thereof according to claim 1, wherein
X is N;
$R_1$ is hydrogen;
$R_2$ is fluoro;
A is

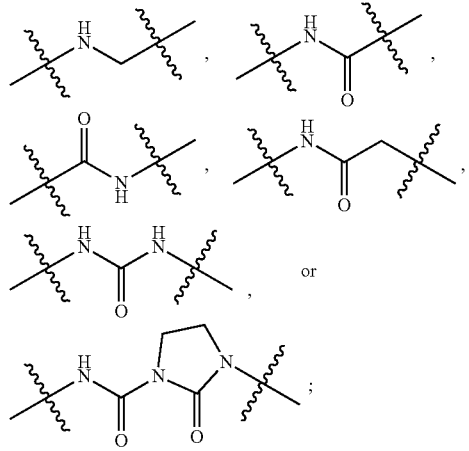

and
B is $C_{1-8}$ alkyl, aryl, or heteroaryl;
wherein one or more hydrogen atoms in the aryl or heteroaryl can be each independently substituted with a substituent selected from the group consisting of halogen, —$CF_3$, —$NO_2$, —CN, —$NR_3R_4$, —NHC(O)$OR_5$, —$SO_2R_6$, $C_{1-8}$ alkoxy, $C_{1-8}$ alkyl, $C_{3-6}$ cycloalkyl, 3- to 6-membered heterocycloalkyl, $C_{5-8}$ aryl, and 5- to 8-membered heteroaryl;
wherein
one or more hydrogen atoms in the $C_{1-8}$ alkoxy among the substituents can be each independently substituted with halogen,
one or more hydrogen atoms in the $C_{1-8}$ alkyl or $C_{3-6}$ cycloalkyl among the substituents can be each independently substituted with 3- to 6-membered heterocycloalkyl which is unsubstituted or substituted with $C_{1-8}$ alkyl, —CN, or —C(O)$NH_2$,
one or more hydrogen atoms in the 3- to 6-membered heterocycloalkyl among the substituents can be each independently substituted with $C_{1-8}$ alkyl or —OH,
one or more hydrogen atoms in the $C_{5-8}$ aryl or 5- to 8-membered heteroaryl among the substituents can be each independently substituted with halogen, —$CF_3$, —$NO_2$, —CN, —$NR_3R_4$, —NHC(O)$OR_5$, —C(O)$NR_3R_4$, $C_{1-8}$ alkoxy, or $C_{1-8}$ alkyl, wherein $R_3$, $R_4$, $R_5$, and $R_6$ are each independently hydrogen or $C_{1-6}$ alkyl, wherein one or more atoms in the $C_{1-6}$ alkyl can be substituted with halogen.

3. The pyridine derivative or pharmaceutically acceptable salt thereof according to claim 1, wherein, in formula UM,
X is N;
$R_1$ is hydrogen;
$R_2$ is fluoro;
A is

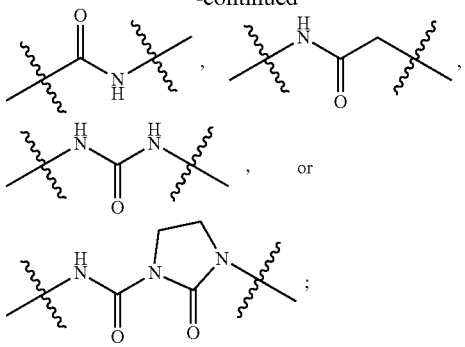

and
B is $C_{1-8}$ alkyl, aryl, or heteroaryl;
wherein one or more hydrogen atoms in the aryl or heteroaryl can be each independently substituted with a substituent selected from the group consisting of halogen, —$CF_3$, —$NO_2$, —CN, —$NR_3R_4$, —NHC(O)$OR_5$, —$SO_2R_6$, $C_{1-4}$ alkoxy, $C_{1-4}$ alkyl, $C_{3-6}$ cycloalkyl, 3- to 6-membered heterocycloalkyl, $C_{5-8}$ aryl, and 5- to 8-membered heteroaryl;
one or more hydrogen atoms in the $C_{1-4}$ alkoxy among the substituents can be each independently substituted with halogen;
one or more hydrogen atoms in the $C_{1-4}$ alkyl or $C_{3-6}$ cycloalkyl among the substituents can be each independently substituted with 3- to 6-membered heterocycloalkyl which is unsubstituted or substituted with $C_{1-4}$ alkyl, —CN, or —C(O)$NH_2$,
one or more hydrogen atoms in the 3- to 6-membered heterocycloalkyl among the substituents can be each independently substituted with $C_{1-8}$ alkyl or —OH,
one or more hydrogen atoms in the $C_{5-8}$ or 5- to 8-membered heteroaryl among the substituents can be each independently substituted with halogen or $C_{1-4}$ alkyl.

4. The pyridine derivative or pharmaceutically acceptable salt thereof according to claim 1, wherein
X is N;
$R_1$ is hydrogen;
$R_2$ is fluoro;
A is

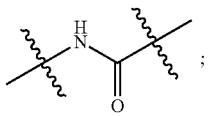 [SMILES: *NC(*)=O]

and
B is aryl;
wherein one or more hydrogen atoms in the aryl can be each independently substituted with a substituent selected from the group consisting of halogen, —$CF_3$, $C_{1-4}$ alkoxy, or $C_{1-4}$ alkyl;
wherein one or more hydrogen atoms in the $C_{1-4}$ alkyl among the substituents can be each independently substituted with —CN or —C(O)$NH_2$.

5. The pyridine derivative or pharmaceutically acceptable salt thereof according to claim 1, wherein the pyridine derivative is selected from the group consisting of the following compounds:

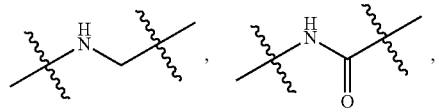

(21) N-(5-(3-(9H-purin-6-yl)pyridin-2-ylamino)-2-fluorophenyl)-3-(2-cyanopropan-2-yl)benzamide;
(30) N-(5-(3-(9H-purin-6-yl)pyridin-2-ylamino)-2-fluorophenyl)-3-(trifluoromethyl)benzamide;
(33) N-(5-(3-(9H-purin-6-yl)pyridin-2-ylamino)-2-fluorophenyl)-3-(2-cyanopropan-2-yl)-5-fluorobenzamide;
(36) N-(5-(3-(9H-purin-6-yl)pyridin-2-ylamino)-2-fluorophenyl)-3-fluoro-5-(trifluoromethyl)benzamide;
(61) 4-chloro-N-{2-fluoro-5-[3-(9H-purin-6-yl)pyridin-2-ylamino]phenyl}-3-(trifluoromethyl)benzamide;
(62) N-{2-fluoro-5-[3-(9H-purin-6-yl)pyridin-2-ylamino]phenyl}-3-nitro-5-(trifluoromethyl)benzamide;
(63) N-{2-fluoro-5-[3-(9H-purin-6-yl)pyridin-2-ylamino]phenyl}-3-methoxy-5-(trifluoromethyl)benzamide;
(64) N-{2-fluoro-5-[3-(9H-purin-6-yl)pyridin-2-ylamino]pheny}-6-(6-methylpyridin-2-yl)benzamide;
(65) N-{2-fluoro-5-[3-(9H-purin-6-yl)pyridin-2-ylamino]phenyl}-3,5-bis(trifluoromethyl)benzamide;
(73) 2-fluoro-5-[3-(9H-purin-6-yl)pyridin-2-ylamino]-N-(3-trifluoromethylphenyl)benzamide;
(74) 1-(4-chloro-3-trifluoromethylphenyl)-3-{2-fluoro-5-[3-(9H-purin-6-yl)pyridin-2-ylamino]phenyl} urea;
(76) N-{2-fluoro-5-[3-(9H-purin-6-yl)pyridin-2-ylamino]phenyl}-2-(3-trifluoromethylphenyl)acetamide;
(111) N-5-[(3-(9H-purin-6-yl)pyridin-2-yl)amino]-2-fluorophenyl-4-fluoro-3-(trifluoromethyl)benzamide;
(112) 5-[3-(9H-purin-6-yl)amino]-N-[3-(2-cyanopropan-2-yl)phenyl]-2-fluorobenzamide;
(113) N-5-[(3-(9H-purin-6-yl)pyridin-2-yl)amino]-2-fluorophenyl-3-fluorobenzamide;
(114) 5-[3-(9H-purin-6-yl)pyridin-2-yl]amino-N-(3,4-difluorophenyl)-2-fluorobenzamide;
(115) 5-[3-(9H-purin-6-yl)pyridin-2-yl]amino-N-(3,5-difluorophenyl)-2-fluorobenzamide;
(116) N-5-[(3-(9H-purin-6-yl)pyridin-2-yl)amino]-2-fluorophenyl-3-(2-cyanopropan-2-yl)-4-fluorobenzamide;
(117) N-5-[(3-(9H-purin-6-yl)pyridin-2-yl)amino]-2-fluorophenyl-4-chloro-3-(2-cyanopropan-2-yl)benzamide;
(118) 1-5-[(3-(9H-purin-6-yl)pyridin-2-yl)amino]-2-fluorophenyl-3-[3-(trifluoromethyl)phenyl]urea;
(119) N-5-[(3-(9H-purin-6-yl)pyridin-2-yl)amino]-2-fluorophenyl-6-(2-cyanopropan-2-yl)picolinamide;
(120) N-5-[(3-(9H-purin-6-yl)pyridin-2-yl)amino]-2-fluorophenyl-2-fluoro-5-(trifluoromethyl)benzamide;
(121) N-5-[(3-(9H-purin-6-yl)pyridin-2-yl)amino]-2-fluorophenyl-2-fluoro-3-(trifluoromethyl)benzamide;
(123) 1-5-[(3-(9H-purin-6-yl)pyridin-2-yl)amino]-2-fluorophenyl-3-[4-(trifluoromethyl)phenyl]urea;
(125) N-5-[(3-(9H-purin-6-yl)pyridin-2-yl)amino]-2-fluorophenyl-3-(methylthio)benzamide;
(126) N-5-[(3-(9H-purin-6-yl)pyridin-2-yl)amino]-2-fluorophenyl-3-(methylsulfonyl)benzamide;
(128) N-5-[(3-(9H-purin-6-yl)pyridin-2-yl)amino]-2-fluorophenyl-2,4-bis(trifluoromethyl)benzamide;
(129) N-5-[(3-(9H-purin-6-yl)pyridin-2-yl)amino]-2-fluorophenyl-3,4-bis(trifluoromethyl)benzamide;
(130) N-5-[(3-(9H-purin-6-yl)pyridin-2-yl)amino]-2-fluorophenyl-2,5-bis(trifluoromethyl)benzamide;
(131) N-5-[(3-(9H-purin-6-yl)pyridin-2-yl)amino]-2-fluorophenyl-3-(trifluoromethyoxy)benzamide;
(132) N-5-[(3-(9H-purin-6-yl)pyridin-2-yl)amino]-2-fluorophenyl-3,5-dimethoxybenzamide;
(133) N-5-[(3-(9H-purin-6-yl)pyridin-2-yl)amino]-2-fluorophenyl-3-fluoro-4-(trifluoromethyl)benzamide;
(134) N-5-[(3-(9H-purin-6-yl)pyridin-2-yl)amino]-2-fluorophenyl-4-methoxy-3-(trifluoromethyl)benzamide;
(135) N-5-[(3-(9H-purin-6-yl)pyridin-2-yl)amino]-2-fluorophenyl-3-chloro-5-(trifluoromethyl)benzamide;
(136) N-5-[(3-(9H-purin-6-yl)pyridin-2-yl)amino]-2-fluorophenyl-6-(trifluoromethyl)picolinamide;
(137) N-5-[(3-(9H-purin-6-yl)pyridin-2-yl)amino]-2-fluorophenyl-4-fluoro-3-methylbenzamide;
(138) N-5-[(3-(9H-purin-6-yl)pyridin-2-yl)amino]-2-fluorophenyl-4-methyl-3-(trifluoromethyl)benzamide;
(139) N-5-[(3-(9H-purin-6-yl)pyridin-2-yl)amino]-2-fluorophenyl-3-methyl-5-(trifluoromethyl)benzamide;
(140) N-5-[(3-(9H-purin-6-yl)pyridin-2-yl)amino]-2-fluorophenyl-3-methoxy-5-(trifluoromethoxy)benzamide;
(141) N-5-[(3-(9H-purin-6-yl)pyridin-2-yl)amino]-2-fluorophenyl-3-cyclopropylbenzamide;
(142) N-5-[(3-(9H-purin-6-yl)pyridin-2-yl)amino]-2-fluorophenyl-3-chloro-5-(trifluoromethoxy)benzamide;
(143) N-5-[(3-(9H-purin-6-yl)pyridin-2-yl)amino]-2-fluorophenyl-4-fluoro-3-(trifluoromethoxy)benzamide;
(144) N-5-[(3-(9H-purin-6-yl)pyridin-2-yl)amino]-2-fluorophenyl-4-(trifluoromethyl)picolinamide;
(145) N-5-[(3-(9H-purin-6-yl)pyridin-2-ylamino]-2-fluorophenyl-3-methylbenzamide;
(146) N-5-[(3-(9H-purin-6-yl)pyridin-2-ylamino]-2-fluorophenyl-3-chlorobenzamide;
(147) N-5-[(3-(9H-purin-6-yl)pyridin-2-ylamino]-2-fluorophenyl-4-chloro-3-(trifluoromethoxy)benzamide;
(148) N-5-[(3-(9H-purin-6-yl)pyridin-2-yl)amino]-2-fluorophenyl-3-fluoro-2-(trifluoromethyl)isonicotinamide;
(149) N-5-[(3-(9H-purin-6-yl)pyridin-2-yl)amino]-2-fluorophenyl-5-(trifluoromethyl)nicotinamide;
(150) N-5-[(3-(9H-purin-6-yl)pyridin-2-yl)amino]-2-fluorophenyl-4-methoxy-3-(trifluoromethoxy)benzamide;
(151) N-5-[(3-(9H-purin-6-yl)pyridin-2-yl)amino]-2-fluorophenyl-2-(trifluoromethyl)isonicotinamide;
(154) N-5-[(3-(9H-purin-6-yl)pyridin-2-yl)amino]-2-fluorophenyl-3-(2-cyanopropan-2-yl)-5-(trifluoromethyl)benzamide;
(155) N-5-[(3-(9H-purin-6-yl)pyridin-2-yl)amino]-2-fluorophenyl-3-(2-cyanopropan-2-yl)-5-methylbenzamide;
(156) N-5-[(3-(9H-purin-6-yl)pyridin-2-yl)amino]-2-fluorophenyl-2-bromo-3-(2-cyanopropan-2-yl)-5-methoxybenzamide;
(157) N-5-[(3-(9H-purin-6-yl)pyridin-2-yl)amino]-2-fluorophenyl-3-cyano-5-(trifluoromethyl)benzamide; and
(158) N-5-[(3-(9H-purin-6-yl)pyridin-2-yl)amino]-2-fluorophenyl-3-bromo-5-(trifluoromethyl)benzamide.

6. A pharmaceutical composition for treatment of an abnormal cell growth disease caused by RAS mutation, the composition containing, as an active ingredient, the pyridine derivative or pharmaceutically acceptable salt thereof according to claim 1, wherein the abnormal cell growth disease caused by RAS mutation is any one selected from the group consisting of lung cancer, liver cancer, colorectal cancer, pancreatic cancer, melanoma, cervical cancer, ovarian cancer, thyroid cancer, renal cancer, and bladder cancer.

7. A method for treating an abnormal cell growth disease caused by RAS mutation, comprising administering a therapeutically effective amount of the pyridine derivative or pharmaceutically acceptable salt thereof according to claim 1, wherein the abnormal cell growth disease caused by RAS mutation is any one selected from the group consisting of lung cancer, liver cancer, colorectal cancer, pancreatic cancer, melanoma, cervical cancer, ovarian cancer, thyroid cancer, renal cancer, and bladder cancer.

* * * * *

UNITED STATES PATENT AND TRADEMARK OFFICE
CERTIFICATE OF CORRECTION

PATENT NO. : 10,844,062 B2  
APPLICATION NO. : 16/074950  
DATED : November 24, 2020  
INVENTOR(S) : Eui Hwan Cho et al.

Page 1 of 1

It is certified that error appears in the above-identified patent and that said Letters Patent is hereby corrected as shown below:

In the Claims

At Column 169, Claim 3, Line 57:  
Delete "UM"  
Insert --I--

At Column 171, Claim 5, Line 22:  
Delete character space between "}" and "urea"

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*